(12) United States Patent
Tarui et al.

(10) Patent No.: US 7,091,247 B2
(45) Date of Patent: Aug. 15, 2006

(54) BIPHENYL COMPOUND

(75) Inventors: Naoki Tarui, Nara (JP); Takashi Santo, Kobe (JP); Hiroyuki Watanabe, Kobe (JP); Kazuyoshi Aso, Takatsuki (JP); Tetsuo Miwa, Kobe (JP); Shiro Takekawa, Nishinomiya (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 249 days.

(21) Appl. No.: 10/312,015

(22) PCT Filed: Jun. 28, 2001

(86) PCT No.: PCT/JP01/05541

§ 371 (c)(1),
(2), (4) Date: Dec. 20, 2002

(87) PCT Pub. No.: WO02/00606

PCT Pub. Date: Jan. 3, 2002

(65) Prior Publication Data

US 2004/0106792 A1  Jun. 3, 2004

(30) Foreign Application Priority Data

Jun. 28, 2000 (JP) .............................. 2000-200118

(51) Int. Cl.
*A61K 31/166* (2006.01)
*C07C 233/64* (2006.01)
*C07C 237/28* (2006.01)
(52) U.S. Cl. ..................................... 514/616; 564/156
(58) Field of Classification Search ............... 564/156; 514/616
See application file for complete search history.

(56) References Cited

FOREIGN PATENT DOCUMENTS

| EP | 0 533 266 A1 | 3/1993 |
| WO | WO 98/47882 | 10/1998 |
| WO | WO 01/25189 | 4/2001 |
| WO | WO 01/66143 | 9/2001 |

OTHER PUBLICATIONS

Ried, Von Walter et al. "Umzetzung von Carboiimiden mit langerkettigen Dicarbonsauredichloriden" Chemiker-Zeitung 114, Jahrgang (1990) Nr. 9: 287-289.

*Primary Examiner*—Taofiq Solola
(74) *Attorney, Agent, or Firm*—Elaine M. Ramesh; Mark Chao

(57) ABSTRACT

A novel biphenyl compound having GPR 14 antagonistic activity. It is a compound represented by the formula (I):

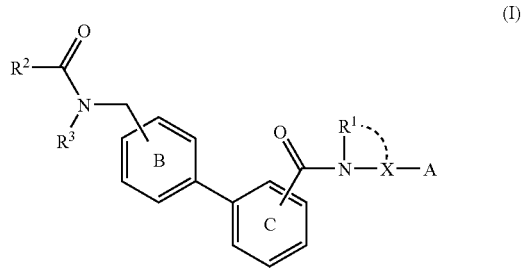

wherein $R^1$ represents hydrogen, etc.; X represents 1 to 12 spacers; A represents amino, etc., $R^2$ and $R^3$ each represents a hydrocarbon group, etc.; and rings B and C each represents an optionally further substituted benzene ring, or a salt thereof.

22 Claims, No Drawings

SEQUENCE LISTING

<160> NUMBER OF SEQ ID NOS: 6

<210> SEQ ID NO 1
<211> LENGTH: 37
<212> TYPE: DNA
<213> ORGANISM: Artificial Sequence
<220> FEATURE:
<223> OTHER INFORMATION: Synthetic DNA for screening cDNA coding human
      GPR14 protein

<400> SEQUENCE: 1
tcgtgagtcg accaccatgg cgctgacccc cgagtcc                              37

<210> SEQ ID NO 2
<211> LENGTH: 33
<212> TYPE: DNA
<213> ORGANISM: Artificial Sequence
<220> FEATURE:
<223> OTHER INFORMATION: Syhthetic DNA for screening cDNA coding human
      GPR14 protein

<400> SEQUENCE: 2
gcctggacta gtgccgcccc tccgcgtgct cac                                  33

<210> SEQ ID NO 3
<211> LENGTH: 1215
<212> TYPE: DNA
<213> ORGANISM: Human

<400> SEQUENCE: 3
tcgtgagtcg accaccatgg cgctgacccc cgagtccccg agcagcttcc ctgggctggc     60
cgccaccggc agctctgtgc cggagccgcc tggcggcccc aacgcaaccc tcaacagctc    120
ctgggccagc ccgaccgagc ccagctccct ggaggacctg gtggccacgg caccattgg    180 gactctgctg tcggccatgg gcgtggtggg cgtggtgggc aacgcctaca cgctggtggt    240
cacctgccgc tccctgcgtg cggtggcctc catgtacgtc tacgtggtca acctggcgct    300
ggccgacctg ctgtacctgc tcagcatccc cttcatcgtg gccacctacg tcaccaagga    360
gtggcacttc ggggacgtgg gctgccgcgt gctcttcggc ctggacttcc tgaccatgca    420
cgccagcatc ttcacgctga ccgtcatgag cagcgagcgc tacgctgcgg tgctgcggcc    480
gctggacacc gtgcagcgcc caagggcta ccgcaagctg ctggcgctgg cacctggct    540 gctggcgctg ctgctgacgc tgcccgtgat gctggccatg cggctggtgc gccggggtcc    600
caagagcctg tgcctgcccg cctggggccc gcgcgcccac cgcgcctacc tgacgctgct    660
cttcgccacc agcatcgcgg ggcccgggct gctcatcggg ctgctctacg cgcgcctggc    720
ccgcgcctac cgccgctcgc agcgcgcctc cttcaagcgg gcccggcggc cggggcgcg    780 cgcgctgcgc ctggtgctgg gcatcgtgct gctcttctgg gcctgcttcc tgcccttctg    840
gctgtggcag ctgctcgccc agtaccacca ggccccgctg gcgccgcgga cggcgcgcat    900
cgtcaactac ctgaccacct gcctcaccta cggcaacagc tgcgccaacc ccttcctcta    960
cacgctgctc accaggaact accgcgacca cctgcgcggc cgcgtgcggg cccgggcag   1020 cggggaggc cggggcccg ttccctccct gcagccccgc gcccgcttcc agcgctgttc   1080
gggccgctcc ctgtcttcct gcagcccaca gcccactgac agcctcgtgc tggccccagc   1140 ggcccggcc cgacctgccc ccagggtcc cagggcccg gcgtgagcac gcggagggc   1200 ggcactagtc caggc                                                    1215

<210> SEQ ID NO 4
<211> LENGTH: 389
<212> TYPE: PRT
<213> ORGANISM: Human

<400> SEQUENCE: 4

```
Met Ala Leu Thr Pro Glu Ser Pro Ser Phe Pro Gly Leu Ala Ala
 1               5                  10                  15

Thr Gly Ser Ser Val Pro Glu Pro Pro Gly Gly Pro Asn Ala Thr Leu
                20                  25                  30

Asn Ser Ser Trp Ala Ser Pro Thr Glu Pro Ser Ser Leu Glu Asp Leu
            35                  40                  45

Val Ala Thr Gly Thr Ile Gly Thr Leu Leu Ser Ala Met Gly Val Val
        50                  55                  60

Gly Val Val Gly Asn Ala Tyr Thr Leu Val Val Thr Cys Arg Ser Leu
65                  70                  75                  80

Arg Ala Val Ala Ser Met Tyr Val Tyr Val Val Asn Leu Ala Leu Ala
                85                  90                  95

Asp Leu Leu Tyr Leu Leu Ser Ile Pro Phe Ile Val Ala Thr Tyr Val
                100                 105                 110

Thr Lys Glu Trp His Phe Gly Asp Val Gly Cys Arg Val Leu Phe Gly
            115                 120                 125

Leu Asp Phe Leu Thr Met His Ala Ser Ile Phe Thr Leu Thr Val Met
        130                 135                 140

Ser Ser Glu Arg Tyr Ala Ala Val Leu Arg Pro Leu Asp Thr Val Gln
145                 150                 155                 160

Arg Pro Lys Gly Tyr Arg Lys Leu Leu Ala Leu Gly Thr Trp Leu Leu
                165                 170                 175

Ala Leu Leu Leu Thr Leu Pro Val Met Leu Ala Met Arg Leu Val Arg
                180                 185                 190

Arg Gly Pro Lys Ser Leu Cys Leu Pro Ala Trp Gly Pro Arg Ala His
            195                 200                 205

Arg Ala Tyr Leu Thr Leu Leu Phe Ala Thr Ser Ile Ala Gly Pro Gly
        210                 215                 220

Leu Leu Ile Gly Leu Leu Tyr Ala Arg Leu Ala Arg Ala Tyr Arg Arg
225                 230                 235                 240

Ser Gln Arg Ala Ser Phe Lys Arg Ala Arg Pro Gly Ala Arg Ala
                245                 250                 255

Leu Arg Leu Val Leu Gly Ile Val Leu Leu Phe Trp Ala Cys Phe Leu
                260                 265                 270

Pro Phe Trp Leu Trp Gln Leu Leu Ala Gln Tyr His Gln Ala Pro Leu
            275                 280                 285

Ala Pro Arg Thr Ala Arg Ile Val Asn Tyr Leu Thr Thr Cys Leu Thr
        290                 295                 300

Tyr Gly Asn Ser Cys Ala Asn Pro Phe Leu Tyr Thr Leu Leu Thr Arg
305                 310                 315                 320

Asn Tyr Arg Asp His Leu Arg Gly Arg Val Arg Gly Pro Gly Ser Gly
                325                 330                 335

Gly Gly Arg Gly Pro Val Pro Ser Leu Gln Pro Arg Ala Arg Phe Gln
            340                 345                 350

Arg Cys Ser Gly Arg Ser Leu Ser Ser Cys Ser Pro Gln Pro Thr Asp
        355                 360                 365

Ser Leu Val Leu Ala Pro Ala Ala Pro Ala Arg Pro Ala Pro Glu Gly
```

```
                      370                 375                 380
Pro Arg Ala Pro Ala
385

<210> SEQ ID NO 5
<211> LENGTH: 28
<212> TYPE: DNA
<213> ORGANISM: Artificial Sequence
<220> FEATURE:
<223> OTHER INFORMATION: Synthetic DNA oligomer S5-1 based on human SSTR
      cDNA

<400> SEQUENCE: 5
ggtcgaccac catggagccc ctgttccc                                      28

<210> SEQ ID NO 6
<211> LENGTH: 26
<212> TYPE: DNA
<213> ORGANISM: Artificial Sequence
<220> FEATURE:
<223> OTHER INFORMATION: Synthetic DNA oligomer S5-2 based on human SSTR
      cDNA

<400> SEQUENCE: 6
ccgtcgacac tctcacagct tgctgg                                        26
```

BIPHENYL COMPOUND

This application is the national phase of PCT/JP01/05541 filed 28 Jun. 2001.

TECHNICAL FIELD

The present invention relates to novel biphenyl compounds having GPR 14-antagonizing activity or somatostatin receptor function regulatory activity, or salts thereof, and their use.

BACKGROUND OF THE INVENTION

Urotensin II was discovered as one of peptide hormones having a potent vasoconstrictive activity, and has been proved to have far higher vasoconstrictive activity than endothelin, which is the most potent vasoconstrictor among those which are currently known to have vasoconstrictive activity on mammal arteria. Further, it has been revealed that the receptor for urotensin II is GPR 14 protein, which is one of the orphan receptors (see, Nature, vol. 401, p. 282 (1999)).

On the other hand, somatostatin has been isolated and identified from sheep hypothalamus tissue as a factor for strongly suppressing secretion of growth hormone and is a peptide composed of 14 amino acids (SST-14). At present, somatostatin composed of 28 amino acids (SST-28) is also isolated and identified. This somatostatin is a brain-gut peptide widely distributed in not only hypothalamus, but also in brain, limbic system, spinal cord, vagus nerve, autonomic neuroganglion, gastrointestinal mucosa, pancreas Langerhans islets, etc., and suppresses secretion of pituitary-gastrointestinal hormones such as growth hormone, thyroid stimulating hormone, gastrin, insulin, glucagon, etc. Further, it suppresses secretion of gastric juice, pancreatic exocrine, and gastrointestinal movement and blood flow. As somatostatin receptors, up to the present, type 1 to type 5 (SSTR1, SSTR2, SSTR3, SSTR4, SSTR5) have been known and it is recognized that each of them shows different expression.
[1. Life Science, Vol. 57, No. 13, p. 1249 (1995)
2. Journal of Clinical Endocrinology and Metabolism, Vol. 80, No. 6, pp. 1789–1793
3. The New England Journal of Medicine, Jan. 25, 1996
4. Eur. J. Clin. Pharmacol., 1996, 51, 139–144
5. Exp. Opin. Ther. Patents (1998) 8 (7): 855–870]

As compounds having somatostatin receptor regulating activity, there are peptide compounds described in Life Science, 31, 1133–1140 (1982), Nature, 292, 55–58 (1981) and the like; and non peptide compounds described in JP 2000-191615 A, JP 2000-191648 A, JP 2000-226373 A, JP 11-209356 A and the like. As compounds having somatostatin receptor regulating activity and containing biphenyl in their structures, there are compounds described in JP 2000-226373 and the like.

Further, as biphenyl compounds, for example, JP 6-107649 A discloses biphenyl compounds having 5-HT (serotonin) receptor antagonistic activity and its Example 10 discloses 4'-[[(methoxyacetyl)methylamino]methyl]-N-[4-methoxy-3-(4-methoxy-3-(4-methyl-1-piperazinyl)phenyl]-2'-methyl-[1,1'-biphenyl]-4-carboxamide hydrochloride.

SUMMARY OF THE INVENTION

An antagonist of urotensin II receptor GPR 14 may possibly be developed as a novel vasoactive drug (a therapeutic agent for treating ischemic myocardial infarction, congestive heart failure and the like). However, none of such antagonists have been reported yet.

The present invention provides novel biphenyl compounds having GPR 14-antagonizing activity or somatostatin receptor function regulatory activity, or salts thereof and, based on GPR 14-antagonizing activity, a vasoactive agent, in particular, a vasoconstriction inhibitor which is useful for preventing and/or treating, for example, hypertension, arteriosclerosis, hypercardia, myocardial infarction, heart failure and the like. Further, based on somatostatin receptor function regulatory activity, it provides an agent for preventing and/or treating diabetes, obesity, diabetic complication, intractable diarrhea, glaucoma, acromegaly, depression, tumor and the like.

The present inventors have intensively examined compounds having GPR 14-antagonizing activity or somatostatin receptor function regulatory activity. As a result, it has been found that a compound having the formula (I) below or salts thereof (hereinafter sometimes referred to as "compound (I)") can exhibit an excellent GPR 14-antagonizing activity or somatostatin receptor function regulatory activity. Thus, the present invention has been completed.

The present invention relates to:

1) A compound represented by the formula (I):

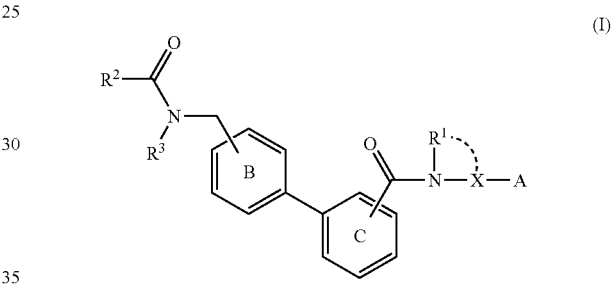

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substituted nitrogen-containing heterocyclic group; $R^2$ represents an optionally substituted hydrocarbon group or an optionally substituted amino group; $R^3$ represents an optionally substituted hydrocarbon group; and rings B and C each represents a further optionally substituted benzene ring, or a salt thereof, provided that (1) a compound represented by the formula:

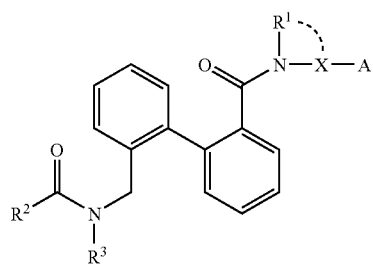

wherein each symbol is as defined above and (2) 4'-[[(methoxyacetyl)methylamino]methyl]-N-[4-methoxy-3-(4-methyl-1-piperazinyl)phenyl]-2'-methyl-[1,1'-biphenyl]-4-carboxamide are excluded;

2) A compound represented by formula (I):

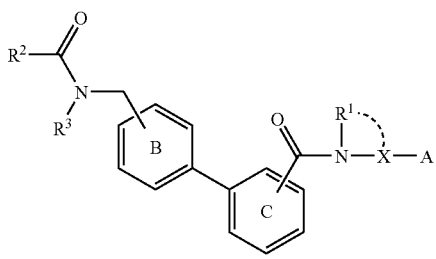

wherein $R^1$ represents hydrogen atom or an optionally substituted hydrocarbon group; X represents a spacer whose linear chain moiety is composed of 1 to 8 atoms; $R^1$ and X may be bound to each other to form a ring; A represents an optionally substituted amino group or an optionally substituted nitrogen-containing heterocyclic group; $R^2$ and $R^3$ each represent an optionally substituted hydrocarbon group, and rings B and C each represent a further optionally substituted benzene ring, or a salt thereof, provided that 4'-[[(methoxyacetyl)methylamino]methyl]-N-[4-methoxy-3-(4-methyl-1-piperazinyl)phenyl]-2'-methyl-[1,1'-biphenyl]-4-carboxamide is excluded;

3) The compound according to the above 2), which is represented by the formula (I):

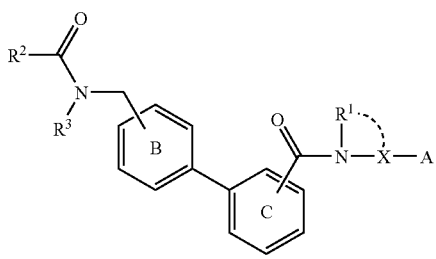

wherein $R^1$ represents a hydrogen atom or an optionally substituted hydrocarbon group, X represents a spacer whose linear chain moiety is composed of 1 to 8 atoms, $R^1$ and X may be bound to each other to form a ring, A represents an optionally substituted amino group or an optionally substituted nitrogen-containing heterocyclic group, $R^2$ and $R^3$ each represents an optionally substituted hydrocarbon group, and rings B and C each represents a further optionally substituted benzene ring, or a salt thereof, provided that a compound represented by the formula:

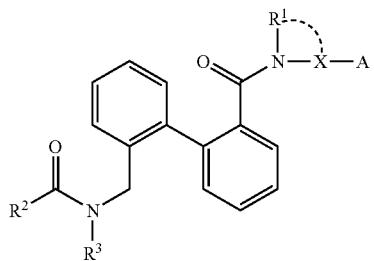

wherein each symbol is as defined above, is excluded;

4) The compound according to the above 1), wherein $R^1$ is (1) hydrogen atom; (2) $C_{1-10}$alkyl which may have 1 to 3 substituents selected from (1') halogen atom, (2') nitro, (3') cyano, (4') oxo, (5') hydroxyl group, (6') thiol, (7') $C_{1-4}$alkylthio, (8') amino group, (9') mono-$C_{1-4}$alkylamino, (10') di-$C_{1-4}$alkylamino, (11') 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (12') phenyl-$C_{1-4}$alkyl, (13') $C_{3-7}$cycloalkyl, (14') carboxyl, (15') $C_{1-4}$alkoxy-carbonyl, (16') $C_{7-10}$aralkyloxy-carbonyl, (17') carbamoyl, (18') mono-$C_{1-4}$alkylcarbamoyl, (19') di-$C_{1-4}$alkylcarbamoyl, (20') $C_{1-4}$alkyl which may be substituted with a halogen atom or $C_{1-4}$alkoxy, (21') $C_{1-4}$alkoxy which may be substituted with a halogen atom or $C_{1-4}$alkoxy, (22') $C_{1-4}$alkylenedioxy, (23') formyl, (24') $C_{2-4}$alkanoyl, (25') $C_{1-4}$alkylsulfonyl, (26') $C_{1-4}$alkylsulfinyl, (27') sulfamoyl, (28') mono-$C_{1-4}$alkylsulfamoyl, (29') di-$C_{1-4}$alkylsulfamoyl, (30') $C_{6-14}$aryl (which may be substituted with a substituent(s) selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole and imidazole, (11") phenyl-$C_{1-4}$alkyl, (12") $C_{3-7}$cycloalkyl, (13") carboxyl group, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl and (29") 5- to 6-membered aromatic monocyclic heterocyclic group), and (31') 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1") halogen, (2") nitro, (3") cyano, (4") oxo, (5") hydroxyl group, (6") thiol, (7") $C_{1-4}$alkylthio, (8") amino, (9") mono-$C_{1-4}$alkylamino, (10") di-$C_{1-4}$alkylamino, (11") 5- to 6-membered cyclic amino selected from tetrahydropyrrole, piperazine, piperidine, morpholine, thiomorpholine, pyrrole and imidazole, (12") phenyl-$C_{1-4}$alkyl, (14") $C_{3-7}$cycloalkyl, (15") carboxyl, (16") $C_{1-4}$alkoxy-carbonyl, (17") $C_{7-10}$aralkyloxy-carbonyl, (18") carbamoyl, (19") mono-$C_{1-4}$alkyl-carbamoyl, (20") di-$C_{1-4}$alkyl-carbamoyl, (21") $C_{1-4}$alkyl which may be substituted with a halogen atom or $C_{1-4}$alkoxy, (22") $C_{1-4}$alkoxy which may be substituted with a halogen atom or $C_{1-4}$alkoxy, (23") $C_{1-4}$alkylenedioxy, (24") formyl, (25") $C_{2-4}$alkanoyl, (26") $C_{1-4}$alkylsulfonyl, and (27") $C_{1-4}$alkylsulfinyl) (hereinafter referred to as substituent group A); (3) $C_{3-8}$cycloalkyl which may have 1 to 3 substituents selected from the substituent group A; (4) $C_{2-10}$alkenyl which may have 1 to 3 substituents selected from the substituent group A; (5) $C_{3-8}$cycloalkenyl which may have 1 to 3 substituents selected from the substituent group A; (6) $C_{2-10}$alkynyl which may have 1 to 3 substituents selected from the substituent group A; (7) $C_{6-14}$aryl which may have 1 to 3 substituents selected from the substituent group A; (8) $C_{6-14}$aryl-$C_{1-6}$alkyl which may have 1 to 3 substituents selected from the substituent group A; (9) di-$C_{6-14}$aryl-$C_{1-6}$alkyl which may have 1 to 3 substituents selected from the substituent group A; (10) tri-$C_{6-14}$aryl-$C_{1-6}$alkyl which may have 1 to 3 substituents selected from the substituent group A; (11) a group represented by the formula —X'''—G—(CH$_2$)$_n$—J wherein X''' represents C$_{1-4}$alkylene or C$_{2-4}$alkenylene, G is a bond, —O—, —S—, —CO—NH— or —NH—CO—, n is an integer of 0 to 3, J represents (a) C$_{6-14}$aryl (which may have 1 to 3 substituents selected from (1'') halogen, (2'') nitro, (3'') cyano, (4'') hydroxyl group, (5'') thiol, (6'') C$_{1-4}$alkylthio, (7'') amino, (8'') mono-C$_{1-4}$alkylamino, (9'') di-C$_{1-4}$alkylamino, (10'') 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (11'') phenyl-C$_{1-4}$alkyl, (12'') C$_{3-7}$cycloalkyl, (13'') carboxyl, (14'') C$_{1-4}$alkoxy-carbonyl, (15'') C$_{7-10}$aralkyloxy-carbonyl, (16'') carbamoyl, (17'') mono-C$_{1-4}$alkyl-carbamoyl, (18'') di-C$_{1-4}$alkyl-carbamoyl, (19'') C$_{1-4}$alkyl which may be substituted with a halogen atom or C$_{1-4}$alkoxy, (20'') C$_{1-4}$alkoxy which may be substituted with a halogen atom or C$_{1-4}$alkoxy, (21'') C$_{1-4}$alkylenedioxy, (22'') formyl, (23'') C$_{2-4}$alkanoyl, (24'') C$_{1-4}$alkylsulfonyl, (25'') C$_{1-4}$alkylsulfinyl, (26'') sulfamoyl, (27'') mono-C$_{1-4}$alkylsulfamoyl, (28'') di-C$_{1-4}$alkylsulfamoyl, (29'') C$_{6-14}$aryl (which may be substituted with a substituent(s) selected from (1''') halogen, (2''') nitro, (3''') cyano, (4''') hydroxyl group, (5''') thiol, (6''') C$_{1-4}$alkylthio, (7''') amino, (8''') mono-C$_{1-4}$alkylamino, (9''') di-C$_{1-4}$alkylamino, (10''') 5- to 6-membered cyclic amino selected from tetrahydropyrrole, piperazine, piperidine, morpholine, thiomorpholine, pyrrole and imidazole, (11''') phenyl-C$_{1-4}$alkyl, (12''') C$_{3-7}$cycloalkyl, (13''') carboxyl group, (14''') C$_{1-4}$alkoxy-carbonyl, (15''') C$_{7-10}$aralkyloxy-carbonyl, (16''') carbamoyl, (17''') mono-C$_{1-4}$alkyl-carbamoyl, (18''') di-C$_{1-4}$alkyl-carbamoyl, (19''') C$_{1-4}$alkyl which may be substituted with a halogen atom or C$_{1-4}$alkoxy, (20''') C$_{1-4}$alkoxy which may be substituted with a halogen atom or C$_{1-4}$alkoxy, (21''') C$_{1-4}$alkylenedioxy, (22''') formyl, (23''') C$_{2-4}$alkanoyl, (24''') C$_{1-4}$alkylsulfonyl, (25''') C$_{1-4}$alkylsulfinyl, (26''') sulfamoyl, (27''') mono-C$_{1-4}$alkylsulfamoyl, (28''') di-C$_{1-4}$alkylsulfamoyl, and (29''') 5- to 6-membered aromatic monocyclic heterocyclic group), and (30'') 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1''') halogen, (2''') nitro, (3''') cyano, (4''') oxo, (5''') hydroxyl group, (6''') thiol, (7''') C$_{1-4}$alkylthio, (8''') amino, (9''') mono-C$_{1-4}$alkylamino, (10''') di-C$_{1-4}$alkylamino, (11''') 5- to 6-membered cyclic amino selected from tetrahydropyrrole, piperazine, piperidine, morpholine, thiomorpholine, pyrrole and imidazole, (12''') phenyl-C$_{1-4}$alkyl, (13''') C$_{3-7}$cycloalkyl, (14''') carboxyl, (15''') C$_{1-4}$alkoxy-carbonyl, (16''') C$_{7-10}$aralkyloxy-carbonyl, (17''') carbamoyl, (18''') mono-C$_{1-4}$alkyl-carbamoyl, (19''') di-C$_{1-4}$alkyl-carbamoyl, (20''') C$_{1-4}$alkyl which may be substituted with a halogen atom or C$_{1-4}$alkoxy, (21''') C$_{1-4}$alkoxy which may be substituted with a halogen atom or C$_{1-4}$alkoxy, (22''') C$_{1-4}$alkylenedioxy, (23'') formyl, (24''') C$_{2-4}$alkanoyl, (25''') C$_{1-4}$alkylsulfonyl and (26''') C$_{1-4}$alkylsulfinyl) (hereinafter referred to as substituent group B), or (b) a 5- to 8-membered aromatic heterocyclic group containing at least one of 1 to 3 kinds of heterocyclic groups selected from oxygen atom, sulfur atom and nitrogen atom (said aromatic heterocyclic group optionally having 1 to 3 substituents selected from the substituent group B); or (12) a group represented by the formula —X''''—L—(CH$_2$)$_n$—M wherein X'''' represents a bond or a C$_{1-4}$alkylene group which may have 1 to 3 substituents selected from the substituent group A, L represents (a) a bond, (b) C$_{6-10}$aryl which may have 1 to 3 substituents selected from the substituent group B, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, and M represents amino group, guanidino group, sulfamoyl group, carbamoyl group or hydroxyl group, X represents the following saturated divalent groups wherein some bonds may have been converted into unsaturated bonds:

(1) —(CH$_2$)$_{f1}$—, wherein f1 represents an integer of 1 to 12, (2) —(CH$_2$)$_{g1}$—X$^1$—(CH$_2$)$_{g2}$—, wherein g1 and g2 are the same or different, and represent an integer of 0 to 11, provided that the sum of g1 and g2 is 0 to 11, and X$^1$ represents NH, O, S, SO or SO$_2$, or (3) —(CH$_2$)$_{h1}$—X$^1$—(CH$_2$)$_{h2}$—X$^2$—(CH$_2$)$_{h3}$— wherein h1, h2 and h3 are the same or different, and represent an integer of 0 to 10, provided that the sum of h1, h2 and h3 is 0 to 10, and X$^1$ and X$^2$ each represents NH, O, S, SO or SO$_2$ provided that when h2 is 0, X$^1$ and/or X$^2$ preferably represent NH, A represents (1) (a) C$_{1-10}$alkyl which may have 1 to 3 substituents selected from (1'') halogen, (2'') nitro, (3'') cyano, (4'') oxo, (5'') hydroxyl group, (6'') thiol, (7'') C$_{1-4}$alkylthio, (8'') amino, (9'') mono-C$_{1-4}$alkylamino, (10'') di-C$_{1-4}$alkylamino, (11'') 5- to 6-membered cyclic amino selected from tetrahydropyrrole, piperazine, piperidine, morpholine, thiomorpholine, pyrrole and imidazole, (12'') phenyl-C$_{1-4}$alkyl, (13'') C$_{3-7}$cycloalkyl, (14'') carboxyl, (15'') C$_{1-4}$alkoxy-carbonyl, (16'') C$_{7-10}$aralkyloxy-carbonyl, (17'') carbamoyl, (18'') mono-C$_{1-4}$alkyl-carbamoyl, (19'') di-C$_{1-4}$alkyl-carbamoyl, (20'') C$_{1-4}$alkyl which may be substituted with a halogen atom or C$_{1-4}$alkoxy, (21'') C$_{1-4}$alkoxy which may be substituted with a halogen atom or C$_{1-4}$alkoxy, (22'') C$_{1-4}$alkylenedioxy, (23'') formyl, (24'') C$_{2-4}$alkanoyl, (25'') C$_{1-4}$alkylsulfonyl and (26'') C$_{1-4}$alkylsulfinyl (hereinafter referred to as substituent group C), (b) C$_{3-8}$cycloalkyl which may have 1 to 3 substituents selected from the substituent group C, (c) C$_{2-10}$alkenyl which may have 1 to 3 substituents selected from the substituent group C, (d) C$_{3-8}$cycloalkenyl which may have 1 to 3 substituents selected from the substituent group C, (e) C$_{2-10}$alkynyl which may have 1 to 3 substituents selected from the substituent group C, (f) C$_{6-14}$aryl which may have 1 to 3 substituents selected from the substituent group C, (g) C$_{6-14}$aryl-C$_{1-6}$alkyl which may have 1 to 3 substituents selected from the substituent group C, (h) di-C$_{6-14}$aryl-C$_{1-6}$alkyl which may have 1 to 3 substituents selected from the substituent group C, (i) tri-C$_{6-14}$aryl-C$_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, C$_{1-10}$alkyl-carbonyl, C$_{3-8}$cycloalkyl-carbonyl, C$_{2-10}$alkenyl-carbonyl, C$_{3-8}$cycloalkenyl-carbonyl, C$_{2-10}$alkynyl-carbonyl, C$_{6-14}$aryl-carbonyl, C$_{6-14}$aryl-C$_{1-6}$alkyl-carbonyl, di-C$_{6-14}$aryl-C$_{1-6}$alkyl-carbonyl, tri-C$_{6-14}$aryl-C$_{1-6}$alkyl-carbonyl, C$_{1-10}$alkylsulfonyl, C$_{3-8}$cycloalkylsulfonyl, C$_{2-10}$alkenylsulfonyl, C$_{3-8}$cycloalkenylsulfonyl, C$_{2-10}$alkynylsulfonyl, C$_{6-14}$arylsulfonyl, C$_{6-14}$aryl-C$_{1-6}$alkylsulfonyl, di-C$_{6-14}$aryl-C$_{1-6}$alkylsulfonyl or tri-C$_{6-14}$aryl-C$_{1-6}$alkylsulfonyl (said acyl optionally having 1 to 3 substituents selected from the substituent group C), or (l) amino which may have 1 to 2 substituents selected from acyl groups wherein a 5- to 8-membered aromatic heterocyclic group or saturated or unsaturated non-aromatic heterocyclic group containing a least one of 1 to 3 kinds of heteroatoms selected from oxygen atom, sulfur atom and nitrogen atom has been bound to carbonyl or sulfonyl (said acyl optionally having 1 to 3 substituents selected from the substituent group C); or (2) cyclic amino which may have 1 to 3 substituents selected from (a) halogen, (b) nitro, (c) cyano, (d) hydroxyl group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl; or (3) a group formed by removing one hydrogen atom from a 5- to 8-membered aromatic monocyclic heterocyclic ring or saturated or unsaturated non-aromatic monocyclic heterocyclic group containing one nitrogen atom and one to three kinds of 1 to 4 heteroatoms selected from oxygen atom, sulfur atom and nitrogen atom or by removing one hydrogen atom from a ring wherein 2 or 3 the same or different rings selected from the above monocyclic rings have been fused (said heterocyclic group optionally having 1 to 3 substituents selected from the substituent group C), $R^2$ represents (1) $C_{1-10}$alkyl which may have 1 to 3 substituents selected from the substituent group A; (2) $C_{3-8}$cycloalkyl which may have 1 to 3 substituents selected from the substituent group A; (3) $C_{2-10}$alkenyl which may have 1 to 3 substituents selected from the substituent group A; (4) $C_{3-8}$cycloalkenyl which may have 1 to 3 substituents selected from the substituent group A; (5) $C_{2-10}$alkynyl which may have 1 to 3 substituents selected from the substituent group A; (6) $C_{6-14}$aryl which may have 1 to 3 substituents selected from the substituent group A; (7) $C_{6-14}$aryl-$C_{1-6}$alkyl which may have 1 to 3 substituents selected from the substituent group A; (8) di-$C_{6-14}$aryl-$C_{1-6}$alkyl which may have 1 to 3 substituents selected from the substituent group A; (9) tri-$C_{6-14}$aryl-$C_{1-6}$alkyl which may have 1 to 3 substituents selected from the substituent group A; (10) a group represented by the formula —X'''—G—(CH$_2$)$_n$—J, wherein X''' represents $C_{1-4}$alkylene or $C_{2-4}$alkenylene, G represents a bond, —O—, —S—, —CO—NH— or —NH—CO—, n is an integer of 0 to 3, and J represents (a) $C_{6-14}$aryl (which may have 1 to 3 substituents selected from the substituent group B) or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group B); (11) a group represented by the formula —X''''—L—(CH$_2$)$_n$—M, wherein X'''' represents a bond or $C_{1-4}$alkylene which may have 1 to 3 substituents selected from the substituent group A, and L represents (a) a bond, (b) $C_{6-10}$aryl which may have 1 to 3 substituents selected from the substituent group B, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, M represents an amino group, guanidino group, sulfamoyl group, carbamoyl group or hydroxyl group; or (12) (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), or (l) amino which may have 1 to 2 substituents selected from acyl groups wherein a 5- to 8-membered aromatic heterocyclic group or saturated or unsaturated non-aromatic heterocyclic group containing a least one of 1 to 3 kinds of heteroatoms selected from oxygen atom, sulfur atom and nitrogen atom has been bound to a carbonyl or sulfonyl group (said acyl optionally having 1 to 3 substituents selected from the substituent group C), and $R^3$ represents (1) $C_{1-10}$alkyl which may have 1 to 3 substituents selected the substituent group A; (2) $C_{3-8}$cycloalkyl which may have 1 to 3 substituents selected from the substituent group A; (3) $C_{2-10}$alkenyl which may have 1 to 3 substituents selected from the substituent group A; (4) $C_{3-8}$cycloalkenyl which may have 1 to 3 substituents selected from the substituent group A; (5) $C_{2-10}$alkynyl which may have 1 to 3 substituents selected from the substituent group A; (6) $C_{6-14}$aryl which may have 1 to 3 substituents selected from the substituent group A; (7) $C_{6-14}$aryl-$C_{1-6}$alkyl which may have 1 to 3 substituents selected from the substituent group A; (8) di-$C_{6-14}$aryl-$C_{1-6}$alkyl which may have 1 to 3 substituents selected from the substituent group A; (9) tri-$C_{6-14}$aryl-$C_{1-6}$alkyl which may have 1 to 3 substituents selected from the substituent group A; (10) a group represented by the formula —X'''—G—(CH$_2$)$_n$—J, wherein X''' represents $C_{1-4}$alkylene or $C_{2-4}$alkenylene, G represents a bond, —O—, —S—, —CO—NH— or —NH—CO—, n is an integer of 0 to 3, and J represents (a) a $C_{6-14}$aryl group (which may have 1 to 3 substituents selected from the substituent group B) or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group B); or (11) a group represented by the formula —X''''—L—(CH$_2$)$_n$—M, wherein X'''' represents a bond or $C_{1-4}$alkylene which may have 1 to 3 substituents selected from the substituent group A, and L represents (a) a bond, (b) $C_{6-10}$aryl (which may have 1 to 3 substituents selected from the substituent group B), or (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, M represents amino group, guanidino group, sulfamoyl group, carbamoyl group or hydroxyl group;

5) The compound according to the above 2), wherein $R^1$ is (1) hydrogen atom; (2) $C_{1-10}$alkyl which may have 1 to 3 substituents selected from (1') halogen atom, (2') nitro, (3') cyano, (4') oxo, (5') hydroxyl group, (6') thiol, (7') $C_{1-4}$alkylthio, (8') amino group, (9') mono-$C_{1-4}$alkylamino, (10') di-$C_{1-4}$alkylamino, (11') 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (12') phenyl-$C_{1-4}$alkyl, (13') $C_{3-7}$cycloalkyl, (14') carboxyl, (15') $C_{1-4}$alkoxycarbonyl, (16') $C_{7-10}$aralkyloxy-carbonyl, (17') carbamoyl, (18') mono-$C_{1-4}$alkylcarbamoyl, (19') di-$C_{1-4}$alkylcarbamoyl, (20') $C_{1-4}$alkyl which may be substituted with a halogen atom or $C_{1-4}$alkoxy, (21') $C_{1-4}$alkoxy which may be substituted with a halogen atom or $C_{1-4}$alkoxy, (22') $C_{1-4}$alkylenedioxy, (23') formyl, (24') $C_{2-4}$alkanoyl, (25') $C_{1-4}$alkylsulfonyl, (26') $C_{1-4}$alkylsulfinyl, (27') sulfamoyl, (28') mono-$C_{1-4}$alkylsulfamoyl, (29') di-$C_{1-4}$alkylsulfamoyl, (30') $C_{6-14}$aryl (which may be substituted with a substituent(s) selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole and imidazole, (11") phenyl-$C_{1-4}$alkyl, (12") $C_{3-7}$cycloalkyl, (13") carboxyl group, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl, and (29') 5- to 6-membered aromatic monocyclic heterocyclic group), or (31') 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1") halogen, (2") nitro, (3") cyano, (4") oxo, (5") hydroxyl group, (6") thiol, (7") $C_{1-4}$alkylthio, (8") amino, (9") mono-$C_{1-4}$alkylamino, (10") di-$C_{1-4}$alkylamino, (11") 5- to 6-membered cyclic amino selected from tetrahydropyrrole, piperazine, piperidine, morpholine, thiomorpholine, pyrrole and imidazole, (12") phenyl-$C_{1-4}$alkyl, (14") $C_{3-7}$cycloalkyl, (15") carboxyl, (16") $C_{1-4}$alkoxy-carbonyl, (17") $C_{7-10}$aralkyloxy-carbonyl, (18") carbamoyl, (19") mono-$C_{1-4}$alkyl-carbamoyl, (20") di-$C_{1-4}$alkyl-carbamoyl, (21") $C_{1-4}$alkyl which may be substituted with a halogen atom or $C_{1-4}$alkoxy, (22") $C_{1-4}$alkoxy which may be substituted with a halogen atom or $C_{1-4}$alkoxy, (23") $C_{1-4}$alkylenedioxy, (24") formyl, (25") $C_{2-4}$alkanoyl, (26") $C_{1-4}$alkylsulfonyl and (27") $C_{1-4}$alkylsulfinyl) (hereinafter referred to as substituent group D); (3) $C_{3-8}$cycloalkyl which may have 1 to 3 substituents selected from the substituent group D; (4) $C_{2-10}$alkenyl which may have 1 to 3 substituents selected from the substituent group D; (5) $C_{3-8}$cycloalkenyl which may have 1 to 3 substituents selected from the substituent group D; (6) $C_{2-10}$alkynyl which may have 1 to 3 substituents selected from the substituent group D; (7) $C_{6-14}$aryl which may have 1 to 3 substituents selected from the substituent group D; (8) $C_{6-14}$aryl-$C_{1-6}$alkyl which may have 1 to 3 substituents selected from the substituent group D; (9) di-$C_{6-14}$aryl-$C_{1-6}$alkyl which may have 1 to 3 substituents selected from the substituent group D; (10) tri-$C_{6-14}$aryl-$C_{1-6}$alkyl which may have 1 to 3 substituents selected from the substituent group D; (11) a group represented by the formula —X'''—G—(CH$_2$)$_n$—J, wherein X''' represents $C_{1-4}$alkylene or $C_{2-4}$alkenylene, G is a bond, —O—, —S—, —CO—NH— or —NH—CO—, n is an integer of 0 to 3, J represents (a) $C_{6-14}$aryl (which may have 1 to 3 substituents selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (11") phenyl-$C_{1-4}$alkyl, (12") $C_{3-7}$cycloalkyl, (13") carboxyl, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl, (29") $C_{6-14}$aryl (which may be substituted with a substituent selected from (1"') halogen, (2"') nitro, (3"') cyano, (4"') hydroxyl group, (5"') thiol, (6"') $C_{1-4}$alkylthio, (7"') amino, (8"') mono-$C_{1-4}$alkylamino, (9"') di-$C_{1-4}$alkylamino, (10"') 5- to 6-membered cyclic amino selected from tetrahydropyrrole, piperazine, piperidine, morpholine, thiomorpholine, pyrrole and imidazole, (11"') phenyl-$C_{1-4}$alkyl, (12"') $C_{3-7}$cycloalkyl, (13"') carboxyl group, (14"') $C_{1-4}$alkoxy-carbonyl, (15"') $C_{7-10}$aralkyloxy-carbonyl, (16"') carbamoyl, (17"') mono-$C_{1-4}$alkyl-carbamoyl, (18"') di-$C_{1-4}$alkyl-carbamoyl, (19"') $C_{1-4}$alkyl which may be substituted with a halogen atom or $C_{1-4}$alkoxy, (20"') $C_{1-4}$alkoxy which may be substituted with a halogen atom or $C_{1-4}$alkoxy, (21"') $C_{1-4}$alkylenedioxy, (22"') formyl, (23"') $C_{2-4}$alkanoyl, (24"') $C_{1-4}$alkylsulfonyl, (25"') $C_{1-4}$alkylsulfinyl, (26"') sulfamoyl, (27"') mono-$C_{1-4}$alkylsulfamoyl, (28"') di-$C_{1-4}$alkylsulfamoyl and (29"') 5- to 6-membered aromatic monocyclic heterocyclic group, or (30") 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1"') halogen, (2"') nitro, (3"') cyano, (4"') oxo, (5"') hydroxyl group, (6"') thiol, (7"') $C_{1-4}$alkylthio, (8"') amino, (9"') mono-$C_{1-4}$alkylamino, (10"') di-$C_{1-4}$alkylamino, (11"') 5- to 6-membered cyclic amino selected from tetrahydropyrrole, piperazine, piperidine, morpholine, thiomorpholine, pyrrole and imidazole, (12"') phenyl-$C_{1-4}$alkyl, (13"') $C_{3-7}$cycloalkyl, (14"') carboxyl, (15"') $C_{1-4}$alkoxy-carbonyl, (16"') $C_{7-10}$aralkyloxy-carbonyl, (17"') carbamoyl, (18"') mono-$C_{1-4}$alkyl-carbamoyl, (19"') di-$C_{1-4}$alkyl-carbamoyl, (20"') $C_{1-4}$alkyl which may be substituted with a halogen atom or $C_{1-4}$alkoxy, (21"') $C_{1-4}$alkoxy which may be substituted with a halogen atom or $C_{1-4}$alkoxy, (22"') $C_{1-4}$alkylenedioxy, (23"') formyl, (24"') $C_{2-4}$alkanoyl, (25"') $C_{1-4}$alkylsulfonyl and (26"') $C_{1-4}$alkylsulfinyl) (hereinafter referred to as substituent group E), or (b) a 5- to 8-membered heterocyclic group containing at least one of 1 to 3 kinds of heterocyclic groups selected from oxygen atom, sulfur atom and nitrogen atom, said aromatic heterocyclic group optionally having 1 to 3 substituents selected from the substituent group E; or (12) a group represented by the formula —X''''—L—(CH$_2$)$_n$—M, wherein X'''' represents a bond or a C$_{1-4}$alkylene group which may have 1 to 3 substituents selected from the substituent group D, L represents (a) a bond, (b) C$_{6-10}$aryl which may have 1 to 3 substituents selected from the substituent group E, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group E), (d) —O—, (e) —S—, (f) —CO—NH— or (g) —NH—CO—, n is an integer of 0 to 3, and M represents an amino group, guanidino group, sulfamoyl group, carbamoyl group or hydroxyl group, X represents the following saturated divalent groups wherein some bonds may have been converted into unsaturated bonds:

(1) —(CH$_2$)$_{f1}$—, wherein f1 represents an integer of 1 to 8, (2) —(CH$_2$)$_{g1}$—X$^1$—(CH$_2$)$_{g2}$—, wherein g1 and g2 are the same or different, and represent an integer of 0 to 7, provided that the sum of g1 and g2 is 0 to 7, and X$^1$ represents NH, O, S, SO or SO$_2$, or (3) —(CH$_2$)$_{h1}$—X$^1$—(CH$_2$)$_{h2}$—X$^2$—(CH$_2$)$_{h3}$—, wherein h1, h2 and h3 are the same or different, and represent an integer of 0 to 6, provided that the sum of h1, h2 and h3 is 0 to 6, and X$^1$ and X$^2$ each represent NH, O, S, SO or SO$_2$ provided that when h2 is 0, X$^1$ and/or X$^2$ preferably represent NH, A represents (1) (a) C$_{1-10}$alkyl which may have 1 to 3 substituents selected from (1'') halogen, (2'') nitro, (3'') cyano, (4'') oxo, (5'') hydroxyl group, (6'') thiol, (7'') C$_{1-4}$alkylthio, (8'') amino, (9'') mono-C$_{1-4}$alkylamino, (10'') di-C$_{1-4}$alkylamino, (11'') 5- to 6-membered cyclic amino selected from tetrahydropyrrole, piperazine, piperidine, morpholine, thiomorpholine, pyrrole and imidazole, (12'') phenyl-C$_{1-4}$alkyl, (13'') C$_{3-7}$cycloalkyl, (14'') carboxyl, (15'') C$_{1-4}$alkoxy-carbonyl, (16'') C$_{7-10}$aralkyloxy-carbonyl, (17'') carbamoyl, (18'') mono-C$_{1-4}$alkyl-carbamoyl, (19'') di-C$_{1-4}$alkyl-carbamoyl, (20'') C$_{1-4}$alkyl which may be substituted with a halogen atom or C$_{1-4}$alkoxy, (21'') C$_{1-4}$alkoxy which may be substituted with a halogen atom or C$_{1-4}$alkoxy, (22'') C$_{1-4}$alkylenedioxy, (23'') formyl, (24'') C$_{2-4}$alkanoyl, (25'') C$_{1-4}$alkylsulfonyl and (26'') C$_{1-4}$alkylsulfinyl (hereinafter referred to as substituent group F), (b) C$_{3-8}$cycloalkyl which may have 1 to 3 substituents selected from the substituent group F, (c) C$_{2-10}$alkenyl which may have 1 to 3 substituents selected from the substituent group F, (d) C$_{3-8}$cycloalkenyl which may have 1 to 3 substituents selected from the substituent group F, (e) C$_{2-10}$alkynyl which may have 1 to 3 substituents selected from the substituent group F, (f) C$_{6-14}$aryl which may have 1 to 3 substituents selected from the substituent group F, (g) C$_{6-14}$aryl-C$_{1-6}$alkyl which may have 1 to 3 substituents selected from the substituent group F, (h) di-C$_{6-14}$aryl-C$_{1-6}$alkyl which may have 1 to 3 substituents selected from the substituent group F, (i) tri-C$_{6-14}$aryl-C$_{1-6}$alkyl which may have 1 to 3 substituents selected from the substituent group F, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group F, (k) acyl selected from formyl, C$_{1-10}$alkyl-carbonyl, C$_{3-8}$cycloalkyl-carbonyl, C$_{2-10}$alkenyl-carbonyl, C$_{3-8}$cycloalkenyl-carbonyl, C$_{2-10}$alkynyl-carbonyl, C$_{6-14}$aryl-carbonyl, C$_{6-14}$aryl-C$_{1-6}$alkyl-carbonyl, di-C$_{6-14}$aryl-C$_{1-6}$alkyl-carbonyl, tri-C$_{6-14}$aryl-C$_{1-6}$alkyl-carbonyl, C$_{1-10}$alkylsulfonyl, C$_{3-8}$cycloalkylsulfonyl, C$_{2-10}$alkenylsulfonyl, C$_{3-8}$cycloalkenylsulfonyl, C$_{2-10}$alkynylsulfonyl, C$_{6-14}$arylsulfonyl, C$_{6-14}$aryl-C$_{1-6}$alkylsulfonyl, di-C$_{6-14}$aryl-C$_{1-6}$alkylsulfonyl or tri-C$_{6-14}$aryl-C$_{1-6}$alkylsulfonyl (said acyl optionally having 1 to 3 substituents selected from the substituent group F, or (l) amino which may have 1 to 2 substituents selected from acyl wherein a 5- to 8-membered aromatic heterocyclic group or saturated or unsaturated non-aromatic heterocyclic group containing a least one of 1 to 3 kinds of heteroatoms selected from oxygen atom, sulfur atom and nitrogen atom has been bound to carbonyl or sulfonyl (said acyl optionally having 1 to 3 substituents selected from the substituent group F); or (2) cyclic amino which may have 1 to 3 substituents selected from (a) halogen, (b) nitro, (c) cyano, (d) hydroxyl group, (e) thiol, (f) amino, (g) carboxyl, (h) optionally halogenated C$_{1-4}$alkyl, (i) optionally halogenated C$_{1-4}$alkoxy, (j) formyl, (k) C$_{2-4}$alkanoyl and (l) C$_{1-4}$alkylsulfonyl; or (3) a group formed by removing one hydrogen atom from a 5- to 8-membered aromatic monocyclic heterocyclic ring or saturated or unsaturated non-aromatic monocyclic heterocyclic ring containing one nitrogen atom and one to three kinds of 1 to 4 heteroatoms selected from an oxygen atom, a sulfur atom and a nitrogen atom or by removing one hydrogen atom from a ring wherein 2 or 3 of the same or different rings selected from the above monocyclic rings have been condensed (said heterocyclic group optionally having 1 to 3 substituents selected from the substituent group F), R$^2$ and R$^3$ each represents (1) C$_{1-10}$alkyl which may have 1 to 3 substituents selected from the substituent group D; (2) C$_{3-8}$cycloalkyl which may have 1 to 3 substituents selected from the substituent group D; (3) C$_{2-10}$alkenyl which may have 1 to 3 substituents selected from the substituent group D; (4) C$_{3-8}$cycloalkenyl which may have 1 to 3 substituents selected from the substituent group D; (5) C$_{2-10}$alkynyl which may have 1 to 3 substituents selected from the substituent group D; (6) C$_{6-14}$aryl which may have 1 to 3 substituents selected from the substituent group D; (7) C$_{6-14}$aryl-C$_{1-6}$alkyl which may have 1 to 3 substituents selected from the substituent group D; (8) di-C$_{6-14}$ aryl-C$_{1-6}$ alkyl which may have 1 to 3 substituents selected from the substituent group D; (9) tri-C$_{6-14}$aryl-C$_{1-6}$alkyl which may have 1 to 3 substituents selected from the substituent group D; (10) a group represented by the formula —X'''—(CH$_2$)$_n$—J, wherein X''' represents C$_{1-4}$alkylene or C$_{2-4}$alkenylene, G represents a bond, —O—, —S—, —CO—NH— or —NH—CO—, n is an integer of 0 to 3, and J represents (a) C$_{6-14}$aryl which may have 1 to 3 substituents selected from the substituent group E or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group E), or (11) a group represented by the formula —X''''—L—(CH$_2$)$_n$—M, wherein X'''' represents a bond or C$_{1-4}$alkylene which may have 1 to 3 substituents selected from the substituent group D, and L represents (a) a bond, (b) C$_{6-10}$aryl which may have 1 to 3 substituents selected from the substituent group E, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group E), (d) —O—, (e) —S—, (f) —CO—

NH— or (g) —NH—CO—, n is an integer of 0 to 3, M represents an amino group, guanidino group, sulfamoyl group, carbamoyl group or hydroxyl group;

6) A compound represented by the formula:

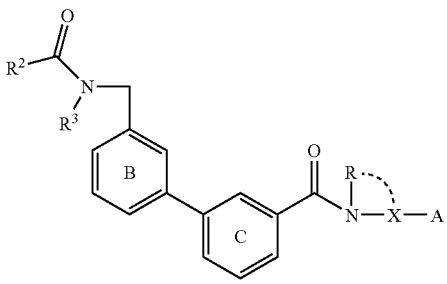

wherein each symbol is as defined in the above 2), or a salt thereof;

7) A compound represented by the formula:

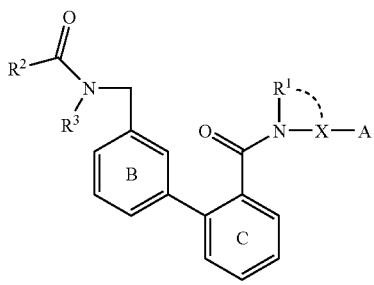

wherein each symbol is as defined in the above 2), or a salt thereof;

8) A compound represented by the formula:

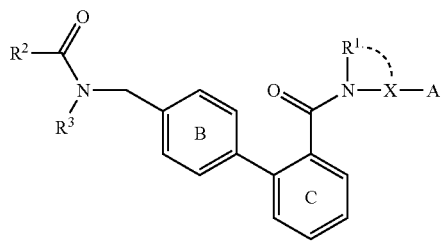

wherein each symbol is as defined in the above 2), or a salt thereof;

9) The compound according to the above 2), wherein the group represented by the formula:

is a group represented by the formula:

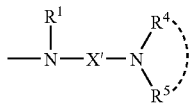

wherein $R^1$ represents (1) hydrogen atom, (2) $C_{1-10}$alkyl, (3) $C_{3-8}$cycloalkyl, (4) $C_{2-10}$alkenyl, (5) $C_{3-8}$cycloalkenyl, (6) $C_{2-10}$alkynyl, (7) $C_{6-14}$aryl, (8) $C_{6-14}$aryl-$C_{1-6}$alkyl, (9) di-$C_{6-14}$aryl-$C_{1-6}$alkyl, (10) tri-$C_{6-14}$aryl-$C_{1-6}$alkyl, (11) a group represented by the formula —X'''—G—(CH$_2$)$_n$—J, wherein X''' represents a $C_{1-4}$alkylene group or $C_{2-4}$alkenylene group, G represents a bond, —O—, —S—, —CO—NH— or —NH—CO—, n is an integer of 0 to 3, J represents (a) $C_{6-14}$aryl or (b) a 5- to 8-membered aromatic heterocyclic group containing at least one of 1 to 3 kinds of heteroatoms selected from oxygen atom, sulfur atom and nitrogen atom, or (12) a group represented by the formula —X''''—L—(CH$_2$)$_n$—M, wherein X'''' represents a bond or a $C_{1-4}$alkylene group, L represents (a) a bond, (b) $C_{6-10}$aryl, (c) a 5- to 8-membered aromatic heterocyclic group containing at least one of 1 to 3 kinds of heteroatoms selected from oxygen atom, sulfur atom and nitrogen atom, (d) —O—, (e) —S—, (f) —CO—NH— or (g) —NH—CO—, n is an integer of 0 to 3, and M represents an amino group, guanidino group, sulfamoyl group, carbamoyl group or hydroxyl group, X' represents $C_{1-6}$alkylene, $R^4$ and $R^5$ each represents hydrogen atom or $C_{1-6}$alkyl (which may have 1 to 3 substituents selected from (i) halogen, (ii) nitro, (iii) cyano, (iv) hydroxyl group, (v) thiol, (vi) $C_{1-4}$alkylthio, (vii) amino, (viii) mono-$C_{1-4}$alkylamino, (ix) di-$C_{1-4}$alkylamino, (x) 5- to 6-membered cyclic amino selected from tetrahydropyrrole, piperazine, piperidine, morpholine, thiomorpholine, pyrrole and imidazole, (xi) carboxyl, (xii) $C_{1-4}$alkoxy-carbonyl, (xiii) $C_{7-10}$aralkyloxy-carbonyl, (xiv) carbamoyl, (xv) mono-$C_{1-4}$alkyl-carbamoyl, (xvi) di-$C_{1-4}$alkyl-carbamoyl, (xvii) $C_{1-4}$alkyl which may be substituted with a halogen atom or $C_{1-4}$alkoxy, (xviii) $C_{1-4}$alkoxy which may be substituted with a halogen atom or $C_{1-4}$alkoxy, (xix) $C_{1-4}$alkylenedioxy, (xx) phenyl-$C_{1-4}$alkyl, (xxi) $C_{3-7}$cycloalkyl, (xxii) formyl, (xxiii) $C_{2-4}$alkanoyl, (xxiv) $C_{1-4}$alkylsulfonyl and (xxv) $C_{1-4}$alkylsulfinyl), and $R^4$ and $R^5$ together with their adjacent nitrogen atom may be bound to each other to form a 3- to 8-membered cyclic amino group;

10) The compound according to the above 9), wherein each of $R^4$ and $R^5$ is hydrogen atom;

11) The compound according to the above 9), wherein $R^4$ and $R^5$ are bound to each other to form a 3- to 8-membered saturated nitrogen-containing heterocyclic ring;

12) The compound according to the above 2), wherein the group represented by the formula:

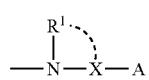

is a group represented by the formula:

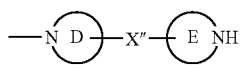

wherein X" represents a bond or $C_{1-4}$alkylene, and rings D and E each represents a 3- to 8-membered saturated nitrogen-containing heterocyclic ring;

13) The compound according to the above 2), wherein $R^2$ is a group represented by the formula —X'"—G—$(CH_2)_n$—J wherein X'" represents a $C_{1-4}$alkylene group or $C_{2-4}$alkenylene group, G represents a bond, —O—, —S—, —CO—NH— or —NH—CO—, n is an integer of 0 to 3, J represents (a) a $C_{6-14}$aryl group (which may have 1 to 3 substituents selected from (i) halogen, (ii) hydroxyl group, (iii) $C_{1-4}$alkyl which may be substituted with a halogen atom or $C_{1-4}$alkoxy, (iv) $C_{1-4}$alkoxy which may be substituted with a halogen atom or $C_{1-4}$alkoxy and (v) sulfamoyl), or (b) a 5- to 8-membered aromatic heterocyclic group containing at least one of 1 to 3 kinds of heteroatoms selected from oxygen atom, sulfur atom and nitrogen atom;

14) The compound according to the above 2), wherein $R^2$ is a group represented by the formula —X""—L—$(CH_2)_n$—M wherein X"" represents a bond or a $C_{1-4}$alkylene group, L represents (a) a bond, (b) $C_{6-14}$aryl, (c) a 5- to 8-membered aromatic heterocyclic group containing at least one of 1 to 3 kinds of heteroatoms selected from oxygen atom, sulfur atom and nitrogen atom, (d) —O—, (e) —S—, (f) —CO—NH— or (g) —NH—CO—, n is an integer of 0 to 3, and M represents an amino group, guanidino group, sulfamoyl group, carbamoyl group or hydroxyl group;

15) The compound according to the above 2), wherein $R^3$ represents a group represented by the formula —$(CH_2)_p$—T, wherein p is an integer of 1 to 6, T represents (a) $C_{6-14}$aryl (which may have 1 to 3 substituents selected from (i) halogen, (ii) hydroxyl group, (iii) phenyl-$C_{1-4}$alkyl, (iv) carboxyl, (v) $C_{1-4}$alkoxy-carbonyl, (vi) $C_{1-4}$alkyl which may be substituted with a halogen atom or $C_{1-4}$alkoxy, (vii) $C_{1-4}$alkoxy which may be substituted with a halogen atom or $C_{1-4}$alkoxy, (viii) $C_{1-4}$alkylenedioxy, (ix) sulfamoyl, (x) $C_{1-4}$alkylsulfamoyl, (xi) di-$C_{1-4}$alkylsulfamoyl and (xii) a 5- to 8-membered heterocyclic group or saturated or unsaturated non-aromatic heterocyclic group containing at least one of 1 to 3 kinds of heteroatoms selected from oxygen atom, sulfur atom and nitrogen atom, or (b) a 5- to 8-membered aromatic heterocyclic group containing at least one of 1 to 3 kinds of heteroatoms selected from oxygen atom, sulfur atom and nitrogen atom;

16) The compound according to the above 14), wherein T is phenyl group substituted with hydroxyl group, sulfamoyl, $C_{1-4}$alkylsulfamoyl or di-$C_{1-4}$alkylsulfamoyl;

17) 3'-{[{2-[4-(Aminosulfonyl)phenyl]ethyl}(4-phenylbutanoyl)amino]methyl}-N-[2-(1-pyrrolidinyl)ethyl]-[1,1'-biphenyl]-3-carboxamide or a salt thereof;

18) 3'-({{2-[4-(Aminosulfonyl)phenyl]ethyl}-[(benzyloxy)acetyl]amino}methyl)-N-[2-(1-pyrrolidinyl)-ethyl][1,1'-biphenyl]-3-carboxamide or a salt thereof;

19) N-(2-Aminoethyl)-3'-{[[3-({[amino(imino)methyl]amino}methyl)benzoyl](1-naphthylmethyl)amino]methyl}-1,1'-biphenyl-2-carboxamide or a salt thereof;

20) N-(2-Aminoethyl)-3'-{[[4-(aminosulfonyl)benzoyl]-(1-naphthylmethyl)amino]methyl}-1,1'-biphenyl-2-carboxamide or a salt thereof;

21) A prodrug of the compound according to the above 1) or 2) or a salt thereof;

22) A pharmaceutical composition comprising a compound represented by the formula (I):

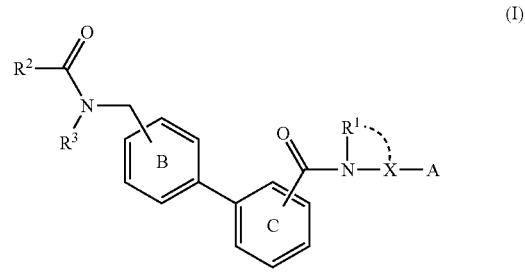

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substituted nitrogen-containing heterocyclic group; $R^2$ represents an optionally substituted hydrocarbon group or an optionally substituted amino group; $R^3$ represents an optionally substituted hydrocarbon group; and rings B and C each represents a further optionally substituted benzene ring, provided that (1) a compound represented by the formula:

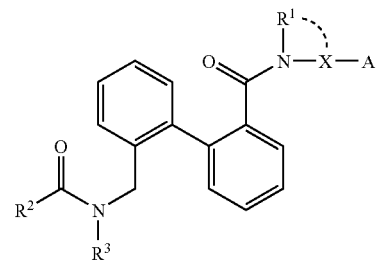

wherein each symbol has the same meaning as defined above, and (2) 4'-[[(methoxyacetyl)methylamino]methyl]-N-[4-methoxy-3-(4-methyl-1-piperazinyl)phenyl]-2'-methyl-[1,1'-biphenyl]-4-carboxamide are excluded, or a salt thereof or a prodrug thereof;

23) A GPR14 antagonist comprising a compound represented by the formula (I):

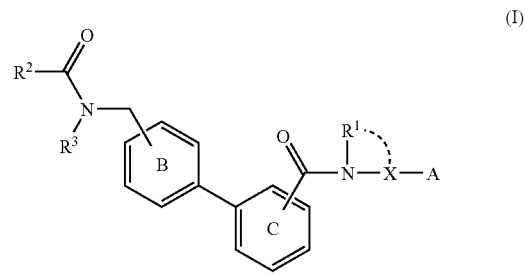

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substituted nitrogen-containing heterocyclic group; $R^2$ represents an optionally substituted hydrocarbon group or an optionally substituted amino group; $R^3$ represents an optionally substituted hydrocarbon group; and rings B and C each represents a further optionally substituted benzene ring, or a salt thereof or a prodrug thereof;

24) A vasoconstriction inhibitor comprising a compound represented by the formula (I):

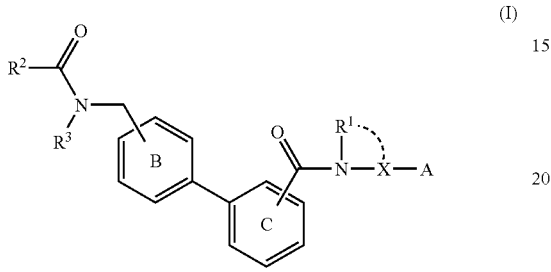

(I)

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substituted nitrogen-containing heterocyclic group; $R^2$ represents an optionally substituted hydrocarbon group or an optionally substituted amino group; $R^3$ represents an optionally substituted hydrocarbon group; and rings B and C each represents a further optionally substituted benzene ring, or a salt thereof or a prodrug thereof;

25) An agent for preventing and/or treating hypertension, arteriosclerosis, cardiac hypertrophy, myocardial infarction or heart failure, comprising a compound represented by the formula (I):

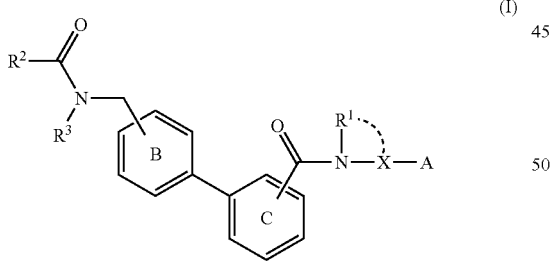

(I)

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substituted nitrogen-containing heterocyclic group; $R^2$ represents an optionally substituted hydrocarbon group or an optionally substituted amino group; $R^3$ represents an optionally substituted hydrocarbon group; and rings B and C each represents a further optionally substituted benzene ring, or a salt thereof or a prodrug thereof;

26) A regulator for a somatostatin receptor function comprising a compound represented by the formula (I):

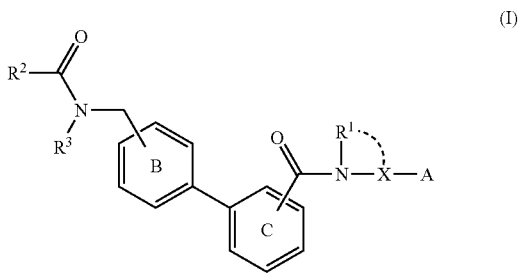

(I)

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substituted nitrogen-containing heterocyclic group, $R^2$ represents an optionally substituted hydrocarbon group or an optionally substituted amino group; $R^3$ represents an optionally substituted hydrocarbon group; and rings B and C each represents a further optionally substituted benzene ring, or a salt thereof or a prodrug thereof;

27) The regulator for a somatostatin receptor function according to the above 26) which is a somatostatin receptor agonist;

28) The regulator for a somatostatin receptor function according to the above 26) which is a somatostatin receptor antagonist;

29) The regulator for a somatostatin receptor function according to the above 26), which is a somatostatin type 5 receptor function regulator;

30) The regulator for a somatostatin receptor function according to the above 26), which is an agent for preventing and/or treating diabetes, obesity, diabetic complications, diseases in the central nervous system, diseases in the digestive organs, glaucoma, acromegaly or tumors;

31) A method of antagonizing GPR14, which comprises administering, into a mammal, an effective amount of a compound represented by the formula (I):

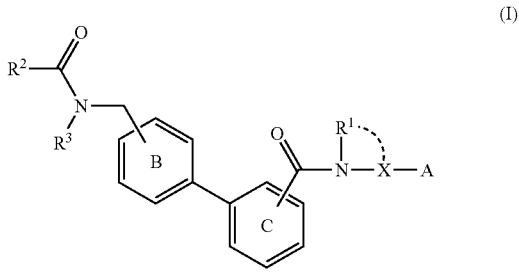

(I)

wherein $R^1$ represents hydrogen atom or an optionally substituted hydrocarbon group; X represents a spacer whose linear chain moiety is composed of 1 to 12 atoms; $R^1$ and X may be bound to each other to form a ring; A represents an optionally substituted amino group or an optionally substi tuted nitrogen-containing heterocyclic group; R² represents an optionally substituted hydrocarbon group or an optionally substituted amino group; R³ represents an optionally substituted hydrocarbon group; and rings B and C each represents a further optionally substituted benzene ring, or a salt thereof;

32) A method of regulating a somatostatin receptor function which comprises administering, into a mammal, an effective amount of a compound represented by the formula (I):

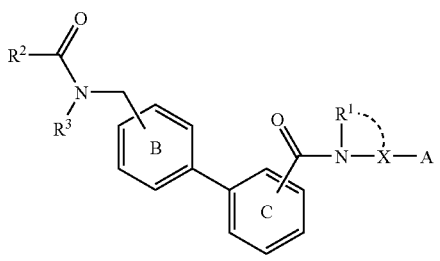

wherein R¹ represents hydrogen atom or an optionally substituted hydrocarbon group; X represents a spacer whose linear chain moiety is composed of 1 to 12 atoms; R¹ and X may be bound to each other to form a ring; A represents an optionally substituted amino group or an optionally substituted nitrogen-containing heterocyclic group; R² represents an optionally substituted hydrocarbon group or an optionally substituted amino group; R³ represents an optionally substituted hydrocarbon group; and rings B and C each represents a further optionally substituted benzene ring, or a salt thereof;

33) Use of a compound represented by the formula (I):

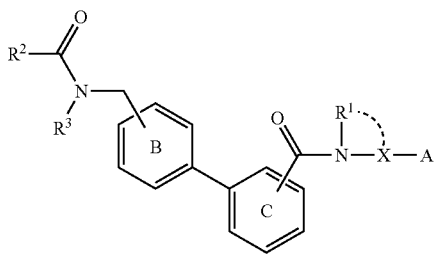

wherein R¹ represents hydrogen atom or an optionally substituted hydrocarbon group; X represents a spacer whose linear chain moiety is composed of 1 to 12 carbon atoms; R¹ and X may be bound to each other to form a ring; A represents an optionally substituted amino group or an optionally substituted nitrogen-containing heterocyclic group; R² represents an optionally substituted hydrocarbon group or an optionally substituted amino group; R³ represents an optionally substituted hydrocarbon group; and rings B and C each represents a further optionally substituted benzene ring, or a salt thereof, for the manufacture of a GPR14 antagonist;

34) Use of a compound represented by the formula (I):

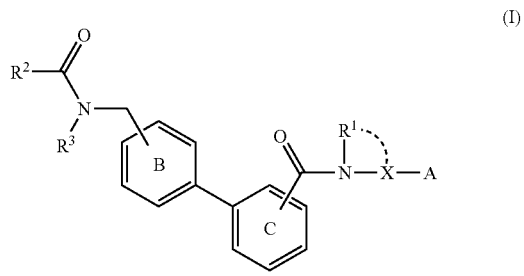

wherein R¹ represents hydrogen atom or an optionally substituted hydrocarbon group; X represents a spacer whose linear chain moiety is composed of 1 to 12 carbon atoms; R¹ and X may be bound to each other to form a ring; A represents an optionally substituted amino group or an optionally substituted nitrogen-containing heterocyclic group; R² represents an optionally substituted hydrocarbon group or an optionally substituted amino group; R³ represents an optionally substituted hydrocarbon group; and rings B and C each represents a further optionally substituted benzene ring, or a salt thereof, for the manufacture of a somatostatin receptor regulator;

35) A process for producing the compound according to the above 1) or a salt thereof, which comprises (i) reacting a compound represented by the formula:

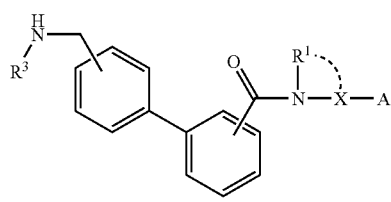

wherein each symbol is as defined in the above 1), or a salt thereof, with a compound represented by the formula: R²COOH wherein R² is as defined in the above 1), or a salt thereof, or a reactive derivative thereof, or (ii) reacting a compound represented by formula:

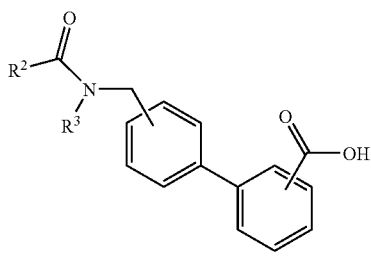

wherein each symbol is as defined in the above 1), or a salt thereof or a reactive derivative thereof, with a compound represented by the formula:

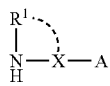

wherein each symbol is as defined in the above 1), or a salt thereof; and the like.

EMBODIMENTS FOR CARRYING OUT THE INVENTION

The term "GPR 14-antagonizing activity" used herein refers to an activity to competitively or non-competitively inhibit the binding of a ligand (e.g., urotensin II, etc.) to GPR14 protein on a cell membrane.

The present invention provides, based on such GPR 14-antagonizing activity, drugs which exhibit a variety of effects on blood vessels (e.g., accentuation or suppression of vasoconstriction, etc.). Among them, vasoconstriction inhibitors may preferably be used which reduce urotensin II-induced potent vasoconstriction. The vasoconstriction inhibitors can be used for preventing and/or treating a variety of diseases. Particularly, they may preferably be used for preventing and/or treating hypertension, arteriosclerosis, hypercardia, myocardial infarction, heart failure and the like, and more preferably, ischemic myocardial infarction, congestive heart failure and the like.

In the above-described formula (I), "a further optionally substituted benzene ring" represented by B or C is a benzene ring which may be substituted in addition to the substituent shown in the formula (I) and examples of the substituent (other than the substituent shown in the formula (I)) include hydrocarbon group which may be substituted; heterocyclic group which may be substituted; nitro group; a halogen atom; amino group which may be substituted; a group represented by the formula: $R^6$—Y— (wherein Y is oxygen atom or sulfur atom which may be oxidized (e.g., S, S(O), S(O)$_2$, etc.) and $R^6$ is a hydrocarbon group which may be substituted or a heterocyclic group which may be substituted); cyano group; acyl group which may be substituted; carboxyl group which may be esterified or amidated; and the like.

Examples of the hydrocarbon group in the "hydrocarbon group which may be substituted" as the substituent of the benzene ring of "a further optionally substituted benzene ring" represented by B or C, and in the "hydrocarbon group which may be substituted" represented by $R^6$ include (1) alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl or decyl, etc., and preferably lower ($C_{1-6}$) alkyl, etc.);

(2) cycloalkyl (e.g., $C_{3-8}$cycloalkyl such as cyclopropyl, cyclobutyl, cyclopentyl, cyclohexyl, cycloheptyl, etc.), wherein the cycloalkyl may be condensed with a benzene ring to form indan (e.g., indan 1-yl, indan 2-yl, etc.), tetrahydronaphthalene (e.g., tetrahydronaphthalene-5-yl, tetrahydronaphthalene-6-yl, etc.) (preferably indan, etc.), and wherein the cycloalkyl may be crosslinked with via a $C_{1-2}$ linear atomic chain to form a crosslinked cyclic hydrocarbon group such as bicyclo[2.2.1]heptyl, bicyclo[2.2.2]octyl, bicyclo [3.2.1]octyl, bicyclo[3.2.2]nonyl, etc. (preferably cyclohexyl having a crosslinkage via a $C_{1-2}$ linear atomic chain, etc., and more preferably bicyclo[2.2.1]heptyl, etc.);

(3) alkenyl (e.g., $C_{2-10}$alkenyl such as vinyl, allyl, crotyl, 2-pentenyl or 3-hexenyl, etc., preferably lower ($C_{2-6}$) alkenyl);

(4) cycloalkenyl (e.g., $C_{3-8}$cycloalkenyl such as 2-cyclopentenyl, 2-cyclohexenyl, 2-cyclopentenylmethyl, 2-cyclohexenylmethyl, etc.);

(5) alkynyl (e.g., $C_{2-10}$alkynyl such as ethynyl, 1-propynyl, 2-propynyl, 1-butynyl, 2-pentynyl, 3-hexynyl, etc., preferably lower ($C_{2-6}$) alkynyl, etc.);

(6) aryl (e.g., $C_{6-14}$aryl such as phenyl or naphthyl, etc., preferably $C_{6-10}$aryl, and more preferably phenyl, etc.);

(7) aralkyl (e.g., $C_{1-6}$alkyl having 1 to 3 $C_{6-14}$allyl groups, preferably phenyl-$C_{1-4}$alkyl (e.g., benzyl, phenethyl, etc.). Particularly, alkyl is preferable, and $C_{1-4}$alkyl (e.g., methyl, ethyl, etc.) is more preferable with methyl being most preferable.

The hydrocarbon group may have substituent(s). Examples of the substituent(s) include halogen (e.g., fluorine, chlorine, bromine, iodine, etc.), nitro, cyano, oxo, hydroxy group, thiol group which may be substituted (e.g., thiol, $C_{1-4}$alkylthio, etc.), amino group which may be substituted (e.g., amino, mono-$C_{1-4}$alkylamino, di-$C_{1-4}$alkylamino, mono-$C_{2-5}$alkanoylamino, or 5- or 6-membered cyclic amino such as tetrahydropyrrole, piperazine, piperidine, morpholine, thiomorpholine, pyrrole, imidazole, etc.), phenyl-lower ($C_{1-4}$) alkyl, $C_{3-7}$cycloalkyl, carboxyl group which may be esterified or amidated (e.g., carboxyl, $C_{1-4}$alkoxy-carbonyl, lower ($C_{7-10}$) aralkyloxy-carbonyl, carbamoyl, mono-$C_{1-4}$alkyl-carbamoyl, di-$C_{1-4}$alkyl-carbamoyl, etc.), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—CH$_2$—O—, —O—CH$_2$—CH$_2$—O—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), $C_{1-4}$alkylsulfinyl (e.g., methanesulfinyl, ethanesulfinyl, etc.), etc. The number of the substituents is preferably 1 to 3.

Examples of the heterocyclic group in the "heterocyclic group which may be substituted" as the substituent of the benzene ring of "a further optionally substituted benzene ring" represented by B or C, and in the "heterocyclic group which may be substituted" represented by $R^6$ include those which may be formed by removing one hydrogen atom from a 5- to 8-membered aromatic heterocyclic ring and saturated or unsaturated non-aromatic (aliphatic) heterocyclic ring containing at least 1 (preferably 1 to 4, and more preferably 1 or 2) of 1 to 3 (preferably 1 or 2) kinds of heteroatom(s) selected from the group consisting of oxygen, sulfur and nitrogen atoms.

Examples of the "aromatic heterocyclic ring" include 5- to 8-membered (preferably 5- or 6-membered) aromatic monocyclic heterocyclic rings (e.g., furan, thiophene, pyrrole, oxazole, isoxazole, thiazole, isothiazole, imidazole, pyrazole, 1,2,3-oxadiazole, 1,2,4-oxadiazole, 1,3,4-thiadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine or triazine, etc.). Examples of the "non-aromatic heterocyclic ring" include 5- to 8-membered (preferably 5- or 6-membered) saturated or unsaturated monocyclic non-aromatic heterocyclic ring (aliphatic heterocyclic ring) such as pyrrolidine, tetrahydrofuran, tetrahydrothiophene, thiolane, dithiolane, oxathiolane, pyrroline, imidazolidine, imidazoline, pyrazolidine, pyrazoline, oxazine, oxadiazine, thiazine, thiadiazine, piperidine, morpholine, thiomorpholine, tetrahydropyran, piperazine, pyran, oxepine, thiepine, azepine, etc.; and 5- to 8-membered non-aromatic heterocyclic rings comprising any of the above-described aromatic monocyclic heterocyclic rings with all or a portion of double bonds therein being saturated.

Examples of the "heterocyclic group" in the "heterocyclic group which may be substituted" as the substituent of the benzene ring of "a further optionally substituted benzene ring" represented by B or C, and in "heterocyclic group which may be substituted" represented by $R^6$ also include those formed by removing one hydrogen atom from a condensed ring formed by condensation of two or three (preferably two) rings selected from the group consisting of the above-listed monocyclic heterocyclic rings (monocyclic aromatic heterocyclic rings and monocyclic non-aromatic heterocyclic rings) and 5- to 8-membered cyclic hydrocarbons (e.g., 5- to 8-membered (preferably 5- or 6-membered) saturated or unsaturated alicyclic hydrocarbons such as $C_{5-8}$cycloalkane, $C_{5-8}$cycloalkene, $C_{5-8}$cycloalkadiene, etc., and 6-membered aromatic hydrocarbon such as benzene. Those condensed rings may be saturated, partially unsaturated or aromatic.

Preferable examples of such condensed ring include those comprising two identical or different heterocyclic rings (preferably one is a heterocyclic ring and the other an aromatic heterocyclic ring, and more preferably two identical or different aromatic heterocyclic rings), and those comprising one heterocyclic ring and one homocyclic ring (preferably one is a heterocyclic ring and the other a benzene ring, and more preferably one is an aromatic heterocyclic ring and the other a benzene ring). Specific examples of such condensed ring include indole, benzothiophene, benzofuran, benzimidazole, imidazo[1,2-a]pyridine, quinoline, isoquinoline, cinnoline, etc.

The "heterocyclic group" in the "heterocyclic group which may be substituted" as the substituent of the benzene ring of "a further optionally substituted benzene ring" represented by B or C, and in "heterocyclic group which may be substituted" represented by $R^6$ may have substituent(s). Examples thereof include those similar to the above-listed substituents of the "hydrocarbon group which may be substituted" as the substituent of the benzene ring of "a further optionally substituted benzene ring" represented by B or C.

Examples of the "halogen atom" as the substituent of benzene ring of "a further optionally substituted benzene ring" represented by B or C include fluorine, chlorine, bromine and iodine.

Examples of the "amino group which may be substituted" as the substituent of the benzene ring of "a further optionally substituted benzene ring" represented by B or C include that similar to the "amino group which may be substituted" represented by A described hereinafter. Among them, preferred are amino group having one or two substituents selected from the group consisting of "hydrocarbon group which may be substituted" (those similar to the above-listed "hydrocarbon group which may be substituted" as the substituent of the benzene ring of "a further optionally substituted benzene ring" represented by B or C); "heterocyclic group which may be substituted" (those similar to the above-listed "heterocyclic group which may be substituted" as the substituent of the benzene ring of "a further optionally substituted benzene ring" represented by B or C); and "acyl group which may be substituted" (those similar to the "acyl group which may be substituted" as the substituent of the benzene ring of "a further optionally substituted benzene ring" represented by B or C). Particularly preferred are amino group which may have one or two alkyl groups which may be substituted [e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, which may have 1 to 3 substituent(s) selected from the group consisting of halogen (e.g., fluorine, chlorine, bromine, iodine, etc.), nitro, cyano, hydroxy group, thiol group which may be substituted (e.g., thiol or $C_{1-4}$alkylthio), amino group which may be substituted (e.g., amino, mono-$C_{1-4}$alkylamino, di-$C_{1-4}$alkylamino, 5- or 6-membered cyclic amino such as tetrahydropyrrole, piperazine, piperidine, morpholine, thiomorpholine, pyrrole, imidazole, etc.), phenyl lower ($C_{1-4}$) alkyl, $C_{3-7}$cycloalkyl, carboxyl group which may be esterified or amidated (e.g., carboxyl, $C_{1-4}$alkoxycarbonyl, lower ($C_{7-10}$) aralkyloxy-carbonyl, carbamoyl, mono-$C_{1-4}$alkylcarbamoyl, di-$C_{1-4}$alkylcarbamoyl, etc.), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—CH$_2$—O—, —O—CH$_2$—CH$_2$—O—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), $C_{1-4}$alkylsulfinyl (e.g., methanesulfinyl, ethanesulfinyl, etc.), and the like].

The "amino group which may be substituted" as the substituent of the benzene ring of "a further optionally substituted benzene ring" represented by B or C may also be an amino group in which the substituents of the amino group are bonded to each other to form a cyclic amino group (e.g., a cyclic amino group formed by removing one hydrogen atom from constituent nitrogen atom of a 5- or 6-membered ring with a bond on its nitrogen atom (e.g., tetrahydropyrrole, piperazine, piperidine, morpholine, thiomorpholine, pyrrole, imidazole, etc.). The cyclic amino group may be substituted and examples thereof include halogen (e.g., fluorine, chlorine, bromine, iodine, etc.), nitro, cyano, hydroxy group, thiol group, amino group, carboxyl group, $C_{1-4}$alkyl which may be halogenated (e.g., trifluoromethyl, methyl, ethyl, etc.), $C_{1-4}$alkoxy which may be halogenated (e.g., methoxy, ethoxy, propoxy, butoxy, trifluoromethoxy, trifluoroethoxy, etc.), formyl, $C_{2-4}$alkanoyl (e.g., acetyl, propionyl, etc.) or $C_{1-4}$alkylsulfonyl (e.g., methanesulfonyl, ethanesulfonyl, etc.) and the like. The number of the substituents is preferably 1 to 3.

Examples of the "acyl group which may be substituted" as the substituent of the benzene ring of "a further optionally substituted benzene ring" represented by B or C include that comprising carbonyl group or sulfonyl group bonded with, for example: hydrogen; "hydrocarbon group which may be substituted" (e.g., that similar to the above-listed "hydrocarbon group which may be substituted" as the substituent of the benzene ring of "a further optionally substituted benzene ring" represented by B or C); or "heterocyclic group which may be substituted" (e.g., that similar to the above-listed "heterocyclic group which may be substituted" as the substituent of the benzene ring of "a further optionally substituted benzene ring" represented by B or C), and the like.

Preferred examples are those comprising carbonyl group or sulfonyl group bonded with, for example:

(1) hydrogen;

(2) alkyl which may be substituted (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl);

(3) cycloalkyl which may be substituted (e.g., $C_{3-7}$cycloalkyl such as cyclopropyl, cyclobutyl, cyclopentyl, cyclohexyl or cycloheptyl, etc.);

(4) alkenyl which may be substituted (e.g., $C_{2-10}$alkenyl such as allyl, crotyl, 2-pentenyl, 3-hexenyl, etc., preferably lower ($C_{2-6}$) alkenyl);

(5) cycloalkenyl which may be substituted (e.g., $C_{3-7}$cycloalkenyl such as 2-cyclopentenyl, 2-cyclohexenyl, 2-cyclopentenylmethyl, 2-cyclohexenylmethyl, etc.); and (6) 5- or 6-membered monocyclic aromatic group which may be substituted (e.g., phenyl, pyridyl, etc.), including acetyl, propionyl, butyryl, isobutyryl, valeryl, isovaleryl, pivaloyl, hexanoyl, heptanoyl, octanoyl, cyclobutane carbonyl, cyclopentane carbonyl, cyclohexane carbonyl, cycloheptane carbonyl, crotonyl, 2-cyclohexene carbonyl, benzoyl, nicotinoyl, methanesulfonyl, ethanesulfonyl, etc.

Examples of the substituent(s) of the above-described (2) alkyl which may be substituted, (3) cycloalkyl which may be substituted, (4) alkenyl which may be substituted, (5) cycloalkenyl which may be substituted, and (6) 5- or 6-membered monocyclic aromatic group which may be substituted include halogen (e.g., fluorine, chlorine, bromine or iodine); nitro; cyano; hydroxy group; thiol group which may be substituted (e.g., thiol, $C_{1-4}$alkylthio, etc.); amino group which may be substituted (e.g., amino, mono-$C_{1-4}$alkylamino, di-$C_{1-4}$alkylamino, 5- or 6-membered cyclic amino such as tetrahydropyrrole, piperazine, piperidine, morpholine, thiomorpholine, pyrrole, imidazole, etc.); carboxyl group which may be esterified or amidated (e.g., carboxyl, $C_{1-4}$alkoxy-carbonyl, carbamoyl, mono-$C_{1-4}$alkyl-carbamoyl, di-$C_{1-4}$alkyl-carbamoyl, etc.); $C_{1-4}$alkyl which may be substituted by halogen atom or $C_{1-4}$alkoxy (e.g., trifluoromethyl, methyl, ethyl, etc.); $C_{1-4}$alkoxy which may be substituted by halogen atom or $C_{1-4}$alkoxy (e.g., methoxy, ethoxy, trifluoromethoxy, trifluoroethoxy, etc.); formyl; $C_{2-4}$alkanoyl (e.g., acetyl, propionyl, etc.); $C_{1-4}$alkylsulfonyl (e.g., methanesulfonyl, ethanesulfonyl, etc.); and $C_{1-4}$alkylsulfinyl (e.g., methanesulfinyl, ethanesulfinyl, etc.), etc. The number of the substituent(s) is preferably 1 to 3.

Examples of the "carboxyl group which may be esterified" as the substituent of the benzene ring of "a further optionally substituted benzene ring" represented by B or C include that comprising a carbonyl group bonded with, for example, hydrogen atom, "hydrocarbon group which may be substituted" (e.g., that similar to the above-listed "hydrocarbon group which may be substituted" as the substituent of the benzene ring of "a further optionally substituted benzene ring" represented by B or C) and preferred examples include:

(1) hydrogen;

(2) alkyl which may be substituted (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl);

(3) cycloalkyl which may be substituted (e.g., $C_{3-7}$cycloalkyl such as cyclopropyl, cyclobutyl, cyclopentyl, cyclohexyl or cycloheptyl, etc.);

(4) alkenyl which may be substituted (e.g., $C_{2-10}$alkenyl such as allyl, crotyl, 2-pentenyl, 3-hexenyl, etc., preferably lower ($C_{2-6}$) alkenyl);

(5) cycloalkenyl which may be substituted (e.g., $C_{3-7}$cycloalkenyl such as 2-cyclopentenyl, 2-cyclohexenyl, 2-cyclopentenylmethyl, 2-cyclohexenylmethyl, etc.); and (6) aryl which may be substituted (e.g., phenyl, naphthyl, etc.); more preferably, carboxyl, lower ($C_{1-6}$) alkoxy-carbonyl, aryloxycarbonyl (e.g., methoxycarbonyl, ethoxycarbonyl, butoxycarbonyl, phenyoxycarbonyl, naphthoxycarbonyl) and the like. Examples of the substituent(s) of the above-described (2) alkyl which may be substituted, (3) cycloalkyl which may be substituted, (4) alkenyl which may be substituted, (5) cycloalkenyl which may be substituted, and (6) aryl which may be substituted include halogen (e.g., fluorine, chlorine, bromine or iodine); nitro; cyano; hydroxy group; thiol group which may be substituted (e.g., thiol, $C_{1-4}$alkylthio, etc.); amino group which may be substituted (e.g., amino, mono-$C_{1-4}$alkylamino, di-$C_{1-4}$alkylamino, 5- or 6-membered cyclic amino such as tetrahydropyrrole, piperazine, piperidine, morpholine, thiomorpholine, pyrrole, imidazole, etc.); carboxyl group which may be esterified or amidated (e.g., carboxyl, $C_{1-4}$alkoxy-carbonyl, carbamoyl, mono-$C_{1-4}$alkyl-carbamoyl, di-$C_{1-4}$alkyl-carbamoyl, etc.); $C_{1-4}$alkyl which may be substituted by halogen atom or $C_{1-4}$alkoxy (e.g., trifluoromethyl, methyl, ethyl, etc.); $C_{1-4}$alkoxy which may be substituted by halogen atom or $C_{1-4}$alkoxy (e.g., methoxy, ethoxy, trifluoromethoxy, trifluoroethoxy, etc.); formyl; $C_{2-4}$alkanoyl (e.g., acetyl, propionyl, etc.); $C_{1-4}$alkylsulfonyl (e.g., methanesulfonyl, ethanesulfonyl, etc.); and $C_{1-4}$alkylsulfinyl (e.g., methanesulfinyl, ethanesulfinyl, etc.), etc. The number of the substituent(s) is preferably 1 to 3.

Examples of the "carboxyl group which may be amidated" as the substituent of the benzene ring of "a further optionally substituted benzene ring" represented by B or C include that comprising a carbonyl group bonded with, for example:

(1) hydroxy group; or (2) "amino group which may be substituted" (e.g., that similar to the above-listed "amino group which may be substituted" as the substituent of the benzene ring of "a further optionally substituted benzene ring" represented by B or C), and the like.

The benzene ring of "a further optionally substituted benzene ring" represented by B or C may have 1 to 4 the same or different substituent(s) (preferably 1 or 2 substituent(s)) at any position(s) of the ring. When the benzene ring of "a further optionally substituted benzene ring" represented by B or C have two or more substituents, any two of the substituents may be bonded to each other to form, for example, lower ($C_{1-6}$) alkylene (e.g., trimethylene, tetramethylene, etc.), lower ($C_{1-6}$) alkyleneoxy (e.g., —CH$_2$—O—CH$_2$—, —O—CH$_2$—CH$_2$—, etc.), lower ($C_{1-6}$) alkylenedioxy (e.g., —O—CH$_2$—O—, —O—CH$_2$—CH$_2$—O—, etc.), lower ($C_{2-6}$) alkenylene (e.g., —CH$_2$—CH=CH—, —CH$_2$—CH$_2$—CH=CH—, —CH$_2$—CH=CH—CH$_2$—, etc.), lower ($C_{4-6}$) alkadienylene (e.g., —CH=CH—CH=CH—, etc.).

Preferred examples of the substituent of the benzene ring of "a further optionally substituted benzene ring" represented by B or C include: hydrocarbon group which may be substituted; heterocyclic group which may be substituted; nitro group; halogen atom; amino group which may be substituted; and a group represented by the formula: $R^6$—Y— (wherein Y is oxygen atom or sulfur atom which may be oxidized and $R^6$ is a hydrocarbon group which may be substituted or heterocyclic group which may be substituted). More preferable are hydrocarbon group which may be substituted, heterocyclic group which may be substituted, halogen atom, amino group which may be substituted and a group represented by the formula $R^6$—Y— (wherein Y is oxygen atom or sulfur atom which may be oxidized and $R^6$ is a hydrocarbon group which may be substituted or heterocyclic group which may be substituted), etc. Most preferable are lower ($C_{1-4}$) alkyl and halogen atom, etc.

Preferably, the "further optionally substituted benzene rings" represented by B or C are benzene rings which do not have any substituent other than that shown in the formula, respectively.

In the above-described formula (I), examples of the hydrocarbon group in the "hydrocarbon group which may be substituted" represented by $R^1$, $R^2$ and $R^3$ include (1) alkyl (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl or decyl, etc., and preferably lower ($C_{1-6}$) alkyl, etc.);

(2) cycloalkyl (e.g., $C_{3-8}$cycloalkyl such as cyclopropyl, cyclobutyl, cyclopentyl, cyclohexyl, cycloheptyl, etc.), wherein the cycloalkyl may be condensed with a benzene ring to form indan (e.g., indan 1-yl, indan 2-yl, etc.), tetrahydronaphthalene (e.g., tetrahydronaphthalene-5-yl, tetrahydronaphthalene-6-yl, etc.) (preferably indan, etc.), and wherein the cycloalkyl may be crosslinked with via a $C_{1-2}$ linear atomic chain to form a closslinked cyclic hydrocarbon group such as bicyclo[2.2.1]heptyl, bicyclo[2.2.2]octyl, bicyclo[3.2.1]octyl, bicyclo[3.2.2]nonyl, etc. (preferably cyclohexyl having a crosslinkage via a $C_{1-2}$ linear atomic chain, etc., and more preferably bicyclo[2.2.1]heptyl, etc.);

(3) alkenyl (e.g., $C_{2-10}$alkenyl such as vinyl, allyl, crotyl, 2-pentenyl or 3-hexenyl, etc., preferably lower ($C_{2-6}$) alkenyl);

(4) cycloalkenyl (e.g., $C_{3-8}$cycloalkenyl such as 2-cyclopentenyl, 2-cyclohexenyl, 2-cyclopentenylmethyl, 2-cyclohexenylmethyl, etc.);

(5) alkynyl (e.g., $C_{2-10}$alkynyl such as ethynyl, 1-propynyl, 2-propynyl, 1-butynyl, 2-pentynyl, 3-hexynyl, etc., preferably lower ($C_{2-6}$) alkynyl, etc.);

(6) aryl (e.g., $C_{6-14}$aryl such as phenyl or naphthyl, etc., preferably $C_{6-10}$aryl, and more preferably phenyl, etc.);

(7) aralkyl (e.g., $C_{1-6}$alkyl having 1 to 3 $C_{6-14}$allyl groups, preferably phenyl-$C_{1-4}$alkyl (e.g., benzyl, phenethyl, etc.);

(8) a group represented by the formula: —X'''—G—$(CH_2)_n$—J, wherein X''' represents a $C_{1-4}$alkylene group or a $C_{2-4}$alkenylene group, G represents a bond, —O—, —S—, —CO—NH— or —NH—CO—, n represents an integer of 0 to 3, and J represents an aromatic ring group which may be substituted; or (9) a group represented by the formula: —X''''—L—$(CH_2)_n$—M, wherein X'''' represents a bond or a $C_{1-4}$alkylene group, L represents (a) a bond, (b) an aromatic ring group which may be substituted, (c) —O—, (d) —S—, (e) —CO—NH— or (f) —NH—CO—, n represents an integer of 0 to 3, M represents amino group, guanidino group, sulfamoyl group, carbamoyl group or hydroxyl group; and the like.

In the above-described formula, examples of the aromatic ring group represented by J and L include an aryl group which may be substituted, an aromatic heterocyclic group which may be substituted, and the like.

Preferably, examples of the "aryl" of the "aryl group which may be substituted" represented by J and L include $C_{6-14}$aryl such as phenyl, naphthyl, etc., more preferably phenyl, etc.

Examples of the "aromatic heterocyclic group" of the "aromatic heterocyclic group which may be substituted" represented by J and L include those similar to "an aromatic heterocyclic group which may be substituted" of the "heterocyclic group which may be substituted" exemplified with respect to $R^6$ and, among them, a 5- or 6-membered aromatic monocyclic heterocyclic ring is preferred. Examples of the 5- or 6-membered aromatic monocyclic heterocyclic ring include furan, thiophene, pyrrole, oxazole, isoxazole, thiazole, isothiazole, imidazole, pyrazole, 1,2,3-oxadiazole, 1,2,4-oxadizaole, 1,3,4-oxadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.

The "aromatic ring group" of the "aromatic ring group which may be substituted represented by J and L may have substituent(s). Examples of such substituent include halogen (e.g., fluorine, chlorine, bromine, iodine, etc.), nitro, cyano, hydroxy group, thiol group which may be substituted (e.g., thiol, $C_{1-4}$alkylthio, etc.), amino group which may be substituted (e.g., amino, mono-$C_{1-4}$alkylamino, di-$C_{1-4}$alkylamino, or 5- or 6-membered cyclic amino such as tetrahydropyrrole, piperazine, piperidine, morpholine, thiomorpholine, pyrrole, imidazole, 2-oxo-1-pyrrolidinyl, 2-oxo-1-piperidinyl, etc.), phenyl-lower ($C_{1-4}$) alkyl, $C_{3-7}$cycloalkyl, carboxyl group which may be esterified or amidated (e.g., carboxyl, $C_{1-4}$alkoxy-carbonyl, lower ($C_{7-10}$) aralkyloxy-carbonyl, carbamoyl, mono-$C_{1-4}$alkyl-carbamoyl, di-$C_{1-4}$alkyl-carbamoyl, etc.), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—$CH_2$—O—, —O—$CH_2$—$CH_2$—O—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), $C_{1-4}$alkylsulfinyl (e.g., methanesulfinyl, ethanesulfinyl, etc.), sulfamoyl which may be substituted (e.g., sulfamoyl, mono-$C_{1-4}$alkylsulfamoyl, di-$C_{1-4}$alkylsulfamoyl, etc), an aryl group which may be substituted, a heterocyclic group which may be substituted, and the like. The number of the substituents is preferably 1 to 3.

The "hydrocarbon group" of the "hydrocarbon group which may be substituted represented by $R^1$, $R^2$ and $R^3$ may have substituent(s). Examples of such substituent include halogen (e.g., fluorine, chlorine, bromine, iodine, etc.), nitro, cyano, oxo, hydroxy group, thiol group which may be substituted (e.g., thiol, $C_{1-4}$alkylthio, etc.), amino group which may be substituted (e.g., amino, mono-$C_{1-4}$alkylamino, di-$C_{1-4}$alkylamino, or 5- or 6-membered cyclic amino such as tetrahydropyrrole, piperazine, piperidine, morpholine, thiomorpholine, pyrrole, imidazole, 2-oxo-1-pyrrolidinyl, 2-oxo-1-piperidinyl, etc.), phenyl-lower ($C_{1-4}$) alkyl, $C_{3-7}$cycloalkyl, carboxyl group which may be esterified or amidated (e.g., carboxyl, $C_{1-4}$alkoxy-carbonyl, lower ($C_{7-10}$) aralkyloxy-carbonyl, carbamoyl, mono-$C_{1-4}$alkyl-carbamoyl, di-$C_{1-4}$alkyl-carbamoyl, etc.), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—$CH_2$—O—, —O—$CH_2$—$CH_2$—O—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), $C_{1-4}$alkylsulfinyl (e.g., methanesulfinyl, ethanesulfinyl, etc.), sulfamoyl which may be substituted (e.g., sulfamoyl, mono-$C_{1-4}$alkylsulfamoyl, di-$C_{1-4}$alkylsulfamoyl, etc), an aryl group which may be substituted, a heterocyclic group which may be substituted, and the like. The number of the substituents is preferably 1 to 3.

Examples of the "aryl group" in the "aryl group which may be substituted" as the substituent of the "hydrocarbon group which may be substituted" represented by $R^1$, $R^2$ and $R^3$ include $C_{6-14}$aryl such as phenyl, naphthyl, etc., preferably $C_{6-10}$aryl, more preferably phenyl, etc.

Examples of the substituent(s) of the "aryl group" include halogen (e.g., fluorine, chlorine, bromine, iodine, etc.), nitro, cyano, hydroxy group, thiol group which may be substituted (e.g., thiol, $C_{1-4}$alkylthio, etc.), amino group which may be substituted (e.g., amino, mono-$C_{1-4}$alkylamino, di-$C_{1-4}$alkylamino, or 5- or 6-membered cyclic amino such as tetrahydropyrrole, piperazine, piperidine, morpholine, thiomorpholine, pyrrole, imidazole, etc.), phenyl-lower ($C_{1-4}$) alkyl, $C_{3-7}$cycloalkyl, carboxyl group which may be esterified or amidated (e.g., carboxyl, $C_{1-4}$alkoxy-carbonyl, lower ($C_{7-10}$) aralkyloxy-carbonyl, carbamoyl, mono-$C_{1-4}$alkyl-carbamoyl, di-$C_{1-4}$alkyl-carbamoyl, etc.), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—$CH_2$—O—, —O—$CH_2$—$CH_2$—O—, etc.), formyl, $C_{2-4}$alkanoyl (e.g., acetyl, propionyl, etc.), $C_{1-4}$alkylsulfonyl (e.g., methanesulfonyl, ethanesulfonyl, etc.), $C_{1-4}$alkylsulfinyl (e.g., methanesulfinyl, ethanesulfinyl, etc.), sulfamoyl which may be substituted (e.g., sulfamoyl, mono-$C_{1-4}$alkylsulfamoyl, di-$C_{1-4}$alkylsulfamoyl, etc), a heterocyclic group which may be substituted (e.g., furan, thiophene, pyrrole, oxazole, isoxazole, thiazole, isothiazole, imidazole, pyrazole, 1,2,3-oxadiazole, 1,2,4-oxadizaole, 1,3,4-oxadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.), and the like. The number of the substituents is preferably 1 to 3.

Examples of the "heterocyclic group which may be substituted" as the substituent of the "hydrocarbon group which may be substituted" represented by $R^1$, $R^2$ and $R^3$ include those similar to the "heterocyclic group which may be substituted" represented by the above-described $R^6$.

In the above-described formula (I), preferred examples of the substituent(s) of the "amino group" of the "amino group which may be substituted" represented by $R^2$ include a hydrocarbon group, a heterocyclic group, and an acyl group each of which may be substituted, and the like. When the "amino group" is substituted, the number of the substituent(s) is 1 to 2.

Examples of the hydrocarbon group as the substituent of the "amino group which may be substituted" represented by $R^2$ include:

(1) alkyl which may be substituted (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$) alkyl, etc.);

(2) cycloalkyl which may be substituted (e.g., $C_{3-8}$cycloalkyl such as cyclopropyl, cyclobutyl, cyclopentyl, cyclohexyl, cycloheptyl, cyclooctyl, etc.), wherein the cycloalkyl may be condensed with a benzene ring to form indan (e.g., indan-1-yl, indan-2-yl, etc.), tetrahydronaphthalene (e.g., tetrahydronaphthalene-5-yl, tetrahydronaphthalene-6-yl, etc.) etc. (preferably indan etc.), and wherein the cycloalkyl may be crosslinked via a $C_{1-2}$ linear atomic chain to form a crosslinked cyclic hydrocarbon group such as bicyclo[2.2.1]heptyl, bicyclo[2.2.2]octyl, bicyclo[3.2.1]octyl, bicyclo[3.2.2]nonyl etc. (preferably, cyclohexyl being crosslinked via a $C_{1-2}$ linear atomic chain, etc., and more preferably bicyclo[2.2.1]heptyl, etc.);

(3) alkenyl which may be substituted (e.g., $C_{2-10}$alkenyl such as allyl, crotyl, 2-pentenyl, 3-hexenyl, etc., and preferably lower ($C_{2-6}$) alkenyl);

(4) cycloalkenyl which may be substituted (e.g., $C_{3-7}$cycloalkenyl such as 2-cyclopentenyl, 2-cyclohexenyl, 2-cyclopentenylmethyl, 2-cyclohexenylmethyl, etc.);

(5) alkynyl (e.g., $C_{2-10}$alkynyl such as ethynyl, 1-propynyl, 2-propynyl, 1-butynyl, 2-pentynyl, 3-hexynyl, etc., preferably lower ($C_{2-6}$) alkynyl, etc.);

(6) aryl (e.g., $C_{6-14}$aryl such as phenyl or naphthyl, etc., preferably $C_{6-10}$aryl, and more preferably phenyl, etc.);

(7) aralkyl (e.g., $C_{1-6}$alkyl having 1 to 3 $C_{6-14}$allyl groups, preferably phenyl-$C_{1-4}$alkyl (e.g., benzyl, phenethyl, etc.); and the like.

Examples of the heterocyclic group as the substituent of the "amino group which may be substituted" represented by $R^2$ include that similar to the "heterocyclic group" in "heterocyclic group which may be substituted" as the substituent of the benzene ring of "a further optionally substituted benzene ring" represented by B or C, and in "heterocyclic group which may be substituted" represented by $R^6$, and the like.

Preferred examples of the acyl group as the substituent of the "amino group which may be substituted" represented by $R^2$ include that comprising carbonyl group or sulfonyl group bonded with, for example, (1) hydrogen or a hydrocarbon group (that similar to the hydrocarbon group as the substituent of the "amino group which may be substituted" represented by the above-described $R^2$, etc.), (2) a heterocyclic group (that similar to the heterocyclic group as the substituent of the "heterocyclic group which may be substituted" represented by $R^2$, etc.), and the like.

Examples of the substituents of the "hydrocarbon group which may be substituted", "heterocyclic group which may be substituted" and "acyl group which may be substituted" as the substituent of the "amino group which may be substituted" include the "hydrocarbon group which may be substituted" as the substituent of the benzene ring of "a further optionally substituted benzene ring" represented by B or C and the substituent of the "hydrocarbon group" of the "hydrocarbon group which may be substituted" represented by $R^6$. The number of the substituent(s) is preferably 1 to 3.

In the above-described formula (I), as $R^1$, hydrogen atom or optionally substituted $C_{1-6}$alkyl are preferred, and hydrogen atom or optionally substituted $C_{1-4}$alkyl are further preferred and, in particular, hydrogen atom is used.

In the above-described formula (I), as the "hydrocarbon group which may be substituted" represented by $R^2$, the group represented by the formula: $-X'''-G-(CH_2)_n-J$ wherein $X'''$ represents $C_{1-4}$alkylene or $C_{2-4}$alkenylene, G is a bond, $-O-$, $-S-$, $-CO-NH-$ or $-NH-CO-$, n is an integer of 0 to 3, J represents an aromatic ring group which may be substituted, or the group represented by the formula: $-X''''-L-(CH_2)_n-M$ wherein $X''''$ represents a bond or a $C_{1-4}$alkylene group, L represents (a) a bond, (b) an aromatic ring group which may be substituted, (c) $-O-$, (d) $-S-$, (e) $-CO-NH-$ or (f) $-NH-CO-$, n is an integer of 0 to 3, and M represents amino group, guanidino group, sulfamoyl group, carbamoyl group or hydroxyl group are preferred. As the aromatic ring group which may be substituted represented by J and L, preferred are an optionally substituted phenyl, a 5- or 6-membered monocyclic aromatic heterocyclic group, etc.

In the above-described formula (I), as the "hydrocarbon group which may be substituted" represented by $R^3$, $C_{1-6}$alkyl which may be substituted is preferred. Among them, a group represented by the formula: $-(CH_2)_p-T$ wherein p is an integer of 1 to 6 and T is an aromatic ring group which may be substituted is preferred.

While, as the "aromatic ring group which may be substituted" represented by T, there are the same groups as the "aromatic ring group which may be substituted" represented by the above-described J, as the substituent of the "aromatic ring group" of the "aromatic ring group which may be substituted" represented by T, preferred are hydroxyl group, sulfamoyl group which may be substituted (e.g., sulfamoyl, mono-$C_{1-4}$alkylsulfamoyl, di-$C_{1-4}$alkyl sulfamoyl, etc.), etc.

In the above-described formula (I), when $R^1$ and X bind together to form a ring, the ring is not specifically limited in so far as it is a nitrogen-containing heterocyclic ring and both saturated and unsaturated rings are included therein regardless of particular size of the ring. Among them, a 3- to 8-membered nitrogen-containing heterocyclic ring is preferred and, in particular, a saturated 3- to 8-membered nitrogen-containing heterocyclic ring, i.e., a ring represented by the formula:

wherein D ring represents a saturated 3- to 8-membered nitrogen-containing heterocyclic ring is preferred.

Examples of the "3- to 8-membered nitrogen-containing heterocyclic ring" include a 3- to 8-membered nitrogen-containing heterocyclic ring containing one nitrogen atom which may further contain one to three kinds (preferably 1 or 2 kinds) of 1 to 4 (preferably 1 or 2) heteroatoms selected from oxygen atom, sulfur atom and nitrogen atom and the like. Specific examples thereof include a 3- to 8-membered (preferably 5- to 6-membered) saturated or unsaturated (preferably saturated) mono-cyclic non-aromatic heterocyclic ring (aliphatic heterocyclic ring) such as pyrrolidine, pyrroline, imidazolidine, imidazoline, pyrazolidine, pyrazoline, oxazine, oxaziadine, thiazine, thiaziadine, piperidine, morpholine, thiomorpholine, piperazine, azepine, etc.

The "3- to 8-membered nitorgen-containing heterocyclic ring" may have substituent(s) and examples of the substituents include those similar to the substituent of the "hydrocarbon group which may be substituted" as the substituent of the benzene ring of "a further optionally substituted benzene ring" represented by the above-described B and C.

Further, in the above-described formula (I), $R^1$ may bind to the "amino group which may be substituted" represented by A to form a ring, and the ring is not specifically limited in so far as it is a heterocyclic ring having at least 2 nitrogen atoms and may be a saturated or unsaturated ring regardless of particular size of the ring. Among them, a 3- to 8-membered nitrogen-containing heterocyclic ring is preferred, in particular, a saturated 3- to 8-membered heterocyclic ring, i.e., a ring represented by the formula:

wherein A' represents nitrogen atom which may be substituted, and F represents a saturated 3- to 8-membered heterocyclic ring.

In the above-described formula, examples of the substituent of the "nitrogen atom" of the "nitrogen atom which may be substituted" represented by A' include that similar to the substituent of the "amino group" of the "amino group which may be substituted" represented by A described hereinafter.

Examples of the "3- to 8-membered nitrogen-containing heterocyclic ring" include a 3- to 8-membered nitrogen-containing heterocyclic ring containing two nitrogen atoms which may further contain one to three kinds (preferably 1 or 2 kinds) of 1 to 4 (preferably 1 or 2) heteroatoms selected from oxygen atom, sulfur atom and nitrogen atom and the like. Specific examples thereof include a 3- to 8-membered (preferably 5- to 6-membered) saturated or unsaturated (preferably saturated) mono-cyclic non-aromatic heterocyclic ring (aliphatic heterocyclic ring) such as imidazolidine, imidazoline, pyrazolidine, pyrazoline, oxaziadine, thiaziadine, piperazine, diazepine, etc.

The "3- to 8-membered nitorgen-containing heterocyclic ring" may have substituent(s) and examples of the substituents include those similar to the substituent of the "hydrocarbon group which may be substituted" as the substituent of the benzene ring of "a further optionally substituted benzene ring" represented by the above-described B and C.

In the above-described formula, the spacer whose linear chain moiety is composed of 1 to 12 atoms represented by X is not specifically limited in so far as it is a divalent group "whose linear chain moiety is composed of 1 to 12 atoms" and examples thereof include a saturated divalent group such as (1) $-(CH_2)_{f1}-$ (f1 is an integer of 1 to 12, preferably an integer of 1 to 8, more preferably an integer of 1 to 6, in particular, an integer of 1 to 4);

(2) $-(CH_2)_{g1}-X^1-(CH_2)_{g2}-$ (g1 and g2 are the same or different and are integers 0 to 11 provided that the sum of g1 and g2 is 0 to 11, and $X^1$ is NH, O, S, SO or $SO_2$);

(3) $-(CH_2)_{h1}-X^1-(CH_2)_{h2}-X^2-(CH_2)_{h3}-$ (h1, h2 and h3 are the same or different integers 0 to 10 provided that the sum of h1, h2 and h3 is 0 to 10, and $X^1$ and $X^2$ independently represent NH, O, S, SO or $SO_2$ provided that, when h2 is 0, at least one of $X^1$ and $X^2$ is preferably NH); etc., and these divalent groups wherein some bonds have been converted into unsaturated bonds. Specific examples thereof include a divalent group such as $-O-(CH_2)_{k3}-$ (k3 is an integer of 0 to 11), $-(CH_2)_{k3}-O-$ (k3 is an integer of 0 to 11), $-S-(CH_2)_{k3}-$ (k3 is an integer of 0 to 11), $-(CH_2)_{k3}-S-$ (k3 is an integer of 0 to 11), $-NH-$ $(CH_2)_{k3}$— (k3 is an integer of 0 to 11), —$(CH_2)_{k3}$—NH— (k3 is an integer of 0 to 11), —$(CH_2)_{k4}$— (k4 is an integer of 1 to 12), —CH=CH—, —C.C—, —CO—NH—, —$SO_2$—NH— etc.

More preferably, X is a divalent group whose linear chain moiety is composed of 1 to 4 carbon atoms. Among them, preferred are $C_{1-4}$alkylene, $C_{2-4}$alkenylene, etc., in particular, $C_{1-4}$alkylene is preferably used.

The divalent group as X may have substituent(s) at any position (preferably on carbon atom(s)) and such substituent(s) are not specifically limited in so far as they can bind to the divalent chain which constitutes the linear chain moiety. Examples thereof include substituents similar to those of the benzene ring in "a further optionally substituted benzene ring" represented by the above-described B and C, as well as oxo, etc. Such substituent(s) may be the same or different 1 to 4 (preferably 1 to 2) substituents at any position(s) of the divalent group. Further, the substituents of the divalent group as X can bind to each other to form a ring. Examples of such "ring" include $C_{5-7}$cycloalkane such as cyclopentane, cyclohexane, cycloheptane, etc.; benzene; and the like.

Examples of the substituent of the divalent group as X include lower ($C_{1-6}$) alkyl (e.g., methyl, ethyl, propyl, isopropyl, butyl, isobutyl, sec-butyl, tert-butyl, pentyl, isopentyl, neopentyl, hexyl, etc.); lower ($C_{3-7}$) cycloalkyl (e.g., cyclopropyl, cyclobutyl, cyclopentyl, cyclohexyl, cycloheptyl, etc.); formyl; lower ($C_{2-7}$) alkanoyl (e.g., acetyl, propionyl butyryl, etc.); lower ($C_{2-7}$) lower alkoxy-carbonyl; lower ($C_{1-6}$); lower alkoxy; hydroxy group; oxo, etc.

Examples of "amino group which may be substituted" represented by A in the above-described formula include amino group which may have one or two substituents selected from the group consisting of: "hydrocarbon group which may be substituted" (e.g., those similar to the above-described "hydrocarbon group which may be substituted" as the substituent of the benzene ring of "a further optionally substituted benzene ring" represented by B or C), "heterocyclic group which may be substituted" (e.g., those similar to the above-described "heterocyclic group which may be substituted" as the substituent of the benzene ring of "a further optionally substituted benzene ring" represented by B or C) and "acyl group which may be substituted" (e.g., those similar to the above-described "acyl group which may be substituted" as the substituent of the benzene ring of "a further optionally substituted benzene ring" represented by B or C), and the like. In the "amino group which may be substituted" represented by A, the substituents of the amino group may be bonded to each other to form a cyclic amino group (e.g., a cyclic amino group formed by removing one hydrogen atom from a constituent nitrogen atom of 5- or 6-membered ring such as tetrahydropyrrole, piperazine, piperidine, morpholine, thiomorpholine, pyrrole or imidazole, having a bond on the nitrogen atom). The cyclic amino group may have substituent(s), and examples thereof include halogen (e.g., fluorine, chlorine, bromine, iodine, etc.), nitro, cyano, hydroxy group, thiol group, amino group, carboxyl group, $C_{1-4}$alkyl which may be halogenated (e.g., trifluoromethyl, methyl, ethyl, etc.), $C_{1-4}$alkoxy which may be halogenated (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.), etc. The number of the substituents is preferably 1 to 3.

Examples of substituent which the "amino group which may be substituted" represented by A may have preferably include (1) alkyl which may be substituted (e.g., $C_{1-10}$alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., and preferably lower ($C_{1-6}$) alkyl, etc.);

(2) cycloalkyl which may be substituted (e.g., $C_{3-8}$cycloalkyl such as cyclopropyl, cyclobutyl, cyclopentyl, cyclohexyl, cycloheptyl, cyclooctyl, etc.), wherein the cycloalkyl may be condensed with a benzene ring to form indan (e.g., indan-1-yl, indan-2-yl, etc.), tetrahydronaphthalene (e.g., tetrahydronaphthalene-5-yl, tetrahydronaphthalene-6-yl, etc.) etc. (preferably indan etc.), and wherein the cycloalkyl may be crosslinked via a $C_{1-2}$ linear atomic chain to form a crosslinked cyclic hydrocarbon-group such as bicyclo[2.2.1] heptyl, bicyclo[2.2.2]octyl, bicyclo[3.2.1]octyl, bicyclo [3.2.2]nonyl etc. (preferably, cyclohexyl being crosslinked via a $C_{1-2}$ linear atomic chain, etc., and more preferably bicyclo[2.2.1]heptyl, etc.);

(3) alkenyl which may be substituted (e.g., $C_{2-10}$alkenyl such as allyl, crotyl, 2-pentenyl, 3-hexenyl, etc., and preferably lower ($C_{2-6}$) alkenyl);

(4) cycloalkenyl which may be substituted (e.g., $C_{3-7}$cycloalkenyl such as 2-cyclopentenyl, 2-cyclohexenyl, 2-cyclopentenylmethyl, 2-cyclohexenylmethyl, etc.);

(5) aralkyl which may be substituted (e.g., phenyl-$C_{1-4}$alkyl such as benzyl, phenethyl, etc.);

(6) formyl or acyl which may be substituted (e.g., $C_{2-4}$alkanoyl such as acetyl, propionyl, butyryl, isobutyryl, etc., and $C_{1-4}$alkylsulfonyl such as methanesulfonyl, ethanesulfonyl, etc.);

(7) aryl which may be substituted (e.g., phenyl, naphthyl, etc.);

(8) heterocyclic group which may be substituted (e.g., a group formed by eliminating one hydrogen atom from a 5- or 6-membered aromatic heterocyclic ring comprising 1 to 4 heteroatom(s) of 1 or 2 species selected from the nitrogen, sulfur and oxygen atoms (e.g. furan, thiophene, pyrrole, imidazole, pyrazole, thiazole, oxazole, isothiazole, isoxazole, tetrazole, pyridine, pyrazine, pyrimidine, pyridazine, triazine, etc.); and a group formed by eliminating one hydrogen atom from a 5- or 6-membered non-aromatic heterocyclic ring comprising 1 to 4 heteroatom(s) of 1 or 2 species selected from the nitrogen, sulfur and oxygen atoms (e.g. tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, etc.)).

Examples of the substituents of the above-described (1) alkyl which may be substituted, (2) cycloalkyl which may be substituted, (3) alkenyl which may be substituted, (4) cycloalkenyl which may be substituted, (5) aralkyl which may be substituted, (6) acyl which may be substituted, (7) aryl which may be substituted, and (8) heterocyclic group which may be substituted include halogen (e.g., fluorine, chlorine, bromine, iodine, etc.); $C_{1-4}$alkyl which may be substituted by halogen atom or $C_{1-4}$alkoxy; $C_{1-4}$alkoxy which may be substituted by halogen atom or $C_{1-4}$alkoxy (e.g., methoxy, ethoxy, propoxy, butoxy, trifluoromethoxy, trifluoroethoxy, etc.); $C_{1-4}$alkylenedioxy (e.g., —O—$CH_2$—O—, —O—$CH_2$—$CH_2$—O—, etc.); formyl, $C_{2-4}$alkanoyl (e.g., acetyl, propionyl, etc.); $C_{1-4}$alkylsulfonyl (e.g., methanesulfonyl, ethanesulfonyl, etc.); phenyl-lower ($C_{1-4}$) alkyl; $C_{3-7}$cycloalkyl; cyano; nitro; hydroxy group; thiol group which may be substituted (e.g., thiol, $C_{1-4}$alkylthio, etc.); amino group which may be substituted (e.g., amino, mono-$C_{1-4}$alkylamino, di-$C_{1-4}$alkylamino, 5- or 6-membered cyclic amino such as tetrahydropyrrole, piperazine, piperidine, morpholine, thiomorpholine, pyrrole, imidazole, etc.); carboxyl group; lower ($C_{1-4}$) alkoxy-carbonyl; lower ($C_{7-10}$) aralkyloxy-carbonyl; carbamoyl; mono-$C_{1-4}$alkyl-carbamoyl; di-$C_{1-4}$alkyl-carbamoyl (preferably halogen, lower ($C_{1-4}$) alkyl which may be halogenated, lower ($C_{1-4}$) alkoxy which may be halogenated, phenyl-lower ($C_{1-4}$) alkyl, $C_{3-7}$cycloalkyl, cyano, hydroxy group, etc.); etc. The number of the substituents is preferably 1 to 3.

Particularly, examples of "amino group which may be substituted" represented by A include amino group which may have one or two alkyl which may be substituted [e.g., $C_{1-10}$alkyl (such as methyl, ethyl, propyl, isopropyl, butyl, isobutyl, sec-butyl, tert-butyl, pentyl, isopentyl, neopentyl, hexyl, heptyl, octyl, nonyl, decyl, preferably lower ($C_{1-6}$) alkyl) which may have 1 to 3 substituent(s) selected from the group consisting of halogen (e.g., fluorine, chlorine, bromine, iodine, etc.), nitro, cyano, hydroxy group, thiol group which may be substituted (e.g., thiol, $C_{1-4}$alkylthio, etc.), amino group which may be substituted (e.g., amino, mono-$C_{1-4}$alkylamino, di-$C_{1-4}$alkylamino, 5- or 6-membered cyclic amino such as tetrahydropyrrole, piperazine, piperidine, morpholine, thiomorpholine, pyrrole, imidazole, etc.), carboxyl group which may be esterified or amidated (e.g., carboxyl, $C_{1-4}$alkoxy-carbonyl, lower ($C_{7-10}$) aralkyloxy-carbonyl, carbamoyl, mono-$C_{1-4}$alkyl-carbamoyl or di-$C_{1-4}$ alkyl-carbamoyl), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—CH$_2$—O—, —O—CH$_2$—CH$_2$—O—, etc.), phenyl-lower ($C_{1-4}$) alkyl, $C_{3-7}$cycloalkyl, formyl, $C_{2-4}$alkanoyl (e.g., acetyl, propionyl, etc.), $C_{1-4}$alkylsulfonyl (e.g., methanesulfonyl, ethanesulfonyl, etc.) or $C_{1-4}$alkylsulfinyl (e.g., methanesulfinyl, ethanesulfinyl, etc.), etc.].

In the above-described formula, examples of the "nitrogen-containing heterocyclic group" of the "nitrogen-containing heterocyclic group which may be substituted" represented by A include those which may be formed by removing one hydrogen atom from a 5- to 8-membered aromatic monocyclic heterocyclic ring, saturated or unsaturated non-aromatic monocyclic heterocyclic ring (aliphatic heterocyclic ring), etc. containing one nitrogen atom and further 1 to 4 (preferably 1 or 2) of 1 to 3 (preferably 1 or 2) kinds of heteroatom(s) selected from the group consisting of oxygen, sulfur and nitrogen atoms; a ring formed by condensing the same or different rings selected from these monocyclic rings; or the like. While the "nitrogen-containing heterocyclic group which may be substituted" represented by A may bind to X through any of nitrogen atom or carbon atom, preferably, it binds to X through carbon atom.

Examples of "aromatic monocyclic heterocyclic ring" include a 5- to 8-membered (preferably 5- or 6-membered) aromatic monocyclic heterocyclic ring (e.g., pyrrole, oxazole, isoxazole, thiazole, isothiazole, imidazole, pyrazole, 1,2,3-oxadiazole, 1,2,4-oxadiazole, 1,3,4-thiadiazole, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine, etc.). Examples of "non-aromatic monocyclic heterocyclic ring" include a 5- to 8-membered (preferably 5- or 6-membered) saturated or unsaturated monocyclic non-aromatic heterocyclic ring (aliphatic heterocyclic ring) such as pyrrolidine, pyrroline, imidazolidine, imidazoline, pyrazolidine, pyrazoline, oxazine, oxadiazine, thiazine, thiadiazine, piperidine, morpholine, thiomorpholine, piperazine, azepine, etc.; a 5- to 8-membered non-aromatic heterocyclic ring comprising any of the above-described aromatic monocyclic heterocyclic rings with all or portion of double bonds therein being saturated; and the like.

Examples of the substituent of the "nitrogen-containing heterocyclic ring" of the "nitrogen-containing heterocyclic ring which may be substituted" represented by A include that similar to the above-described substituent of the "hydrocarbon group which may be substituted" as the substituent of the benzene ring of "a further optionally substituted benzene ring" represented by B or C.

As the "nitrogen-containing heterocyclic group" of the "nitrogen-containing heterocyclic group" represented by A, a 5- to 6-membered nitrogen-containing heterocyclic group is preferred and a saturated 5- to 6-membered nitrogen-containing heterocyclic group is more preferred. Among them, particularly preferred are pyrrolidine, piperidine, piperazine (preferably a saturated 5- to 6-membered nitrogen-containing heterocyclic ring), etc.

In the above-described formula, preferred examples of the group represented by the formula:

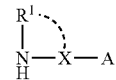

include a group represented by the formula:

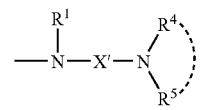

wherein $R^1$ is as defined above, X' represents $C_{1-6}$alkylene group which may be substituted, $R^4$ and $R^5$ are hydrogen atom or $C_{1-6}$alkyl group which may be substituted, respectively, and $R^4$ and $R^5$ bind to each other to form a ring, a group represented by the formula:

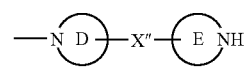

wherein X" is a bond or C1–4alkylene group which may be substituted, ring D and ring E represent a saturated 3- to 8-membered nitrogen-containing heterocyclic ring, respectively; and the like.

Examples of the substituent of "$C_{1-6}$alkylene group (preferably $C_{1-4}$alkylene group)" in the "$C_{1-6}$alkylene group which may be substituted" represented by X' include that similar to the substituent of the divalent group as X.

In the above-described formula, examples of the "$C_{1-6}$ alkyl group which may be substituted" represented by $R^4$ and $R^5$ include lower ($C_{1-6}$) alkyl group such as methyl, ethyl, propyl, isopropyl, butyl, isobutyl, sec-butyl, tert-butyl, pentyl, isopentyl, neopentyl, hexyl, etc., which may have 1 to 3 substituent(s) selected from the group consisting of halogen (e.g., fluorine, chlorine, bromine, iodine, etc.), nitro, cyano, hydroxy group, thiol group which may be substituted (e.g., thiol or $C_{1-4}$alkylthio), amino group which may be substituted (e.g., amino, mono-$C_{1-4}$alkylamino, di-$C_{1-4}$alkylamino, 5- or 6-membered cyclic amino such as tetrahydropyrrole, piperazine, piperidine, morpholine, thiomorpholine, pyrrole, imidazole, etc.), carboxyl group which may be esterified or amidated (e.g., carboxyl, $C_{1-4}$alkoxy-carbonyl, lower ($C_{7-10}$) aralkyloxy-carbonyl, carbamoyl, mono-$C_{1-4}$alkyl-carbamoyl, di-$C_{1-4}$alkyl-carbamoyl, etc.), $C_{1-4}$alkyl which may be substituted by halogen atom or $C_{1-4}$alkoxy (e.g., trifluoromethyl, methyl, ethyl, etc.), $C_{1-4}$alkoxy which may be substituted by halogen atom or $C_{1-4}$alkoxy (e.g., methoxy, ethoxy, trifluoromethoxy, trifluoroethoxy, etc.), $C_{1-4}$alkylenedioxy (e.g., —O—CH$_2$—O—, —O—CH$_2$—CH$_2$—O—, etc.), phenyl-lower ($C_{1-4}$) alkyl, $C_{3-7}$cycloalkyl, formyl, $C_{2-4}$alkanoyl (e.g., acetyl, propionyl, etc.), $C_{1-4}$alkylsulfonyl (e.g., methanesulfonyl, ethanesulfonyl, etc.), $C_{1-4}$alkylsulfinyl (e.g., methanesulfinyl, ethanesulfinyl, etc.) and the like.

In the above-described formula, $R^4$ and $R^5$ may bind to each other to form together with the adjacent nitrogen atom a cyclic amino group (e.g., a cyclic amino group formed by removing one hydrogen atom from constituent nitrogen atom of a 5- or 6-membered ring with a bond on its nitrogen atom, such as tetrahydropyrrole, piperazine, piperidine, morpholine, thiomorpholine, pyrrole, imidazole, etc.; preferably a saturated 5- to 6-membered cyclic amino group such as pyrrolidino, piperazino, piperidino, etc.; more preferably pyrrolidino, etc.). The cyclic amino group may have substituent(s) and examples thereof include halogen (e.g., fluorine, chlorine, bromine, iodine, etc.), nitro, cyano, hydroxy group, thiol group, amino group, carboxyl group, $C_{1-4}$alkyl which may be halogenated (e.g., trifluoromethyl, methyl, ethyl, etc.), $C_{1-4}$alkoxy which may be halogenated (e.g., methoxy, ethoxy, propoxy, butoxy, trifluoromethoxy, trifluoroethoxy, etc.), formyl, $C_{2-4}$alkanoyl (e.g., acetyl, propionyl, etc.), $C_{1-4}$alkylsulfonyl (e.g., methanesulfonyl, ethanesulfonyl, etc.), etc. The number of the substituents is preferably 1 to 3.

In the above-described formula, examples of the substituent of the "$C_{1-4}$alkylene group" of the "$C_{1-4}$alkylene group which may be substituted" include that similar to the substituent of the divalent group as X.

Examples of the "saturated 3- to 8-membered nitrogen-containing heterocyclic ring represented by X" include a 3- to 8-membered nitrogen-containing heterocyclic ring containing one nitrogen atom which may further contain one to three kinds (preferably 1 or 2 kinds) of 1 to 4 (preferably 1 or 2) heteroatoms selected from oxygen atom, sulfur atom and nitrogen atom and the like. Specific examples thereof include a 3- to 8-membered (preferably 5- to 6-membered) saturated or unsaturated (preferably saturated) mono-cyclic non-aromatic heterocyclic ring (aliphatic heterocyclic ring) such as pyrrolidine, pyrroline, imidazolidine, imidazoline, pyrazolidine, pyrazoline, oxazine, oxaziadine, thiazine, thiaziadine, piperidine, morpholine, thiomorpholine, piperazine, azepine, etc.

The "3- to 8-membered nitrogen-containing heterocyclic ring" may have substituent(s) and examples of the substituents include those similar to the substituent of the "hydrocarbon group which may be substituted" as the substituent of the benzene ring of "a further optionally substituted benzene ring" represented by the above-described B and C.

Further, while the "3- to 8-membered nitrogen-containing heterocyclic group which may be substituted" represented by ring D and ring E may bind to X" through any of nitrogen atom or carbon atom, preferably, it binds to X" through carbon atom.

In the above-described formula (I), while the substituents of ring B and ring C shown in the formula may be substituted at any possible positions, preferably, a compound represented by the formula (I) or a salt thereof has any of the following structures:

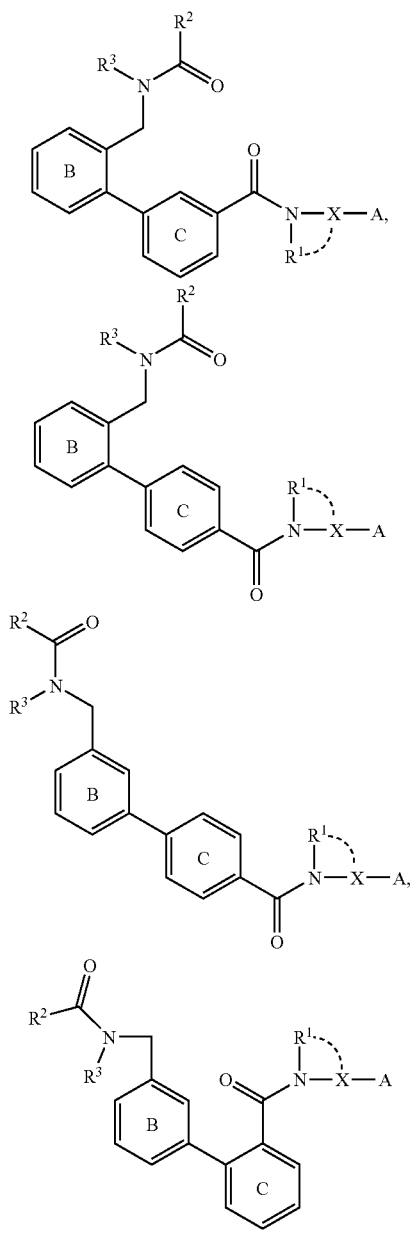

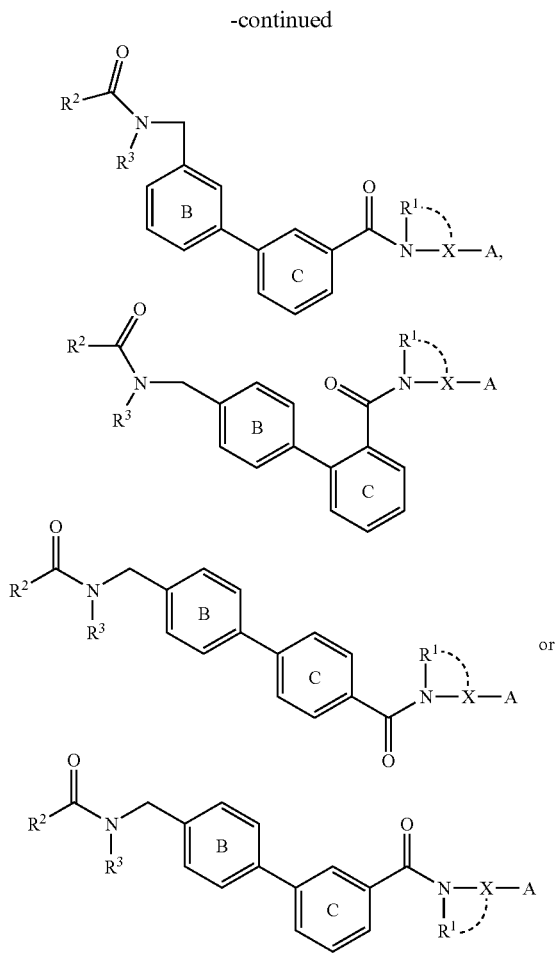

wherein each symbol is as defined above.

Among them, preferably, the compound has the following structure:

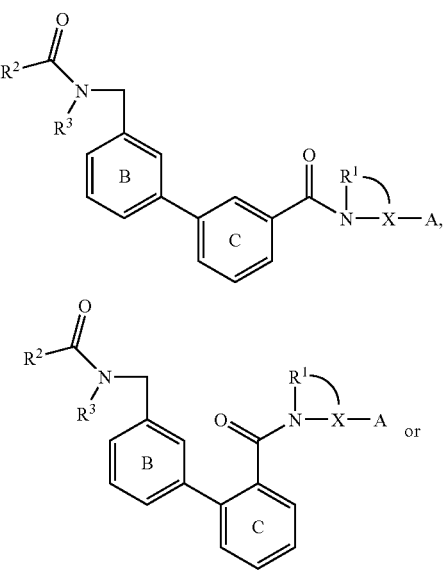

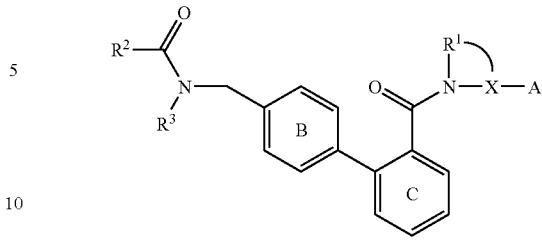

In particular, among the compounds represented by the formula (I), 3'-{[{2-[4-(aminosulfonyl)phenyl]ethyl}(4-phenylbutanoyl)amino]methyl}-N-[2-(1-pyrrolidinyl) ethyl]-[1,1'-biphenyl]-3-carboxamide, 3'-({{2-[4-(amino-sulfonyl)phenyl]ethyl}-[(benzyloxy)acetyl]amino}methyl)-N-[2-(1-pyrrolidinyl)-ethyl][1,1'-biphenyl]-3-carboxamide, N-(2-aminoethyl)-3'-{[[3-({[amino(imino)methyl]-amino}methyl)benzoyl](1-naphthylmethyl)amino]methyl}-1,1'-biphenyl]-2-carboxamide, N-(2-Aminoethyl)-3'-{[[4-(aminosulfonyl)benzoyl]-(1-naphthylmethyl)amino] methyl}-1,1'-biphenyl-2-carboxamide, and the like are preferably used.

Salts of the compound represented by the formula (I) and used in the present invention are preferably pharmaceutically acceptable salts, for example, salts with inorganic base, organic base, inorganic acid, organic acid, or basic or acidic amino acid.

Preferred examples of salts with inorganic base include alkaline metal salts such as sodium salts or potassium salts; alkaline earth metal salts such as calcium salts or magnesium salts; and aluminium salts and ammonium salts, etc.

Preferred examples of salts with organic base include salts with, for example, trimethylamine, triethylamine, pyridine, picoline, ethanolamine, diethanolamine, triethanolamine, dicyclohexylamine or N,N'-dibenzylethylenediamine, etc.

Preferred examples of salts with inorganic acid include salts with, for example, hydrochloric acid, hydrobromic acid, nitric acid, sulfuric acid or phosphoric acid, etc.

Preferred examples of salts with organic acid include salts with, for example, formic acid, acetic acid, trifluoroacetic acid, fumaric acid, oxalic acid, tartaric acid, maleic acid, citric acid, succinic acid, malic acid, methansulfonic acid, benzenesulfonic acid or p-toluenesulfonic acid, etc.

Preferred examples of salts with basic amino acid include salts with, for example, arginine, lysine or ornithine, etc. Preferred examples of salts with acidic amino acid include salts with, for example, aspartic acid or glutamic acid, etc.

The compound represented by the formula (I) to be used in the present invention may be hydrates or non-hydrates. Further, the compound represented by the formula (I) to be used in the present invention can be individually isolated by any known means for separation and/or purification as desired when it is present as configurational isomers, diastereoisomers or conformers. Furthermore, the compound represented by the formula (I) to be used in the present invention can be separated into S-form and R-form by any conventional optical resolution means when it is present as racemic modifications. All of those optically active substances and racemic modifications are encompassed by the present invention.

The compound represented by the formula (I) to be used in the present invention and a salt thereof [hereinafter sometimes referred to as compound (I)] may be used as prodrugs. Examples of such prodrugs may include a compound which may be converted into compound (I) through, for example, enzyme- or gastric acid-mediated reaction in vivo under physiological conditions, i.e., a compound which may be enzymatically oxidized, reduced and/or hydrolyzed to be converted into compound (I), and a compound which may be hydrolyzed by gastric acid and the like to be converted into compound (I). Examples of the prodrug of compound (I) include a compound such as compound (I) whose amino group has been acylated, alkylated or phosphorylated (e.g., a compound such as compound (I) whose amino group has been eicosanoylated, alanylated, pentylamino carbonylated, (5-methyl-2-oxo-1,3-dioxolene-4-yl) methoxycarbonylated, tetrahydrofuranylated, pyrrolidylmethylated, pivaloyloxymethylated, tert-butylated, etc.); a compound such as compound (I) whose hydroxy group has been acylated, alkylated, phosphorylated or borated (e.g., a compound such as compound (I) whose hydroxy group has been acetylated, palmitoylated, propanoylated, pivaloylated, succinylated, fumarylated, alanylated, dimethylaminomethylcarbonylated, etc.); a compound such as compound (I) whose carboxyl group has been esterified or amidated (e.g., a compound such as compound (I) whose carboxyl group has been ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolene-4-yl)methyl esterified, cyclohexyloxycarbonylethyl esterified, methylamidated, etc.), etc. These compounds can be prepared from compound (I) using any known method.

Further, prodrugs of compound (I) may be compounds which may be converted into compound (I) under physiological conditions as described in "Development of pharmaceuticals (Iyakuhinn no Kaihatsu)", vol. 7, Molecular Design pp. 163–198, Hirokawa Shoten (1990).

Furthermore, compound (I) may be labeled with any suitable isotope such as $^3H$, $^{14}C$, $^{35}S$, $^{125}I$, etc.

Compound (I) of the present invention may be used alone or in combination with pharmaceutically acceptable carrier or carriers, to formulate solid preparations such as tablet, capsule, granule, powder, etc.; or liquid preparations such as syrup, injectable preparation, etc., which can then be administered orally or parenterally.

Dosage forms for parenteral administration include, for example, injectable preparations, instillation and suppository.

Examples of pharmaceutically acceptable carrier include various organic or inorganic carrier materials which have been conventionally used as formulation bases. Excipient, lubricant, binder, disintegrator, etc., may be used for solid preparations, while solvent, dissolution adjuvant, suspending agent, isotonizing agent, buffer, soothing agent, etc., may be used for liquid preparations. Additive or additives may be added when required, including preservative, anti-oxidant, colorant, sweetening agent, etc. Preferred examples of excipient include lactose, saccharose, D-mannitol, starch, crystalline cellulose, light anhydrous silicic acid, etc. Preferred examples of lubricant include, for example, magnesium stearate, calcium stearate, talc, colloidal silica, etc. Preferred examples of binder include, for example, crystalline cellulose, saccharose, D-mannitol, dextrin, hydroxypropylcellulose, hydroxypropylmethylcellulose, polyvinylpyrrolidone, etc. Preferred examples of disintegrator include, for example, starch, carboxymethyl cellulose, carboxy methylcellulose calcium, crosscarmellose sodium, sodium carboxymethyl starch, etc. Preferred examples of solvent include, for example, water for injection, alcohol, propylene glycol, macrogol, sesame oil, corn oil, etc. Preferred examples of dissolution adjuvant include, for example, polyethylene glycol, propylene glycol, D-mannitol, benzyl benzoate, ethanol, trisaminomethane, cholesterol, triethanolamine, sodium carbonate, sodium citrate, etc. Preferred examples of suspending agent include: surfactants such as stearyl triethanolamine, sodium lauryl sulfate, laurylamino propionate, lecitin, benzalkonium chloride, benzethonium chloride, glyceryl monostearate, etc; and hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose, etc. Preferred examples of isotonizing agent include, for example, sodium chloride, glycerine, D-mannitol, etc. Preferred examples of buffer include buffer solution of, for example, phosphate, acetate, carbonate, citrate, etc. Preferred examples of soothing agent include, for example, benzyl alcohol, etc. Preferred examples of preservative include, for example, p-hydroxybenzoic esters, chlorobutanol, benzyl alcohol, phenethyl alcohol, dehydroacetic acid, sorbic acid, etc. Preferred examples of anti-oxidant include, for example, sulfite, ascorbic acid, etc.

A process for producing a compound represented by the formula (I) or a salt thereof will be described below. Starting compounds and intermediates shown in the following process may form their salts similar to those of a compound represented by the formula (I).

Production Process

A compound represented by the formula (I) or a salt thereof can be produced, for example, according to Scheme 1:

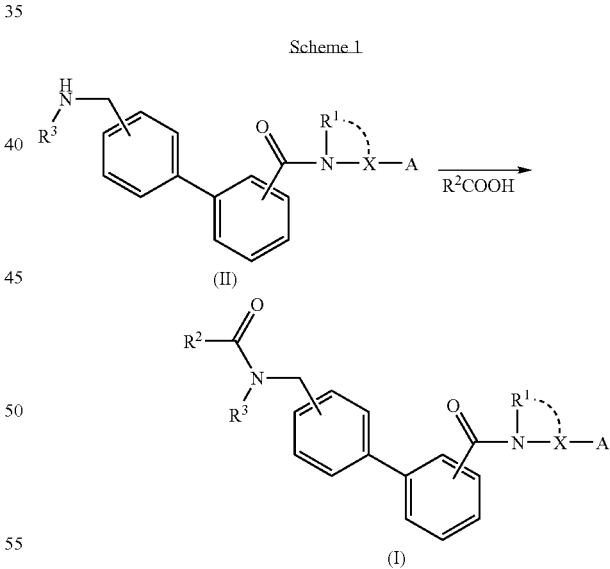

wherein each symbol is as defined above.

The compound represented by the formula (I) or a salt thereof can be produced by reacting a compound represented by the formula (II) and a carboxylic acid represented by the formula: $R^2COOH$, a reactive derivative thereof or a salt thereof in a solvent, if necessary, in the presence of a base, by using a condensation agent. Examples of the reactive derivative of the carboxylic acid include acid anhydrides, active esters (e.g., p-nitrophenyl ester, N-hydroxysuccinim ide ester, pentafluorophenyl ester, 1-hydroxybenzotriazol ester, etc.), acid halides (e.g., acid chloride, acid bromide, etc.), imidazolides and mixed acid anhydrides (e.g., anhydride with methyl carbonate, anhydride with ethyl carbonate, etc.), etc. Specific examples thereof include a compound whose group corresponding to that represented by the formula —COOH is a group represented by the formula —COQ [wherein, Q is a leaving group (e.g., a halogen atom (fluorine, chlorine, bromine, iodine, etc.), methanesulfonyloxy, benzenesulfonyloxy, p-toluenesulfonyloxy, etc.)], etc. Examples of the solvent to be used include ether solvents (e.g., diethyl ether, tetrahydrofuran, dioxane, etc.), hydrocarbon solvents (e.g., benzene, toluene, hexane, heptane, etc.), halogen solvents (e.g., dichloromethane, dichloroethane, chloroform, tetrachloromethane, etc.), acetonitrile, N,N-dimethylformamide, etc. Examples of the base to be used include organic bases such as triethylamine, 4-dimethylaminopyridine, N,N-diisopropylethylamine, triethylenediamine, and 4-methylmorpholine, carbonates of alkali metals or alkali earth metals (e.g., sodium carbonate, potassium carbonate, etc.), hydrogencarbonates of alkali metals or alkali earth metals (e.g., sodium hydrogencarbonate, potassium hydrogencarbonate, etc.), hydroxides of alkali metals or alkali earth metals (e.g., sodium hydroxide, potassium hydroxide, etc.), etc. As the condensation agent to be used, there are those used for peptide synthesis, etc. Specific examples thereof include dicyclohexylcarbodiimide, diisopropylcarbodiimide, N-ethyl-N'-3-dimethylaminopropylcarbodiimide and hydrochloride thereof, benzotriazol-1-yl-tris(dimethylamino)phosphonium hexafluorophosphate, benzotriazol-1-yl-trispyrrolidinophosphonium hexafluorophosphate, diethyl cyanophosphate, diphenylphosphorylazide, N-hydroxy-5-norbornene-2,3-carboxyimide, etc. These may be used alone or in combination with 1-hydroxybenzotriazol, 1-hydroxy-7-azabenzotriazol, etc. In this case, the carboxylic acid represented by the formula: $R^2COOH$ or a salt thereof is used in an amount of 0.5 to 10 mole equivalents, preferably 1 to 5 mole equivalents, and the condensation agent is used in an amount of 0.5 to 10 mole equivalents, preferably 1 to 6 equivalent, based on 1 mole of the compound represented by the formula (II) or a salt thereof. In this case, the reaction temperature is −50 to 200° C., preferably −20 to 100° C., and the reaction time is 0.5 to 96 hours, preferably from 0.5 to 72 hours, more preferably from 1 to 24 hours.

A compound expressed by the formula (I) or a salt thereof can also be produced, for example, according to Scheme 2:

Scheme 2

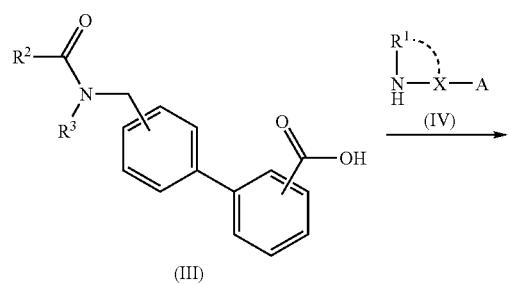

(III)

-continued

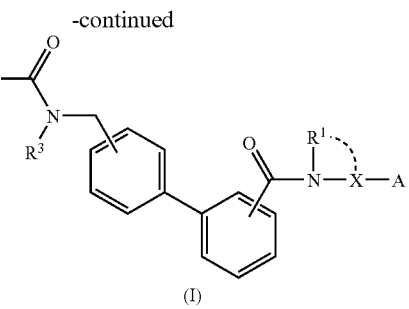

(I)

wherein each symbol is as defined above.

The compound represented by the formula (I) or a salt thereof can be produced by reacting a compound represented by the formula (III), a reactive derivative thereof or a salt thereof, and a compound represented by the formula (IV) or a salt thereof in a solvent, if necessary, in the presence of a base, by means of a condensation agent. Examples of the reactive derivative of the compound represented by the formula (III) include acid anhydrides, active esters (e.g., p-nitrophenyl ester, N-hydroxysuccinimide ester, pentafluorophenyl ester, 1-hydroxybenzotriazol ester, etc.), acid halides (e.g., acid chloride, acid bromide, etc.), imidazolides, mixed acid anhydrides (e.g., anhydride with methyl carbonate, anhydride with ethyl carbonate, etc.), etc. Specific examples thereof include a compound whose group corresponding that represented by the formula: —COOH is a group represented by the formula: —COQ [wherein, Q is a leaving group (e.g., halogen atom (fluorine, chlorine, bromine, iodine, etc.), methanesulfonyloxy, benzenesulfonyloxy, p-toluenesulfonyloxy, etc.)], etc. Examples of the solvent to be used include ether solvents (e.g., diethyl ether, tetrahydrofuran, dioxane, etc.), hydrocarbon solvents (e.g., benzene, toluene, hexane, heptane, etc.), halogen solvents (e.g., dichloromethane, dichloroethane, chloroform, tetrachloromethane, etc.), acetonitrile, N,N-dimethylformamide, etc. Examples of the base to be used include organic bases such as triethylamine, 4-dimethylaminopyridine, N,N-diisopropylethylamine, triethylenediamine, and 4-methylmorpholine, carbonates of alkali metals or alkali earth metals (e.g., sodium carbonate, potassium carbonate, etc.), hydrogencarbonates of alkali metals or alkali earth metals (e.g., sodium hydrogencarbonate, potassium hydrogencarbonate, etc.), hydroxides of alkali metals or alkali earth metals (e.g., sodium hydroxide, potassium hydroxide, etc.), etc. As the condensation agent to be used, there are those for use in peptide synthesis, etc. Specific examples thereof include dicyclohexylcarbodiimide, diisopropylcarbodiimide, N-ethyl-N'-3-dimethylaminopropylcarbodiimide and hydrochloride thereof, benzotriazol-1-yl-tris(dimethylamino)phosphoniumhexafluorophosphate, benzotriazol-1-yl-trispyrrolidinophosphoniumhexafluorophosphate, diethyl cyanophosphate, diphenylphosphorylazide, etc. These may be used alone or in combination with 1-hydroxybenzotriazol, 1-hydroxy-7-azabenzotriazol, etc. In this case, the compound represented by the formula (IV) or a salt thereof is used in an amount of 0.5 to 10 mole equivalents, preferably 1 to 5 mole equivalents, and the condensation agent is used in an amount of 0.5 to 10 mole equivalents, preferably 1 to 6 more equivalents, based on 1 mole of a compound represented by the formula (III) or a salt thereof. In this case, the reaction temperature is −50 to 200° C., preferably −20 to 100° C., and the reaction time is 0.5 to 96 hours, preferably 0.5 to 72 hours, and more preferably 1 to 24 hours.

A compound expressed by the formula (II) or a salt thereof can be produced, for example, according to Scheme 3:

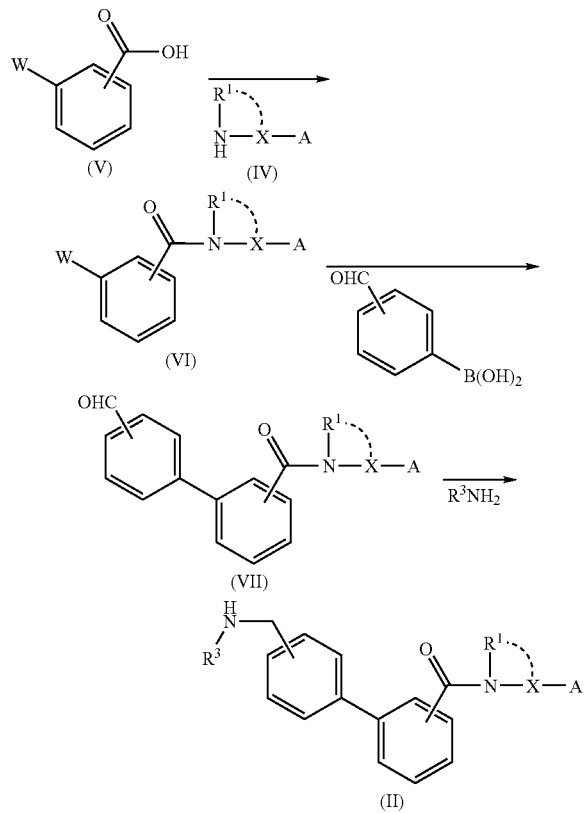

wherein W represents a halogen atom (for example, fluorine, chlorine, bromine, iodine, etc.) or trifluoromethanesulfonyloxy group, and each of the other symbols is as defined above.

A compound represented by the formula (VI) or a salt thereof can be produced by reacting a compound represented by the formula (V), a reactive derivative thereof or a salt thereof, with a compound represented by the formula (IV) or a salt thereof. This reaction is carried out under the same conditions, etc. as those for the condensation reaction in the above-described Scheme 2 above.

The compound represented by the formula (VII) or a salt thereof can be produced by reacting a compound represented by the formula (VI) or a salt thereof with formylbenzeneboronic acid or ester thereof or anhydride thereof in a solvent under basic conditions in the presence of a transition metal catalyst. Examples of the solvent to be used include water, alcohol solvents (e.g., methanol, ethanol, n-propanol, isopropanol, etc.), ether solvents (e.g., diethyl ether, tetrahydrofuran, 1,2-dimethoxyethane, etc.), hydrocarbon solvents (e.g., benzene, toluene, hexane, heptane, etc.), N,N-dimethylformamide, etc. These solvents may be used alone or, as necessary, as a mixture prepared by mixing two species or more in appropriate ratios. Examples of the base to be used include carbonates of alkali metals or alkali earth metals (e.g., sodium carbonate, potassium carbonate, etc.), hydrogencarbonates of alkali metals or alkali earth metals (e.g., sodium hydrogencarbonate, potassium hydrogencarbonate, etc.), hydroxides of alkali metals or alkali earth metals (e.g., sodium hydroxide, potassium hydroxide, etc.), triethylamine, 4-dimethylaminopyridine, N,N-diisopropylethylamine, triethylenediamine, 4-methylmorpholine, etc. Examples of the transition metal catalyst to be used include palladium catalysts [e.g., tetrakis(triphenylphosphine)palladium, 1,1-bis(diphenylphosphine)ferrocene dichloropalladium, dichlorobis(triphenylphosphine)palladium etc.], etc. In this case, formylbenzeneboronic acid or ester thereof or anhydride thereof is used in an amount of 0.5 to 10 mole equivalents, preferably 1 to 5 mole equivalents, and the transition metal catalyst is used in an amount of 0.01 to 1 mole equivalent, preferably 0.05 to 0.2 equivalent, based on 1 mole of the compound represented by the formula (VI) or a salt thereof. In this case, the reaction temperature is 0 to 200° C., preferably 50 to 100° C., and the reaction time is 0.5 to 48 hours, preferably 1 to 24 hours.

The compound represented by the formula (II) or a salt thereof can be produced by reacting a compound represented by the formula (VII) or a salt thereof and an amine represented by the formula: $R^3NH_2$ or a salt thereof under reductive amination conditions. This reductive amination can be carried out by reacting a compound represented by the formula (VII) or a salt thereof with the amine represented by the formula: $R^3NH_2$ or a salt thereof in the presence of a metal hydrogen complex (e.g., sodium boron hydride, cyano sodium boron hydride, triacetoxy sodium boron hydride, etc.) in a solvent such as an ether solvent (e.g., diethyl ether, tetrahydrofuran, dioxane, etc.), a hydrocarbon solvent (e.g., benzene, toluene, hexane, heptane, etc.), a halogen solvent (e.g., dichloromethane, dichloroethane, chloroform, tetrachloromethane, etc.), an alcohol solvent (e.g., methanol, ethanol, n-propanol, isopropanol, etc.), acetonitrile, N,N-dimethylformamide or acetic acid, etc., or in a mixed solvent thereof. In this case, the amine represented by the formula: $R^3NH_2$ or a salt thereof is used in an amount of 0.5 to 10 mole equivalents, preferably 1 to 5 mole equivalents, and the metal hydrogen complex is used in an amount of 0.5 to 10 mole equivalents, preferably 1 to 5 equivalents, based on 1 mole of a compound indicated by the formula (VII) or a salt thereof. In this case, the reaction temperature is 0 to 200° C., preferably 20 to 100° C., and the reaction time is 0.5 to 96 hours, preferably 1 to 24 hours.

The compound represented by the formula (II) or a salt thereof can also be produced, for example, in accordance with Scheme 4:

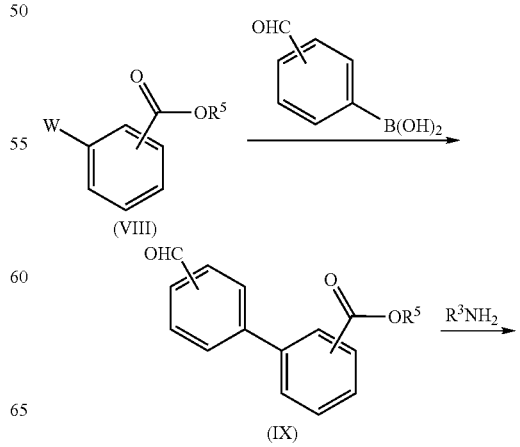

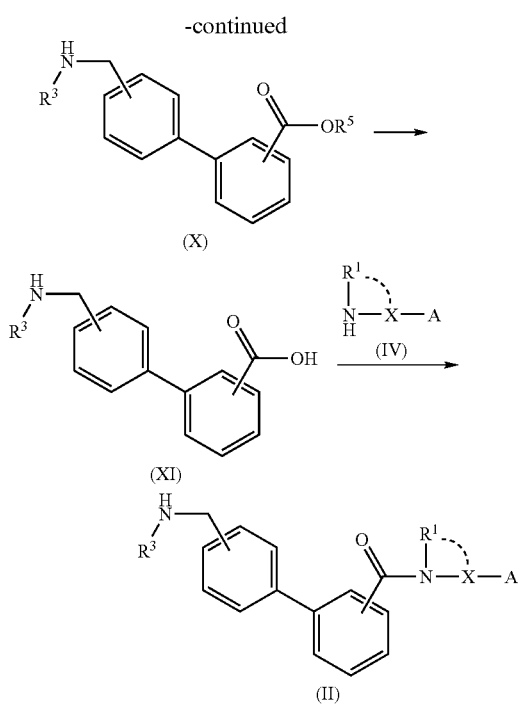

wherein $R^5$ represents $C_{1-6}$alkyl (e.g., methyl, ethyl, propyl, isopropyl, butyl, tert-butyl, etc.), phenyl, trityl, silyl, etc., which may be substituted, and each of the other symbols is as defined above.

A compound represented by the formula (IX) or a salt thereof can be produced by reacting a compound represented by the formula (VIII) or a salt thereof with formylbenzeneboronic acid or ester thereof or anhydride thereof in a solvent under basic conditions in the presence of a transition metal catalyst. This reaction is carried out under the same conditions, etc. as those illustrated in the reaction from the compound represented by the formula (VI) or a salt thereof to the compound represented by the formula (VII) or a salt thereof in the above-described Scheme 3.

A compound represented by the formula (X) or a salt thereof can be produced by reacting a compound represented by the formula (IX) or a salt thereof with an amine represented by the formula: $R^3NH_2$ or a salt thereof under reductive amination conditions. This reaction is carried out under the same conditions, etc. as those illustrated in the reaction from the compound represented by the formula (VII) or a salt thereof to the compound represented by the formula (II) or a salt thereof in the above-described Scheme 3.

A compound represented by the formula (XI) or a salt thereof can be produced by treating the compound represented by the formula (X) or a salt thereof with an acid or base. That is, the desired compound or a salt thereof can be produced by the reaction of the compound represented by the formula (X) or a salt thereof, and a mineral acid (e.g., nitric acid, hydrochloric acid, hydrobromic acid, iodic acid, sulfuric acid, etc.) or a hydroxide of an alkali metal (e.g., sodium hydroxide, potassium hydroxide, lithium hydroxide, etc.) in a solvent, for example, water, an ether solvent (e.g., diethyl ether, tetrahydrofuran, dioxane, etc.), an alcohol solvent (e.g., methanol, ethanol, n-propanol, isopropanol, etc.), etc., or in a mixed solvent thereof, at 0 to 150° C., preferably at 20 to 50° C. In this case, the strength of the acid or base is suitably about 0.1 to 10 N, and the reaction time is 1 to 72 hours.

The compound represented by the formula (II) or a salt thereof can be produced by reacting the compound represented by the formula (XI), a reactive derivative thereof or a salt thereof with the compound represented by the formula (IV) or a salt thereof. This reaction is carried out under the same conditions, etc. as those illustrated in the above-described condensation reaction of Scheme 2.

The compound represented by the formula (III) or a salt thereof can be produced, for example, according to Scheme 5:

Scheme 5

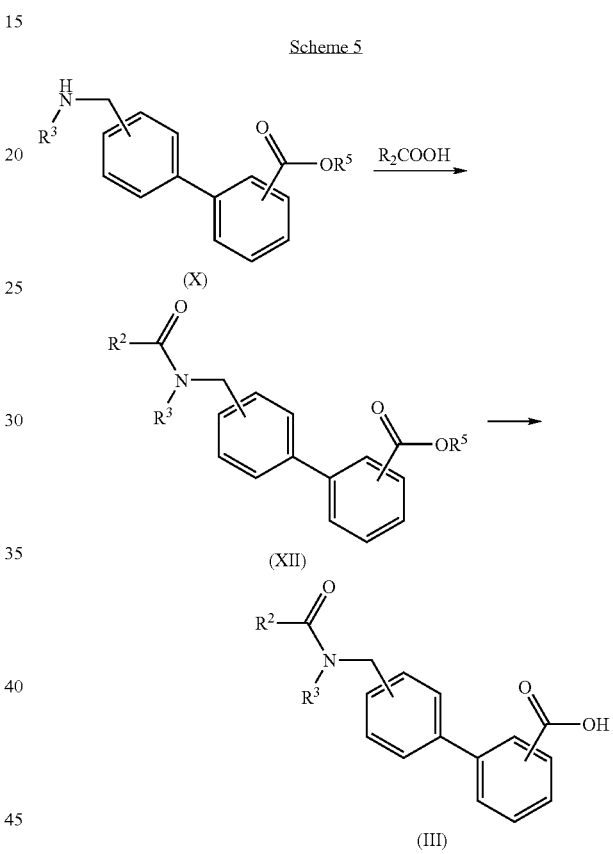

wherein each symbol is as defined above.

A compound represented by the formula (XII) or a salt thereof can be produced by reacting the compound represented by the formula (X), whose production process has been illustrated in the above-described Scheme 4, with the carboxylic acid represented by the formula: $R^2COOH$, a reactive derivative thereof or a salt thereof in a solvent, if necessary, in the presence of a base using a condensation agent. This reaction uses is carried out under the same conditions, etc., as those illustrated in the condensation reaction of the above-described Scheme 1.

The compound represented by the formula (III) or a salt thereof can be produced by treating the compound represented by Formula (XII) or a salt thereof with an acid or base. This reaction is carried out under the same conditions, etc., as those illustrated in the reaction from the compound represented by the formula (X) or a salt thereof to the compound represented by the formula (XI) or a salt thereof in the above-described Scheme 4.

Compound (I) obtained in this manner can be isolated and purified by means of a known separation and purification means such as, for example, condensation, vacuum concentration, solvent extraction, crystallization, recrystallization, conversion dissolution, chromatography, etc.

The compounds used in each of the above-described production processes may form salts similar to those of compound (I) in so far as they do not interfere with the reaction.

Further, in each of the above-described reactions, when a starting compound has as a substituent amino group, carboxyl group, or hydroxyl group, it may be protected by introducing a protective group generally used in peptide chemistry, etc. and the desired compound can be obtained by removing the protective group, if necessary, after the reaction.

Examples of the protective group for amino group to be used include $C_{1-6}$alkyl carbonyl (e.g., acetyl, propionyl, etc.), formyl, phenylcarbonyl, $C_{1-6}$alkyloxycarbonyl (e.g., methoxycarbonyl, ethoxycarbonyl, t-butoxycarbonyl, etc.) phenyloxycarbonyl (e.g., benzoxycarbonyl, etc.), $C_{7-10}$aralkyloxycarbonyl (e.g., benzyloxycarbonyl, etc.), trityl, phthaloyl, etc., each of which may be substituted. Examples of the substituent(s) to be used include a halogen atom (e.g., fluorine, chlorine, bromine, iodine, etc.), $C_{1-6}$alkyl carbonyl (e.g., acetyl, propionyl, butyryl, etc.), nitro group, etc., and the number of substituents is about 1 to 3.

Examples of the protective group for carboxyl group to be used include $C_{1-6}$alkyl (e.g., methyl, ethyl, propyl, isopropyl, butyl, tert-butyl, etc.), phenyl, trityl, silyl, etc., each of which may be substituted. Examples of the substituent(s) to be used include a halogen atom (e.g., fluorine, chlorine, bromine, iodine, etc.), $C_{1-6}$alkyl carbonyl (e.g., acetyl, propionyl, butyryl, etc.), formyl, nitro group, etc., and the number of substituents is about 1 to 3.

Examples of the protective group for hydroxyl group to be used include $C_{1-6}$alkyl (e.g., methyl, ethyl, propyl, isopropyl, butyl, tert-butyl, etc.), phenyl, $C_{7-10}$aralkyl (e.g., benzyl, etc.), $C_{1-6}$alkyl carbonyl (e.g., acetyl, propionyl, etc.), formyl, phenyloxycarbonyl, $C_{7-10}$aralkyloxycarbonyl (e.g., benzyloxycarbonyl, etc.), pyranyl, furanyl and silyl, each of which may be substituted. Examples of the substituent(s) to be used include a halogen atom (e.g., fluorine, chlorine, bromine, iodine, etc.), $C_{1-6}$alkyl, phenyl, $C_{7-10}$aralkyl, nitro group, etc., and the number of substituent groups is about 1 to 4.

In addition, while a per se known method or a modification method thereof (for example, the method described in Protective Groups in Organic Chemistry (J. F. W. MacOmie et al., Plenum Press Corp.) can be used as a method of introducing or removing the protective group, as a removing method, for example, there can be used a method wherein treatment is carried out with an acid, a base, reduction, ultraviolet ray, hydrazine, phenylhydrazine, sodium N-methylthiocarbamate, tetrabutylammonium fluoride, palladium acetate, etc.

Since compound (I) of the present invention has a potent GPR 14 antagonizing activity, it can be used as a therapeutic agent for expressing various vasoactivities (such as accentuation or inhibition of vasoconstriction), and preferably as a vasoconstriction inhibitor.

Further, compound (I) of the present invention can be used as an agent for preventing and/or treating various diseases (e.g., circulatory system-associated diseases). Among them, it is preferably used as an agent for preventing and/or treating hypertension, arteriosclerosis, hypertension, hypercardia, myocardial infarction, heart failure, septic shock, etc., in particular, an agent for preventing and/or treating ischemic myocardial infarction or congestive heart failure.

Further, compound (I) of the present invention has very low toxicity and thus can be used safely.

Daily dose of compound (I) of the present invention as a GPR 14 antagonist may depend on various factors such as the condition and weight of the patient to be treated and administration manner. For oral administration, the compound may be administered at an amount of about 0.1 to 100 mg, preferably about 1 to 50 mg, more preferably about 1 to 20 mg as an active component [(e.g., compound (I)] per an adult (50 kg) and it can be administered once to three times a day.

Compound (I) of the present invention may be used in combination with other therapeutic agent(s) (particularly with a therapeutic agent for preventing and/or treating hypertension, etc.). In this case, these agents may separately be formulated into different preparations, or may be formulated together into one preparation, by blending with any pharmaceutically acceptable carrier, excipient, binder and/or diluent, and then administered orally or parenterally. When these agents are separately formulated into different preparations, these preparations may be administered to a subject after mixing together by using diluent just prior to use. Alternatively, these preparations may separately be administered to the subject simultaneously or with a certain time interval. A kit product for mixing separate preparations using diluent and the like just prior to use for administration (e.g., a kit for injection which contains two or more ampoules each containing a different powdery drug and a diluent for mixing the drugs just prior to use) as well as a kit product for administering separate preparations to a subject simultaneously or separately with a certain time interval (e.g., a kit for administering two or more types of separate tables to a subject simultaneously or separately with a certain time interval wherein tablets each containing a different drug are packed in the same bag or different bags, and a column is provided on the bag in which a time interval for drug administration can be written) are encompassed by the pharmaceutical compositions of the present invention.

Specific examples of other therapeutic agents which can be used in combination with compound having GPR 14 antagonizing activity or a salt thereof according to the present invention include:

drugs for treating hypertension such as diuretic [e.g., furosemide (Lasix), bumetanide (Lunetoron) or azosemide (Diart), etc.], antihypertensive drug [e.g., ACE inhibitor such as enalapril maleate (Renivace) or delapril hydrochloride, etc.] and Ca antagonist (manidipine or amlodipine), or •- or •-receptor blocker, etc.] etc.;

drugs for treating chronic heart failure such as cardiotonic drug [e.g., cardiotonic glycoside (e.g., digoxin), •-receptor stimulator (catecholamine preparation such as denopamine or dobutamine), PDE inhibitor, etc.], diuretic [e.g., furosemide (Lasix) or spironolactone (Aldactone), etc.], ACE inhibitor [e.g., enalapril maleate (Renivace), etc.], Ca antagonist [e.g., amlodipine, etc.], •-receptor blocker, etc.;

antiarrhythmic drugs such as disopyramide, lidocaine, quinidine sulfate, flecainide acetate, mexiletine hydrochloride, amiodarone hydrochloride, as well as •-blocker, Ca antagonist, etc.;

drugs for preventing and/or treating thrombogenesis: coagulation inhibitor [e.g., heparin sodium, heparin calcium, warfarin calcium (warfarin), blood coagulation factor Xa inhibitor and drugs capable of balancing coagulation fibrinolytic system], thrombolytic agent [e.g., tPA, urokinase, prourokinase, etc.], antiplatelet drug [e.g., aspirin, sulfinpyrazolo (Anturan), dipyridamole (Persantin), ticlopidine (Panaldine), cilostazol (Pletaal) and GP IIb/IIIa antagonist (ReoPro), etc.], etc.;

coronary vasodilators such as nifedipine, diltiazem, nicorandil, nitrite agent, etc.;

cardioplegic drugs such as opener for cardiac ATP-K, Na—H exchange inhibitor, endothelin antagonist, urotensin antagonist, etc; and the like.

Further, compound (I) of the present invention has somatostatin acceptor regulatory activity (somatostatin acceptor agonistic and/or antagonistic activity). That is, compound (I) acts through somatostatin-relating various intracellular information transmission systems. Examples of the "intracellular information transmission systems" include intracellular information transmission systems involving transcription factors such as adenylate cyclase, the $K^+$ channel, the $Ca^{2+}$ channel, protein dephosphate oxidation, the phospholipase C/inositol3-phosphoric acid producing system, MAP kinase, the $Na^+/H^+$ exchange system, phospholipase A2, and NF-•B etc., and the like. Further, compound (I) also regulates direct or indirect cell growth suppression activity or apoptosis activity involving somatostatin.

Furthermore, compound (I) has low in toxicity and acts on each somatostatin acceptor (for example, antagonistic or agonistic activity) of a mammal (e.g., human, cow, horse, dog, cat, monkey, mouse, rat, etc., particularly human) to accelerate or suppress the production and/or secretion of a variety of hormones, growth factors, physiologically active substances, etc.

Examples of the "hormones" include growth hormone (GH), growth hormone relieving hormone (GHRH), thyroid-stimulating hormone(TSH), prolactin, insulin, glucagon, etc. Examples of the "growth factors" include insulin-like growth factor-1 (IGF-1), vascular endothelial growth factor (VEGF), etc. Examples of the "physiologically active substances" include interleukins such as vasoactive intestinal polypeptide (VIP), gastrin, glucagon-like peptide-1, amylin, substance-P, CCK (cholecystokinin), amylase, interleukin-6 (IL-6), interleukin-1 (IL-1), cytokines such as TNF-•, cardiotropin, etc.

Therefore, compound (I) is safe and useful for abnormality of the above-described intracellular information transmission systems (e.g., diseases along with excessive acceleration or suppression, etc.), diseases associated with abnormality of cell growth control, diseases along with the abnormality of the production and/or secretion of hormones, growth factors physiologically active substances, etc., acceleration of growth, immunity, stomach and intestines, metabolism function, etc.

For example, compound (I) is useful (1) as a therapeutic drug for tumors of acromegaly, TSH producing tumor, non-secretion (non-functionality) hypophysoma, dystopic ACTH (adrenocorticotopin) producing tumor, medullary thyroid cancer, VIP producing tumor, glucagon producing tumor, gastorin producing tumor, insulinoma, carcinoid, etc.; (2) as a therapeutic drug for insulin dependent or independent diabete or a variety of diseases associated with these diabetes, i.e., diabetes complications (e.g., diabetic retinosis, diabetic nephropathy, diabetic neuropathy, dawn phenomenon, orthostatic hypotension, etc.); (3) as a therapeutic drug for obesity and polyphagia caused by improvement of hyperinsulinemia or suppression of appetite, etc.; (4) as a therapeutic drug for acute pancreatitis, chronic pancreatitis, pancreas/intestine stomy, hemorrhagic tumors, peptic tumors, gastritis, chlorhydria, regurgitant esophagitis, etc.; (5) as a improving drug for a variety of symptoms in association with *Helicobacter pylori* infection (e.g., suppressing agent for gastrin secretion acceleration, etc.); (6) as a secretion suppressing drug for amylase associated with endoscopy cholangiopancreatography and further a therapeutic drug for the prognosis of the pancreas surgery; (7) as a therapeutic drug for decrease in absorption ability of small intestines, diarrhea due to secretion acceleration or the abnormality of movement ability of digestive tracts (e.g., short bowel syndromes, etc.), diarrhea caused by a drug for use in cancer chemotherapy, diarrhea due to congenital small intestine atrophy, diarrhea due to neuroendocrine tumors such as VIP producing tumors, diarrhea due to AIDS, diarrhea due to anti-host graft reaction associated with marrow transplantation, etc., diarrhea due to diabetes, diarrhea due to coeliac plexus block, diarrhea due to systemic scelosis, diarrhea due to eosinophilia, etc.; (8) as a therapeutic drug for damping complex, hypersensitive colitis, Crohn's disease, inflammatory enteropathy, etc.; (9) as a therapeutic drug for tumors or cancer (e.g., thyroid cancer, colon cancer, mastocarcinoma, prostate cancer, small cell lung carcinoma, non-small cell lung carcinoma pancreas cancer, stomach cancer, cholangioma, liver cancer, bladder cancer, oophoron cancer, melanoma, osteosarcoma, chondrosarcoma, malignant pheochromocytoma, neuroblastoma, encephalophyma, thymoma, kidney cancer, etc.), leukemia (e.g., leukemia of basiphilic leucocyte and chronic lymphemia, chronic myelogenic leukemia, Hodgkin's disease, non-Hodgkin lymphoma, etc.), etc., the therapeutic drug being usable singly or in combination with other carcinostatic drugs (e.g., tamoxifen, LHRH agonist, LHRH antagonist, interferon •, •, and •, interleukin-2, etc.); (10) as a preventive or therapeutic drug for hypertrophic cardiomyopathy, arteriosclerosis, the valvular disease of the heart, myocardial infarction (particularly, cardiac infarction after the formation surgery for the transdermal per tubam coronary artery), and re-vascularization; (11) as a therapeutic drug for esophageal vein cancer bleeding, hepatocirrhosis, peripheral vasculopathy diseases; (12) as a therapeutic drug for diseases based on the control action on secretion of physiologically active substances (e.g., substance P, tachykinin, cytokine, etc.) acting on the immune system, for example, diseases in association with systemic or local inflammation (e.g., polyarteritis, rheumatoid arthritis, psoriatic, sunburn, eczema, allergy (e.g., asthma, atopic dermatitis, allergic rhinitis, etc.), etc.); (13) as a therapeutic drug for diseases such as, for example, dementia (e.g., Alzheimer's disease, Alzheimer type senescense dementia, vascular multiple dementia, etc.), schizophrenia, epilepsia, ademonia, general anxiety disorder, sleep disorder, multiple sclerosis, etc., which affect the production and secretion of nerve controlling factors; (14) as a therapeutic drug for eye diseases (e.g., glaucoma, etc.); (15) as a preventive or therapeutic drug for acute bacteria meningitis, acute virus cerebritis, the adult respiration pressing syndromes, bacteria pneumonia, severe systemic fungus infectious diseases, tuberculosis, spine damage, fracture, liver failure, pneumonia, alcoholic hepatitis, hepatitis A, hepatitis B, hepatitis C, AIDS contagious diseases, human papilloma virus infectious diseases, influenza infectious disease, cancer metastasis, multiple myeloma, chondrification disease, osteoporosis, bone Behchet's disease, nephritis, renal failure, septicemia, septicemia shock, hypercalcemia, hypercholesterolemia, hyperglyceridemia, hyperlipemia, systemic lupus erythematosus, transient brain ischemic attack, alcoholic hepatitis, etc.; (16) for treatment of organ transplant, burn, vulnus, alopecia, etc.; (17) as a lenitive for suppressing or relieving chronic or acute aches (e.g., aches after surgery, inflammatory aches, teeth aches, and aches associated with bone diseases (e.g., arthritis, rheumatism, osteoporosis, etc.)). Furthermore, the compound (I) is usable for (18) imaging of a tumor having a somatostatin acceptor formed by introducing a radioactive substance (e.g., $^{123}$I, $^{125}$I, $^{111}$In, etc.) into the compound (I) directly or via an appropriate spacer, or (19) targeting for a tumor having a somatostatin acceptor formed by introducing a carcinostatic into the compound (I) directly or via an appropriate spacer.

Also, somatostatin associates with, for example, secretion of growth hormones (particularly, SSTR2), and compound (I) can have the same effect or use as that of growth hormone itself when it is used directly or for the purpose of promoting secretion of growth hormone. Therefore, compound (I) can be used for prevention or treatment of diseases or symptoms attributable to the shortage of growth hormone or IGF-1.

Examples of the "prevention or treatment of diseases or symptoms attributable to the shortage of growth hormone or IGF-1" include treatment of insulin dependent (I type) or independent (II type) diabetes, or a variety of diseases associated with diabetes, i.e., diabetes complications (e.g., diabetic retinitis, diabetic nephrosis, diabetic neuropathy, dawn phenomenon, orthostatic hypotension, etc.); prevention of the catabolic side-effect of glucocorticoid, prevention or treatment of osteoporosis, stimulation of the immune system (increase and enhancement of blood cells such as lymph cells, enhancement of antibacterial action or antivirus action), promotion of healing of burn or vulnus, acceleration of fracture curing, treatment of acute or chronic kidney diseases, treatment or improvement of diseases or symptoms (short height, growth delay) associated with growth hormone shortage in adulthood or infancy, treatment of obesity, promotion of recovery after surgery, improvement of growth delay associated with Prader-Willi syndromes or Turner syndromes, treatment of intrauterine growth delay or bone formation abnormality, treatment of peripheral nerve diseases, treatment of Noonan syndromes, schizophrenia, ademonia, etc., treatment or prevention of nerve degeneration diseases such as Alzheimer's disease and Parkinson's disease, treatment of lung failure or ventilation dependency disease, treatment of absorption failure syndromes, improvement of cachexia or protein loss due to cancer, AIDS, etc., promotion of weight increase and protein attachment for patient during total parenteral nutrition (TPN), treatment of hyperinsulinism, promotion of ovulation induction, improvement of climacteric disorders, improvement of senile constitution, etc.

In addition, with mammals like cattle as well, the compound is useful for promotion of growth, increase of milk production, enhancement of anti-bacterial or anti-viral action by stimulation of the immune system, stimulation of wool growth in sheep, etc.

Compound (I) may be used with various preparations for combination use.

For example, in the treatment of osteoporosis, it can also be used in combination with other osteoporosis treatment preparations (e.g., bisphosphonate drugs, vitamin D preparations, calcitonin preparations, PTH preparations, ostein, etc.).

In the treatment of diabetes or associated diseases thereof, the compound is usable in combination with other diabetes treating drugs (e.g., troglitazone, pioglytazone, or hydrochlorides thereof, rosiglitazone or thiazolidinedione drugs such as maleate thereof; glucagon antagonists; ●-glucosidase inhibitors such as acarbose, and voglibose; insulin preparations; insulin secretion promoting agents such as sulfonylurea agents or sulfonamide agents (e.g., glibenclamide, tolbutamide, glyclopyramide, acetohexamide, tolazamide, gliclazide, glybuzole, glymepyride, etc.), lepaglynide, natheglynide, and michiglynide; biguanide agents such as metformin and buformin, etc.).

Further, the compound can also be used in combination with other hormones that promote growth hormone secretion (e.g., GHRH), GH, or IGF-1.

In the improvement of climacterium disorders, the compound is usable in combination with, for example, hormone supplementation therapy (e.g., therapies by means of estrogen drugs, raloxifene, and tamoxifen).

For the purpose of accelerating the immune system, the compound can be used in combination with cytokines or agents for enhancing cytokine actions as well.

When compound (I) of the present invention is used for adult acromegalia patients, diabetes complications, inveterate diarrhea, diabetes, or obesity, daily dose thereof may depend on various factors such as the condition and weight of the patient to be treated and administration manner. For oral administration, the compound may be administered at an amount of about 0.05 to 1000 mg, preferably about 10 to 150 mg as an active component [(e.g., compound (I)] per an adult (50 kg).

Although the present invention will be described in more detail by referring to Experimental Examples, Preparation Examples, Reference Example and Synthesis Examples, these examples are provided to illustrate the invention but not to limit its scope.

Brief description of SEQ ID NOS used herein will be provided below:

[SEQ ID NO: 1]
A synthetic DNA used for screening cDNA encoding human GPR14 protein.

[SEQ ID NO: 2]
A synthetic DNA used for screening cDNA encoding human GPR14 protein.

[SEQ ID NO: 3]
An entire nucleotide sequence of cDNA encoding human GPR14 protein to which nucleotide sequences recognized by restriction enzymes Sal I and Spe I have been added at the 5'- and 3'-termini, respectively.

[SEQ ID NO: 4]
An amino acid sequence of human GPR14 protein confirmed in Reference Example 2.

[SEQ ID NO: 5]
A nucleotide sequence of DNA oligomer S5-1 based on the nucleotide sequence of human•SSTR cDNA synthesized in Reference Example 4.

[SEQ ID NO: 6]
A nucleotide sequence of DNA oligomer S5-2 based on the nucleotide sequence of human•SSTR cDNA synthesized in Reference Example 4.

REFERENCE EXAMPLE 1

Amplifying cDNA for Human GPR14 Receptor by PCR Method Using Human Skeletal Muscle-Derived cDNA PCR amplification was performed by using cDNA derived from human skeletal muscle (Clontech) as a template and two synthetic DNA primers (SEQ ID NOS: 1 and 2). The synthetic DNA primers were designed so that the gene in the region which is to be translated into receptor protein would be amplified, and such that nucleotide sequences which may be recognized by restriction enzymes Sal I and Spe I were added at the 5'- and 3'-termini of the gene, respectively. Reaction solution included 2.5 μl of cDNA template, synthetic DNA primers (0.2 μM each), 0.2 mM dNTPs, 1 μl of Advantage 2 polymerase mix (Clontech) and the buffer appended to the enzyme (total reaction volume of 50 μl). Thermocycler (Perkin-Elmer Corp.) was used for amplification. The amplification cycle consisted of heating at 95° C. for 60 seconds, followed by 5 rounds of 95° C. for 30 seconds and 72° C. for 3 minutes, 5 rounds of 95° C. for 30 seconds and 70° C. for 3 minutes, and then 20 rounds of 95° C. for 30 seconds and 68° C. for 3 minutes, and finally heating at 68° C. for 3 minutes. The resultant PCR amplification products were confirmed by purification by electrophoresis on a 0.8% agarose gel followed by staining with ethidium bromide.

REFERENCE EXAMPLE 2

Subcloning of PCR Product into Plasmid Vector and Confirming Amplified cDNA by Reading the Nucleotide Sequence of cDNA Insert PCR reaction products obtained in Reference Example 1 were separated on a 0.8% low-melting agarose gel, a gel containing bands was excised using a razor, and DNA was collected using GENECLEAN SPIN (BIO 101, Inc.). According to the prescription included in Eukaryotic TOPO™ TA Cloning kit (Invitrogen), the collected DNA was cloned into a plasmid vector for expression in animal cells, pcDNA3.1/V5/His, to construct a plasmid for protein expression, pcDNA3.1-hGPR14 which was then introduced into *Escherichia coli* DH5α competent cells (Toyobo Co., Ltd.) for transformation. Then, clone which contained cDNA insert fragment was selected on an ampicillin-containing LB agar medium, and separated using a sterilized toothpick to obtain transformant *E. coli* DH5α/pcDNA3.1-hGPR14. Each clone was cultured overnight on an ampicillin-containing LB medium, and Quiawell 8 Ultra Plasmid kit (Qiagen) was used to prepare plasmid DNA. Portion of DNA prepared was digested with restriction enzyme Sal I, and the size and direction of receptor cDNA fragment inserted were determined. The sequences of nucleotides were determined by using DyeDeoxy Terminator Cycle Sequence Kit (Perkin-Elmer Corp.) and then reading in a fluorescence automatic sequencer. The sequence of clone obtained was analyzed and confirmed to be consistent with a genetic sequence comprising the sequence of human GPR14 gene, of which entire sequence has been reported (EP 0 859 052 A1), and Sal I and Spe I recognition sequences added to the 5'- and 3'-termini of the sequence, respectively (SEQ ID NOS: 3 and 4). It should be noted that although the 1133rd base in the sequence of human GPR14 gene (SEQ ID NO: 3) was identified as C in the report (EP 0 859 052 A1) while it was identified as G in the present Example though the amino acids which would be translated from these sequences may be the same.

REFERENCE EXAMPLE 3

Preparing Human GPR14-Expressing CHO Cell

After the transformant *E. coli* DH5α/pcDNA3.1-hGPR14 prepared in Reference Example 2 was cultured, plasmid DNA for pcDNA3.1-hGPR14 was prepared by using Plasmid Midi Kit (Qiagen). The plasmid DNA was introduced into CHO dhfr⁻ cells using CellPhect Transfection Kit (Amersham Pharmacia Biotech) according to the protocol appended thereto. 10 μg of DNA was co-precipitated with calcium phosphate to prepare a suspension which was then added to a 10 cm petri dish on which $5 \times 10^5$ or $1 \times 10^6$ CHO dhfr⁻ cells had previously been inoculated 24 hours before then. Cells were cultured in a MEMα medium containing 10% fetal bovine serum for one day, subcultured, and cultured in a selection medium, a MEMA medium containing 0.4 mg/ml G418 (GIBCO BRL) and 10% dialysis fetal bovine serum. Colonies of transformed cells (CHO/hGPR14), which were human GPR14-expessing CHO cells growing in the selection medium, were selected.

EXPERIMENTAL EXAMPLE 1

Preparing Human GPR14-Expressing Cell Fraction

To $1 \times 10^8$ CHO/GPR14 cells were added 10 ml of homogenate buffer (10 mM NaHCO$_3$, 5 mM EDTA, 0.5 mM PMSF, 1 μg/ml pepstatin, 4 μg/ml E64, 20 μg/ml leupeptin), and disrupted using Polytron (12,000 rpm, 1 minute). Cell debris solution was centrifuged at 1,000 g for 15 minutes to obtain a supernatant. The supernatant was then ultra-sonicated (in Beckman type 30 rotor, 30,000 rpm, 1 hour), and the resultant precipitant was collected as human GPR14-expressing CHO cell fraction.

EXPERIMENTAL EXAMPLE 2

Preparing Isotope-Labeled Human Urotensin II

Isotope-labeled human urotensin II to be used in experiments for testing inhibition of binding was prepared as described below. 5 μg of human urotensin II (available from Peptide Institute, Inc.) was dissolved in 25 μl of 0.4 M sodium acetate (pH 5.6). To the solution was added 200 ng of lactoperoxidase (Wako Pure Chemical Industries, Ltd.) followed by 1 mCi [$^{125}$I]-sodium iodide (Amersham Pharmacia Biotech) and 200 ng of hydrogen peroxide (10 μl). The solution was left to stand at room temperature for 10 minutes, another 200 ng of hydrogen peroxide (10 μl) was added thereto and then the solution was left to stand for 10 minutes. The mixture was then purified by HPLC using TSKgel ODS-80T$_s$ column (4.6 mm×25 cm, Toso Co., Ltd.) to obtain [$^{125}$I]-labeled human urotensin II.

EXPERIMENTAL EXAMPLE 3

Experiment for Testing the Ability of Test Compound to Inhibit Binding of Urotensin II to GPR14 Using Human GPR14-Expressing Cell Fraction and Isotope-Labeled Urotensin II Human GPR14-expressing CHO cell fraction was diluted in a membrane diluting buffer (20 mM phosphate buffer (pH 7.3), 150 mM NaCl, 5 mM MgCl$_2$, 0.1% BSA, 0.05% CHAPS, 0.5 mM PMSF, 0.1 μg/ml Pepstatin, 20 μg/ml Leupeptin, 4 μg/ml E-64) to prepare a solution of cell membrane fraction (protein concentration: 3 μg/ml) for assay. The membrane fraction solution for assay was dispensed in 96-well microplates (85 μl each) which were left for stand for reaction at 25° C. for 3 hours after adding: 10 μl of membrane diluting buffer containing 1 nM [$^{125}$I]-labeled human urotensin II and 5 μl of di-methylsulfoxide diluted 5-times (by volume) in membrane diluting buffer for examining the total binding; 10 μl of membrane diluting buffer containing 1 nM [$^{125}$I]-labeled human urotensin II and 5 μl of 20% dimethylsulfoxide-containing membrane diluting buffer containing 20 μM human urotensin II without isotope-labeling for examining non-specific binding; and 5 μl of a solution of test compound in di-methylsulfoxide diluted 5-times (by volume) in membrane diluting buffer and 10 μl of membrane diluting solution containing 1 nM [$^{125}$I]-labeled-human urotensin II for testing the ability of test compounds to inhibit binding. The mixture solution was filtrated through a filter plate (GF/C, Watman). Next, the filter was washed three times with membrane diluting buffer (0.2 ml), added with 20 μl of Microscinti 20 (Packard), and determined for radioactivity in Topcount (Packard). Specific-binding is calculated by subtracting non-specific binding from the total binding. The ability of test compound to inhibit binding of urotensin II to human GPR14 is represented by the ratio of [(total binding)–(the radio activity of the cell fraction to which test compound was added)] vs [specific binding]. Concentrations of test compounds at which the compounds showed 50% inhibition of human GPR14 binding activity are shown.

Results are shown in Table 1.

TABLE 1

| Test compound | Inhibitory concentration |
| --- | --- |
| Compound of Example 4 | 10 nM |
| Compound of Example 6 | 13 nM |

EXPERIMENTAL EXAMPLE 4

Change in Calcium Concentration in Human GPR14-Expressing CHO Cell Caused by Test Compound GPR14-expressing CHO cells were inoculated on a 96-well plate at 1×10$^4$ cell/well, cultured for 48 hours, and then washed with 0.1 ml of HBSS containing 20 mM HEPES(pH 7.4), 1% FCS and 1% penicillin-streptomycin (hereinafter referred to as "wash buffer"). Next, 100 μl of another wash buffer containing 4 μM Fluo3, 0.04% pluronic acid and 2.5 mM probenicid (hereinafter referred to as "reaction buffer") was added thereto for reaction at 37° C. for 1 hour. The reaction buffer was then removed and the plate was washed three times with 0.2 ml of wash buffer. Then, 90 μl of wash buffer and 10 μl of a solution of test compound in dimethylsulfoxide diluted 10 times (by volume) in membrane diluting buffer were added for agonist activity assay, while, for antagonist activity assay, furthermore 10 μl of 10 nM urotensin II was additionally added to determine change in intracellular calcium concentration in FLIPR (Japan Molecular Device). The test compound (compound of Example 71) inhibited urotensin II-induced increase in intracellular calcium concentration.

A vasoactive agent (e.g., an agent for preventing and/or treating myocardial infarction, heart failure and the like) comprising as an active component the compound having GPR 14 antagonistic activity of the present invention can be produced, for example, as follows.

PREPARATION EXAMPLES

| 1. Capsules | |
| --- | --- |
| (1) Compound obtained in Example 1 | 40 mg |
| (2) Lactose | 70 mg |
| (3) Microcrystalline cellulose | 9 mg |
| (4) Magnesium stearate | 1 mg |
| 1 capsule | 120 mg |

(1), (2), (3) and ½ of (4) are mixed and then granulated. The remainder of (4) is added to the granules, and the whole is sealed in a gelatin capsule.

| 2. Tablets | |
| --- | --- |
| (1) Compound obtained in Example 1 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 tablet | 120 mg |

(1), (2), (3), ⅔ of (4) and ½ of (5) are mixed and then granulated. The remainders of (4) and (5) are added to the granules, and the whole is pressure-molded into a tablet.

SYNTHESIS EXAMPLES

In the following Examples, measurement in HPLC was carried under the following condition A or B:

Measuring instrument: Shimadzu Corporation LC-10 Avp system

Condition A

Column: CAPCELL PAK C18UG120, S-3 •m, 2.0×50 mm

Solvent: Solution A, 0.1% aqueous trifluoroacetic acid;

Solution B, 0.1% trifluoroacetic acid in acetonitrile

Gradient cycle: 0.00 min. (Solution A/Solution B=90/10), 4.00 min. (Solution A/Solution B=5/95), 5.50 min. (Solution A/Solution B=5/95), 5.51 min. (Solution A/Solution B=90/10), 8.00 min. (Solution A/Solution B=90/10)

Injection volume: 2 •l; flow rate: 0.5 ml/min.; detection method: UV 220 nm

Condition B

Column: CAPCELL PAK C18UG120, S-3 •m, 2.0×35 mm

Solvent: Solution A, 0.1% aqueous trifluoroacetic acid;

Solution B, 0.1% trifluoroacetic acid in acetonitrile

Gradient cycle: 0.00 min. (Solution A/Solution B=90/10), 2.00 min. (Solution A/Solution B=5/95), 2.75 min. (Solution A/Solution B=5/95), 2.76 min. (Solution A/Solution B=90/10), 3.60 min. (Solution A/Solution B=90/10)

Injection volume: 5 •l; flow rate: 1.0 ml/min.; detection method: UV 220 nm

In the Examples below, measurement by mass spectrometry (MS) was carried out under the following conditions.

Measuring instrument: Micromass Ltd. Platform II

Ionization method: Atmospheric Pressure Chemical Ionization (APCI) or Electron Spray Ionization (ESI)

In the following Examples, purification by preparative HPLC was carried out under the following conditions.

Instrument: Gilson Ltd. High-Throughput Purification System

Column: YMC CombiPrep ODS-A, S-5 •m, 50×20 mm

Solvent: Solution A, 0.1% aqueous trifluoroacetic acid;

Solution B, 0.1% trifluoroacetic acid in acetonitrile

Gradient cycle: 0.00 min. (Solution A/Solution B=90/10), 1.00 min. (Solution A/Solution B=90/10), 4.20 min. (Solution A/Solution B=10/90), 5.40 min. (Solution A/Solution B=10/90), 5.50 min. (Solution A/Solution B=90/10), 5.60 min. (Solution A/Solution B=90/10)

Flow rate: 25 ml/min.; detection method: UV 220 nm

EXAMPLE 1

3'-{({2-[4-(Aminosulfonyl)phenyl]ethyl}[(E)-3-phenyl-2-propenoyl]amino)methyl}-N-[2-(1-pyrrolidinyl)ethyl][1,1'-biphenyl]-3-carboxamide

1) 3-Bromo-N-[2-(1-pyrrolidinyl)ethyl]phenylcarboxamide 1-(2-Aminoethyl)pyrrolidine (4.34 g), diethyl cyanophosphate (5.57 ml) and triethylamine (10.4 ml) were added to a solution of 3-bromobenzoic acid (5.00 g) in N,N-dimethylformamide (DMF; 60 ml), and the mixture was stirred at room temperature for 16 hours. The reaction mixture was diluted with water and then extracted with diethyl ether. The extract was dried over anhydrous magnesium sulfate, and then the solvent was evaporated under reduced pressure. The residues were crystallized from hexane to give the title compound (6.31 g).

$^1$H-NMR (CDCl$_3$) •: 1.70–1.90 (4H, m), 2.50–2.60 (4H, m), 2.70 (2H, t, J=6.0 Hz), 3.45–3.60 (2H, m), 6.86 (1H, s), 7.30 (1H, t, J=8.0 Hz), 7.60 (1H, dm, J=8.0 Hz), 7.70 (1H, dm, 8.0 Hz), 7.93 (1H, t, J=1.6 Hz).

2) 3'-Formyl-N-[2-(1-pyrrolidinyl)ethyl][1,1'-biphenyl]-3-carboxamide

Palladium tetrakistriphenyl phosphine (735 mg) and 2 M aqueous sodium carbonate (21.2 ml) were added to a solution of 3-bromo-N-[2-(1-pyrrolidinyl)ethyl]phenylcarboxamide (6.31 g) in toluene (50 ml), and then a solution of 3-formylphenylboric acid (3.49 g) in ethanol (15 ml) was added thereto, and the mixture was stirred at 90° C. for 15 hours. The reaction solution was diluted with water and then extracted with diethyl ether. The extract was washed with brine and then dried over anhydrous magnesium sulfate. The solvent was evaporated under reduced pressure, whereby the title compound (6.83 g) was obtained.

$^1$H-NMR (CDCl$_3$) •: 1.95–2.35 (4H, m), 2.95 (2H, m), 3.30–3.50 (2H, m), 3.80–3.40 (4H, m), 7.40–7.60 (2H, m), 7.76 (1H, dm, J=8.0 Hz), 7.85 (1H, dm, J=8.0 Hz), 8.00 (1H, dm, 8.0 Hz), 8.09 (1H, dm, J=8.0 Hz), 8.25 (1H, bs), 8.40 (1H, bs), 8.41 (1H, m), 10.10 (1H, s).

3. 3'-[{2-[4-(Aminosulfonyl)phenyl]ethyl}aminomethyl]-N-[2-(1-pyrrolidinyl)ethyl]-[1,1'-biphenyl]-3-carboxamide 4-(2-Aminoethyl)benzene sulfonamide (2.37 g) and molecular sieves 3A (4.0 g) were added to a solution of 3'-formyl-N-[2-(1-pyrrolidinyl)ethyl][1,1'-biphenyl]-3-carboxamide (3.81 g) in methanol (50 ml), and the mixture was stirred at room temperature for 1.5 hours. After the reaction mixture was diluted with tetrahydrofuran (THF), the molecular sieves were filtered off, and the filtrate was concentrated under reduced pressure. The residues were dissolved in a mixed solvent (100 ml) of methanol-THF (1:1), and sodium borohydride (0.89 g) was added thereto. The reaction mixture was stirred at room temperature for 5 hours, and then the solvent was evaporated under reduced pressure. The residues were diluted with water and extracted with ethyl acetate. The extract was washed with brine and then dried over anhydrous magnesium sulfate, and the solvent was evaporated under reduced pressure. The residues were crystallized from hexane, whereby the title compound (3.71 g) was obtained.

$^1$H-NMR (CDCl$_3$) •: 1.75–1.85 (4H, m), 2.55–2.65 (4H, m), 2.78 (2H, t, J=6.0 Hz), 2.85–3.00 (4H, m), 3.60–3.65 (2H, m), 3.87 (2H, s), 7.05–7.15 (1H, m), 7.20–7.60 (6H, m), 7.65–7.85 3H, m), 7.84 (2H, d, J=8.4 Hz), 8.05 (1H, s).

4) 3'-{({2-[4-(Aminosulfonyl)phenyl]ethyl}[(E)-3-phenyl-2-propenoyl]amino)methyl}-N-[2-(1-pyrrolidinyl)ethyl][1,1'-biphenyl]-3-carboxamide 3'-[{2-[4-(Aminosulfonyl)phenyl]ethyl}aminomethyl]-N-[2-(1-pyrrolidinyl)ethyl]-[1,1'-biphenyl]-3-carboxamide (506 mg), trans-cinnamic acid (163 mg), 1-ethyl-3-(3-dimethylaminopropyl)carbodiimide hydrochloride (EDCI.HCl; 211 mg) and 1-hydroxybenzotriazole (HOBT; 149 mg) were dissolved in a mixed solvent of dichloromethane (15 ml) and DMF (7 ml), and the mixture was stirred at room temperature for 18 hours. The solvent was evaporated under reduced pressure, and water was added to the residues which were then extracted with ethyl acetate. The extract was washed with brine and dried over anhydrous magnesium sulfate, and the solvent was evaporated under reduced pressure. The residues were purified by silica gel column chromatography (dichloromethane/methanol=98/2), whereby the title compound (284 mg) was obtained.

$^1$H-NMR (CDCl$_3$) •: 1.73 (4H, m), 2.52 (4H, m), 2.69 (2H, t, J=6.0 Hz), 2.85–3.00 (2H, m), 3.50–3.60 (2H, m), 3.66 (2H, t, J=7.0 Hz), 4.60 (2H,s), 6.57 (1H, d, J=15.6 Hz), 6.85 (1H, d, J=15.6 Hz), 7.10–7.90 (16H, m), 8.05 (1H, s).

MS (APCI+): 637 (M+H)

EXAMPLE 2

3'-{-({2-[4-(Aminosulfonyl)phenyl]ethyl}[(E)-3-phenyl-2-propenoyl]amino)methyl}-N-[2-(1-pyrrolidinyl)ethyl][1,1'-biphenyl]-3-carboxamide hydrochloride 3'-{({2-[4-(Aminosulfonyl)phenyl]ethyl}[(E)-3-phenyl-2-propenoyl]amino)methyl}-N-[2-(1-pyrrolidinyl)ethyl][1,1'-biphenyl]-3-carboxamide (200 mg) was treated with 4 N hydrogen chloride in ethyl acetate to give the title compound (198 mg).

$^1$H-NMR (DMSO-d$_6$) •: 1.80–2.10 (4H, m), 2.90–3.10 (4H, m), 3.30–3.50 (2H, m), 3.55–3.90 (6H, m), 4.73 (2H,s), 7.05–8.00 (18H, m), 8.25 (1H, s), 9.03 (1H, m).

Elemental analysis (molecular formula C$_{37}$H$_{40}$N$_4$O$_4$S.HCl.1.5H$_2$O):
  Theoretical: C: 63.46; H: 6.33; N: 8.00; Cl: 5.08
  Found: C: 63.65; H: 6.51; N: 7.86; Cl: 5.25

EXAMPLE 3

3'-{({2-[4-(Aminosulfonyl)phenyl]ethyl}[4-phenylbutanoyl]amino)methyl}-N-[2-(1-pyrrolidinyl)ethyl][1,1'-biphenyl]-3-carboxamide The title compound (277 mg) was obtained in the same manner as in Example 1.
  $^1$H-NMR (DMSO-d$_6$) •: 1.75–1.85 (8H, m), 2.20–2.40 (2H, m), 2.45–2.60 (2H, m), 2.60–2.95 (4H, m), 3.20–3.60 (6H, m), 4.62 (2H,s), 7.05–7.95 (18H, m), 8.13 (1H, s), 8.71 (1H, m).
  MS (ESI+): 653 (M+H)

EXAMPLE 4

3'-{({2-[4-(Aminosulfonyl)phenyl]ethyl}[4-phenylbutanoyl]amino)methyl}-N-[2-(1-pyrrolidinyl)ethyl][1,1'-biphenyl]-3-carboxamide hydrochloride The title compound (185 mg) was obtained in the same manner as in Example 2.
  $^1$H-NMR (DMSO-d$_6$) •: 1.75–2.10 (8H, m), 2.25–2.45 (2H, m), 2.45–2.60 (2H, m), 2.80–2.90 (2H, m), 2.95–3.10 (2H, m), 3.20–3.50 (2H, m), 3.50–3.75 (4H, m), 4.61 (2H,s), 7.05–8.00 (18H, m), 8.23 (1H, s), 9.02 (1H, m).
  Elemental analysis (molecular formula C$_{38}$H$_{44}$N$_4$O$_4$S.HCl.H$_2$O)
  Theoretical: C: 64.53; H: 6.70; N: 7.92; Cl: 5.01
  Found: C: 64.39; H: 6.82; N: 7.86; Cl: 5.20

EXAMPLE 5

3'-{({2-[4-(Aminosulfonyl)phenyl]ethyl}[(benzyloxy)acetyl]amino)methyl}-N-[2-(1-pyrrolidinyl)ethyl][1,1'-biphenyl]-3-carboxamide Pyridine (0.16 ml) and benzyloxyacetyl chloride (0.16 ml) were added to a solution of 3'-[{2-[4-(aminosulfonyl)phenyl]ethyl}aminomethyl]-N-[2-(1-pyrrolidinyl)ethyl]-[1,1'-biphenyl]-3-carboxamide (506 mg) in DMF (10 ml). The reaction mixture was stirred at room temperature for 16 hours, then diluted with water and extracted with ethyl acetate. The extract was washed with brine and dried over anhydrous magnesium sulfate, and the solvent was evaporated under reduced pressure. The residues were purified by silica gel column chromatography (dichloromethane/methanol=98/2), whereby the title compound (257 mg) was obtained.
  $^1$H-NMR (CDCl$_3$) •: 1.74 (4H, m), 2.60–2.80 (4H, m), 2.88 (2H, m), 3.20–3.40 (8H, m), 4.17 (2H,s), 4.47 (2H, s), 4.62 (2H, s), 6.57 (1H, d, J=15.6 Hz), 7.20–7.90 (18H, m), 8.11 (1H, s), 8.65 (1H, m).
  MS (ESI+): 655 (M+H)

EXAMPLE 6

3'-{({2-[4-(Aminosulfonyl)phenyl]ethyl}[(benzyloxy)acetyl]amino)methyl}-N-[2-(1-pyrrolidinyl)ethyl][1,1'-biphenyl]-3-carboxamide hydrochloride The title compound (155 mg) was obtained in the same manner as in Example 2.
  $^1$H-NMR (DMSO-d$_6$) •: 1.80–2.10 (4H, m), 3.80–3.15 (6H, m), 3.20–3.50 (2H, m), 3.60–3.75 (4H, m), 4.19 (2H, s), 4.48 (2H, s), 4.62 (2H, s), 7.20–7.90 (18H, m), 8.11 (1H, s), 8.65 (1H, m).
  Elemental analysis (molecular formula C$_{37}$H$_{42}$N$_4$O$_5$S.HCl.1.5H$_2$O)
  Theoretical: C: 61.87; H: 6.45; N: 7.80; Cl: 4.94
  Found: C: 61.76; H: 6.31; N: 7.73; Cl: 5.25

EXAMPLE 7

N-{[4-(Aminomethyl)cyclohexyl]methyl}-3'-{[[(E)-3-(4-bromophenyl)-2-propenoyl](4-hydroxyphenethyl)amino]methyl}[1,1'-biphenyl]-3-carboxamide trifluoroacetate 1) Methyl 3'-[{(4-hydroxyphenetyl)imino}methyl][1,1'-biphenyl]-3-carboxylate Tyramine (10.0 g) and molecular sieves 3A (40 g) were added to a solution of methyl 3'-formyl[1,1'-biphenyl]-3-carboxylate (10.0 g) in methanol (200 ml), and the mixture was stirred at room temperature for 1 hour. After the reaction mixture was diluted with tetrahydrofuran (THF), the molecular sieves were filtered off and the filtrate was concentrated under reduced pressure, whereby the title compound (15.0 g) was obtained.
  $^1$H-NMR (CDCl$_3$) •: 2.94 (2H, t, J=7.0 Hz), 3.85 (2H, t, J=7.0 Hz), 3.94 (3H, s), 6.76 (2H, d, J=8.4 Hz), 7.04 (2H, d, J=8.4 Hz).

2) Methyl 3'-[{(4-Wang resin phenethyl)imino}methyl][1,1'-biphenyl]-3-carboxylate A solution of sodium methoxide in methanol (4.8 M; 8.7 ml) was added to a solution of methyl 3'-[{(4-hydroxyphenethyl)imino}methyl][1,1'-biphenyl]-3-carboxylate (15.0 g) in DMF (300 ml), and after the mixture was stirred at room temperature for 1 hour, a suspension of Wang bromoresin (15.9 g) in DMF (200 ml) was added thereto. The reaction mixture was stirred at 80° C. for 17 hours and diluted with water, and the solvent was removed by filtration. The resultant resin was washed with a mixed solvent of DMF-water (1:1), DMF, THF and methanol in this order and dried at 50° C. under reduced pressure, whereby the title compound (19.9 g) was obtained.
  Magnetic Angle Spinning (MAS)—NMR (CDCl$_3$) •: 3.83 (methyl carboxylate), 8.13 (imine)
  IR (KBr): 1643 cm$^{-1}$
  Amount of the compound carried on the resin: 0.83 mmol/g (elemental analysis: calculated from 1.16% N)

3) Methyl 3'-[{(4-Wang resin phenetyl)amino}methyl][1,1'-biphenyl]-3-carboxylate Sodium borohydride (1.87 g) was added to a mixture of methyl 3'-[{(4-Wang resin phenethyl)imino}methyl][1,1'-biphenyl]-3-carboxylate (19.9 g) and a mixed solvent (400 ml) of methanol-THF (1:1), and the mixture was stirred at room temperature for 18 hours. After the reaction solution was diluted with water, the solvent was removed by filtration, and the resultant resin was washed with THF, a mixed solvent of THF-water (1:1), THF and methanol in this order and then dried at 50° C. under reduced pressure, to give the title compound (20.4 g).
  MAS-NMR (CDCl$_3$) δ: 3.83 (methyl carboxylate)

4) 3'-[{(4-Wang resin phenethyl)amino}methyl][1,1'-biphenyl]-3-carboxylic acid A mixture of methyl 3'-[{(4-Wang resin phenethyl)amino}methyl][1,1'-biphenyl]-3-carboxylate (20.0 g), 1 N aqueous sodium hydroxide (165 ml) and dioxane (330 ml) was stirred at 80° C. for 62 hours. The solvent was removed by filtration, and the resultant resin was washed with THF, a mixed solvent of THF-acetic acid (1:1), THF and methanol in this order and then dried at 50° C. under reduced pressure, to give the title compound (19.5 g). The resultant resin (5 beads) was treated with trifluoroacetic acid-dichloromethane (1:1, 50 ml) to give 3'-[{(4-hydroxyphenethyl)amino}methyl][1,1'-biphenyl]-3-carboxylic acid which was then analyzed in HPLC and measured by mass spectrometry.

HPLC analysis (condition A): purity 96% (retention time: 2.612 min.)
MS (APCI+): 348 (M+H)

5) N-{[4-(tert-Butoxycarbonylaminomethyl)cyclohexyl]methyl}-3'-{[(4-Wang resin phenethyl)amino]methyl}[1,1'-biphenyl]-3-carboxamide tert-Butyl [4-(aminomethyl)cyclohexyl]methyl carbamate (61 mg), benzotriazol-1-yl-oxy-tris-pyrrolidinophosphonium hexafluorophosphate (PyBOP; 133 mg) and N,N-diisopropylethylamine (DIEA; 44 ml) were added to a suspension of 3'-[{(4-Wang resin phenethyl)amino}methyl][1,1'-biphenyl]-3-carboxylic acid (30 mg) in DMF (1.5 ml), and the mixture was stirred at room temperature for 38 hours. The solvent was removed by filtration, and the resultant resin was washed with DMF, THF and methanol in this order and dried at 50° C. under reduced pressure to give the title compound (30 mg). The resultant resin (5 beads) was treated with trifluoroacetic acid-dichloromethane (1:1, 50 ml) to give N-{[4-(aminomethyl)cyclohexyl]methyl}-3'-{[(4-hydroxyphenethyl)amino]methyl}[1,1'-biphenyl]-3-carboxamide which was then analyzed in HPLC and measured by mass spectrometry.

HPLC analysis (condition A): purity 64% (retention time: 2.391 min.)
MS (APCI+): 472 (M+H)

6) N-{[4-(Aminomethyl)cyclohexyl]methyl}-3'-{[[(E)-3-(4-bromophenyl)-2-propenoyl](4-hydroxyphenethyl)amino]methyl}[1,1'-biphenyl]-3-carboxamide trifluoroacetate 4-Bromocinnamic acid (29 mg), N,N'-diisopropylcarbodiimide (DIPCI; 24 ml) and 1-hydroxy-7-benzotriazole (HOAT; 21 mg) were added to a suspension of N-{[4-(tert-butoxycarbonylaminomethyl)cyclohexyl]methyl}-3'-{[(4-Wang resin phenethyl)amino]methyl}[1,1'-biphenyl]-3-carboxamide (30 mg) in DMF (2 ml), and the mixture was stirred at room temperature for 20 hours. The solvent was removed by filtration, and the resultant resin was washed with DMF, THF and methanol in this order and dried at 50° C. under reduced pressure. The resultant resin was treated with trifluoroacetic acid-dichloromethane (1:1; 1 ml) and purified by preparative HPLC to give the title compound (6.6 mg).

$^1$H-NMR (Acetone-$d_6$) •: 1.00–1.10 (2H, m), 1.50–1.70 (4H, m), 1.80–2.00 (4H, m), 2.50–2.65 (2H, m), 2.80–2.95 (2H, m), 3.25–3.80 (4H, m), 4.79 (2H,s), 6.76 (2H, d, J=8.4 Hz), 7.02 (1H, d, J=14.4 Hz), 7.08 (2H, d, J=8.4 Hz), 7.20–8.00 (13H, m), 8.13 (1H, s).

HPLC analysis (condition B): purity 100% (retention time: 1.730 min.)
MS (APCI+): 680 (M+H), 682

The following compounds were produced in the same manner as in Example 7.

EXAMPLE 8

3'-{([4-Hydroxyphenethyl][(E)-3-phenyl-2-propenoyl]amino)methyl}-N-[2-(1-pyrrolidinyl)ethyl][1,1'-biphenyl]-3-carboxamide trifluoroacetate Yield: 6.8 mg
HPLC analysis (condition A): purity 100% (retention time: 3.239 min.)
MS (APCI+): 574 (M+H)

EXAMPLE 9

3'-{([4-Hydroxyphenethyl][(benzyloxy)acetyl]amino)methyl}-N-[2-(1-pyrrolidinyl)ethyl][1,1'-biphenyl]-3-carboxamide trifluoroacetate Yield: 6.7 mg
HPLC analysis (condition A): purity 98% (retention time: 3.166 min.)
MS (APCI+): 592 (M+H)

EXAMPLE 10

3'-{([4-Hydroxyphenethyl][4-phenylbutanoyl]amino)methyl}-N-[2-(1-pyrrolidinyl)ethyl][1,1'-biphenyl]-3-carboxamide trifluoroacetate Yield: 6.8 mg
HPLC analysis (condition A): purity 100% (retention time: 3.330 min.)
MS (APCI+): 590 (M+H)

EXAMPLE 11

3'-{([4-Hydroxyphenethyl][3-(1H-indol-3-yl)propanoyl]amino)methyl}-N-[2-(1-pyrrolidinyl)ethyl][1,1'-biphenyl]-3-carboxamide trifluoroacetate Yield: 1.1 mg
HPLC analysis (condition A): purity 97% (retention time: 3.225 min.)
MS (APCI+): 615 (M+H)

EXAMPLE 12

3'-{([4-Hydroxyphenethyl][2-(1H-indol-3-yl)acetyl]amino)methyl}-N-[2-(1-pyrrolidinyl)ethyl][1,1'-biphenyl]-3-carboxamide trifluoroacetate Yield: 1.5 mg
HPLC analysis (condition A): purity 98% (retention time: 3.146 min.)
MS (APCI+): 601 (M+H)

EXAMPLE 13

3'-{([(E)-3-(2-Furyl)-2-propenoyl][4-hydroxyphenethyl]amino)methyl}-N-[2-(1-pyrrolidinyl)ethyl][1,1'-biphenyl]-3-carboxamide trifluoroacetate Yield: 6.6 mg
HPLC analysis (condition A): purity 98% (retention time: 3.136 min.)
MS (APCI+): 564 (M+H)

EXAMPLE 14

3'-{([2-(3-Bromophenyl)acetyl][4-hydroxyphenethyl]amino)methyl}-N-[2-(1-pyrrolidinyl)ethyl][1,1'-biphenyl]-3-carboxamide trifluoroacetate Yield: 4.6 mg
HPLC analysis (condition A): purity 95% (retention time: 3.309 min.)
MS (APCI+): 640 (M+H), 642

EXAMPLE 15

3'-{([4-Hydroxyphenethyl][2-(4-methoxyphenyl)acetyl]amino)methyl}-N-[2-(1-pyrrolidinyl)ethyl][1,1'-biphenyl]-3-carboxamide trifluoroacetate Yield: 5.5 mg
HPLC analysis (condition B): purity 100% (retention time: 1.538 min.)
MS (APCI+): 592 (M+H)

EXAMPLE 16

(E)-N-(4-Hydroxyphenethyl)-3-phenyl-N-{[3'-({4-[3-(4-piperidinyl)propyl]-1-piperidinyl}carbonyl)[1,1'-biphenyl]-3-yl]methyl}-2-propenamide trifluoroacetate Yield: 3.8 mg
HPLC analysis (condition A): purity 100% (retention time: 3.465 min.)
MS (APCI+): 670 (M+H)

EXAMPLE 17

2-(4-Bromophenyl)-N-(4-hydroxyphenethyl)-N-{[3'-({4-[3-(4-piperidinyl)propyl]-1-piperidinyl}carbonyl)[1,1'-biphenyl]-3-yl]methyl}acetamide trifluoroacetate Yield: 3.5 mg
HPLC analysis (condition A): purity 99% (retention time: 3.538 min.)
MS (APCI+): 736 (M+H), 738

EXAMPLE 18

2-(Benzyloxy)-N-(4-hydroxyphenethyl)-N-{[3'-({4-[3-(4-piperidinyl)propyl]-1-piperidinyl}carbonyl)[1,1'-biphenyl]-3-yl]methyl}acetamide trifluoroacetate Yield: 3.8 mg
HPLC analysis (condition A): purity 99% (retention time: 3.416 min.)
MS (APCI+): 688 (M+H)

EXAMPLE 19

N-(4-Hydroxyphenethyl)-4-phenyl-N-{[3'-({4-[3-(4-piperidinyl)propyl]-1-piperidinyl}carbonyl)[1,1'-biphenyl]-3-yl]methyl}butanamide trifluoroacetate Yield: 4.5 mg
HPLC analysis (condition A): purity 100% (retention time: 3.555 min.)
MS (APCI+): 686 (M+H)

EXAMPLE 20

N-[2-((4-Hydroxyphenethyl){[3'-({4-[3-(4-piperidinyl)propyl]-1-piperidinyl}carbonyl)[1,1'-biphenyl]-3-yl]methyl}amino)-2-oxyethyl]benzamide trifluoroacetate Yield: 3.0 mg
HPLC analysis (condition A): purity 98% (retention time: 3.281 min.)
MS (APCI+): 701 (M+H)

EXAMPLE 21

N-(4-Hydroxyphenethyl)-3-(1H-indol-3-yl)-N-{[3'-({4-[3-(4-piperidinyl)propyl]-1-piperidinyl}carbonyl)[1,1'-biphenyl]-3-yl]methyl}propanamide trifluoroacetate Yield: 1.0 mg
HPLC analysis (condition A): purity 96% (retention time: 3.455 min.)
MS (APCI+): 711 (M+H)

EXAMPLE 22

N-(4-Hydroxyphenethyl)-2-(1H-indol-3-yl)-N-{[3'-({4-[3-(4-piperidinyl)propyl]-1-piperidinyl}carbonyl)[1,1'-biphenyl]-3-yl]methyl}acetamide trifluoroacetate Yield: 0.9 mg
HPLC analysis (condition A): purity 90% (retention time: 3.371 min.)
MS (APCI+): 697 (M+H)

EXAMPLE 23

N-(4-Hydroxyphenethyl)-4-methyl-N-{[3'-({4-[3-(4-piperidinyl)propyl]-1-piperidinyl}carbonyl)[1,1'-biphenyl]-3-yl]methyl}pentanamide trifluoroacetate Yield: 4.6 mg
HPLC analysis (condition A): purity 100% (retention time: 3.483 min.)
MS (APCI+): 638 (M+H)

EXAMPLE 24

(E)-3-(2-Furyl)-N-(4-hydroxyphenethyl)-N-{[3'-({4-[3-(4-piperidinyl)propyl]-1-piperidinyl}carbonyl)[1,1'-biphenyl]-3-yl]methyl}-2-propenamide trifluoroacetate Yield: 1.8 mg
HPLC analysis (condition A): purity 95% (retention time: 3.391 min.)
MS (APCI+): 660 (M+H)

EXAMPLE 25

(E)-N-(4-Hydroxyphenethyl)-N-{[3'-({4-[3-(4-piperidinyl)propyl]-1-piperidinyl}carbonyl)[1,1'-biphenyl]-3-yl]methyl}-3-(3-pyridyl)-2-propenamide trifluoroacetate Yield: 4.2 mg
HPLC analysis (condition A): purity 95% (retention time: 2.907 min.)
MS (APCI+): 671 (M+H)

EXAMPLE 26

2-(3-Bromophenyl)-N-(4-hydroxyphenethyl)-N-{[3'-({4-[3-(4-piperidinyl)propyl]-1-piperidinyl}carbonyl)[1,1'-biphenyl]-3-yl]methyl}acetamide trifluoroacetate Yield: 2.1 mg
HPLC analysis (condition A): purity 94% (retention time: 3.538 min.)
MS (APCI+): 736 (M+H), 738

EXAMPLE 27

2-(2-Bromophenyl)-N-(4-hydroxyphenethyl)-N-{[3'-({4-[3-(4-piperidinyl)propyl]-1-piperidinyl}carbonyl)[1,1'-biphenyl]-3-yl]methyl}acetamide trifluoroacetate Yield: 3.2 mg
HPLC analysis (condition A): purity 93% (retention time: 3.518 min.)
MS (APCI+): 736 (M+H), 738

EXAMPLE 28

N-(4-Hydroxyphenethyl)-N-{[3'-({4-[3-(4-piperidinyl)propyl]-1-piperidinyl}carbonyl)[1,1'-biphenyl]-3-yl]methyl}-2-(4-pyridynylsulfanyl)acetamide trifluoroacetate Yield: 6.5 mg
HPLC analysis (condition B): purity 100% (retention time: 1.427 min.)
MS (APCI+): 691 (M+H)

EXAMPLE 29

N-(4-Hydroxyphenethyl)-2-(4-methoxyphenyl)-N-{[3'-({4-[3-(4-piperidinyl)propyl]-1-piperidinyl}carbonyl)[1,1'-biphenyl]-3-yl]methyl}acetamide trifluoroacetate Yield: 2.9 mg
HPLC analysis (condition B): purity 100% (retention time: 1.666 min.)
MS (APCI+): 688 (M+H)

EXAMPLE 30

(E)-N-(4-Hydroxyphenethyl)-3-(4-methoxyphenyl)-N-{[3'-({4-[3-(4-piperidinyl)propyl]-1-piperidinyl}carbonyl)[1,1'-biphenyl]-3-yl]methyl}-2-propenamide trifluoroacetate Yield: 4.0 mg
HPLC analysis (condition B): purity 100% (retention time: 1.709 min.)
MS (APCI+): 700 (M+H)

EXAMPLE 31

N-(5-Aminopentyl)-3'-{[[2-(4-bromophenyl)acetyl](4-hydroxyphenethyl)amino]methyl}[1,1'-biphenyl]-3-carboxamide trifluoroacetate Yield: 8.1 mg
HPLC analysis (condition B): purity 100% (retention time: 1.633 min.)
MS (APCI+): 628 (M+H), 630

EXAMPLE 32

N-(5-Aminopentyl)-3'-{[(4-hydroxyphenethyl)(4-phenylbutanoyl)amino]methyl}[1,1'-biphenyl]-3-carboxamide trifluoroacetate Yield: 6.5 mg
HPLC analysis (condition B): purity 100% (retention time: 1.629 min.)
MS (APCI+): 578 (M+H)

EXAMPLE 33

N-(5-Aminopentyl)-3'-{[(4-hydroxyphenethyl)[3-(1H-indol-3-yl)propanoyl]amino]methyl}[1,1'-biphenyl]-3-carboxamide trifluoroacetate Yield: 1.2 mg
HPLC analysis (condition B): purity 100% (retention time: 1.568 min.)
MS (APCI+): 603 (M+H)

EXAMPLE 34

N-(5-Aminopentyl)-3'-{[[2-(2-bromophenyl)acetyl](4-hydroxyphenethyl)amino]methyl}[1,1'-biphenyl]-3-carboxamide trifluoroacetate Yield: 8.1 mg
HPLC analysis (condition B): purity 100% (retention time: 1.607 min.)
MS (APCI+): 628 (M+H), 630

EXAMPLE 35

N-(5-Aminopentyl)-3'-{[[(E)-3-(4-bromophenyl)-2-propenoyl](4-hydroxyphenethyl)amino]methyl}[1,1'-biphenyl]-3-carboxamide trifluoroacetate Yield: 10.8 mg
HPLC analysis (condition B): purity 100% (retention time: 1.689 min.)
MS (APCI+): 640 (M+H), 642

EXAMPLE 36

N-(6-Aminohexyl)-3'-{[(4-hydroxyphenethyl)(4-phenylbutanoyl)amino]methyl}[1,1'-biphenyl]-3-carboxamide trifluoroacetate Yield: 7.0 mg
HPLC analysis (condition B): purity 100% (retention time: 1.660 min.)
MS (APCI+): 592 (M+H)

EXAMPLE 37

N-(6-Aminohexyl)-3'-{[(4-hydroxyphenethyl)[3-(1H-indol-3-yl)propanoyl]amino]methyl}[1,1'-biphenyl]-3-carboxamide trifluoroacetate Yield: 1.3 mg
HPLC analysis (condition B): purity 100% (retention time: 1.594 min.)
MS (APCI+): 617 (M+H)

EXAMPLE 38

N-(6-Aminohexyl)-3'-{[[(E)-3-(2-furyl)-2-propenoyl](4-hydroxyphenethyl)amino]methyl}[1,1'-biphenyl]-3-carboxamide trifluoroacetate Yield: 6.1 mg
HPLC analysis (condition B): purity 100% (retention time: 1.562 min.)
MS (APCI+): 566 (M+H)

EXAMPLE 39

N-(6-Aminohexyl)-3'-{[[2-(3-bromophenyl)acetyl](4-hydroxyphenethyl)amino]methyl}[1,1'-biphenyl]-3-carboxamide trifluoroacetate Yield: 8.0 mg
HPLC analysis (condition B): purity 100% (retention time: 1.640 min.)
MS (APCI+): 644 (M+H), 646

EXAMPLE 40

N-{[3-(Aminomethyl)cyclohexyl]methyl}-3'-{[[2-(4-bromophenyl)acetyl](4-hydroxyphenethyl)amino]methyl}[1,1'-biphenyl]-3-carboxamide trifluoroacetate Yield: 6.6 mg
HPLC analysis (condition B): purity 100% (retention time: 1.678 min.)
MS (APCI+): 668 (M+H), 670

EXAMPLE 41

N-{[3-(Aminomethyl)cyclohexyl]methyl}-3'-{[[2-(benzyloxy)acetyl](4-hydroxyphenethyl)amino]methyl}[1,1'-biphenyl]-3-carboxamide trifluoroacetate Yield: 5.9 mg
HPLC analysis (condition B): purity 100% (retention time: 1.604 min.)
MS (APCI+): 620 (M+H)

EXAMPLE 42

N-{[3-(Aminomethyl)cyclohexyl]methyl}-3'-{[(4-hydroxyphenethyl)(4-phenylbutanoyl)amino]methyl}[1,1'-biphenyl]-3-carboxamide trifluoroacetate Yield: 5.8 mg
HPLC analysis (condition B): purity 100% (retention time: 1.685 min.)
MS (APCI+): 618 (M+H)

EXAMPLE 43

N-{[3-(Aminomethyl)cyclohexyl]methyl}-3'-{[(4-hydroxyphenethyl)[3-(1H-indol-3-yl)propanoyl]amino]methyl}[1,1'-biphenyl]-3-carboxamide trifluoroacetate Yield: 0.9 mg
HPLC analysis (condition B): purity 100% (retention time: 1.623 min.)
MS (APCI+): 643 (M+H)

EXAMPLE 44

N-{[3-(Aminomethyl)cyclohexyl]methyl}-3'-{[(4-hydroxyphenethyl)[2-(1H-indol-3-yl)acetyl]amino]methyl}[1,1'-biphenyl]-3-carboxamide trifluoroacetate Yield: 1.3 mg
HPLC analysis (condition B): purity 100% (retention time: 1.587 min.)
MS (APCI+): 629 (M+H)

EXAMPLE 45

N-{[3-(Aminomethyl)cyclohexyl]methyl}-3'-{[[(E)-3-(2-furyl)-2-propenoyl](4-hydroxyphenethyl)amino]methyl}[1,1'-biphenyl]-3-carboxamide trifluoroacetate Yield: 3.9 mg
HPLC analysis (condition B): purity 100% (retention time: 1.591 min.)
MS (APCI+): 592 (M+H)

EXAMPLE 46

N-{[3-(Aminomethyl)cyclohexyl]methyl}-3'-{[[2-(3-bromophenyl)acetyl](4-hydroxyphenethyl)amino]methyl}[1,1'-biphenyl]-3-carboxamide trifluoroacetate Yield: 6.7 mg
HPLC analysis (condition B): purity 100% (retention time: 1.673 min.)
MS (APCI+): 668 (M+H), 670

EXAMPLE 47

N-{[3-(Aminomethyl)cyclohexyl]methyl}-3'-{[[(E)-3-(4-bromophenyl)-2-propenoyl](4-hydroxyphenethyl)amino]methyl}[1,1'-biphenyl]-3-carboxamide trifluoroacetate Yield: 8.3 mg
HPLC analysis (condition B): purity 100% (retention time: 1.746 min.)
MS (APCI+): 680 (M+H), 682

EXAMPLE 48

N-{[4-(Aminomethyl)cyclohexyl]methyl}-3'-{[(4-hydroxyphenethyl)[(E)-3-phenyl-2-propenoyl]amino]methyl}[1,1'-biphenyl]-3-carboxamide trifluoroacetate Yield: 4.9 mg
HPLC analysis (condition B): purity 100% (retention time: 1.630 min.)
MS (APCI+): 602 (M+H)

EXAMPLE 49

N-{[4-(Aminomethyl)cyclohexyl]methyl}-3'-{[[2-(4-bromophenyl)acetyl](4-hydroxyphenethyl)amino]methyl}[1,1'-biphenyl]-3-carboxamide trifluoroacetate Yield: 5.2 mg
HPLC analysis (condition B): purity 100% (retention time: 1.668 min.)
MS (APCI+): 668 (M+H), 670

EXAMPLE 50

N-{[4-(Aminomethyl)cyclohexyl]methyl}-3'-{[[2-(benzyloxy)acetyl](4-hydroxyphenethyl)amino]methyl}[1,1'-biphenyl]-3-carboxamide trifluoroacetate Yield: 4.0 mg
HPLC analysis (condition B): purity 100% (retention time: 1.593 min.)
MS (APCI+): 620 (M+H)

EXAMPLE 51

N-{4-(Aminomethyl)cyclohexyl]methyl}-3'-{[(4-hydroxyphenethyl)(4-phenylbutanoyl)amino]methyl}[1,1'-biphenyl]-3-carboxamide trifluoroacetate Yield: 4.0 mg
HPLC analysis (condition B): purity 100% (retention time: 1.680 min.)
MS (APCI+): 618 (M+H)

EXAMPLE 52

N-{4-(Aminomethyl)cyclohexyl]methyl}-3'-{[[2-(benzoylamino)acetyl](4-hydroxyphenethyl)amino]methyl}[1,1'-biphenyl]-3-carboxamide trifluoroacetate Yield: 4.2 mg
HPLC analysis (condition B): purity 100% (retention time: 1.521 min.)
MS (APCI+): 633 (M+H)

EXAMPLE 53

N-{[4-(Aminomethyl)cyclohexyl]methyl}-3'-{[(4-hydroxyphenethyl)[3-(1H-indol-3-yl)propanoyl]amino]methyl}[1,1'-biphenyl]-3-carboxamide trifluoroacetate Yield: 1.0 mg
HPLC analysis (condition B): purity 100% (retention time: 1.608 min.)
MS (APCI+): 643 (M+H)

EXAMPLE 54

N-{[4-(Aminomethyl)cyclohexyl]methyl}-3'-{[(4-hydroxyphenethyl)[2-(1H-indol-3-yl)acetyl]amino]methyl}[1,1'-biphenyl]-3-carboxamide trifluoroacetate Yield: 1.0 mg
HPLC analysis (condition B): purity 100% (retention time: 1.570 min.)
MS (APCI+): 629 (M+H)

EXAMPLE 55

N-{[4-(Aminomethyl)cyclohexyl]methyl}-3'-{[[(E)-3-(2-furyl)-2-propenoyl](4-hydroxyphenethyl)amino]methyl}[1,1'-biphenyl]-3-carboxamide trifluoroacetate Yield: 3.5 mg
HPLC analysis (condition B): purity 100% (retention time: 1.577 min.)
MS (APCI+): 592 (M+H)

EXAMPLE 56

N-{[4-(Aminomethyl)cyclohexyl]methyl}-3'-{[(4-hydroxyphenethyl)[(E)-3-(3-pyridyl)-2-propenoyl]amino]methyl}[1,1'-biphenyl]-3-carboxamide trifluoroacetate Yield: 5.8 mg
HPLC analysis (condition B): purity 100% (retention time: 1.305 min.)
MS (APCI+): 603 (M+H)

EXAMPLE 57

N-{[4-(Aminomethyl)cyclohexyl]methyl}-3'-{[[2-(3-bromophenyl)acetyl](4-hydroxyphenethyl)amino]methyl}[1,1'-biphenyl]-3-carboxamide trifluoroacetate Yield: 5.3 mg
HPLC analysis (condition B): purity 100% (retention time: 1.667 min.)
MS (APCI+): 668 (M+H), 670

EXAMPLE 58

N-{[4-(Aminomethyl)cyclohexyl]methyl}-3'-{[[2-(2-bromophenyl)acetyl](4-hydroxyphenethyl)amino]methyl}[1,1'-biphenyl]-3-carboxamide trifluoroacetate Yield: 5.6 mg
HPLC analysis (condition B): purity 100% (retention time: 1.648 min.)
MS (APCI+): 668 (M+H), 670

EXAMPLE 59

N-{[4-(Aminomethyl)cyclohexyl]methyl}-3'-{[(4-hydroxyphenethyl)[2-(4-methoxyphenyl)acetyl]amino]methyl}[1,1'-biphenyl]-3-carboxamide trifluoroacetate Yield: 5.4 mg
HPLC analysis (condition B): purity 100% (retention time: 1.570 min.)
MS (APCI+): 620 (M+H)

EXAMPLE 60

N-(4-Aminocyclohexyl)-3'-{[[2-(4-bromophenyl)acetyl](4-hydroxyphenethyl)amino]methyl}[1,1'-biphenyl]-3-carboxamide trifluoroacetate Yield: 5.7 mg
HPLC analysis (condition B): purity 100% (retention time: 1.617 min.)
MS (APCI+): 640 (M+H), 642

EXAMPLE 61

N-(3-Aminopropyl)-3'-{[[2-(4-bromophenyl)acetyl](4-hydroxyphenethyl)amino]methyl}[1,1'-biphenyl]-3-carboxamide trifluoroacetate Yield: 9.4 mg
HPLC analysis (condition B): purity 100% (retention time: 1.590 min.)
MS (APCI+): 600 (M+H), 602

EXAMPLE 62

N-(3-Aminopropyl)-3'-{[[2-(benzyloxy)acetyl](4-hydroxyphenethyl)amino]methyl}[1,1'-biphenyl]-3-carboxamide trifluoroacetate Yield: 7.2 mg
HPLC analysis (condition B): purity 100% (retention time: 1.527 min.)
MS (APCI+): 552 (M+H)

EXAMPLE 63

N-(3-Aminopropyl)-3'-{[(4-hydroxyphenethyl)(4-phenylbutanoyl)amino]methyl}[1,1'-biphenyl]-3-carboxamide trifluoroacetate Yield: 8.7 mg
HPLC analysis (condition B): purity 100% (retention time: 1.610 min.)
MS (APCI+): 550 (M+H)

EXAMPLE 64

N-(3-Aminopropyl)-3'-{[(4-hydroxyphenethyl)[3-(1H-indol-3-yl) propanoyl]amino]methyl}[1,1'-biphenyl]-3-carboxamide trifluoroacetate Yield: 7.5 mg
HPLC analysis (condition B): purity 100% (retention time: 1.541 min.)
MS (APCI+): 575 (M+H)

EXAMPLE 65

N-(3-Aminopropyl)-3'-{[(4-hydroxyphenethyl)[2-(1H-indol-3-yl)acetyl]amino]methyl}[1,1'-biphenyl]-3-carboxamide trifluoroacetate Yield: 1.5 mg
HPLC analysis (condition B): purity 100% (retention time: 1.503 min.)
MS (APCI+): 561 (M+H)

EXAMPLE 66

N-(3-Aminopropyl)-3'-{[(4-hydroxyphenethyl)(4-methylpentanoyl)amino]methyl}[1,1'-biphenyl]-3-carboxamide trifluoroacetate Yield: 9.6 mg
HPLC analysis (condition B): purity 100% (retention time: 1.555 min.)
MS (APCI+): 502 (M+H)

EXAMPLE 67

N-(3-Aminopropyl)-3'-{[[2-(3-bromophenyl)acetyl](4-hydroxyphenethyl)amino]methyl}[1,1'-biphenyl]-3-carboxamide trifluoroacetate Yield: 10.3 mg
HPLC analysis (condition B): purity 100% (retention time: 1.592 min.)
MS (APCI+): 600 (M+H), 602

EXAMPLE 68

N-(3-Aminopropyl)-3'-{[[2-(2-bromophenyl)acetyl](4-hydroxyphenethyl)amino]methyl}[1,1'-biphenyl]-3-carboxamide trifluoroacetate Yield: 9.4 mg
HPLC analysis (condition B): purity 100% (retention time: 1.569 min.)
MS (APCI+): 600 (M+H), 602

EXAMPLE 69

N-(3-Aminopropyl)-3'-{[(4-hydroxyphenethyl)[2-(4-methoxyphenyl)acetyl]amino]methyl}[1,1'-biphenyl]-3-carboxamide trifluoroacetate Yield: 9.4 mg
HPLC analysis (condition B): purity 100% (retention time: 1.498 min.)
MS (APCI+): 552 (M+H)

EXAMPLE 70

N-(3-Aminopropyl)-3'-{[[(E)-3-(4-bromophenyl)-2-propenoyl](4-hydroxyphenethyl)amino]methyl}[1,1'-biphenyl]-3-carboxamide trifluoroacetate Yield: 10.1 mg
HPLC analysis (condition B): purity 100% (retention time: 1.658 min.)
MS (APCI+): 612 (M+H), 614

EXAMPLE 71

N-(2-Aminoethyl)-3'-({[4-(aminosulfonyl)phenethyl][(E)-3-phenyl-2-propenoyl]amino}methyl)[1,1'-biphenyl]-3-carboxamide trifluoroacetate 1) 2-[(3-Bromobenzoyl)amino]ethylcarbamic acid Wang resin ester A mixture of 4-nitrophenoxycarbonyl Wang resin (7.00 g), N-(2-aminoethyl)-3-bromobenzamide (3.52 g), DIEA (4.26 ml) and DMF (60 ml) was stirred at room temperature for 20 hours. The solvent was removed by filtration, and the resultant resin was washed with DMF, THF and methanol in this order and then dried at 50° C. under reduced pressure to give the title compound (6.8 g). The amount of the compound carried on the resin was 0.94 mmol/g (elemental analysis: calculated from 7.51% Br). The resultant resin (5 beads) was treated with trifluoroacetic acid-dichloromethane (1:1; 50 ml) to give N-(2-aminoethyl)-3-bromobenzamide which was then analyzed in HPLC and measured by mass spectrometry.
HPLC analysis (condition A): purity 96% (retention time: 1.208 min.)
MS (APCI+): 243 (M+H), 245

2) 2-{[(3'-Formyl[1,1'-biphenyl]-3-yl)carbonyl]amino}ethylcarbamic acid Wang resin ester Palladium tetrakistriphenyl phosphine (706 mg) and 2 M aqueous sodium carbonate (30.6 ml) were added to a suspension of 2-[(3-bromobenzoyl)amino]ethylcarbamic acid Wang resin ester (6.50 g) in 1,2-dimethoxyethane (200 ml), and 3-formylphenylboric acid (4.58 g) was further added thereto, and the mixture was stirred at 80° C. for 20 hours. The solvent was removed by filtration, and the resultant resin was washed with DMF, THF and methanol in this order and then dried at 50° C. under reduced pressure to give the title compound (6.68 g). The resultant resin (5 beads) was treated with trifluoroacetic acid-dichloromethane (1:1; 50 ml) to give N-(2-aminoethyl)-3'-formyl[1,1'-biphenyl]-3-carboxamide which was then analyzed in HPLC and measured by mass spectrometry.

HPLC analysis (condition A): purity 95% (retention time: 2.295 min.)
MS (APCI+): 269 (M+H)

3) 2-{[(3'-{[(4-(Aminosulfonyl)phenethyl)amino]methyl}[1,1'-biphenyl]-3-yl)carbonyl]amino}ethylcarbamic acid Wang resin ester A mixture of 2-{[(3'-formyl[1,1'-biphenyl]-3-yl)carbonyl]amino}ethylcarbamic acid Wang resin ester (30 mg), 4-(2-aminosulfonyl)benzenesulfonamide (28 mg) and a solution of 5% acetic acid in dichloromethane (2 ml) was stirred at room temperature for 30 minutes, and sodium triacetoxy borohydride (30 mg) was further added thereto, and the mixture was stirred at room temperature for 15 hours. The solvent was removed by filtration, and the resultant resin was washed with DMF, a mixed solvent of DMF-water (1:1), DMF, THF and methanol in this order and then dried at 50° C. under reduced pressure to give the title compound (30 mg). The resultant resin (5 beads) was treated with trifluoroacetic acid-dichloromethane (1:1; 50 ml) to give N-(2-aminoethyl)-3'-({[4-(aminosulfonyl)phenethyl]amino}methyl)[1,1'-biphenyl]-3-carboxamide which was then analyzed in HPLC and measured by mass spectrometry.

HPLC analysis (condition A): purity 88% (retention time: 0.857 min.)
MS (APCI–): 451 (M–H)

4) N-(2-Aminoethyl)-3'-({[4-(aminosulfonyl)phenethyl][(E)-3-phenyl-2-propenoyl]amino}methyl)[1,1'-biphenyl]-3-carboxamide trifluoroacetate Cinnamic acid (29 mg), DIPCI (27 ml) and HOAT (23 mg) were added to a suspension of 2-{[(3'-{[(4-(aminosulfonyl)phenethyl)amino]methyl}[1,1'-biphenyl]-3-yl)carbonyl]amino}ethylcarbamic acid Wang resin ester (30 mg) in DMF (2 ml), and the mixture was stirred at room temperature for 15 hours. The solvent was removed by filtration, and the resultant resin was washed with DMF, THF and methanol in this order and then dried at 50° C. under reduced pressure. The resultant resin was treated with trifluoroacetic acid-dichloromethane (1:1; 1 ml) and then purified by preparative HPLC to give the title compound (5.4 mg).

¹H-NMR (Acetone-d₆) •: 3.00–3.20 (2H, m), 3.70–3.90 (4H, m), 4.00–4.15 (2H, m), 4.85 (2H,s), 6.45–6.60 (1H, m), 7.05–7.20 (1H, m), 7.25–8.00 (17H, m), 8.31 (1H, s).
HPLC analysis (condition B): purity 97% (retention time: 1.492 min.)
MS (APCI–): 581 (M–H)

The following compounds were produced in the same manner as in Example 71.

EXAMPLE 72

N-(2-Aminoethyl)-3'-{[(4-(aminosulfonyl)phenethyl][2-(4-bromophenyl)acetyl]amino}methyl)[1,1'-biphenyl]-3-carboxamide trifluoroacetate Yield: 6.9 mg
HPLC analysis (condition B): purity 100% (retention time: 1.535 min.)
MS (APCI–): 647 (M–H), 649

EXAMPLE 73

N-(2-Aminoethyl)-3'-({[4-(aminosulfonyl)phenethyl][2-(benzyloxy)acetyl]amino}methyl}[1,1'-biphenyl]-3-carboxamide trifluoroacetate Yield: 8.0 mg
HPLC analysis (condition B): purity 100% (retention time: 1.445 min.)
MS (APCI–): 599 (M–H)

EXAMPLE 74

N-(2-Aminoethyl)-3'-({[4-(aminosulfonyl)phenethyl](4-phenylbutanoyl)amino}methyl)[1,1'-biphenyl]-3-carboxamide trifluoroacetate Yield: 8.0 mg
HPLC analysis (condition B): purity 100% (retention time: 1.540 min.)
MS (APCI–): 597 (M–H)

EXAMPLE 75

N-(2-Aminoethyl)-3'-({[4-(aminosulfonyl)phenethyl][(E)-3-(2-furyl)-2-propenoyl]amino}methyl)[1,1'-biphenyl]-3-carboxamide trifluoroacetate Yield: 3.6 mg
HPLC analysis (condition B): purity 100% (retention time: 1.427 min.)
MS (APCI–): 571 (M–H)

EXAMPLE 76

N-(2-Aminoethyl)-3'-({[4-(aminosulfonyl)phenethyl][2-(3-bromophenyl)acetyl]amino}methyl)[1,1'-biphenyl]-3-carboxamide trifluoroacetate Yield: 4.5 mg
HPLC analysis (condition B): purity 100% (retention time: 1.524 min.)
MS (APCI–): 647 (M–H), 649

EXAMPLE 77

N-(2-Aminoethyl)-3'-({[4-(aminosulfonyl)phenethyl][2-(2-bromophenyl)acetyl]amino}methyl)[1,1'-biphenyl]-3-carboxamide trifluoroacetate Yield: 9.0 mg
HPLC analysis (condition B): purity 100% (retention time: 1.499 min.)
MS (APCI–): 647 (M–H), 649

EXAMPLE 78

N-(2-Aminoethyl)-3'-({[4-(aminosulfonyl)phenethyl][(E)-3-(4-methoxyphenyl)-2-propenoyl]amino}methyl)[1,1'-biphenyl]-3-carboxamide trifluoroacetate Yield: 6.3 mg
HPLC analysis (condition B): purity 100% (retention time: 1.498 min.)
MS (APCI–): 611 (M–H)

EXAMPLE 79

N-(2-Aminoethyl)-3'-({[4-(aminosulfonyl)phen-ethyl][2-(4-methoxyphenyl)acetyl]amino}methyl)[1,1'-biphenyl]-3-carboxamide trifluoroacetate Yield: 3.8 mg
HPLC analysis (condition B): purity 100% (retention time: 1.431 min.)
MS (APCI−): 599 (M−H)

EXAMPLE 80

N-(2-Aminoethyl)-3'-({[4-(aminosulfonyl)phen-ethyl][2-(4-hydroxyphenyl)acetyl]amino}methyl)[1,1'-biphenyl]-3-carboxamide trifluoroacetate Yield: 3.8 mg
HPLC analysis (condition B): purity 100% (retention time: 1.325 min.)
MS (APCI−): 585 (M−H)

EXAMPLE 81

N-(2-Aminoethyl)-3'-({[4-(aminosulfonyl)phen-ethyl][(E)-3-(4-hydroxyphenyl)-2-propenoyl]amino}methyl)[1,1'-biphenyl]-3-carboxamide trifluoroacetate Yield: 5.0 mg
HPLC analysis (condition B): purity 100% (retention time: 1.347 min.)
MS (APCI−): 597 (M−H)

EXAMPLE 82

N-(2-Aminoethyl)-3'-({[4-(aminosulfonyl)phen-ethyl][3-(4-hydroxyphenyl)propanoyl]amino}methyl)[1,1'-biphenyl]-3-carboxamide trifluoroacetate Yield: 4.4 mg
HPLC analysis (condition B): purity 100% (retention time: 1.592 min.)
MS (APCI−): 599 (M−H)

EXAMPLE 83

N-(2-Aminoethyl)-3'-({[4-(aminosulfonyl)benzyl][(E)-3-phenyl-2-propenoyl]amino}methyl)[1,1'-biphenyl]-3-carboxamide trifluoroacetate Yield: 6.2 mg
HPLC analysis (condition B): purity 100% (retention time: 1.476 min.)
MS (APCI−): 567 (M−H)

EXAMPLE 84

N-(2-Aminoethyl)-3'-({[4-(aminosulfonyl)benzyl][(E)-3-(4-methoxyphenyl)-2-propenoyl]amino}methyl)[1,1'-biphenyl]-3-carboxamide trifluoroacetate Yield: 5.0 mg
HPLC analysis (condition B): purity 100% (retention time: 1.478 min.)
MS (APCI−): 597 (M−H)

EXAMPLE 85

N-(2-Aminoethyl)-3'-({[3-(1H-indol-3-yl)propanoyl][2-(4-pyridinyl)ethyl]amino}methyl)[1,1'-biphenyl]-3-carboxamide trifluoroacetate Yield: 1.4 mg
HPLC analysis (condition B): purity 100% (retention time: 1.335 min.)
MS (APCI−): 544 (M−H)

EXAMPLE 86

N-(2-Aminoethyl)-3'-({[2-(1H-indol-3-yl)acetyl][2-(2-oxo-1-pyrrolidinyl)ethyl]amino}methyl)[1,1'-biphenyl]-3-carboxamide trifluoroacetate Yield: 1.1 mg
HPLC analysis (condition B): purity 100% (retention time: 1.425 min.)
MS (APCI−): 550 (M−H)

EXAMPLE 87

N-(2-Aminoethyl)-3'-({[4-phenylbutanoyl][2-(2-thienyl)ethyl]amino}methyl)[1,1'-biphenyl]-3-carboxamide trifluoroacetate Yield: 2.9 mg
HPLC analysis (condition B): purity 100% (retention time: 1.722 min.)
MS (APCI−): 524 (M−H)

EXAMPLE 88

N-(2-Aminoethyl)-3'-({[2-(3-bromophenyl)acetyl][2-(2-thienyl)ethyl]amino}methyl)[1,1'-biphenyl]-3-carboxamide trifluoroacetate Yield: 2.3 mg
HPLC analysis (condition B): purity 100% (retention time: 1.722 min.)
MS (APCI+): 576 (M+H), 578

EXAMPLE 89

N-(2-Aminoethyl)-3'-({[(E)-3-(4-hydroxyphenyl)-2-propenoyl][2-(2-thienyl)ethyl]amino}methyl)[1,1'-biphenyl]-3-carboxamide trifluoroacetate Yield: 2.6 mg
HPLC analysis (condition B): purity 100% (retention time: 1.549 min.)
MS (APCI−): 524 (M−H)

EXAMPLE 90

N-(2-Aminoethyl)-3'-({[(E)-3-phenyl-2-propenoyl][4-(1,2,3-thiadiazol-4-yl]amino}methyl)[1,1'-biphenyl]-3-carboxamide trifluoroacetate Yield: 5.0 mg
HPLC analysis (condition B): purity 100% (retention time: 1.652 min.)
MS (APCI+): 574 (M+H)

EXAMPLE 91

N-(2-Aminoethyl)-3'-({[(E)-3-(4-methoxyphenyl)-2-propenoyl][4-(1,2,3-thiadiazol-4-yl]amino}methyl)[1,1'-biphenyl]-3-carboxamide trifluoroacetate Yield: 5.6 mg
HPLC analysis (condition B): purity 100% (retention time: 1.647 min.)
MS (APCI+): 604 (M+H)

EXAMPLE 92

N-(2-Aminoethyl)-3'-({[(E)-3-phenyl-2-propenoyl](3-phenylpropyl)amino}methyl)[1,1'-biphenyl]-3-carboxamide trifluoroacetate Yield: 4.4 mg
HPLC analysis (condition B): purity 100% (retention time: 1.743 min.)
MS (APCI−): 516 (M−H)

EXAMPLE 93

N-(2-Aminoethyl)-3'-({[(E)-3-(4-methoxyphenyl)-2-propenoyl](3-phenylpropyl)amino}methyl)[1,1'-biphenyl]-3-carboxamide trifluoroacetate Yield: 7.4 mg
HPLC analysis (condition B): purity 100% (retention time: 1.740 min.)
MS (APCI−): 546 (M−H)

EXAMPLE 94

3'-({[4-(Aminosulfonyl)phenethyl][(E)-3-(4-methoxyphenyl)-2-propenoyl]amino}methyl)-N-[2-(1-pyrrolidinyl)ethyl][1,1'-biphenyl]-3-carboxamide trifluoroacetate 1) 3-Bromo-N-formyl resin-N-[2-(1-pyrrolidinyl)ethyl]benzamide A mixture of 4-(4-formyl-3-methoxyphenoxy)butyrylaminomethyl resin (formyl resin: 4.20 g), 1-(2-aminoethyl)pyrrolidine (2.13 ml) and a solution of 5% acetic acid in dichloromethane (100 ml) was stirred at room temperature for 30 minutes, and then sodium triacetoxy borohydride (3.56 g) was added thereto, and the mixture was further stirred at room temperature for 15 hours. The solvent was removed by filtration, and the resin was washed with DMF, a mixed solvent of DMF-water (1:1), DMF, THF and methanol in this order and then dried at 50° C. under reduced pressure. The resultant resin was suspended in DMF (80 ml), and 3-bromobenzoic acid (3.38 g), PyBOP (8.74 g) and DIEA (2.93 ml) were added thereto, and the mixture was stirred at room temperature for 15 hours. The solvent was removed by filtration, and the resultant resin was washed with DMF, THF and methanol in this order and dried at 50° C. under reduced pressure to give the title compound (6.18 g). The amount of the compound carried on the resin was 0.95 mmol/g (elemental analysis: calculated from 7.55% Br). The resultant resin (5 beads) was treated with trifluoroacetic acid-dichloromethane (1:1; 50 ml) to give 3-bromo-N-[2-(1-pyrrolidinyl)ethyl]benzamide which was then analyzed in HPLC and measured by mass spectrometry.

HPLC analysis (condition B): purity 98% (retention time: 1.460 min.)
MS (APCI+): 297 (M+H), 299

2) 3'-Formyl-N-formyl resin-N-[2-(1-pyrrolidinyl)ethyl][1,1'-biphenyl]-3-carboxamide The title compound was produced in the same manner as in 2) in Example 71.
HPLC analysis (condition B): purity 95% (retention time: 1.214 min.)
MS (APCI+): 323 (M+H)

3) 3'-({[4-(Aminosulfonyl)phenethyl]amino}methyl)-N-formyl resin-N-[2-(1-pyrrolidinyl)ethyl][1,1'-biphenyl]-3-carboxamide The title compound was produced in the same manner as in 3) in Example 71.
Yield: 30 mg
HPLC analysis (condition B): purity 73% (retention time: 1.030 min.)
MS (APCI+): 507 (M+H)

4) 3'-({[4-(Aminosulfonyl)phenethyl][(E)-3-(4-methoxyphenyl)-2-propenoyl]amino}methyl)-N-[2-(1-pyrrolidinyl)ethyl][1,1'-biphenyl]-3-carboxamide trifluoroacetate The title compound was produced in the same manner as in 4) in Example 71.
Yield: 4.7 mg
$^1$H-NMR (Acetone-$d_6$) •: 1.90–2.20 (4H, m), 3.05 (2H, m), 3.22 (2H, m), 3.40–3.65 (7H, m), 3.70–4.00 (4H, m), 4.80 (2H,s), 6.40–6.60 (1H, m), 6.90–7.05 (2H, m), 7.20–8.00 (15H, m), 8.22 (1H, s).
HPLC analysis (condition B): purity 100% (retention time: 1.543 min.)
MS (APCI−): 667 (M1H)

The following compounds were produced in the same manner as in Example 94.

EXAMPLE 95

3'-({[4-(Aminosulfonyl)phenethyl][2-(4-bromophenyl)acetyl]amino}methyl)-N-[2-(1-pyrrolidinyl)ethyl][1,1'-biphenyl]-3-carboxamide trifluoroacetate Yield: 1.7 mg
HPLC analysis (condition B): purity 91% (retention time: 1.577 min.)
MS (APCI+): 703 (M+H), 705

EXAMPLE 96

3'-({[4-(Aminosulfonyl)phenethyl][2-(3-bromophenyl)acetyl]amino}methyl)-N-[2-(1-pyrrolidinyl)ethyl][1,1'-biphenyl]-3-carboxamide trifluoroacetate Yield: 3.7 mg
HPLC analysis (condition B): purity 100% (retention time: 1.571 min.)
MS (APCI+): 703 (M+H), 705

EXAMPLE 97

3'-({[4-(Aminosulfonyl)phenethyl][2-(2-bromophenyl)acetyl]amino}methyl)-N-[2-(1-pyrrolidinyl)ethyl][1,1'-biphenyl]-3-carboxamide trifluoroacetate Yield: 4.2 mg
HPLC analysis (condition B): purity 100% (retention time: 1.543 min.)
MS (APCI+): 703 (M+H), 705

EXAMPLE 98

3'-({[4-(Aminosulfonyl)phenethyl][(E)-3-phenyl-2-propenoyl]amino}methyl)-N-[2-(1-pyrrolidinyl)ethyl][1,1'-biphenyl]-3-carboxamide trifluoroacetate Yield: 4.2 mg
HPLC analysis (condition B): purity 100% (retention time: 1.543 min.)
MS (APCI+): 637 (M+H)

EXAMPLE 99

3'-({[4-(Aminosulfonyl)phenethyl][2-(benzyloxy)acetyl]amino}methyl)-N-[2-(1-pyrrolidinyl)ethyl][1,1'-biphenyl]-3-carboxamide trifluoroacetate Yield: 3.8 mg
HPLC analysis (condition B): purity 100% (retention time: 1.497 min.)
MS (APCI+): 655 (M+H)

EXAMPLE 100

3'-({[4-(Aminosulfonyl)phenethyl](4-phenylbutanoyl)amino}methyl)-N-[2-(1-pyrrolidinyl)ethyl][1,1'-biphenyl]-3-carboxamide trifluoroacetate Yield: 3.7 mg
HPLC analysis (condition B): purity 100% (retention time: 1.581 min.)
MS (APCI+): 653 (M+H)

EXAMPLE 101

3'-({[4-(Aminosulfonyl)phenethyl][3-(1H-indol-3-yl)propanoyl]amino}methyl)-N-[2-(1-pyrrolidinyl)ethyl][1,1'-biphenyl]-3-carboxamide trifluoroacetate Yield: 1.4 mg
HPLC analysis (condition B): purity 100% (retention time: 1.524 min.)
MS (APCI+): 678 (M+H)

EXAMPLE 102

3'-({[4-(Aminosulfonyl)phenethyl][2-(4-methoxyphenyl)acetyl]amino}methyl)-N-[2-(1-pyrrolidinyl)ethyl][1,1'-biphenyl]-3-carboxamide trifluoroacetate Yield: 4.3 mg HPLC analysis (condition B): purity 100% (retention time: 1.467 min.)
MS (APCI+): 655 (M+H)

EXAMPLE 103

3'-({[4-(Aminosulfonyl)phenethyl][2-(3-methoxyphenyl)acetyl]amino}methyl)-N-[2-(1-pyrrolidinyl)ethyl][1,1'-biphenyl]-3-carboxamide trifluoroacetate Yield: 3.5 mg
HPLC analysis (condition B): purity 100% (retention time: 1.491 min.)
MS (APCI+): 655 (M+H)

EXAMPLE 104

3'-({[4-(Aminosulfonyl)phenethyl][2-(3-fluorophenyl)acetyl]amino}methyl)-N-[2-(1-pyrrolidinyl)ethyl][1,1'-biphenyl]-3-carboxamide trifluoroacetate Yield: 3.2 mg
HPLC analysis (condition B): purity 100% (retention time: 1.490 min.)
MS (APCI+): 643 (M+H)

EXAMPLE 105

3'-({[4-(Aminosulfonyl)phenethyl][2-(benzoylamino)acetyl]amino}methyl)-N-[2-(1-pyrrolidinyl)ethyl][1,1'-biphenyl]-3-carboxamide trifluoroacetate Yield: 3.3 mg
HPLC analysis (condition B): purity 100% (retention time: 1.413 min.)
MS (APCI+): 668 (M+H)

EXAMPLE 106

3'-({[4-(Aminosulfonyl)benzyl][2-(4-bromophenyl)acetyl]amino}methyl)-N-[2-(1-pyrrolidinyl)ethyl][1,1'-biphenyl]-3-carboxamide trifluoroacetate Yield: 3.3 mg
HPLC analysis (condition B): purity 100% (retention time: 1.564 min.)
MS (APCI+): 689 (M+H), 691

EXAMPLE 107

3'-({[4-(Aminosulfonyl)benzyl][2-(2-bromophenyl)acetyl]amino}methyl)-N-[2-(1-pyrrolidinyl)ethyl][1,1'-biphenyl]-3-carboxamide trifluoroacetate Yield: 3.4 mg
HPLC analysis (condition B): purity 100% (retention time: 1.534 min.)
MS (APCI+): 689 (M+H), 691

EXAMPLE 108

3'-({[4-(Aminosulfonyl)benzyl][(E)-3-phenyl-2-propenoyl]amino}methyl)-N-[2-(1-pyrrolidinyl)ethyl][1,1'-biphenyl]-3-carboxamide trifluoroacetate Yield: 3.8 mg
HPLC analysis (condition B): purity 100% (retention time: 1.532 min.)
MS (APCI+): 623 (M+H)

EXAMPLE 109

3'-({[4-(Aminosulfonyl)benzyl][2-(benzyloxy)
acetyl]amino}methyl)-N-[2-(1-pyrrolidinyl)ethyl][1,
1'-biphenyl]-3-carboxamide trifluoroacetate Yield: 3.4 mg
HPLC analysis (condition B): purity 100% (retention time: 1.480 min.)
MS (APCI+): 641 (M+H)

EXAMPLE 110

3'-({[4-(Aminosulfonyl)benzyl](4-phenylbutanoyl)
amino}methyl)-N-[2-(1-pyrrolidinyl)ethyl][1,1'-
biphenyl]-3-carboxamide trifluoroacetate Yield: 4.7 mg
HPLC analysis (condition B): purity 100% (retention time: 1.576 min.)
MS (APCI+): 639 (M+H)

EXAMPLE 111

3'-({[4-(Aminosulfonyl)benzyl][3-(1H-indol-3-yl)
propanoyl]amino}methyl)-N-[2-(1-pyrrolidinyl)
ethyl][1,1'-biphenyl]-3-carboxamide trifluoroacetate Yield: 2.0 mg
HPLC analysis (condition B): purity 100% (retention time: 1.503 min.)
MS (APCI+): 664 (M+H)

EXAMPLE 112

3'-({[4-(Aminosulfonyl)benzyl][2-(3-methoxyphe-
nyl)acetyl]amino}methyl)-N-[2-(1-pyrrolidinyl)
ethyl][1,1'-biphenyl]-3-carboxamide trifluoroacetate Yield: 4.5 mg
HPLC analysis (condition B): purity 100% (retention time: 1.485 min.)
MS (APCI−): 641 (M−H)

EXAMPLE 113

3'-({[4-(Aminosulfonyl)benzyl][(E)-3-(4-methox-
yphenyl)-2-propenoyl]amino}methyl)-N-[2-(1-pyr-
rolidinyl)ethyl][1,1'-biphenyl]-3-carboxamide trif-
luoroacetate Yield: 5.6 mg
HPLC analysis (condition B): purity 100% (retention time: 1.527 min.)
MS (APCI+): 653 (M+H)

EXAMPLE 114

3'-({[4-(Aminosulfonyl)benzyl][2-(3-fluorophenyl)
acetyl]amino}methyl)-N-[2-(1-pyrrolidinyl)ethyl][1,
1'-biphenyl]-3-carboxamide trifluoroacetate Yield: 4.3 mg
HPLC analysis (condition B): purity 100% (retention time: 1.494 min.)
MS (APCI+): 629 (M+H)

EXAMPLE 115

3'-({[2-(4-Bromophenyl)acetyl][2-(4-pyridinyl)
ethyl]amino}methyl)-N-[2-(1-pyrrolidinyl)ethyl][1,
1'-biphenyl]-3-carboxamide trifluoroacetate Yield: 4.8 mg
HPLC analysis (condition B): purity 100% (retention time: 1.230 min.)
MS (APCI+): 625 (M+H), 627

EXAMPLE 116

3'-({[2-(3-Bromophenyl)acetyl][2-(4-pyridinyl)
ethyl]amino}methyl)-N-[2-(1-pyrrolidinyl)ethyl][1,
1'-biphenyl]-3-carboxamide trifluoroacetate Yield: 5.2 mg
HPLC analysis (condition B): purity 100% (retention time: 1.236 min.)
MS (APCI+): 625 (M+H), 627

EXAMPLE 117

3'-({[2-(2-Bromophenyl)acetyl][2-(4-pyridinyl)
ethyl]amino}methyl)-N-[2-(1-pyrrolidinyl)ethyl][1,
1'-biphenyl]-3-carboxamide trifluoroacetate Yield: 4.9 mg
HPLC analysis (condition B): purity 100% (retention time: 1.320 min.)
MS (APCI+): 625 (M+H), 627

EXAMPLE 118

3'-({[(E)-3-Phenyl-2-propenoyl][2-(4-pyridinyl)
ethyl]amino}methyl)-N-[2-(1-pyrrolidinyl)ethyl][1,
1'-biphenyl]-3-carboxamide trifluoroacetate Yield: 6.8 mg
HPLC analysis (condition B): purity 100% (retention time: 1.316 min.)
MS (APCI+): 559 (M+H)

EXAMPLE 119

3'-({(4-Phenylbutanoyl)[2-(4-pyridinyl)ethyl]
amino}methyl)-N-[2-(1-pyrrolidinyl)ethyl][1,1'-
biphenyl]-3-carboxamide trifluoroacetate Yield: 5.0 mg
HPLC analysis (condition B): purity 100% (retention time: 1.234 min.)
MS (APCI+): 575 (M+H)

EXAMPLE 120

3'-({[3-(1H-Indol-3-yl)propanoyl][2-(4-pyridinyl)
ethyl]amino}methyl)-N-[2-(1-pyrrolidinyl)ethyl][1,
1'-biphenyl]-3-carboxamide trifluoroacetate Yield: 1.5 mg
HPLC analysis (condition B): purity 100% (retention time: 1.308 min.)
MS (APCI+): 600 (M+H)

EXAMPLE 121

3'-({[2-(4-Methoxyphenyl)acetyl][2-(4-pyridinyl)ethyl]amino}methyl)-N-[2-(1-pyrrolidinyl)ethyl][1,1'-biphenyl]-3-carboxamide trifluoroacetate Yield: 6.6 mg
HPLC analysis (condition B): purity 100% (retention time: 1.264 min.)
MS (APCI+): 577 (M+H)

EXAMPLE 122

3'-({[2-(2-Bromophenyl)acetyl][2-(2-thienyl)ethyl]amino}methyl)-N-[2-(1-pyrrolidinyl)ethyl][1,1'-biphenyl]-3-carboxamide trifluoroacetate Yield: 2.8 mg
HPLC analysis (condition B): purity 100% (retention time: 1.749 min.)
MS (APCI+): 630 (M+H), 632

EXAMPLE 123

3'-({[2-(2-Thienyl)ethyl][(E)-3-phenyl-2-propenoyl]amino}methyl)-N-[2-(1-pyrrolidinyl)ethyl][1,1'-biphenyl]-3-carboxamide trifluoroacetate Yield: 3.3 mg
HPLC analysis (condition B): purity 100% (retention time: 1.728 min.)
MS (APCI+): 564 (M+H)

EXAMPLE 124

3'-({[2-(Benzyloxy)acetyl][2-(2-thienyl)ethyl]amino}methyl)-N-[2-(1-pyrrolidinyl)ethyl][1,1'-biphenyl]-3-carboxamide trifluoroacetate Yield: 3.5 mg
HPLC analysis (condition B): purity 100% (retention time: 1.682 min.)
MS (APCI+): 582 (M+H)

EXAMPLE 125

3'-({(4-Phenylbutanoyl)[2-(2-thienyl)ethyl]amino}methyl)-N-[2-(1-pyrrolidinyl)ethyl][1,1'-biphenyl]-3-carboxamide trifluoroacetate Yield: 3.3 mg
HPLC analysis (condition B): purity 100% (retention time: 1.776 min.)
MS (APCI+): 580 (M+H)

EXAMPLE 126

3'-({[3-(1H-Indol-3-yl)propanoyl][2-(2-thienyl)ethyl]amino}methyl)-N-[2-(1-pyrrolidinyl)ethyl][1,1'-biphenyl]-3-carboxamide trifluoroacetate Yield: 1.7 mg
HPLC analysis (condition B): purity 100% (retention time: 1.701 min.)
MS (APCI+): 605 (M+H)

EXAMPLE 127

3'-({[2-(4-Methoxyphenyl)acetyl][2-(2-thienyl)ethyl]amino}methyl)-N-[2-(1-pyrrolidinyl)ethyl][1,1'-biphenyl]-3-carboxamide trifluoroacetate Yield: 3.0 mg
HPLC analysis (condition B): purity 100% (retention time: 1.667 min.)
MS (APCI+): 582 (M+H)

EXAMPLE 128

3'-({[2-(3-Methoxyphenyl)acetyl][2-(2-thienyl)ethyl]amino}methyl)-N-[2-(1-pyrrolidinyl)ethyl][1,1'-biphenyl]-3-carboxamide trifluoroacetate Yield: 3.2 mg
HPLC analysis (condition B): purity 100% (retention time: 1.672 min.)
MS (APCI+): 582 (M+H)

EXAMPLE 129

3'-({[(E)-3-(4-Methoxyphenyl)-2-propenoyl][2-(2-thienyl)ethyl]amino}methyl)-N-[2-(1-pyrrolidinyl)ethyl][1,1'-biphenyl]-3-carboxamide trifluoroacetate Yield: 3.9 mg
HPLC analysis (condition B): purity 100% (retention time: 1.715 min.)
MS (APCI+): 594 (M+H)

EXAMPLE 130

3'-({[2-(3-Fluorophenyl)acetyl][2-(2-thienyl)ethyl]amino}methyl)-N-[2-(1-pyrrolidinyl)ethyl][1,1'-biphenyl]-3-carboxamide trifluoroacetate Yield: 1.1 mg
HPLC analysis (condition B): purity 100% (retention time: 1.700 min.)
MS (APCI+): 570 (M+H)

EXAMPLE 131

3'-({[2-(Benzoylamino)acetyl][2-(2-thienyl)ethyl]amino}methyl)-N-[2-(1-pyrrolidinyl)ethyl][1,1'-biphenyl]-3-carboxamide trifluoroacetate Yield: 3.5 mg
HPLC analysis (condition B): purity 100% (retention time: 1.583 min.)
MS (APCI+): 595 (M+H)

EXAMPLE 132

3'-({[2-(4-Bromophenyl)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 1.6 mg
HPLC analysis (condition B): purity 100% (retention time: 1.753 min.)
MS (APCI+): 694 (M+H), 696

EXAMPLE 133

3'-({[2-(3-Bromophenyl)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 3.7 mg
HPLC analysis (condition B): purity 100% (retention time: 1.729 min.)
MS (APCI+): 694 (M+H), 696

EXAMPLE 134

3'-({[2-(2-Bromophenyl)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 5.7 mg
HPLC analysis (condition B): purity 98% (retention time: 1.721 min.)
MS (APCI+): 694 (M+H), 696

EXAMPLE 135

3'-({[(E)-3-Phenyl-2-propenoyl][4-(1,2,3-thiadiazol-4-yl]amino}methyl)-N-[2-(1-pyrrolidinyl)ethyl][1,1'-biphenyl]-3-carboxamide trifluoroacetate Yield: 5.4 mg
HPLC analysis (condition B): purity 100% (retention time: 1.705 min.)
MS (APCI+): 628 (M+H)

EXAMPLE 136

3'-({[2-(Benzyloxy)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 2.1 mg
HPLC analysis (condition B): purity 100% (retention time: 1.662 min.)
MS (APCI+): 646 (M+H)

EXAMPLE 137

3'-({(4-Phenylbutanoyl)[4-(1,2,3-thiadiazol-4-yl]amino}methyl)-N-[2-(1-pyrrolidinyl)ethyl][1,1'-biphenyl]-3-carboxamide trifluoroacetate Yield: 1.1 mg
HPLC analysis (condition B): purity 100% (retention time: 1.759 min.)
MS (APCI+): 644 (M+H)

EXAMPLE 138

3'-({[3-(1H-Indol-3-yl)propanoyl][4-(1,2,3-thiadiazol-4-yl]amino}methyl)-N-[2-(1-pyrrolidinyl)ethyl][1,1'-biphenyl]-3-carboxamide trifluoroacetate Yield: 1.8 mg
HPLC analysis (condition B): purity 100% (retention time: 1.680 min.)
MS (APCI+): 669 (M+H)

EXAMPLE 139

3'-({[2-(4-Methoxyphenyl)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 5.4 mg
HPLC analysis (condition B): purity 100% (retention time: 1.652 min.)
MS (APCI+): 646 (M+H)

EXAMPLE 140

3'-({[2-(3-Methoxyphenyl)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 5.0 mg
HPLC analysis (condition B): purity 100% (retention time: 1.651 min.)
MS (APCI+): 582 (M+H)

EXAMPLE 141

3'-({[(E)-3-(4-Methoxyphenyl)-2-propenoyl][4-(1,2,3-thiadiazol-4-yl]amino}methyl)-N-[2-(1-pyrrolidinyl)ethyl][1,1'-biphenyl]-3-carboxamide trifluoroacetate Yield: 5.5 mg
HPLC analysis (condition B): purity 100% (retention time: 1.708 min.)
MS (APCI+): 658 (M+H)

EXAMPLE 142

3'-({[2-(3-Fluorophenyl)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 3.8 mg
HPLC analysis (condition B): purity 100% (retention time: 1.673 min.)
MS (APCI+): 634 (M+H)

EXAMPLE 143

3'-({[2-(Benzoylamino)acetyl][4-(1,2,3-thiadiazol-4-yl]amino}methyl)-N-[2-(1-pyrrolidinyl)ethyl][1,1'-biphenyl]-3-carboxamide trifluoroacetate Yield: 4.4 mg
HPLC analysis (condition B): purity 100% (retention time: 1.566 min.)
MS (APCI+): 659 (M+H)

EXAMPLE 144

3'-({[2-(4-Bromophenyl)acetyl](3-phenylpropyl)amino}methyl)-N-[2-(1-pyrrolidinyl)ethyl][1,1'-biphenyl]-3-carboxamide trifluoroacetate Yield: 4.0 mg
HPLC analysis (condition B): purity 100% (retention time: 1.831 min.)
MS (APCI+): 638 (M+H), 640

EXAMPLE 145

3'-({[2-(3-Bromophenyl)acetyl](3-phenylpropyl)
amino}methyl)-N-[2-(1-pyrrolidinyl)ethyl][1,1'-
biphenyl]-3-carboxamide trifluoroacetate Yield: 3.3 mg
HPLC analysis (condition B): purity 100% (retention time: 1.822 min.)
MS (APCI+): 638 (M+H), 640

EXAMPLE 146

3'-({[2-(2-Bromophenyl)acetyl](3-phenylpropyl)
amino}methyl)-N-[2-(1-pyrrolidinyl)ethyl][1,1'-
biphenyl]-3-carboxamide trifluoroacetate Yield: 1.0 mg
HPLC analysis (condition B): purity 98% (retention time: 1.814 min.)
MS (APCI+): 638 (M+H), 640

EXAMPLE 147

3'-({[(E)-3-Phenyl-2-propenoyl](3-phenylpropyl)
amino}methyl)-N-[2-(1-pyrrolidinyl)ethyl][1,1'-
biphenyl]-3-carboxamide trifluoroacetate Yield: 4.1 mg
HPLC analysis (condition B): purity 100% (retention time: 1.798 min.)
MS (APCI+): 572 (M+H)

EXAMPLE 148

3'-({[2-(Benzyloxy)acetyl](3-phenylpropyl)
amino}methyl)-N-[2-(1-pyrrolidinyl)ethyl][1,1'-
biphenyl]-3-carboxamide trifluoroacetate Yield: 4.6 mg
HPLC analysis (condition B): purity 100% (retention time: 1.754 min.)
MS (APCI+): 590 (M+H)

EXAMPLE 149

3'-({(4-Phenylbutanoyl)(3-phenylpropyl)
amino}methyl)-N-[2-(1-pyrrolidinyl)ethyl][1,1'-
biphenyl]-3-carboxamide trifluoroacetate Yield: 4.8 mg
HPLC analysis (condition B): purity 100% (retention time: 1.844 min.)
MS (APCI+): 588 (M+H)

EXAMPLE 150

3'-({[3-(1H-Indol-3-yl)propanoyl](3-phenylpropyl)
amino}methyl)-N-[2-(1-pyrrolidinyl)ethyl][1,1'-
biphenyl]-3-carboxamide trifluoroacetate Yield: 1.7 mg
HPLC analysis (condition B): purity 100% (retention time: 1.761 min.)
MS (APCI+): 613 (M+H)

EXAMPLE 151

3'-([{2-(4-Methoxyphenyl)acetyl](3-phenylpropyl)
amino}methyl)-N-[2-(1-pyrrolidinyl)ethyl][1,1'-
biphenyl]-3-carboxamide trifluoroacetate Yield: 3.2 mg
HPLC analysis (condition B): purity 100% (retention time: 1.724 min.)
MS (APCI+): 590 (M+H)

EXAMPLE 152

3'-({[2-(3-Methoxyphenyl)acetyl](3-phenylpropyl)
amino}methyl)-N-[2-(1-pyrrolidinyl)ethyl][1,1'-
biphenyl]-3-carboxamide trifluoroacetate Yield: 4.0 mg
HPLC analysis (condition B): purity 100% (retention time: 1.737 min.)
MS (APCI+): 590 (M+H)

EXAMPLE 153

3'-({[(E)-3-(4-Methoxyphenyl)-2-propenoyl](3-phe-
nylpropyl)amino}methyl)-N-[2-(1-pyrrolidinyl)
ethyl][1,1'-biphenyl]-3-carboxamide trifluoroacetate Yield: 4.7 mg
HPLC analysis (condition B): purity 100% (retention time: 1.791 min.)
MS (APCI+): 602 (M+H)

EXAMPLE 154

3'-({[2-(3-Fluorophenyl)acetyl](3-phenylpropyl)
amino}methyl)-N-[2-(1-pyrrolidinyl)ethyl][1,1'-
biphenyl]-3-carboxamide trifluoroacetate Yield: 5.7 mg
HPLC analysis (condition B): purity 100% (retention time: 1.758 min.)
MS (APCI+): 578

EXAMPLE 155

3'-({[2-(Benzoylamino)acetyl](3-phenylpropyl)
amino}methyl)-N-[2-(1-pyrrolidinyl)ethyl][1,1'-
biphenyl]-3-carboxamide trifluoroacetate Yield: 5.0 mg
HPLC analysis (condition B): purity 100% (retention time: 1.648 min.)
MS (APCI+): 603 (M+H)

EXAMPLE 156

Methyl 4-[([2-(4-bromophenyl)acetyl]{[3'-({[2-(1-
pyrrolidinyl)ethyl]amino}carbonyl)[1,1'-biphenyl]-
3-yl]methyl}amino)methyl]benzoate trifluoroacetate Yield: 1.4 mg
HPLC analysis (condition B): purity 100% (retention time: 1.740 min.)
MS (APCI+): 668 (M+H), 670

EXAMPLE 157

Methyl 4-[([2-(3-bromophenyl)acetyl]{[3'-({[2-(1-pyrrolidinyl)ethyl]amino}carbonyl)[1,1'-biphenyl]-3-yl]methyl}amino)methyl]benzoate trifluoroacetate Yield: 3.1 mg
HPLC analysis (condition B): purity 94% (retention time: 1.735 min.)
MS (APCI+): 668 (M+H), 670

EXAMPLE 158

Methyl 4-[([2-(2-Bromophenyl)acetyl]{[3'-({[2-(1-pyrrolidinyl)ethyl]amino}carbonyl)[1,1'-biphenyl]-3-yl]methyl}amino)methyl]benzoate trifluoroacetate Yield: 5.7 mg
HPLC analysis (condition B): purity 95% (retention time: 1.718 min.)
MS (APCI+): 668 (M+H), 670

EXAMPLE 159

Methyl 4-[([(E)-3-phenyl-2-propenoyl]{[3'-({[2-(1-pyrrolidinyl)ethyl]amino}carbonyl)[1,1'-biphenyl]-3-yl]methyl}amino)methyl]benzoate trifluoroacetate Yield: 1.5 mg
HPLC analysis (condition B): purity 97% (retention time: 1.700 min.)
MS (APCI+): 602 (M+H)

EXAMPLE 160

Methyl 4-[([2-(Benzyloxy)acetyl]{[3'-({[2-(1-pyrrolidinyl)ethyl]amino}carbonyl)[1,1'-biphenyl]-3-yl]methyl}amino)methyl]benzoate trifluoroacetate Yield: 1.5 mg
HPLC analysis (condition B): purity 100% (retention time: 1.648 min.)
MS (APCI+): 620 (M+H)

EXAMPLE 161

Methyl 4-[({(4-Phenylbutanoyl){[3'-({[2-(1-pyrrolidinyl)ethyl]amino}carbonyl)[1,1'-biphenyl]-3-yl]methyl}amino)methyl]benzoate trifluoroacetate Yield: 5.0 mg
HPLC analysis (condition B): purity 100% (retention time: 1.748 min.)
MS (APCI+): 618 (M+H)

EXAMPLE 162

Methyl 4-[({[3-(1H-Indol-3-yl)propanoyl]{[3'-({[2-(1-pyrrolidinyl)ethyl]amino}carbonyl)[1,1'-biphenyl]-3-yl]methyl}amino)methyl]benzoate trifluoroacetate Yield: 0.7 mg
HPLC analysis (condition B): purity 100% (retention time: 1.674 min.)
MS (APCI+): 643 (M+H)

EXAMPLE 163

Methyl 4-[({[2-(3-Methoxyphenyl)acetyl]{[3'-({[2-(1-pyrrolidinyl)ethyl]amino}carbonyl)[1,1'-biphenyl]-3-yl]methyl}amino)methyl]benzoate trifluoroacetate Yield: 1.0 mg
HPLC analysis (condition B): purity 100% (retention time: 1.641 min.)
MS (APCI+): 620 (M+H)

EXAMPLE 164

Methyl 4-[({[(E)-3-(4-Methoxyphenyl)-2-propenoyl]{[3'-({[2-(1-pyrrolidinyl)ethyl]amino}carbonyl)[1,1'-biphenyl]-3-yl]methyl}amino)methyl]benzoate trifluoroacetate Yield: 0.9 mg
HPLC analysis (condition B): purity 100% (retention time: 1.697 min.)
MS (APCI+): 632 (M+H)

EXAMPLE 165

Methyl 4-[({[2-(3-Fluorophenyl)acetyl]{[3'-({[2-(1-pyrrolidinyl)ethyl]amino}carbonyl)[1,1'-biphenyl]-3-yl]methyl}amino)methyl]benzoate trifluoroacetate Yield: 4.2 mg
HPLC analysis (condition B): purity 100% (retention time: 1.672 min.)
MS (APCI+): 608 (M+H)

EXAMPLE 166

Methyl 6-[(2-(4-Bromophenyl)acetyl]{[3'-({[2-(1-pyrrolidinyl)ethyl]amino}carbonyl)[1,1'-biphenyl]-3-yl]methyl}amino)hexanoate trifluoroacetate Yield: 3.0 mg
HPLC analysis (condition B): purity 100% (retention time: 1.696 min.)
MS (APCI+): 648 (M+H), 650

EXAMPLE 167

Methyl 6-[(2-(3-Bromophenyl)acetyl]{[3'-({[2-(1-pyrrolidinyl)ethyl]amino}carbonyl)[1,1'-biphenyl]-3-yl]methyl}amino)hexanoate trifluoroacetate Yield: 1.1 mg
HPLC analysis (condition B): purity 100% (retention time: 1.691 min.)
MS (APCI+): 648 (M+H), 650

EXAMPLE 168

Methyl 6-[(2-(2-Bromophenyl)acetyl]{[3'-({[2-(1-pyrrolidinyl)ethyl]amino}carbonyl)[1,1'-biphenyl]-3-yl]methyl}amino)hexanoate trifluoroacetate Yield: 2.9 mg
HPLC analysis (condition B): purity 100% (retention time: 1.670 min.)
MS (APCI+): 648 (M+H), 650

EXAMPLE 169

Methyl 6-([(E)-3-Phenyl-2-propenoyl]{[3'-({[2-(1-pyrrolidinyl)ethyl]amino}carbonyl)[1,1'-biphenyl]-3-yl]methyl}amino)hexanoate trifluoroacetate Yield: 1.0 mg
HPLC analysis (condition B): purity 100% (retention time: 1.655 min.)
MS (APCI+): 582 (M+H)

EXAMPLE 170

Methyl 6-([4-Phenylbutanoyl]{[3'-({[2-(1-pyrrolidinyl)ethyl]amino}carbonyl)[1,1'-biphenyl]-3-yl]methyl}amino)hexanoate trifluoroacetate Yield: 3.4 mg
HPLC analysis (condition B): purity 100% (retention time: 1.699 min.)
MS (APCI+): 598 (M+H)

EXAMPLE 171

Methyl 6-([3-(1H-Indol-3-yl)propanoyl]{[3'-({[2-(1-pyrrolidinyl)ethyl]amino}carbonyl)[1,1'-biphenyl]-3-yl]methyl}amino)hexanoate trifluoroacetate Yield: 1.0 mg
HPLC analysis (condition B): purity 100% (retention time: 1.629 min.)
MS (APCI+): 623 (M+H)

EXAMPLE 172

Methyl 6-([(E)-3-(4-Methoxyphenyl)-2-propenoyl]{[3'-({[2-(1-pyrrolidinyl)ethyl]amino}carbonyl)[1,1'-biphenyl]-3-yl]methyl}amino)hexanoate trifluoroacetate Yield: 3.5 mg
HPLC analysis (condition B): purity 100% (retention time: 1.659 min.) MS (APCI+): 612 (M+H)

EXAMPLE 173

Methyl 6-([2-(3-Fluorophenyl)acetyl]{[3'-({[2-(1-pyrrolidinyl)ethyl]amino}carbonyl)[1,1'-biphenyl]-3-yl]methyl}amino)hexanoate trifluoroacetate Yield: 2.1 mg
HPLC analysis (condition B): purity 100% (retention time: 1.620 min.)
MS (APCI+): 588 (M+H)

EXAMPLE 174

N-[4-(Aminosulfonyl)phenethyl]-2-(4-bromophenyl)-N-{[3'-({4-[3-(4-piperidinyl)propyl]-1-piperidinyl}carbonyl)[1,1'-biphenyl]-3-yl]methyl}acetamide trifluoroacetate 1) 4-{3-[1-(3-Bromobenzoyl)-4-piperidinyl]propyl}-1-piperidine carboxylic acid Wang resin ester A mixture of 4-nitrophenoxycarbonyl Wang resin (6.00 g), (3-bromophenyl){4-[3-(4-piperidinyl)propyl]-1-piperidinyl}methanone hydrochloride (4.66 g), DIEA (3.76 ml) and DMF (50 ml) was stirred at room temperature for 20 hours. The solvent was removed by filtration, and the resultant resin was washed with DMF, THF and methanol in this order and then dried at 50° C. under reduced pressure to give the title compound (6.95 g). The amount of the compound carried on the resin was 0.72 mmol/g (elemental analysis: calculated from 5.77% Br). The resultant resin (5 beads) was treated with trifluoroacetic acid-dichloromethane (1:1; 50 ml) to give (3-bromophenyl){4-[3-(4-piperidinyl)propyl]-1-piperidinyl}methanone which was then analyzed in HPLC and measured by mass spectrometry.

HPLC analysis (condition B): purity 97% (retention time: 1.437 min.)
MS (APCI+): 393 (M+H), 395

2) 4-{3-{1-[(3'-Formyl[1,1'-biphenyl]-3-yl)carbonyl]-4-piperidinyl]propyl}-1-piperidine carboxylic acid Wang resin ester The title compound was obtained in the same manner as in 2) in Example 71.

Yield: 7.60 g
HPLC analysis (condition B): purity 94% (retention time: 1.484 min.)
MS (APCI+): 419 (M+H)

3) 4-{3-{1-[(3'-({[4-(Aminosulfonyl)phenethyl]amino}methyl)[1,1'-biphenyl]-3-yl)carbonyl]-4-piperidinyl]propyl}-1-piperidine carboxylic acid Wang resin ester The title compound was obtained in the same manner as in 3) in Example 71.

Yield: 30 mg
HPLC analysis (condition B): purity 67% (retention time: 1.293 min.)
MS (APCI+): 603 (M+H)

4) N-[4-(Aminosulfonyl)phenethyl]-2-(4-bromophenyl)-N-{[3'-({4-[3-(4-piperidinyl)propyl]-1-piperidinyl}carbonyl)[1,1'-biphenyl]-3-yl]methyl}acetamide trifluoroacetate The title compound was obtained in the same manner as in 4) in Example 71.

Yield: 6.0 mg
$^1$H-NMR (Acetone-$d_6$) •: 1.00–2.00 (16H, m), 2.90–3.40 (8H, m), 3.40–3.60 (2H, m), 3.60–3.80 (2H, m), 3.81 (2H,s), 4.78 (2H, s), 6.55–6.65 (2H, m), 7.14–7.25 (4H, m), 7.30–7.50 (8H, m), 7.60–7.90 (2H, m).
HPLC analysis (condition B): purity 98% (retention time: 1.702 min.)
MS (APCI+): 798 (M+H), 800

The following compounds were produced in the same manner as in Example 174.

EXAMPLE 175

N-[4-(Aminosulfonyl)phenethyl]-2-(3-bromophenyl)-N-{[3'-({4-[3-(4-piperidinyl) propyl]-1-piperidinyl}carbonyl)[1,1'-biphenyl]-3-yl]methyl}acetamide trifluoroacetate Yield: 6.8 mg
HPLC analysis (condition B): purity 100% (retention time: 1.687 min.)
MS (APCI−): 797 (M−H), 799

EXAMPLE 176

N-[4-(Aminosulfonyl)phenethyl]-2-(2-bromophenyl)-N-{[3'-({4-[3-(4-piperidinyl)propyl]-1-piperidinyl}carbonyl)[1,1'-biphenyl]-3-yl]methyl}acetamide trifluoroacetate Yield: 6.4 mg
HPLC analysis (condition B): purity 100% (retention time: 1.677 min.)
MS (APCI-): 797 (M–H), 799

EXAMPLE 177

(E)-N-[4-(Aminosulfonyl)phenethyl]-3-phenyl-N-{[3'-({4-[3-(4-piperidinyl)propyl]-1-piperidinyl}carbonyl)[1,1'-biphenyl]-3-yl]methyl}-2-propenamide trifluoroacetate Yield: 6.0 mg
HPLC analysis (condition B): purity 100% (retention time: 1.656 min.)
MS (APCI-): 731 (M–H)

EXAMPLE 178

N-[4-(Aminosulfonyl)phenethyl]-2-(benzyloxy)-N-{[3'-({4-[3-(4-piperidinyl)propyl]-1-piperidinyl}carbonyl)[1,1'-biphenyl]-3-yl]methyl}acetamide trifluoroacetate Yield: 6.6 mg
HPLC analysis (condition B): purity 100% (retention time: 1.625 min.)
MS (APCI-): 751 (M–H)

EXAMPLE 179

N-[4-(Aminosulfonyl)phenethyl]-4-phenyl-N-{[3'-({4-[3-(4-piperidinyl)propyl]-1-piperidinyl}carbonyl)[1,1'-biphenyl]-3-yl]methyl}butanamide trifluoroacetate Yield: 5.7 mg
HPLC analysis (condition B): purity 100% (retention time: 1.700 min.)
MS (APCI-): 747 (M–H)

EXAMPLE 180

N-[4-(Aminosulfonyl)phenethyl]-2-(4-methoxyphenyl)-N-{[3'-({4-[3-(4-piperidinyl)propyl]-1-piperidinyl}carbonyl)[1,1'-biphenyl]-3-yl]methyl)acetamide trifluoroacetate Yield: 1.7 mg
HPLC analysis (condition B): purity 100% (retention time: 1.615 min.)
MS (APCI-): 749 (M–H)

EXAMPLE 181

N-[4-(Aminosulfonyl)phenethyl]-2-(3-methoxyphenyl)-N-{[3'-({4-[3-(4-piperidinyl)propyl]-1-piperidinyl}carbonyl)[1,1'-biphenyl]-3-yl]methyl}acetamide trifluoroacetate Yield: 1.0 mg
HPLC analysis (condition B): purity 100% (retention time: 1.619 min.)
MS (APCI-): 749 (M–H)

EXAMPLE 182

(E)-N-[4-(Aminosulfonyl)phenethyl]-3-(4-methoxyphenyl)-N-{[3'-({4-[3-(4-piperidinyl)propyl]-1-piperidinyl}carbonyl)[1,1'-biphenyl]-3-yl]methyl}-2-propenamide trifluoroacetate Yield: 1.9 mg
HPLC analysis (condition B): purity 100% (retention time: 1.661 min.)
MS (APCI-): 761 (M–H)

EXAMPLE 183

N-[4-(Aminosulfonyl)phenethyl]-2-(3-fluorophenyl)-N-{[3'-({4-[3-(4-piperidinyl)propyl]-1-piperidinyl}carbonyl)[1,1'-biphenyl]-3-yl]methyl}acetamide trifluoroacetate Yield: 4.9 mg
HPLC analysis (condition B): purity 100% (retention time: 1.633 min.)
MS (APCI-): 737 (M–H)

EXAMPLE 184

N-[2-([4-(Aminosulfonyl)phenethyl]{[3'-({4-[3-(4-piperidinyl)propyl]-1-piperidinyl}carbonyl)[1,1'-biphenyl]-3-yl]methyl}amino)-2-oxyethyl]benzamide trifluoroacetate Yield: 1.2 mg
HPLC analysis (condition B): purity 100% (retention time: 1.563 min.)
MS (APCI-): 762 (M–H)

EXAMPLE 185

N-[4-(Aminosulfonyl)benzyl]-2-(4-bromophenyl)-N-{[3'-({4-[3-(4-piperidinyl)propyl]-1-piperidinyl}carbonyl)[1,1'-biphenyl]-3-yl]methyl}acetamide trifluoroacetate Yield: 1.9 mg
HPLC analysis (condition B): purity 100% (retention time: 1.698 min.)
MS (APCI-): 783 (M–H), 785

EXAMPLE 186

N-[4-(Aminosulfonyl)benzyl]-2-(3-bromophenyl)-N-{[3'-({4-[3-(4-piperidinyl)propyl]-1-piperidinyl}carbonyl)[1,1'-biphenyl]-3-yl]methyl}acetamide trifluoroacetate Yield: 6.5 mg
HPLC analysis (condition B): purity 100% (retention time: 1.686 min.)
MS (APCI-): 783 (M–H), 785

EXAMPLE 187

N-[4-(Aminosulfonyl)benzyl]-2-(2-bromophenyl)-N-{[3'-({4-[3-(4-piperidinyl)propyl]-1-piperidinyl}carbonyl)[1,1'-biphenyl]-3-yl]methyl}acetamide trifluoroacetate Yield: 2.8 mg
HPLC analysis (condition B): purity 100% (retention time: 1.676 min.)
MS (APCI-): 783 (M–H), 785

EXAMPLE 188

(E)-N-[4-(Aminosulfonyl)benzyl]-3-phenyl-N-{[3'-({4-[3-(4-piperidinyl)propyl]-1-piperidinyl}carbonyl)[1,1'-biphenyl]-3-yl]methyl}-2-propenamide trifluoroacetate Yield: 1.0 mg
HPLC analysis (condition B): purity 100% (retention time: 1.615 min.)
MS (APCI−): 717 (M−H)

EXAMPLE 189

N-[4-(Aminosulfonyl)benzyl]-2-(benzyloxy)-N-{[3'-({4-[3-(4-piperidinyl)propyl]-1-piperidinyl}carbonyl)[1,1'-biphenyl]-3-yl]methyl}acetamide trifluoroacetate Yield: 2.0 mg
HPLC analysis (condition B): purity 100% (retention time: 1.622 min.)
MS (APCI−): 735 (M−H)

EXAMPLE 190

N-[4-(Aminosulfonyl)benzyl]-4-phenyl-N-{[3'-({4-[3-(4-piperidinyl)propyl]-1-piperidinyl}carbonyl)[1,1'-biphenyl]-3-yl]methyl}butanamide trifluoroacetate Yield: 5.2 mg
HPLC analysis (condition B): purity 100% (retention time: 1.692 min.)
MS (APCI−): 733 (M−H)

EXAMPLE 191

N-[4-(Aminosulfonyl)benzyl]-2-(4-methoxyphenyl)-N-{[3'-({4-[3-(4-piperidinyl)propyl]-1-piperidinyl}carbonyl)[1,1'-biphenyl]-3-yl]methyl}acetamide trifluoroacetate Yield: 3.8 mg
HPLC analysis (condition B): purity 100% (retention time: 1.603 min.)
MS (APCI−): 735 (M−H)

EXAMPLE 192

N-[4-(Aminosulfonyl)benzyl]-2-(3-methoxyphenyl)-N-{[3'-({4-[3-(4-piperidinyl)propyl]-1-piperidinyl}carbonyl)[1,1'-biphenyl]-3-yl]methyl}acetamide trifluoroacetate Yield: 0.8 mg
HPLC analysis (condition B): purity 100% (retention time: 1.609 min.)
MS (APCI−): 735 (M−H)

EXAMPLE 193

(E)-N-[4-(Aminosulfonyl)benzyl]-3-(4-methoxyphenyl)-N-{[3'-({4-[3-(4-piperidinyl)propyl]-1-piperidinyl)carbonyl)[1,1'-biphenyl]-3-yl]methyl}-2-propenamide trifluoroacetate Yield: 3.6 mg
HPLC analysis (condition B): purity 100% (retention time: 1.647 min.)
MS (APCI−): 747 (M−H)

EXAMPLE 194

N-[4-(Aminosulfonyl)benzyl]-2-(3-fluorophenyl)-N-{[3'-({4-[3-(4-piperidinyl)propyl]-1-piperidinyl}carbonyl)[1,1'-biphenyl]-3-yl]methyl}acetamide trifluoroacetate Yield: 5.1 mg
HPLC analysis (condition B): purity 100% (retention time: 1.624 min.)
MS (APCI−): 723 (M−H)

EXAMPLE 195

N-[2-([4-(Aminosulfonyl)benzyl]{[3'-({4-[3-(4-piperidinyl)propyl]-1-piperidinyl}carbonyl)[1,1'-biphenyl]-3-yl]methyl}amino)-2-oxyethyl]benzamide trifluoroacetate Yield: 1.1 mg
HPLC analysis (condition B): purity 100% (retention time: 1.540 min.)
MS (APCI−): 748 (M−H)

EXAMPLE 196

2-(4-Bromophenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]acetamide trifluoroacetate Yield: 7.7 mg
HPLC analysis (condition B): purity 100% (retention time: 1.469 min.)
MS (APCI+): 721 (M+H), 723

EXAMPLE 197

2-(3-Bromophenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]acetamide trifluoroacetate Yield: 6.4 mg
HPLC analysis (condition B): purity 100% (retention time: 1.491 min.)
MS (APCI+): 721 (M+H), 723

EXAMPLE 198

2-(2-Bromophenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]acetamide trifluoroacetate Yield: 6.7 mg
HPLC analysis (condition B): purity 100% (retention time: 1.470 min.)
MS (APCI+): 721 (M+H), 723

EXAMPLE 199

(E)-3-Phenyl-N-{[3'-({4-[3-(4-piperidinyl)propyl]-1-piperidinyl}carbonyl)[1,1'-biphenyl]-3-yl]methyl}-N-[2-(4-pyridinyl)ethyl]-2-propenamide trifluoroacetate Yield: 6.7 mg
HPLC analysis (condition B): purity 100% (retention time: 1.454 min.)
MS (APCI+): 655 (M+H)

EXAMPLE 200

4-Phenyl-N-{[3'-({4-[3-(4-piperidinyl)propyl]-1-piperidinyl}carbonyl)[1,1'-biphenyl]-3-yl]methyl}-N-[2-(4-pyridinyl)ethyl]butanamide trifluoroacetate Yield: 2.1 mg
HPLC analysis (condition B): purity 100% (retention time: 1.495 min.)
MS (APCI+): 672 (M+H)

EXAMPLE 201

3-(1H-Indol-3-yl)-N-{[3'-({4-[3-(4-piperidinyl)propyl]-1-piperidinyl}carbonyl)[1,1'-biphenyl]-3-yl]methyl}-N-[2-(4-pyridinyl)ethyl]propanamide trifluoroacetate Yield: 2.5 mg
HPLC analysis (condition B): purity 100% (retention time: 1.416 min.)
MS (APCI+): 694 (M+H)

EXAMPLE 202

2-(4-Methoxyphenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]acetamide trifluoroacetate Yield: 5.8 mg
HPLC analysis (condition B): purity 100% (retention time: 1.417 min.)
MS (APCI+): 673 (M+H)

EXAMPLE 203

2-(3-Methoxyphenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]acetamide trifluoroacetate Yield: 4.6 mg
HPLC analysis (condition B): purity 100% (retention time: 1.419 min.)
MS (APCI+): 673 (M+H)

EXAMPLE 204

(E)-3-(4-Methoxyphenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]-2-propenamide trifluoroacetate Yield: 5.1 mg
HPLC analysis (condition B): purity 100% (retention time: 1.447 min.)
MS (APCI+): 685 (M+H)

EXAMPLE 205

2-(3-Fluorophenyl)-N-{[3'-({4-[3-(4-piperidinyl)propyl]-1-piperidinyl}carbonyl)[1,1'-biphenyl]-3-yl]methyl}-N-[2-(4-pyridinyl)ethyl]acetamide trifluoroacetate Yield: 6.1 mg
HPLC analysis (condition B): purity 100% (retention time: 1.430 min.)
MS (APCI+): 661 (M+H)

EXAMPLE 206

N-(2-Oxo-2-{{[3'-({4-[3-(4-piperidinyl)propyl]-1-piperidinyl}carbonyl)[1,1'-biphenyl]-3-yl]methyl}[2-(4-pyridinyl)ethyl]amino}ethyl)benzamide trifluoroacetate Yield: 6.9 mg
HPLC analysis (condition B): purity 100% (retention time: 1.369 min.)
MS (APCI+): 686 (M+H)

EXAMPLE 207

2-(4-Bromophenyl)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 2.3 mg
HPLC analysis (condition B): purity 100% (retention time: 1.871 min.)
MS (APCI+): 726 (M+H), 728

EXAMPLE 208

2-(3-Bromophenyl)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 1.9 mg
HPLC analysis (condition B): purity 100% (retention time: 1.860 min.)
MS (APCI+): 726 (M+H), 728

EXAMPLE 209

2-(2-Bromophenyl)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 1.7 mg
HPLC analysis (condition B): purity 100% (retention time: 1.859 min.)
MS (APCI+): 726 (M+H), 728

EXAMPLE 210

(E)-3-Phenyl-N-{[3'-({4-[3-(4-piperidinyl)propyl]-1-piperidinyl}carbonyl)[1,1'-biphenyl]-3-yl]methyl}-N-[2-(2-thienyl)ethyl]-2-propenamide trifluoroacetate Yield: 2.4 mg
HPLC analysis (condition B): purity 100% (retention time: 1.835 min.)
MS (APCI+): 660 (M+H)

EXAMPLE 211

2-(Benzyloxy)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 2.1 mg
HPLC analysis (condition B): purity 100% (retention time: 1.803 min.)
MS (APCI+): 678 (M+H)

EXAMPLE 212

4-Phenyl-N-{[3'-({4-[3-(4-piperidinyl)propyl]-1-piperidinyl}carbonyl)[1,1'-biphenyl]-3-yl]methyl}-N-[2-(2-thienyl)ethyl]butanamide trifluoroacetate Yield: 1.0 mg
HPLC analysis (condition B): purity 100% (retention time: 1.879 min.)
MS (APCI+): 676 (M+H)

EXAMPLE 213

3-(1H-Indol-3-yl)-N-{[3'-({4-[3-(4-piperidinyl)propyl]-1-piperidinyl}carbonyl)[1,1'-biphenyl]-3-yl]methyl}-N-[2-(2-thienyl)ethyl]propanamide trifluoroacetate Yield: 1.1 mg
HPLC analysis (condition B): purity 100% (retention time: 1.804 min.)
MS (APCI+): 701 (M+H)

EXAMPLE 214

2-(4-Methoxyphenyl)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 1.8 mg
HPLC analysis (condition B): purity 100% (retention time: 1.753 min.)
MS (APCI+): 678 (M+H)

EXAMPLE 215

2-(3-Methoxyphenyl)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 2.3 mg
HPLC analysis (condition B): purity 100% (retention time: 1.781 min.)
MS (APCI+): 678 (M+H)

EXAMPLE 216

(E)-3-(4-Methoxyphenyl)-N-{[3'-({4-[3-(4-piperidinyl)propyl]-1-piperidinyl}carbonyl)[1,1'-biphenyl]-3-yl]methyl}-N-[2-(2-thienyl)ethyl]-2-propenamide trifluoroacetate Yield: 2.6 mg
HPLC analysis (condition B): purity 100% (retention time: 1.830 min.)
MS (APCI+): 690 (M+H)

EXAMPLE 217

2-(3-Fluorophenyl)-N-{[3'-({4-[3-(4-piperidinyl)propyl]-1-piperidinyl}carbonyl)[1,1'-biphenyl]-3-yl]methyl}-N-[2-(2-thienyl)ethyl]acetamide trifluoroacetate Yield: 2.3 mg
HPLC analysis (condition B): purity 100% (retention time: 1.807 min.)
MS (APCI+): 666 (M+H)

EXAMPLE 218

N-(2-Oxo-2-{{[3'-({4-[3-(4-piperidinyl)propyl]-1-piperidinyl}carbonyl)[1,1'-biphenyl]-3-yl]methyl}[2-(2-thienyl)ethyl]amino}ethyl)benzamide trifluoroacetate Yield: 0.9 mg
HPLC analysis (condition B): purity 100% (retention time: 1.698 min.)
MS (APCI+): 691 (M+H)

EXAMPLE 219

2-(4-Bromophenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 5.3 mg
HPLC analysis (condition B): purity 100% (retention time: 1.862 min.)
MS (APCI+): 790 (M+H), 792

EXAMPLE 220

2-(3-Bromophenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 5.3 mg
HPLC analysis (condition B): purity 100% (retention time: 1.852 min.)
MS (APCI+): 790 (M+H), 792

EXAMPLE 221

2-(2-Bromophenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 4.7 mg
HPLC analysis (condition B): purity 100% (retention time: 1.841 min.)
MS (APCI+): 790 (M+H), 792

EXAMPLE 222

(E)-3-Phenyl-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]-2-propenamide trifluoroacetate Yield: 3.9 mg
HPLC analysis (condition B): purity 100% (retention time: 1.809 min.)
MS (APCI+): 724 (M+H)

EXAMPLE 223

2-(Benzyloxy)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 0.9 mg
HPLC analysis (condition B): purity 100% (retention time: 1.781 min.)
MS (APCI+): 742 (M+H)

EXAMPLE 224

4-Phenyl-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]butanamide trifluoroacetate Yield: 4.7 mg
HPLC analysis (condition B): purity 100% (retention time: 1.863 min.)
MS (APCI+): 740 (M+H)

EXAMPLE 225

3-(1H-Indol-3-yl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]propanamide trifluoroacetate Yield: 2.4 mg
HPLC analysis (condition B): purity 92% (retention time: 1.793 min.)
MS (APCI+): 765 (M+H)

EXAMPLE 226

2-(4-Methoxyphenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 2.9 mg
HPLC analysis (condition B): purity 100% (retention time: 1.775 min.)
MS (APCI+): 742 (M+H)

EXAMPLE 227

2-(3-Methoxyphenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 0.8 mg
HPLC analysis (condition B): purity 100% (retention time: 1.773 min.)
MS (APCI+): 742 (M+H)

EXAMPLE 228

(E)-3-(4-Methoxyphenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]-2-propenamide trifluoroacetate Yield: 3.4 mg
HPLC analysis (condition B): purity 100% (retention time: 1.803 min.)
MS (APCI+): 754 (M+H)

EXAMPLE 229

2-(3-Fluorophenyl)-N-{[3'-({4-[3-(4-piperidinyl)propyl]-1-piperidinyl}carbonyl)[1,1'-biphenyl]-3-yl]methyl}-N-[3-(1,2,3-thiadiazol-4-yl)benzyl]acetamide trifluoroacetate Yield: 1.4 mg
HPLC analysis (condition B): purity 100% (retention time: 1.791 min.)
MS (APCI+): 730 (M+H)

EXAMPLE 230

N-(2-Oxo-2-{{[3'-({4-[3-(4-piperidinyl)propyl]-1-piperidinyl}carbonyl)[1,1'-biphenyl]-3-yl]methyl}[3-(1,2,3-thiadiazol-4-yl)benzyl]amino}ethyl)benzamide trifluoroacetate Yield: 1.9 mg
HPLC analysis (condition B): purity 100% (retention time: 1.695 min.)
MS (APCI+): 755 (M+H)

EXAMPLE 231

2-(4-Bromophenyl)-N-(3-phenylpropyl)-N-{[3'-({4-[3-(4-piperidinyl)propyl]-1-piperidinyl}carbonyl)[1,1'-biphenyl]-3-yl]methyl}acetamide trifluoroacetate Yield: 6.4 mg
HPLC analysis (condition B): purity 100% (retention time: 1.925 min.)
MS (APCI+): 734 (M+H), 736

EXAMPLE 232

2-(3-Bromophenyl)-N-(3-phenylpropyl)-N-{[3'-({4-[3-(4-piperidinyl)propyl]-1-piperidinyl}carbonyl)[1,1'-biphenyl]-3-yl]methyl}acetamide trifluoroacetate Yield: 7.0 mg
HPLC analysis (condition B): purity 100% (retention time: 1.829 min.)
MS (APCI+): 734 (M+H), 736

EXAMPLE 233

2-(2-Bromophenyl)-N-(3-phenylpropyl)-N-{[3'-({4-[3-(4-piperidinyl)propyl]-1-piperidinyl}carbonyl)[1,1'-biphenyl]-3-yl]methyl}acetamide trifluoroacetate Yield: 0.9 mg
HPLC analysis (condition B): purity 100% (retention time: 1.904 min.)
MS (APCI+): 734 (M+H), 736

EXAMPLE 234

(E)-3-Phenyl-N-(3-phenylpropyl)-N-{[3'-({4-[3-(4-piperidinyl)propyl]-1-piperidinyl}carbonyl)[1,1'-biphenyl]-3-yl]methyl}-2-propenamide trifluoroacetate Yield: 2.4 mg
HPLC analysis (condition B): purity 100% (retention time: 1.888 min.)
MS (APCI+): 668 (M+H)

EXAMPLE 235

2-(Benzyloxy)-N-(3-phenylpropyl)-N-{[3'-({4-[3-(4-piperidinyl)propyl]-1-piperidinyl}carbonyl)[1,1'-biphenyl]-3-yl]methyl}acetamide trifluoroacetate Yield: 4.9 mg
HPLC analysis (condition B): purity 100% (retention time: 1.844 min.)
MS (APCI+): 686 (M+H)

EXAMPLE 236

4-Phenyl-N-(3-phenylpropyl)-N-{[3'-({4-[3-(4-piperidinyl)propyl]-1-piperidinyl}carbonyl)[1,1'-biphenyl]-3-yl]methyl}butanamide trifluoroacetate Yield: 4.7 mg
HPLC analysis (condition B): purity 100% (retention time: 1.933 min.)
MS (APCI+): 684 (M+H)

EXAMPLE 237

3-(1H-Indol-3-yl)-N-(3-phenylpropyl)-N-{[3'-({4-[3-(4-piperidinyl)propyl]-1-piperidinyl}carbonyl)[1,1'-biphenyl]-3-yl]methyl}propanamide trifluoroacetate Yield: 1.5 mg
HPLC analysis (condition B): purity 100% (retention time: 1.855 min.)
MS (APCI+): 709 (M+H)

EXAMPLE 238

2-(4-Methoxyphenyl)-N-(3-phenylpropyl)-N-{[3'-({4-[3-(4-piperidinyl)propyl]-1-piperidinyl}carbonyl)[1,1'-biphenyl]-3-yl]methyl}acetamide trifluoroacetate Yield: 1.1 mg
HPLC analysis (condition B): purity 100% (retention time: 1.833 min.)
MS (APCI+): 686 (M+H)

EXAMPLE 239

2-(3-Methoxyphenyl)-N-(3-phenylpropyl)-N-{[3'-({4-[3-(4-piperidinyl)propyl]-1-piperidinyl}carbonyl)[1,1'-biphenyl]-3-yl]methyl)acetamide trifluoroacetate Yield: 2.5 mg
HPLC analysis (condition B): purity 100% (retention time: 1.831 min.)
MS (APCI+): 686 (M+H)

EXAMPLE 240

(E)-3-(4-Methoxyphenyl)-N-(3-phenylpropyl)-N-{[3'-({4-[3-(4-piperidinyl)propyl]-1-piperidinyl}carbonyl)[1,1'-biphenyl]-3-yl]methyl}-2-propenamide trifluoroacetate Yield: 1.3 mg
HPLC analysis (condition B): purity 100% (retention time: 1.822 min.)
MS (APCI+): 698 (M+H)

EXAMPLE 241

2-(3-Fluorophenyl)-N-(3-phenylpropyl)-N-{[3'-({4-[3-(4-piperidinyl)propyl]-1-piperidinyl}carbonyl)[1,1'-biphenyl]-3-yl]methyl}acetamide trifluoroacetate Yield: 1.1 mg
HPLC analysis (condition B): purity 100% (retention time: 1.860 min.)
MS (APCI+): 674 (M+H)

EXAMPLE 242

N-[2-Oxo-2-((3-phenylpropyl){3'-({4-[3-(4-piperidinyl)propyl]-1-piperidinyl}carbonyl)[1,1'-biphenyl]-3-yl]methyl}amino)ethyl]benzamide trifluoroacetate Yield: 2.0 mg
HPLC analysis (condition B): purity 100% (retention time: 1.761 min.)
MS (APCI+): 699 (M+H)

EXAMPLE 243

Methyl 4-[([2-(4-bromophenyl)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 6.7 mg
HPLC analysis (condition B): purity 100% (retention time: 1.843 min.)
MS (APCI+): 764 (M+H), 766

EXAMPLE 244

Methyl 4-[([2-(3-bromophenyl)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 6.7 mg
HPLC analysis (condition B): purity 100% (retention time: 1.829 min.)
MS (APCI+): 764 (M+H), 766

EXAMPLE 245

Methyl 4-[([2-(2-bromophenyl)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 5.8 mg
HPLC analysis (condition B): purity 100% (retention time: 1.822 min.)
MS (APCI+): 764 (M+H), 766

EXAMPLE 246

Methyl 4-[([(E)-3-phenyl-2-propenoyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 1.2 mg
HPLC analysis (condition B): purity 100% (retention time: 1.803 min.)
MS (APCI+): 698 (M+H)

EXAMPLE 247

Methyl 4-[([2-(benzyloxy)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 1.2 mg
HPLC analysis (condition B): purity 100% (retention time: 1.760 min.)
MS (APCI+): 716 (M+H)

EXAMPLE 248

Methyl 4-[([4-phenylbutanoyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 4.5 mg
HPLC analysis (condition B): purity 100% (retention time: 1.848 min.)
MS (APCI+): 714 (M+H)

EXAMPLE 249

Methyl 4-[([3-(1H-indol-3-yl)propanoyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 3.3 mg
HPLC analysis (condition B): purity 100% (retention time: 1.784 min.)
MS (APCI+): 739 (M+H)

EXAMPLE 250

Methyl 4-[([2-(4-methoxyphenyl)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 5.2 mg
HPLC analysis (condition B): purity 100% (retention time: 1.753 min.)
MS (APCI+): 716 (M+H)

EXAMPLE 251

Methyl 4-[([2-(3-methoxyphenyl)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 4.5 mg
HPLC analysis (condition B): purity 100% (retention time: 1.765 min.)
MS (APCI+): 716 (M+H)

EXAMPLE 252

Methyl 4-[([(E)-3-(4-methoxyphenyl)-2-propenoyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 5.8 mg
HPLC analysis (condition B): purity 100% (retention time: 1.793 min.)
MS (APCI+): 728 (M+H)

EXAMPLE 253

Methyl 4-[([2-(3-fluorophenyl)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 1.9 mg
HPLC analysis (condition B): purity 100% (retention time: 1.715 min.)
MS (APCI+): 704 (M+H)

EXAMPLE 254

Methyl 4-[([2-(benzoylamino)acetyl]{[3'-({4-[3-(4-piperidinyl)propyl]-1-piperidinyl}carbonyl)[1,1'-biphenyl]-3-yl]methyl}amino)methyl]benzoate trifluoroacetate Yield: 7.4 mg
HPLC analysis (condition B): purity 100% (retention time: 1.670 min.)
MS (APCI+): 729 (M+H)

EXAMPLE 255

Methyl 6-[([2-(4-bromophenyl)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 1.8 mg
HPLC analysis (condition B): purity 96% (retention time: 1.802 min.)
MS (APCI+): 744 (M+H), 746

EXAMPLE 256

Methyl 6-[([2-(3-bromophenyl)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 4.7 mg
HPLC analysis (condition B): purity 100% (retention time: 1.804 min.)
MS (APCI+): 744 (M+H), 746

EXAMPLE 257

Methyl 6-[([2-(2-bromophenyl)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 1.0 mg
HPLC analysis (condition B): purity 100% (retention time: 1.787 min.)
MS (APCI+): 744 (M+H), 746

EXAMPLE 258

Methyl 6-[([(E)-3-phenyl-2-propenoyl]{[3'-({4-[3-(4-piperidinyl)propyl]-1-piperidinyl}carbonyl)[1,1'-biphenyl]-3-yl]methyl}amino)hexanoate trifluoroacetate Yield: 6.0 mg
HPLC analysis (condition B): purity 100% (retention time: 1.760 min.)
MS (APCI+): 678 (M+H)

EXAMPLE 259

Methyl 6-[([2-(benzyloxy)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 4.7 mg
HPLC analysis (condition B): purity 100% (retention time: 1.725 min.)
MS (APCI+): 696 (M+H)

EXAMPLE 260

Methyl 6-[([4-phenylbutanoyl]{[3'-({4-[3-(4-piperidinyl)propyl]-1-piperidinyl}carbonyl)[1,1'-biphenyl]-3-yl]methyl}amino)hexanoate trifluoroacetate Yield: 5.6 mg
HPLC analysis (condition B): purity 100% (retention time: 1.808 min.)
MS (APCI+): 694 (M+H)

EXAMPLE 261

Methyl 6-[([3-(1H-indol-3-yl)propanoyl]{[3'-({4-[3-(4-piperidinyl)propyl]-1-piperidinyl}carbonyl)[1,1'-biphenyl]-3-yl]methyl}amino)hexanoate trifluoroacetate Yield: 0.9 mg
HPLC analysis (condition B): purity 100% (retention time: 1.739 min.)
MS (APCI+): 719 (M+H)

EXAMPLE 262

Methyl 6-[([2-(4-methoxyphenyl)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 5.9 mg
HPLC analysis (condition B): purity 100% (retention time: 1.718 min.)
MS (APCI+): 696 (M+H)

EXAMPLE 263

Methyl 6-[([2-(3-methoxyphenyl)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 3.9 mg
HPLC analysis (condition B): purity 100% (retention time: 1.721 min.)
MS (APCI+): 696 (M+H)

EXAMPLE 264

Methyl 6-[([(E)-3-(4-methoxyphenyl)-2-propenoyl]{[3'-({4-[3-(4-piperidinyl)propyl]-1-piperidinyl}carbonyl)[1,1'-biphenyl]-3-yl]methyl}amino)hexanoate trifluoroacetate Yield: 3.9 mg
HPLC analysis (condition B): purity 100% (retention time: 1.769 min.)
MS (APCI+): 708 (M+H)

EXAMPLE 265

Methyl 6-[([2-(3-fluorophenyl)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 5.4 mg
HPLC analysis (condition B): purity 100% (retention time: 1.7 min.)
MS (APCI+): 684 (M+H)

EXAMPLE 266

Methyl 6-[([2-(benzoylamino)acetyl]{[3'-({4-[3-(4-piperidinyl)propyl]-1-piperidinyl}carbonyl)[1,1'-biphenyl]-3-yl]methyl}amino)hexanoate trifluoroacetate Yield: 1.1 mg
HPLC analysis (condition B): purity 100% (retention time: 1.649 min.)
MS (APCI+): 709 (M+H)

The following compounds were produced in the same manner as in Example 7.

EXAMPLE 267

2-(4-Bromophenyl)-N-(4-hydroxyphenethyl)-N-{[2'-({4-[3-(4-piperidinyl)propyl]-1-piperidinyl}carbonyl)[1,1'-biphenyl]-4-yl]methyl}acetamide trifluoroacetate Yield: 3.5 mg
HPLC analysis (condition A): purity 76% (retention time: 3.408 min.)
MS (APCI−): 734 (M−H), 736

EXAMPLE 268

2-(4-Bromophenyl)-N-(4-hydroxyphenethyl)-N-{[2'-({4-[2-(4-piperidinyl)ethyl]-1-piperidinyl}carbonyl)[1,1'-biphenyl]-3-yl]methyl}acetamide trifluoroacetate Yield: 0.9 mg
HPLC analysis (condition A): purity 100% (retention time: 3.724 min.)
MS (APCI−): 720 (M−H), 722

EXAMPLE 269

2-(4-Bromophenyl)-N-(4-hydroxyphenethyl)-N-{[2'-({4-[3-(4-piperidinyl)propyl]-1-piperidinyl}carbonyl)[1,1'-biphenyl]-3-yl]methyl}acetamide trifluoroacetate Yield: 0.9 mg
HPLC analysis (condition A): purity 98% (retention time: 3.819 min.)
MS (APCI−): 734 (M−H), 736

EXAMPLE 270

N-(4-Hydroxyphenethyl)-2-(2-naphthyl)-N-{[2'-({4-[3-(4-piperidinyl)propyl]-1-piperidinyl}carbonyl)[1,1'-biphenyl]-3-yl]methyl}acetamide trifluoroacetate Yield: 8.2 mg
HPLC analysis (condition A): purity 94% (retention time: 3.815 min.)
MS (APCI+): 708 (M+H)

EXAMPLE 271

N-(4-Hydroxyphenethyl)-3-(1H-indol-3-yl)-N-{[2'-({4-[3-(4-piperidinyl)propyl]-1-piperidinyl}carbonyl)[1,1'-biphenyl]-3-yl]methyl}propanamide trifluoroacetate Yield: 1.5 mg
HPLC analysis (condition A): purity 100% (retention time: 3.755 min.)
MS (APCI+): 711 (M+H)

EXAMPLE 272

N-(4-Hydroxyphenethyl)-4-phenyl-N-{[2'-({4-[3-(4-piperidinyl)propyl]-1-piperidinyl}carbonyl)[1,1'-biphenyl]-3-yl]methyl}butanamide trifluoroacetate Yield: 4.7 mg
HPLC analysis (condition A): purity 100% (retention time: 3.826 min.)
MS (APCI+): 686 (M+H)

EXAMPLE 273

N-{[2'-(1,4'-Bipiperidin-1'-ylcarbonyl)-1,1'-biphenyl-4-yl]methyl}-2-(4-bromophenyl)-N-[2-(4-hydroxyphenyl)ethyl]acetamide trifluoroacetate Yield: 19 mg
HPLC analysis (condition A): purity 85% (retention time: 3.413 min.)
MS (APCI+): 694 (M+H), 696

EXAMPLE 274

4'-({[(4-Bromophenyl)acetyl][2-(4-hydroxyphenyl)ethyl]amino}methyl)-N-(2-pyrrolidin-1-ylethyl)-1,1'-biphenyl-2-carboxamide trifluoroacetate Yield: 19 mg
HPLC analysis (condition A): purity 88% (retention time: 3.413 min.)
MS (APCI+): 640 (M+H), 642

EXAMPLE 275

4'-({[(4-Bromophenyl)acetyl][2-(4-hydroxyphenyl)ethyl]amino}methyl)-N-[2-(dimethylamino)ethyl]-1,1'-biphenyl-2-carboxamide trifluoroacetate Yield: 19 mg
HPLC analysis (condition A): purity 89% (retention time: 3.298 min.)
MS (APCI+): 614 (M+H), 616

EXAMPLE 276

N-(2-Aminoethyl)-4'-({[(4-bromophenyl)acetyl][2-(4-hydroxyphenyl)ethyl]amino}methyl)-1,1'-biphenyl-2-carboxamide trifluoroacetate Yield: 15 mg
HPLC analysis (condition A): purity 83% (retention time: 3.886 min.)
MS (APCI+): 586 (M+H), 588

EXAMPLE 277

N-(3-Amino-2,2-dimethylpropyl)-4'-({[(4-bromophenyl)acetyl][2-(4-hydroxyphenyl)ethyl]amino}methyl)-1,1'-biphenyl-2-carboxamide trifluoroacetate Yield: 17 mg
HPLC analysis (condition A): purity 77% (retention time: 4.071 min.)
MS (APCI+): 628 (M+H), 630

EXAMPLE 278

N-{[2'-(1,4'-Bipiperidin-1'-ylcarbonyl)-1,1'-biphenyl-4-yl]methyl}-N-[2-(4-hydroxyphenyl)ethyl]-N-(phenylacetyl)glycineamide trifluoroacetate Yield: 16 mg
HPLC analysis (condition A): purity 72% (retention time: 2.930 min.)
MS (APCI+): 673 (M+H)

EXAMPLE 279

N-[2-(Dimethylamino)ethyl]-4'-({[2-(4-hydroxyphenyl)ethyl][N-(phenylacetyl)glycyl]amino}methyl)-1,1'-biphenyl-2-carboxamide trifluoroacetate Yield: 22 mg
HPLC analysis (condition A): purity 89% (retention time: 2.819 min.)
MS (APCI+): 593 (M+H)

EXAMPLE 280

N-{[2'-(1,4'-Bipiperidin-1'-ylcarbonyl)-1,1'-biphenyl-3-yl]methyl}-2-(4-bromophenyl)-N-[2-(4-hydroxyphenyl)ethyl]acetamide trifluoroacetate Yield: 19 mg
HPLC analysis (condition A): purity 86% (retention time: 3.327 min.)
MS (APCI+): 694 (M+H), 696

EXAMPLE 281

3'-({[(4-Bromophenyl)acetyl][2-(4-hydroxyphenyl)ethyl]amino}methyl)-N-[2-(dimethylamino)ethyl]-1,1'-biphenyl-2-carboxamide trifluoroacetate Yield: 15 mg
HPLC analysis (condition A): purity 86% (retention time: 3.275 min.)
MS (APCI+): 614 (M+H), 616

EXAMPLE 282

N-{[2'-(1,4'-Bipiperidin-1'-ylcarbonyl)-1,1'-biphenyl-3-yl]methyl}-N-[2-(4-hydroxyphenyl)ethyl]-N-(phenylacetyl)glycineamide trifluoroacetate Yield: 21 mg
HPLC analysis (condition A): purity 85% (retention time: 3.041 min.)
MS (APCI+): 673 (M+H)

EXAMPLE 283

N-[2-(Dimethylamino)ethyl]-3'-({[2-(4-hydroxyphenyl)ethyl][N-(phenylacetyl)glycyl]amino}methyl)-1,1'-biphenyl-2-carboxamide trifluoroacetate Yield: 12 mg
HPLC analysis (condition A): purity 90% (retention time: 2.965 min.)
MS (APCI+): 593 (M+H)

EXAMPLE 284

N-(2-Aminoethyl)-3'-({[(4-bromophenyl)acetyl][2-(4-hydroxyphenyl)ethyl]amino}methyl)-1,1'-biphenyl-2-carboxamide trifluoroacetate Yield: 6.4 mg
HPLC analysis (condition A): purity 100% (retention time: 3.580 min.)
MS (APCI+): 586 (M+H), 588

EXAMPLE 285

N-(3-Amino-2,2-dimethylpropyl)-3'-({[(4-bromophenyl)acetyl][2-(4-hydroxyphenyl)ethyl]amino}methyl)-1,1'-biphenyl-2-carboxamide trifluoroacetate Yield: 1.8 mg
HPLC analysis (condition A): purity 98% (retention time: 3.597 min.)
MS (APCI+): 628 (M+H), 630

EXAMPLE 286

2-({[3'-({[(4-Bromophenyl)acetyl][2-(4-hydroxyphenyl)ethyl]amino}methyl)-1,1'-biphenyl-2-yl]carbonyl}amino)ethyl imidothiocarbamate trifluoroacetate Yield: 9.9 mg
HPLC analysis (condition A): purity 99% (retention time: 3.806 min.)
MS (APCI+): 646 (M+H), 648

EXAMPLE 287

N-{[2'-(1,4'-Bipiperidin-1'-ylcarbonyl)-1,1'-biphenyl-3-yl]methyl}-N-[2-(4-hydroxyphenyl)ethyl]-4-phenylbutanamide trifluoroacetate Yield: 2.4 mg
HPLC analysis (condition A): purity 98% (retention time: 3.711 min.)
MS (APCI+): 644 (M+H)

EXAMPLE 288

N-(2-Aminoethyl)-3'-({[(4-chlorophenyl)acetyl][2-(4-hydroxyphenyl)ethyl]amino}methyl)-1,1'-biphenyl-2-carboxamide trifluoroacetate Yield: 15 mg
HPLC analysis (condition A): purity 91% (retention time: 3.462 min.)
MS (APCI+): 542 (M+H)

EXAMPLE 289

N-(2-Aminoethyl)-3'-({[[2-(4-chlorophenyl)ethyl][2-naphthylacetyl)amino}methyl)-1,1'-biphenyl-2-carboxamide trifluoroacetate Yield: 11 mg
HPLC analysis (condition A): purity 100% (retention time: 3.533 min.)
MS (APCI+): 558 (M+H)

EXAMPLE 290

N-(2-Aminoethyl)-3'-([[2-(4-hydroxyphenyl)ethyl][3-(1H-indol-3-yl)propanoyl]amino]methyl)-1,1'-biphenyl-2-carboxamide trifluoroacetate Yield: 1.5 mg
HPLC analysis (condition A): purity 100% (retention time: 3.490 min.)
MS (APCI+): 561 (M+H)

EXAMPLE 291

N-(2-Aminoethyl)-3'-{[[2-(4-hydroxyphenyl)ethyl][4-phenylbutanoyl)amino]methyl}-1,1'-biphenyl-2-carboxamide trifluoroacetate Yield: 19 mg
HPLC analysis (condition A): purity 90% (retention time: 3.517 min.)
MS (APCI+): 536 (M+H)

EXAMPLE 292

N-(2-Aminoethyl)-3'-({[(2E)-3-(2-fluorophenyl)-2-propenoyl][2-(4-hydroxyphenyl)ethyl]amino}methyl)-1,1'-biphenyl-2-carboxamide trifluoroacetate Yield: 19 mg
HPLC analysis (condition A): purity 90% (retention time: 3.455 min.)
MS (APCI+): 538 (M+H)

EXAMPLE 293

N-(2-Aminoethyl)-3'-{[[2-(4-hydroxyphenyl)ethyl]({[3-(trifluoromethyl)phenyl]amino}carbonyl)amino]methyl}-1,1'-biphenyl-2-carboxamide trifluoroacetate Yield: 18 mg
HPLC analysis (condition A): purity 86% (retention time: 3.575 min.)
MS (APCI+): 577 (M+H)

EXAMPLE 294

N-(6-Aminohexyl)-3'-([[2-(4-hydroxyphenyl)ethyl][3-(1H-indol-3-yl)propanoyl]amino]methyl)-1,1'-biphenyl-2-carboxamide trifluoroacetate Yield: 1.4 mg
HPLC analysis (condition A): purity 99% (retention time: 3.500 min.)
MS (APCI+): 617 (M+H)

EXAMPLE 295

N-(6-Aminohexyl)-3'-{[[2-(4-hydroxyphenyl)ethyl]([{3-(trifluoromethyl)phenyl]amino}carbonyl)amino]methyl)-1,1'-biphenyl-2-carboxamide trifluoroacetate Yield: 4.2 mg
HPLC analysis (condition A): purity 100% (retention time: 3.739 min.)
MS (APCI+): 633 (M+H)

EXAMPLE 296

N-{[4-(Aminoethyl)cyclohexyl]methyl}-3'-([[2-(4-hydroxyphenyl)ethyl][3-(1H-indol-3-yl)propanoyl]amino]methyl)-1,1'-biphenyl-2-carboxamide trifluoroacetate Yield: 1.0 mg
HPLC analysis (condition A): purity 100% (retention time: 3.540 min.)
MS (APCI+): 643 (M+H)

EXAMPLE 297

N-{[4-(Aminoethyl)cyclohexyl]methyl}-3'-{[[2-(4-hydroxyphenyl)ethyl]({[3-(trifluoromethyl)phenyl]amino}carbonyl)amino]methyl}-1,1'-biphenyl-2-carboxamide trifluoroacetate Yield: 6.0 mg
HPLC analysis (condition A): purity 100% (retention time: 3.776 min.)
MS (APCI+): 659 (M+H)

EXAMPLE 298

N-{[2'-(1,4'-Bipiperidin-1'-ylcarbonyl)-1,1'-biphenyl-3-yl]methyl}-N-[2-(4-hydroxyphenyl)ethyl]-4-(2-thienyl)butanamide trifluoroacetate Yield: 4.0 mg
HPLC analysis (condition A): purity 100% (retention time: 3.905 min.)
MS (APCI+): 650 (M+H)

EXAMPLE 299

N-{[2'-(1,4'-Bipiperidin-1'-ylcarbonyl)-1,1'-biphenyl-3-yl]methyl)-N-[2-(4-hydroxyphenyl)ethyl]-4-(1-naphthyloxy)acetamide trifluoroacetate Yield: 12 mg
HPLC analysis (condition A): purity 93% (retention time: 4.050 min.)
MS (APCI+): 682 (M+H)

EXAMPLE 300

(2E)-N-{[2'-(1,4'-Bipiperidin-1'-ylcarbonyl)-1,1'-biphenyl-3-yl]methyl}-3-(3-fluorophenyl)-N-[2-(4-hydroxyphenyl)ethyl]-2-propenamide trifluoroacetate Yield: 10 mg
HPLC analysis (condition A): purity 100% (retention time: 3.958 min.)
MS (APCI+): 646 (M+H)

The following compounds were produced in the same manner as in Example 71.

EXAMPLE 301

N-(2-Aminoethyl)-3'-({[(2E)-3-(4-fluorophenyl)-2-propenoyl](1-naphthylmethyl)amino}methyl)-1,1'-biphenyl-2-carboxamide trifluoroacetate Yield: 15 mg HPLC analysis (condition A): purity 81% (retention time: 3.674 min.)
MS (APCI+): 558 (M+H)

EXAMPLE 302

N-(2-Aminoethyl)-3'-[((1-naphthylmethyl){(2E)-3-[3-(trifluoromethyl)phenyl]-2-propenoyl}amino)methyl]-1,1'-biphenyl-2-carboxamide trifluoroacetate Yield: 14 mg
HPLC analysis (condition A): purity 84% (retention time: 3.882 min.)
MS (APCI+): 608 (M+H)

EXAMPLE 303

N-(2-Aminoethyl)-3'-({(1-naphthylmethyl)[N-(phenylacetyl)glycyl]amino}methyl)-1,1'-biphenyl-2-carboxamide trifluoroacetate Yield: 15 mg
HPLC analysis (condition A): purity 94% (retention time: 3.695 min.)
MS (APCI+): 585 (M+H)

EXAMPLE 304

N-(2-Aminoethyl)-3'-{[(N-benzoylglycyl)(1-naphthylmethyl)amino]methyl}-1,1'-biphenyl-2-carboxamide trifluoroacetate Yield: 16 mg
HPLC analysis (condition A): purity 89% (retention time: 3.848 min.)
MS (APCI+): 571 (M+H)

EXAMPLE 305

N-(2-Aminoethyl)-3'-{[[2-(1H-indol-3-yl)ethyl](4-phenylbutanoyl)amino]methyl}-1,1'-biphenyl-2-carboxamide trifluoroacetate Yield: 1.4 mg
HPLC analysis (condition A): purity 100% (retention time: 3.513 min.)
MS (APCI+): 559 (M+H)

EXAMPLE 306

N-(2-Aminoethyl)-3'-{[[2-(1H-indol-3-yl)ethyl]{4-(2-thienyl)butanoyl}amino]methyl}-1,1'-biphenyl-2-carboxamide trifluoroacetate Yield: 1.3 mg
HPLC analysis (condition A): purity 100% (retention time: 3.400 min.)
MS (APCI+): 565 (M+H)

EXAMPLE 307

N-(2-Aminoethyl)-3'-{{[2-(1H-indol-3-yl)ethyl][3-(1H-indol-3-yl)propanoyl]amino}methyl}-1,1'-biphenyl-2-carboxamide trifluoroacetate Yield: 1.1 mg
HPLC analysis (condition A): purity 98% (retention time: 2.822 min.)
MS (APCI+): 584 (M+H)

EXAMPLE 308

N-(2-Aminoethyl)-3'-({(3,3-diphenylpropyl)[3-(1H-indol-3-yl)propanoyl]amino}methyl)-1,1'-biphenyl-2-carboxamide trifluoroacetate Yield: 1.3 mg
HPLC analysis (condition A): purity 97% (retention time: 3.621 min.)
MS (APCI+): 635 (M+H)

EXAMPLE 309

Methyl {[(2'-{[(2-aminoethyl)amino]carbonyl)-1,1'-biphenyl-3-yl)methyl][(4-bromophenyl)acetyl]amino}(phenyl)acetate trifluoroacetate Yield: 3.7 mg
HPLC analysis (condition A): purity 98% (retention time: 4.935 min.)
MS (APCI+): 614 (M+H), 616

EXAMPLE 310

Methyl [[(2'-{[(2-aminoethyl)amino]carbonyl}-1,1'-biphenyl-3-yl)methyl][(4-phenylbutanoyl)amino](phenyl)acetate trifluoroacetate Yield: 1.3 mg
HPLC analysis (condition A): purity 87% (retention time: 3.337 min.)

MS (APCI+): 564 (M+H)

EXAMPLE 311

Methyl {[(2'-{[(2-aminoethyl)amino]carbonyl}-1,1'-biphenyl-3-yl)methyl][N-(phenylacetyl)glycyl]amino}(phenyl)acetate trifluoroacetate Yield: 2.5 mg
HPLC analysis (condition A): purity 98% (retention time: 3.018 min.)
MS (APCI+): 593 (M+H)

EXAMPLE 312

N-(2-Aminoethyl)-3'-{[(1-benzylpiperidin-4-yl)(4-phenylbutanoyl)amino]methyl}-1,1'-biphenyl-2-carboxamide trifluoroacetate Yield: 21 mg
HPLC analysis (condition A): purity 97% (retention time: 2.863 min.)
MS (APCI+): 589 (M+H)

EXAMPLE 313

N-(2-Aminoethyl)-3'-{[(1-benzylpiperidin-4-yl){4-(2-thienyl)butanoyl}amino]methyl}-1,1'-biphenyl-2-carboxamide trifluoroacetate Yield: 2.6 mg
HPLC analysis (condition A): purity 100% (retention time: 2.825 min.)
MS (APCI+): 595 (M+H)

EXAMPLE 314

N-(2-Aminoethyl)-3'-{[[(2E)-3-(4-fluorophenyl)-2-propenoyl](4-phenoxyphenyl)amino]methyl}-1,1'-biphenyl-2-carboxamide trifluoroacetate Yield: 18 mg
HPLC analysis (condition A): purity 95% (retention time: 3.339 min.)
MS (APCI+): 586 (M+H)

EXAMPLE 315

N-(2-Aminoethyl)-3'-({{4-[(E)-2-(4-methoxyphenyl)ethenyl]phenyl}{N-(phenylacetyl)glycyl}amino}methyl)-1,1'-biphenyl-2-carboxamide trifluoroacetate Yield: 2.3 mg
HPLC analysis (condition A): purity 100% (retention time: 3.455 min.)
MS (APCI+): 653 (M+H)

EXAMPLE 316

N-(2-Aminoethyl)-3'-({(4-benzoylphenyl)[(benzyloxy)acetyl]amino}methyl)-1,1'-biphenyl-2-carboxamide trifluoroacetate Yield: 20 mg
HPLC analysis (condition A): purity 84% (retention time: 3.807 min.)
MS (APCI+): 598 (M+H)

EXAMPLE 317

Ethyl N-[(2'-{[(2-aminoethyl)amino]carbonyl}-1,1'-biphenyl-3-yl)methyl]-N-[(4-bromophenyl)acetyl]tyrosinate trifluoroacetate Yield: 4.1 mg
HPLC analysis (condition A): purity 99% (retention time: 2.818 min.)
MS (APCI+): 658 (M+H), 660

EXAMPLE 318

Ethyl N-[(2'-{[(2-aminoethyl)amino]carbonyl}-1,1'-biphenyl-3-yl)methyl]-N-[(4-methoxyphenyl)acetyl]tyrosinate trifluoroacetate Yield: 1.9 mg
HPLC analysis (condition A): purity 89% (retention time: 3.044 min.)
MS (APCI+): 610 (M+H)

EXAMPLE 319

Ethyl N-(phenylacetyl)glycyl-N-[(2'-{[(2-aminoethyl)amino]carbonyl}-1,1'-biphenyl-3-yl)methyl]tyrosinate trifluoroacetate Yield: 4.3 mg
HPLC analysis (condition A): purity 99% (retention time: 2.987 min.)
MS (APCI+): 637 (M+H)

EXAMPLE 320

Ethyl N-[(2'-{[(2-aminoethyl)amino]carbonyl}-1,1'-biphenyl-3-yl)methyl]-N-[(2-naphthylacetyl)tyrosinate trifluoroacetate Yield: 3.4 mg
HPLC analysis (condition A): purity 88% (retention time: 3.217 min.)
MS (APCI+): 630 (M+H)

EXAMPLE 321

3'-{[(4-Aminobutanoyl)(1-naphthylmethyl)amino]methyl}-N-(2-aminoethyl)-1,1'-biphenyl-2-carboxamide trifluoroacetate Yield: 18 mg
HPLC analysis (condition A): purity 95% (retention time: 2.643 min.)
MS (APCI+): 495 (M+H)

EXAMPLE 322

N-[(2'-{[(2-Aminoethyl)amino]carbonyl}-1,1'-biphenyl-3-yl)methyl]-N-(1-naphthylmethyl)piperidine-4-carboxamide trifluoroacetate Yield: 27 mg
HPLC analysis (condition A): purity 93% (retention time: 2.649 min.)
MS (APCI+): 521 (M+H)

EXAMPLE 323

N-(2-Aminoethyl)-3'-{[{[4-(aminomethyl)cyclohexyl]carbonyl}(1-naphthylmethyl)amino]methyl}-1,1'-biphenyl-2-carboxamide trifluoroacetate Yield: 11 mg
HPLC analysis (condition A): purity 9% (retention time: 2.740 min.)
MS (APCI+): 549 (M+H)

EXAMPLE 324

N-(2-Aminoethyl)-3'-{[[4-({[amino(imino)methyl]amino}methyl)benzoyl](1-naphthylmethyl)amino]methyl}-1,1'-biphenyl-2-carboxamide trifluoroacetate Yield: 7.1 mg
HPLC analysis (condition A): purity 80% (retention time: 2.789 min.)
MS (APCI+): 585 (M+H)

EXAMPLE 325

N-(2-Aminoethyl)-3'-{[[3-({[amino(imino)methyl]amino}methyl)benzoyl](1-naphthylmethyl)amino]methyl}-1,1'-biphenyl-2-carboxamide trifluoroacetate Yield: 9.6 mg
HPLC analysis (condition A): purity 98% (retention time: 2.796 min.)
MS (APCI+): 585 (M+H)

EXAMPLE 326

N-(2-Aminoethyl)-3'-{[[5-{[amino(imino)methyl]amino}pentanoyl)(1-naphthylmethyl)amino]methyl]-1,1'-biphenyl-2-carboxamide trifluoroacetate Yield: 26 mg
HPLC analysis (condition A): purity 91% (retention time: 2.763 min.)
MS (APCI+): 551 (M+H)

EXAMPLE 327

N-(2-Aminoethyl)-3'-{[{[4-({[amino(imino)methyl]amino}methyl)cyclohexyl]carbonyl}(1-naphthylmethyl)amino]methyl}-1,1'-biphenyl-2-carboxamide trifluoroacetate Yield: 7.4 mg
HPLC analysis (condition A): purity 98% (retention time: 2.850 min.)
MS (APCI+): 591 (M+H)

EXAMPLE 328

N-(2-Aminoethyl)-3'-{[[4-(aminosulfonyl)benzoyl](1-naphthylmethyl)amino]methyl}-1,1'-biphenyl-2-carboxamide trifluoroacetate Yield: 8.5 mg
HPLC analysis (condition A): purity 95% (retention time: 3.062 min.)
MS (APCI+): 593 (M+H)

EXAMPLE 329

3'-{[{[2-(Aminocarbonyl)phenoxy]acetyl}(1-naphthylmethyl)amino]methyl}-N-(2-aminoethyl)-1,1'-biphenyl-2-carboxamide trifluoroacetate Yield: 22 mg
HPLC analysis (condition A): purity 96% (retention time: 3.211 min.)
MS (APCI+): 587 (M+H)

EXAMPLE 330

N-(2-Aminoethyl)-3'-{[(1-naphthylmethyl)(tyrosyl)amino]methyl}-1,1'-biphenyl-2-carboxamide trifluoroacetate Yield: 21 mg
HPLC analysis (condition A): purity 94% (retention time: 2.749 min.)
MS (APCI+): 573 (M+H)

EXAMPLE 331

N-(2-Aminoethyl)-3'-{[[2-(4-methoxyphenyl)ethyl](tyrosyl)amino]methyl}-1,1'-biphenyl-2-carboxamide trifluoroacetate Yield: 19 mg
HPLC analysis (condition A): purity 94% (retention time: 2.615 min.)
MS (APCI+): 567 (M+H)

EXAMPLE 332

N-(2-Aminoethyl)-3'-{[[2-(2,4-dichlorophenyl)ethyl](tyrosyl)amino]methyl}-1,1'-biphenyl-2-carboxamide trifluoroacetate Yield: 22 mg
HPLC analysis (condition A): purity 94% (retention time: 2.888 min.)
MS (APCI+): 605 (M+H)

EXAMPLE 333

N-(2-Aminoethyl)-3'-{[(3,3-diphenylpropyl)(tyrosyl)amino]methyl}-1,1'-biphenyl-2-carboxamide trifluoroacetate Yield: 21 mg
HPLC analysis (condition A): purity 97% (retention time: 2.950 min.)
MS (APCI+): 627 (M+H)

EXAMPLE 334

N-(2-Aminoethyl)-3'-{[(4-phenylbutyl)(tyrosyl)amino]methyl}-1,1'-biphenyl-2-carboxamide trifluoroacetate Yield: 9.7 mg
HPLC analysis (condition A): purity 96% (retention time: 2.833 min.)
MS (APCI+): 565 (M+H)

EXAMPLE 335

N-(2-Aminoethyl)-3'-{[{3-[methyl(phenyl)amino]propyl}(tyrosyl)amino]methyl}-1,1'-biphenyl-2-carboxamide trifluoroacetate Yield: 10 mg
HPLC analysis (condition A): purity 96% (retention time: 2.096 min.)
MS (APCI+): 580 (M+H)

EXAMPLE 336

N-(2-Aminoethyl)-3'-({[4-({[amino(imino)methyl]amino}methyl)benzoyl][2-(2,4-dichlorophenyl)ethyl]amino}methyl)-1,1'-biphenyl-3-carboxamide trifluoroacetate Yield: 25 mg
HPLC analysis (condition A): purity 87% (retention time: 2.953 min.)
MS (APCI+): 617 (M+H)

EXAMPLE 337

N-(2-Aminoethyl)-3'-{[[4-({[amino(imino)methyl]amino}methyl)benzoyl](1-naphthylmethyl)amino]methyl}-1,1'-biphenyl-3-carboxamide trifluoroacetate Yield: 2.1 mg
HPLC analysis (condition A): purity 98% (retention time: 2.860 min.)
MS (APCI+): 585 (M+H)

EXAMPLE 338

N-(2-Aminoethyl)-3'-{[[4-({[amino(imino)methyl]amino}methyl)benzoyl](4-phenylbutyl)amino]methyl}-1,1'-biphenyl-3-carboxamide trifluoroacetate Yield: 11 mg
HPLC analysis (condition A): purity 99% (retention time: 2.927 min.)
MS (APCI+): 577 (M+H)

EXAMPLE 339

N-(2-Aminoethyl)-4'-{[[4-({[amino(imino)methyl]amino}methyl)benzoyl](3,3-diphenylpropyl)amino]methyl}-1,1'-biphenyl-2-carboxamide trifluoroacetate Yield: 11 mg
HPLC analysis (condition A): purity 98% (retention time: 2.977 min.)
MS (APCI+): 639 (M+H)

EXAMPLE 340

N-(2-Aminoethyl)-4'-{[[(benzyloxy)acetyl](4-phenoxyphenyl)amino]methyl}-1,1'-biphenyl-2-carboxamide trifluoroacetate Yield: 17 mg
HPLC analysis (condition A): purity 87% (retention time: 3.485 min.)
MS (APCI+): 586 (M+H)

EXAMPLE 341

N-(2-Aminoethyl)-4'-({{4-[(E)-2-(4-methoxyphenyl)ethenyl]phenyl}[N-(phenylacetyl)glycyl]amino}methyl)-1,1'-biphenyl-2-carboxamide trifluoroacetate Yield: 2.0 mg
HPLC analysis (condition A): purity 99% (retention time: 3.462 min.)
MS (APCI+): 653 (M+H)

EXAMPLE 342

N-(2-Aminoethyl)-4'-[((N-benzoylglycyl){4-[(E)-2-(4-methoxyphenyl)ethenyl]phenyl}amino)methyl]-1,1'-biphenyl-2-carboxamide trifluoroacetate Yield: 1.5 mg
HPLC analysis (condition A): purity 99% (retention time: 3.448 min.)
MS (APCI+): 639 (M+H)

EXAMPLE 343

N-(2-Aminoethyl)-4'-[(([(benzyloxy)acetyl]{4-[(E)-2-(4-methoxyphenyl)ethenyl]phenyl}amino)methyl]-1,1'-biphenyl-2-carboxamide trifluoroacetate Yield: 1.8 mg
HPLC analysis (condition A): purity 100% (retention time: 3.604 min.)
MS (APCI+): 626 (M+H)

The compounds obtained in the Examples above, compounds obtained by analogous methods to those in the Examples above, and results of mass spectra (MS) thereof are shown below.

Root Structure
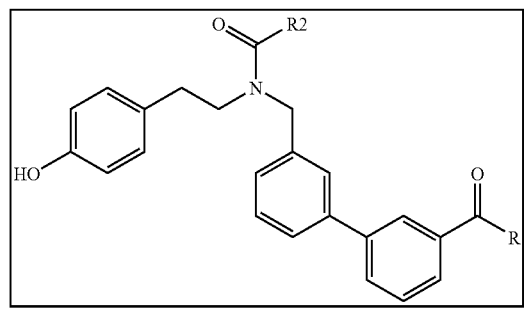
MS (APCI+)
| R2 | R |  |  |
|---|---|---|---|
|  | (CH₃)₂N-CH₂CH₂-NH-* | piperazine | N-methyl-homopiperazine |
| cis-styryl | 548 (M + H) | 546 (M + H) | 547 (M + H) |
| 4-bromobenzyl | 614 (M + H), 616 | 612 (M + H) 614 | 640 (M + H) 642 |
| benzyloxymethyl | 566 (M + H) | 564 (M + H) | 592 (M + H) |
| 3-phenylpropyl | 564 (M + H) | 562 (M + H) | 590 (M + H) |
| benzamidomethyl | 579 (M + H) | 577 (M + H) | 605 (M + H) |
| 2-(indol-3-yl)ethyl | 589 (M + H) | 587 (M + H) | 615 (M + H) |
| (indol-3-yl)methyl | 575 (M + H) | 573 (M + H) | 601 (M + H) |
| isobutyl | 516 (M + H) | 514 (M + H) | 542 (M + H) |

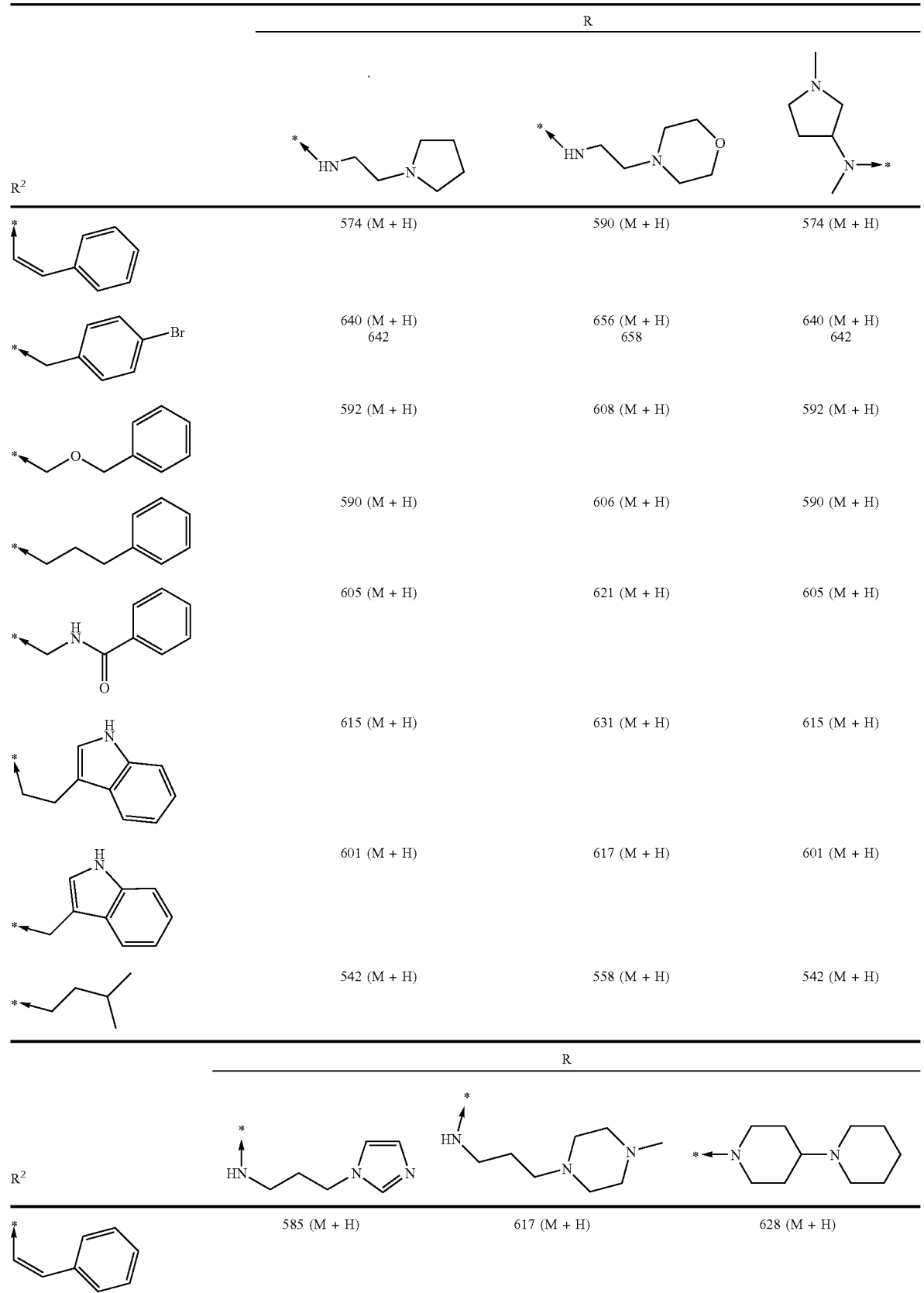

-continued
| R² | | 651 (M + H) 653 | 683 (M + H) 685 | 694 (M + H) 696 |
|---|---|---|---|---|
| 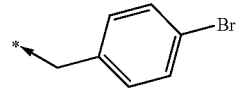 | | 651 (M + H) 653 | 683 (M + H) 685 | 694 (M + H) 696 |
| 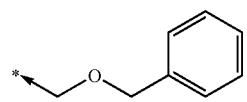 | | 603 (M + H) | 635 (M + H) | 646 (M + H) |
|  | | 601 (M + H) | 633 (M + H) | 644 (M + H) |
| 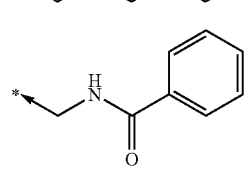 | | 626 (M + H) | 648 (M + H) | 659 (M + H) |
| 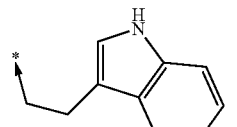 | | 626 (M + H) | 658 (M + H) | 669 (M + H) |
| 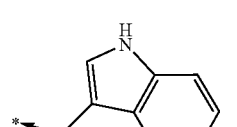 | | 612 (M + H) | 644 (M + H) | 655 (M + H) |
| 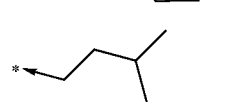 | | 553 (M + H) | 585 (M + H) | 596 (M + H) |
| | R | | |
|---|---|---|---|
| R² | 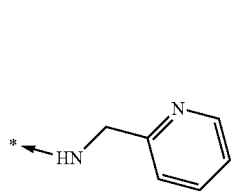 | 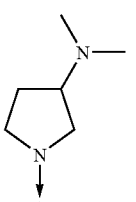 | 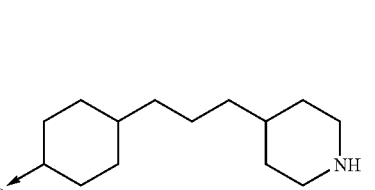 |
| 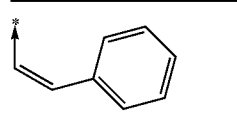 | 568 (M + H) | 574 (M + H) | 670 (M + H) |
| 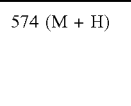 | 638 (M + H) 636 | 640 (M + H) 642 | 736 (M + H) 738 |
| 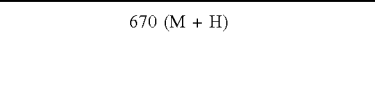 | 586 (M + H) | 592 (M + H) | 688 (M + H) |
| 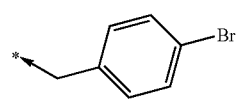 | 584 (M + H) | 590 (M + H) | 686 (M + H) |

-continued
| R² | | | |
|---|---|---|---|
| 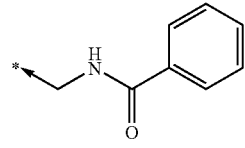 | 599 (M + H) | 605 (M + H) | 701 (M + H) |
| 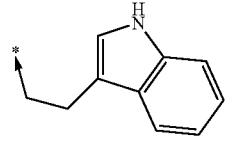 | 609 (M + H) | 615 (M + H) | 711 (M + H) |
| 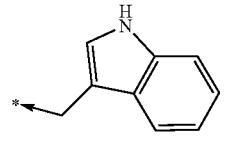 | 595 (M + H) | 601 (M + H) | 697 (M + H) |
| 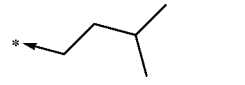 | 536 (M + H) | 542 (M + H) | 638 (M + H) |
| | R | | |
|---|---|---|---|
| R² |  | 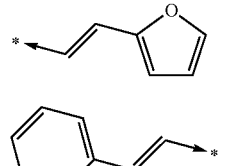 | 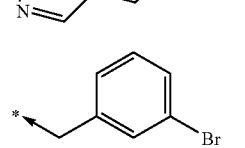 |
|  | 538 (M + H) | 536 (M + H) | 564 (M + H) |
| 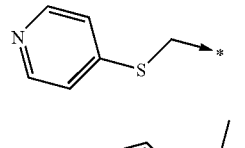 | 549 (M + H) | 547 (M + H) | 575 (M + H) |
| 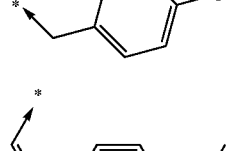 | 614 (M + H) 616 | 612 (M + H) 614 | 640 (M + H) 642 |
| 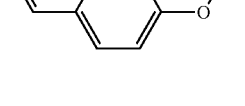 | 614 (M + H) 616 | 612 (M + H) 614 | 640 (M + H) 642 |
|  | 569 (M + H) | 567 (M + H) | 595 (M + H) |
|  | 566 (M + H) | 564 (M + H) | 592 (M + H) |
|  | 578 (M + H) | 576 (M + H) | 604 (M + H) |

-continued
| R² | | | |
|---|---|---|---|
| 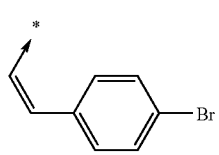 (4-Br styryl) | 626 (M + H) 628 | 624 (M + H) 626 | 652 (M + H) 654 |
| | R | | |
|---|---|---|---|
| R² | 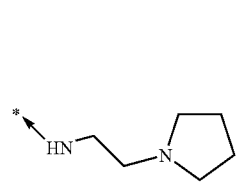 HN-CH₂CH₂-pyrrolidine | 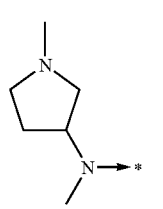 HN-CH₂CH₂-morpholine | 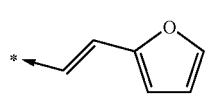 1-methyl-3-(dimethylamino)pyrrolidine |
| 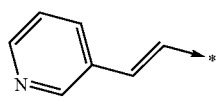 (furyl vinyl) | 564 (M + H) | 580 (M + H) | 564 (M + H) |
| 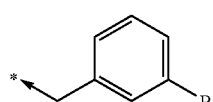 (3-pyridyl vinyl) | 575 (M + H) | 591 (M + H) | 575 (M + H) |
| 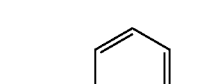 (3-Br benzyl) | 640 (M + H) 642 | 656 (M + H) 658 | 640 (M + H) 642 |
| 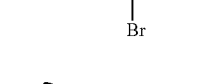 (2-Br benzyl) | 640 (M + H) 642 | 656 (M + H) 658 | 640 (M + H) 642 |
| 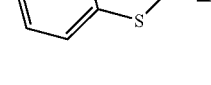 (4-pyridyl-S-CH₂) | 595 (M + H) | 611 (M + H) | 595 (M + H) |
| 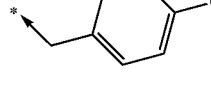 (4-OMe benzyl) | 592 (M + H) | 608 (M + H) | 592 (M + H) |
| (4-OMe styryl) | 604 (M + H) | 620 (M + H) | 604 (M + H) |
| (4-Br styryl) | 652 (M + H) 654 | 668 (M + H) 670 | 652 (M + H) 654 |

-continued

| R₂ | R |||
|---|---|---|---|
| | HN~~~N(imidazole) | HN~~~N(N-methylpiperazine) | piperidinyl-piperidine |
| *furan-CH=CH- | 575 (M + H) | 607 (M + H) | 618 (M + H) |
| 3-pyridyl-CH=CH-* | 586 (M + H) | 618 (M + H) | 629 (M + H) |
| *-CH₂-(3-bromophenyl) | 651 (M + H) 653 | 683 (M + H) 685 | 694 (M + H) 696 |
| *-CH₂-(2-bromophenyl) | 651 (M + H) 653 | 683 (M + H) 685 | 694 (M + H) 696 |
| 4-pyridyl-S-CH₂-* | 606 (M + H) | 638 (M + H) | 649 (M + H) |
| *-CH₂-(4-methoxyphenyl) | 603 (M + H) | 635 (M + H) | 646 (M + H) |
| *-CH=CH-(4-methoxyphenyl) (cis) | 615 (M + H) | 647 (M + H) | 658 (M + H) |
| *-CH=CH-(4-bromophenyl) (cis) | 663 (M + H) 665 | 695 (M + H) 697 | 706 (M + H) 708 |

| R₂ | R |||
|---|---|---|---|
| | *-HN-CH₂-(2-pyridyl) | 3-(dimethylamino)pyrrolidinyl | cyclohexyl-(CH₂)₃-piperidinyl |
| *furan-CH=CH- | 558 (M + H) | 564 (M + H) | 660 (M + H) |

-continued

| R² | | | |
|---|---|---|---|
| [3-pyridyl-CH=CH-*] | 569 (M + H) | 575 (M + H) | 671 (M + H) |
| [3-Br-C₆H₄-CH₂-*] | 634 (M + H) 636 | 640 (M + H) 642 | 736 (M + H) 738 |
| [2-Br-C₆H₄-CH₂-*] | 634 (M + H) 636 | 640 (M + H) 642 | 736 (M + H) 738 |
| [4-pyridyl-S-CH₂-*] | 589 (M + H) | 595 (M + H) | 691 (M + H) |
| [4-MeO-C₆H₄-CH₂-*] | 586 (M + H) | 592 (M + H) | 688 (M + H) |
| [4-MeO-C₆H₄-CH=CH-*] | 598 (M + H) | 604 (M + H) | 700 (M + H) |
| [4-Br-C₆H₄-CH=CH-*] | 646 (M + H) 648 | 652 (M + H) 654 | 748 (M + H) 750 |

| R² | R | | |
|---|---|---|---|
| | H₂N-CH₂CH₂-NH-* | H₂N-CH₂CH₂CH₂-NH-* | H₂N-(CH₂)₄-NH-* |
| [C₆H₅-CH=CH-*] | 520 (M + H) | 534 (M + H) | 548 (M + H) |
| [4-Br-C₆H₄-CH₂-*] | 586 (M + H) 588 | 600 (M + H) 602 | 614 (M + H) 616 |
| [C₆H₅-CH₂-O-CH₂-*] | 538 (M + H) | 552 (M + H) | 566 (M + H) |
| [C₆H₅-CH₂CH₂-CH₂-*] | 536 (M + H) | 550 (M + H) | 564 (M + H) |

| R² | R | | |
|---|---|---|---|
| | H₂N–(CH₂)₅–NH–* | H₂N–(CH₂)₆–NH–* | H₂N-CH₂-(cyclohexyl)-CH₂-NH–* |
| *–CH₂–NH–C(O)–Ph | 551 (M + H) | 565 (M + H) | 579 (M + H) |
| *–CH₂–CH₂–(1H-indol-3-yl) | 561 (M + H) | 575 (M + H) | 589 (M + H) |
| *–CH₂–(1H-indol-3-yl) | 547 (M + H) | 561 (M + H) | 575 (M + H) |
| *–CH₂–CH₂–CH(CH₃)₂ | 488 (M + H) | 502 (M + H) | 516 (M + H) |

| R² | R | | |
|---|---|---|---|
| | H₂N–(CH₂)₅–NH–* | H₂N–(CH₂)₆–NH–* | H₂N-CH₂-(cyclohexyl)-CH₂-NH–* |
| *–CH=CH–Ph | 562 (M + H) | 576 (M + H) | 602 (M + H) |
| *–CH₂–C₆H₄–Br | 628 (M + H); 630 | 642 (M + H); 644 | 668 (M + H); 670 |
| *–CH₂–O–CH₂–Ph | 580 (M + H) | 594 (M + H) | 620 (M + H) |
| *–CH₂–CH₂–CH₂–Ph | 578 (M + H) | 592 (M + H) | 618 (M + H) |
| *–CH₂–NH–C(O)–Ph | 593 (M + H) | 607 (M + H) | 633 (M + H) |
| *–CH₂–CH₂–(1H-indol-3-yl) | 603 (M + H) | 617 (M + H) | 643 (M + H) |
| *–CH₂–(1H-indol-3-yl) | 589 (M + H) | 603 (M + H) | 629 (M + H) |

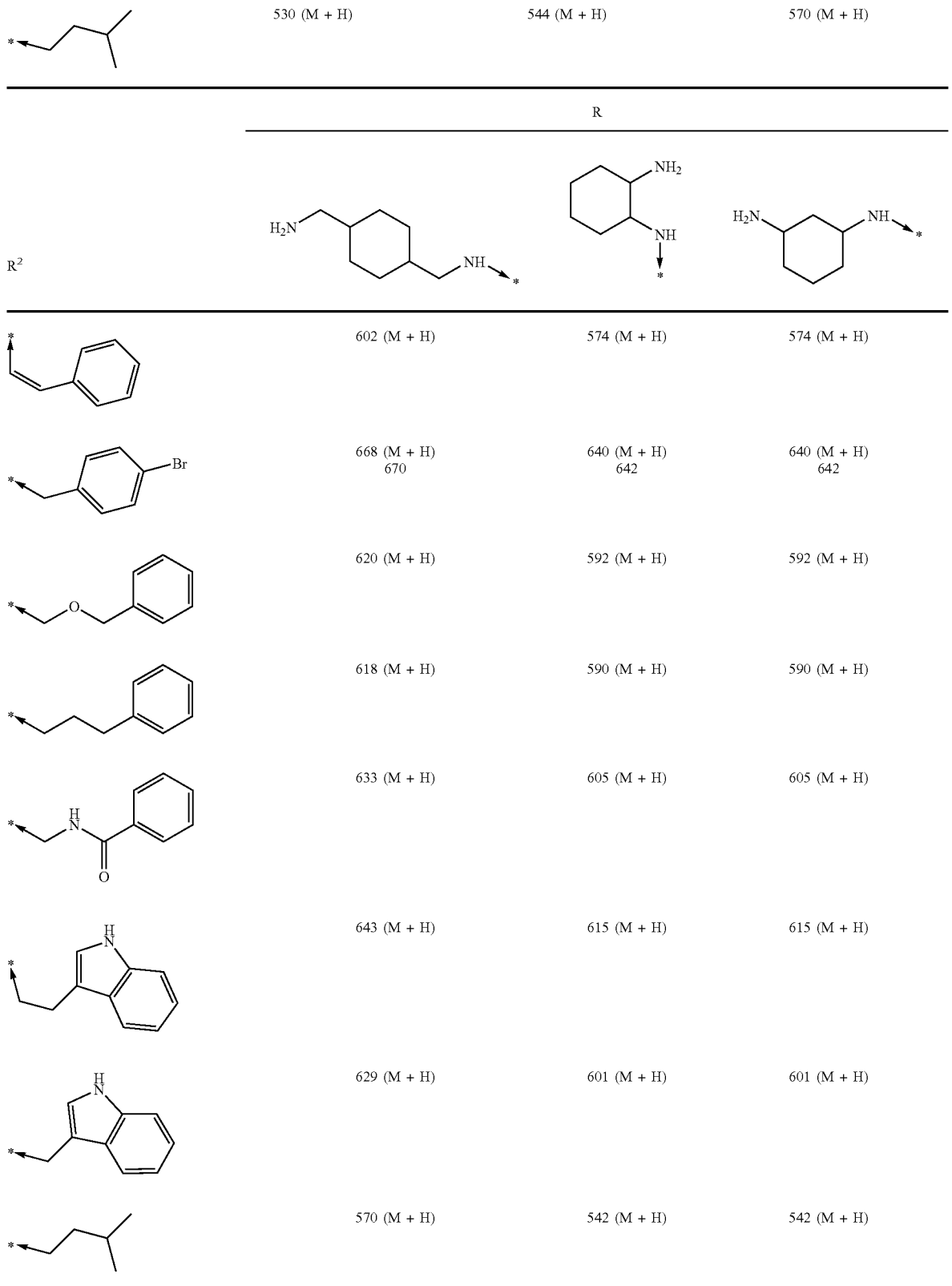

-continued

| R² | R: H₂N-cyclohexyl-NH→* | R: H₂N-CH₂CH₂-N(CH₃)-CH₂CH₂-NH→* |
|---|---|---|
| *←CH=CH-Ph (cis styryl) | 574 (M + H) | 577 (M + H) |
| *←CH₂-C₆H₄-Br | 640 (M + H) <br> 642 | 643 (M + H) <br> 645 |
| *←CH₂-O-CH₂-Ph | 592 (M + H) | 595 (M + H) |
| *←(CH₂)₃-Ph | 590 (M + H) | 593 (M + H) |
| *←CH₂-NH-C(O)-Ph | 605 (M + H) | 608 (M + H) |
| *←(CH₂)₂-(3-indolyl) | 615 (M + H) | 618 (M + H) |
| *←CH₂-(3-indolyl) | 601 (M + H) | 604 (M + H) |
| *←CH₂-CH(CH₃)₂ (isobutyl) | 542 (M + H) | 545 (M + H) |

| R² | R: H₂N-CH₂CH₂-NH→* | R: H₂N-(CH₂)₃-NH→* | R: H₂N-(CH₂)₄-NH→* |
|---|---|---|---|
| *←CH=CH-(2-furyl) | 510 (M + H) | 524 (M + H) | 538 (M + H) |
| *←CH=CH-(3-pyridyl) | 521 (M + H) | 535 (M + H) | 549 (M + H) |

-continued

| R² | H₂N~~~NH→* | H₂N~~~~NH→* | H₂N-CH₂-(cyclohexyl)-CH₂-NH→* |
|---|---|---|---|
| *-CH₂-(3-Br-phenyl) | 586 (M + H) / 588 | 600 (M + H) / 602 | 614 (M + H) / 616 |
| *-CH₂-(2-Br-phenyl) | 586 (M + H) / 588 | 600 (M + H) / 602 | 614 (M + H) / 616 |
| (4-pyridyl)-S-CH₂-* | 541 (M + H) | 555 (M + H) | 569 (M + H) |
| *-CH₂-(4-MeO-phenyl) | 538 (M + H) | 552 (M + H) | 566 (M + H) |
| *-CH=CH-(4-MeO-phenyl) | 550 (M + H) | 564 (M + H) | 578 (M + H) |
| *-CH=CH-(4-Br-phenyl) | 598 (M + H) / 600 | 612 (M + H) / 614 | 626 (M + H) / 628 |

| R² | H₂N~~~~NH→* | H₂N~~~~~NH→* | H₂N-CH₂-(cyclohexyl)-CH₂-NH→* |
|---|---|---|---|
| *-CH=CH-(2-furyl) | 552 (M + H) | 566 (M + H) | 592 (M + H) |
| (3-pyridyl)-CH=CH-* | 563 (M + H) | 577 (M + H) | 603 (M + H) |
| *-CH₂-(3-Br-phenyl) | 628 (M + H) / 630 | 642 (M + H) / 644 | 668 (M + H) / 670 |
| *-CH₂-(2-Br-phenyl) | 628 (M + H) / 630 | 642 (M + H) / 644 | 668 (M + H) / 670 |
| (4-pyridyl)-S-CH₂-* | 583 (M + H) | 597 (M + H) | 623 (M + H) |

-continued
| R² | | | |
|---|---|---|---|
|  | 580 (M + H) | 594 (M + H) | 620 (M + H) |
| 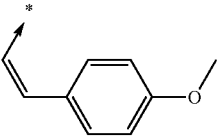 | 592 (M + H) | 606 (M + H) | 632 (M + H) |
| 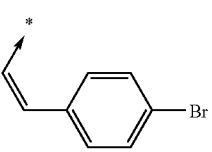 | 640 (M + H)<br>642 | 654 (M + H)<br>656 | 680 (M + H)<br>682 |
| | R | | |
|---|---|---|---|
| R² | 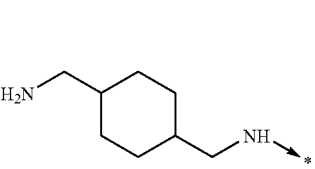 | 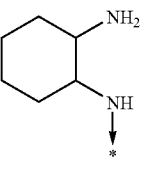 | 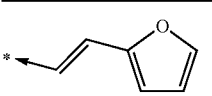 |
| 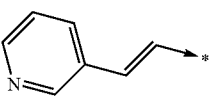 | 592 (M + H) | 564 (M + H) | 564 (M + H) |
| 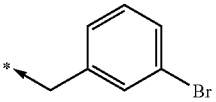 | 603 (M + H) | 675 (M + H) | 675 (M + H) |
| 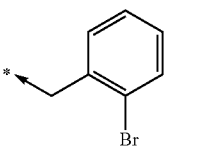 | 668 (M + H)<br>670 | 640 (M + H)<br>642 | 640 (M + H)<br>642 |
| 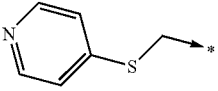 | 668 (M + H)<br>670 | 640 (M + H)<br>642 | 640 (M + H)<br>642 |
| 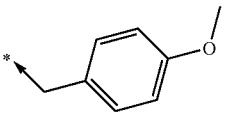 | 623 (M + H) | 595 (M + H) | 595 (M + H) |
| 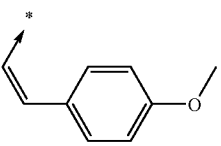 | 620 (M + H) | 592 (M + H) | 592 (M + H) |
| | 632 (M + H) | 604 (M + H) | 604 (M + H) |

-continued
| $R^2$ | | | |
|---|---|---|---|
| 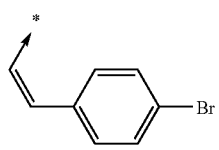 | 680 (M + H) 682 | 652 (M + H) 654 | 652 (M + H) 654 |
| | R | |
|---|---|---|
| | 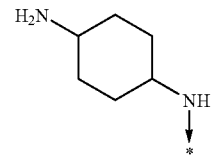 | 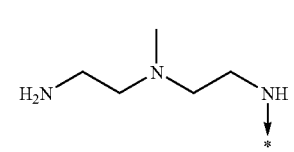 |
| 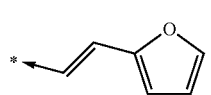 | 564 (M + H) | 567 (M + H) |
| 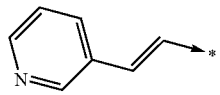 | 675 (M + H) | 678 (M + H) |
| 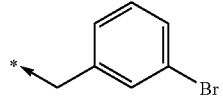 | 640 (M + H) 642 | 643 (M + H) 645 |
| 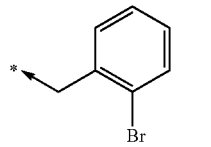 | 640 (M + H) 642 | 643 (M + H) 645 |
| 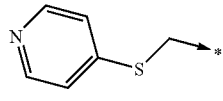 | 595 (M + H) | 598 (M + H) |
| 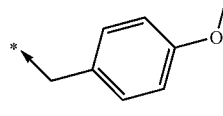 | 592 (M + H) | 595 (M + H) |
|  | 604 (M + H) | 607 (M + H) |
|  | 652 (M + H) 654 | 655 (M + H) 657 |

Root Structure

[Root structure: biphenyl with -C(=O)NH-CH₂CH₂-NH₂ on one ring and -CH₂-N(R³)-C(=O)-R² on the other]

MS (APCI+ or -)

| R² \ R³ | -CH₂CH₂-C₆H₄-SO₂NH₂ | -CH₂-C₆H₄-SO₂NH₂ | -CH₂-(4-pyridyl)-CH₂- | -(CH₂)₃-N(2-oxopyrrolidinyl) |
|---|---|---|---|---|
| cinnamyl (PhCH=CH-CH₂-) | 581 (M − H) | 567 (M − H) | 503 (M − H) | 523 (M − H) |
| 4-bromobenzyl | 647 (M − H), 649 | 633 (M − H), 635 | 571 (M + H), 573 | 589 (M − H), 591 |
| benzyloxymethyl (PhCH₂-O-CH₂-) | 599 (M − H) | 585 (M − H) | 523 (M + H) | 541 (M − H) |
| 4-phenylbutyl | 597 (M − H) | 583 (M − H) | 521 (M + H) | 539 (M − H) |
| PhC(O)NH-CH₂- | 612 (M − H) | 598 (M − H) | 536 (M + H) | 554 (M − H) |
| 2-(1H-indol-3-yl)ethyl | 622 (M − H) | 608 (M − H) | 544 (M − H) | 564 (M − H) |

-continued
| R² | | | | | |
|---|---|---|---|---|---|
| | | 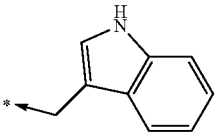 | 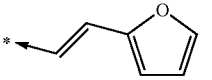 | 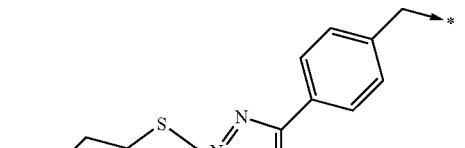 | 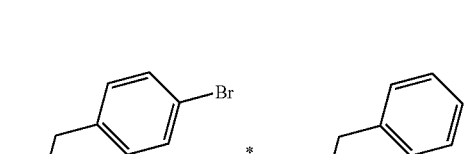 |
| | | | | | |
|---|---|---|---|---|---|
| 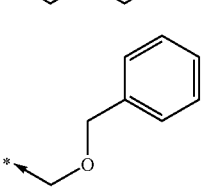 indole-CH₂ | | 608 (M − H) | 694 (M − H) | 530 (M − H) | 550 (M − H) |
| furan-CH=CH | | 571 (M − H) | 557 (M − H) | 495 (M + H) | 513 (M − H) |
R³
| R² | | | | | |
|---|---|---|---|---|---|
| styryl | | 508 (M − H) | 574 (M + H) | 580 (M − H) 582 | 516 (M − H) |
| 4-Br-benzyl | | 574 (M − H) 576 | 640 (M + H) 642 | 648 (M + H) 650 | 582 (M − H) 584 |
| benzyloxymethyl | | 526 (M − H) | 592 (M + H) | 598 (M − H) 600 | 534 (M − H) |
| 3-phenylpropyl | | 524 (M − H) | 590 (M + H) | 596 (M − H) 598 | 532 (M − H) |
| benzamidomethyl | | 539 (M − H) | 605 (M + H) | 613 (M + H) 615 | 547 (M − H) |
| indol-3-yl-propyl | | 549 (M − H) | 615 (M + H) | 623 (M + H) 625 | 557 (M − H) |
| indol-3-yl-methyl | | 535 (M − H) | 601 (MH) | 608 (M + H) 610 | 543 (M − H) |

-continued
| R² | | R³ | | |
|---|---|---|---|---|
| | 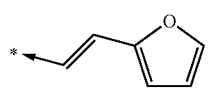 | 498 (M − H) | 564 (M + H) | 572 (M + H) 574 | 506 (M − H) |
| | | 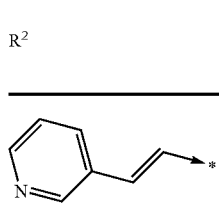 | 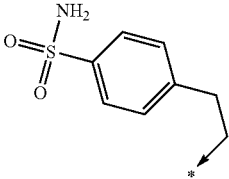 | 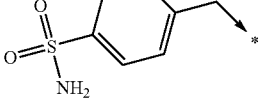 |
|---|---|---|---|---|
| 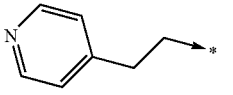 | | 582 (M − H) | 568 (M − H) | 506 (M + H) |
| 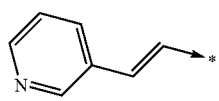 | | 647 (M − H) 649 | 633 (M − H) 635 | 571 (M + H) 573 |
| 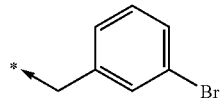 | | 647 (M − H) 649 | 633 (M − H) 635 | 571 (M + H) 573 |
|  | | 611 (M − H) | 597 (M − H) | 535 (M + H) |
| 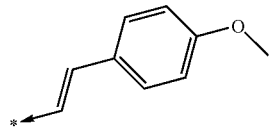 | | 599 (M − H) | 585 (M − H) | 521 (M − H) |
| 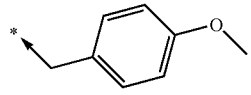 | | 585 (M − H) | 571 (M − H) | 507 (M − H) |
| 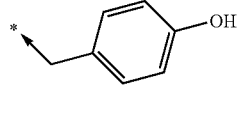 | | 597 (M − H) | 583 (M − H) | 519 (M − H) |
| 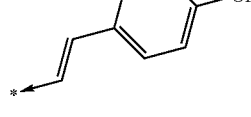 | | 599 (M − H) | 585 (M − H) | 521 (M − H) |

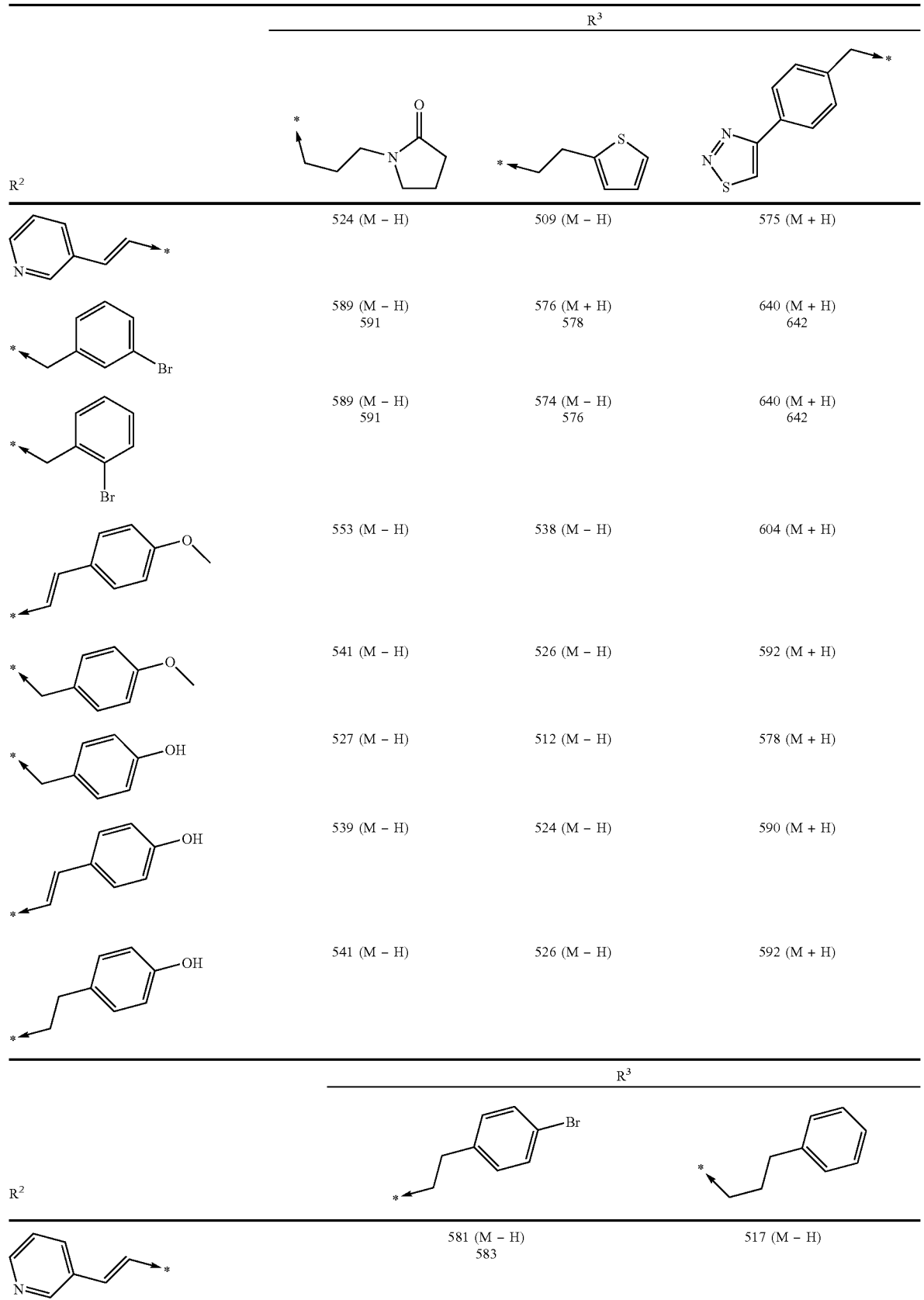

-continued
| R² | | MS (APCI+ or -) | |
|---|---|---|---|
| 3-bromobenzyl | | 646 (M + H) / 648 | 582 (M − H) / 584 |
| 2-bromobenzyl | | 646 (M + H) / 648 | 582 (M − H) / 584 |
| 4-methoxycinnamyl | | 611 (M − H) / 613 | 546 (M − H) |
| 4-methoxybenzyl | | 598 (M − H) / 600 | 534 (M − H) |
| 4-hydroxybenzyl | | 586 (M + H) / 588 | 520 (M − H) |
| 4-hydroxycinnamyl | | 596 (M − H) / 598 | 532 (M − H) |
| 4-hydroxyphenethyl | | 598 (M − H) / 600 | 534 (M − H) |
Root Structure
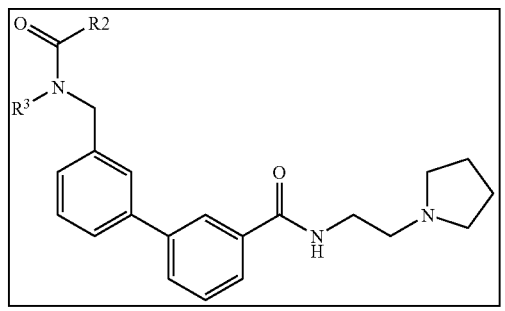
MS (APCI+ or −)
| R² | R³ = 4-sulfamoylphenethyl | R³ = 4-sulfamoylbenzyl | |
|---|---|---|---|
| 4-bromobenzyl | 703 (M + H) / 705 | 689 (M + H) / 691 | 625 (M + H) / 627 |

-continued
| | | | |
|---|---|---|---|
| 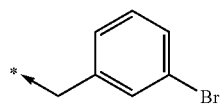 | 703 (M + H) 705 | 689 (M + H) 691 | 625 (M + H) 627 |
| 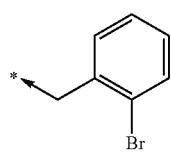 | 703 (M + H) 705 | 689 (M + H) 691 | 625 (M + H) 627 |
| 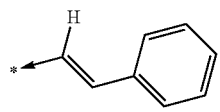 | 637 (M + H) | 623 (M + H) | 559 (M + H) |
| 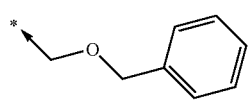 | 655 (M + H) | 641 (M + H) | 677 (M + H) |
| 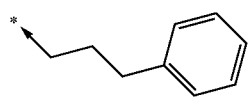 | 653 (M + H) | 639 (M + H) | 575 (M + H) |
| 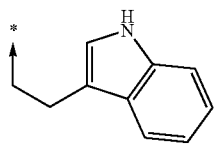 | 678 (M + H) | 664 (M + H) | 600 (M + H) |
| 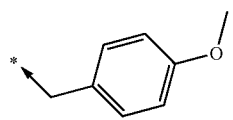 | 655 (M + H) | 641 (M + H) | 577 (M + H) |
| 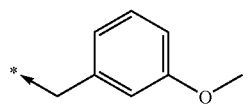 | 655 (M + H) | 639 (M − H) | 577 (M + H) |
| 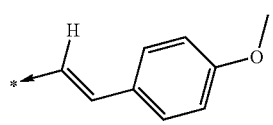 | 667 (M + H) | 653 (M + H) | 589 (M + H) |
| 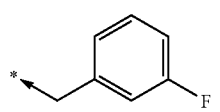 | 643 (M + H) | 629 (M + H) | 565 (M + H) |
| 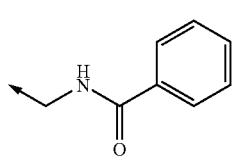 | 668 (M + H) | 654 (M + H) | 590 (M + H) |

-continued

| R² | R³ 2-thienylethyl | R³ 4-(thiadiazolyl)benzyl | R³ 3-phenylpropyl | R³ methyl 4-benzoate |
|---|---|---|---|---|
| 4-bromobenzyl | 630 (M + H) 632 | 694 (M + H) 696 | 638 (M + H) 640 | 668 (M + H) 670 |
| 3-bromobenzyl | 630 (M + H) 632 | 694 (M + H) 696 | 638 (M + H) 640 | 668 (M + H) 670 |
| 2-bromobenzyl | 630 (M + H) 632 | 694 (M + H) 696 | 638 (M + H) 640 | 668 (M + H) 670 |
| styryl | 564 (M + H) | 628 (M + H) | 572 (M + H) | 602 (M + H) |
| benzyloxymethyl | 582 (M + H) | 646 (M + H) | 590 (M + H) | 620 (M + H) |
| 3-phenylpropyl | 580 (M + H) | 644 (M + H) | 588 (M + H) | 618 (M + H) |
| 2-(1H-indol-3-yl)ethyl | 605 (M + H) | 669 (M + H) | 613 (M + H) | 643 (M + H) |
| 4-methoxybenzyl | 582 (M + H) | 646 (M + H) | 590 (M + H) | 620 (M + H) |
| 3-methoxybenzyl | 582 (M + H) | 646 (M + H) | 590 (M + H) | 620 (M + H) |
| 4-methoxystyryl | 594 (M + H) | 658 (M + H) | 602 (M + H) | 632 (M + H) |

-continued
| R² | | | |
|---|---|---|---|
| 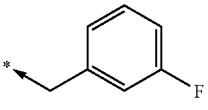  3-F-benzyl | 570 (M + H) | 634 (M + H) | 578 (M + H) | 608 (M + H) |
| 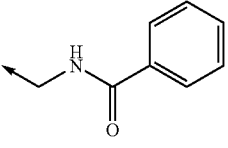  benzamide-CH₂ | 595 (M + H) | 659 (M + H) | 603 (M + H) | 633 (M + H) |
| | R³ | | |
|---|---|---|---|
| R² | 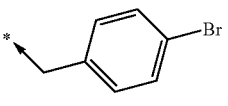 | 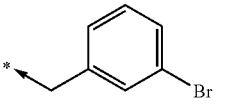 | 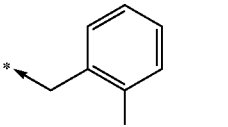 |
| 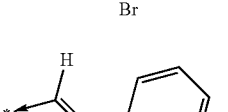 4-Br-benzyl | 648 (M + H) 650 | 652 (M − H) 654 | 632 (M − H) 634 |
| 3-Br-benzyl | 648 (M + H) 650 | 652 (M − H) 654 | 632 (M − H) 634 |
| 2-Br-benzyl | 648 (M + H) 650 | 652 (M − H) 654 | 632 (M − H) 634 |
| 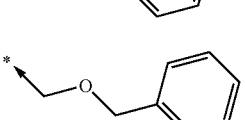 styryl | 582 (M + H) | 598 (M + H) | 566 (M − H) |
| 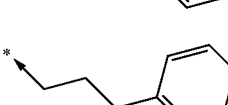 benzyloxymethyl | 600 (M + H) | 604 (M − H) | 584 (M − H) |
| phenylpropyl | 598 (M + H) | 602 (M − H) | 582 (M − H) |
| 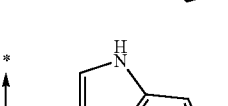 indolylethyl | 623 (M + H) | 627 (M − H) | 607 (M − H) |
|  4-methoxybenzyl | 600 (M + H) | 604 (M − H) | 584 (M − H) |

-continued

| R² | | | |
|---|---|---|---|
| *-CH₂-(3-methoxyphenyl) | 600 (M + H) | 604 (M − H) | 584 (M − H) |
| *-CH=CH-(4-methoxyphenyl) | 612 (M + H) | 616 (M − H) | 596 (M − H) |
| *-CH₂-(3-fluorophenyl) | 588 (M + H) | 592 (M − H) | 572 (M − H) |
| *-CH₂-NH-C(O)-phenyl | 613 (M + H) | 617 (M − H) | 597 (M − H) |

Root Structure

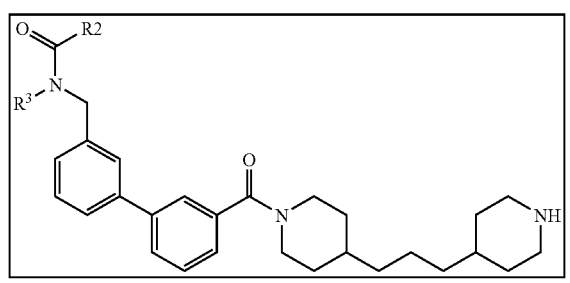

MS (APCI+ or −)

| R² | R³ = 4-(H₂NSO₂)phenylethyl | R³ = 4-(H₂NSO₂)phenylmethyl | R³ = 4-pyridylethyl |
|---|---|---|---|
| *-CH₂-(4-bromophenyl) | 799 (M + H), 801 | 783 (M + H), 785 | 721 (M + H), 723 |
| *-CH₂-(3-bromophenyl) | 797 (M − H), 799 | 783 (M + H), 785 | 721 (M + H), 723 |
| *-CH₂-(2-bromophenyl) | 797 (M − H), 799 | 783 (M + H), 785 | 721 (M + H), 723 |
| *-CH=CH-phenyl | 731 (M − H) | 717 (M − H) | 655 (M + H) |
| *-CH₂-O-CH₂-phenyl | 751 (M + H) | 735 (M − H) | 673 (M + H) |

-continued
| | | | |
|---|---|---|---|
| 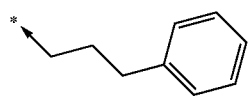 | 747 (M − H) | 733 (M − H) | 671 (M + H) |
| 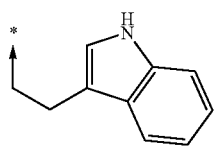 | 772 (M − H) | 758 (M − H) | 694 (M − H) |
| 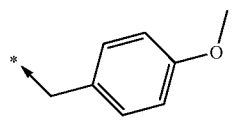 | 749 (M − H) | 735 (M − H) | 673 (M + H) |
| 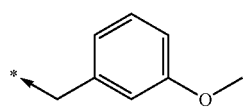 | 749 (M − H) | 735 (M − H) | 673 (M + H) |
| 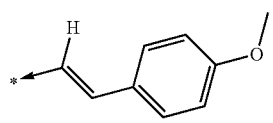 | 761 (M − H) | 747 (M − H) | 685 (M + H) |
| 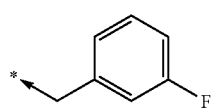 | 737 (M − H) | 723 (M − H) | 661 (M + H) |
| 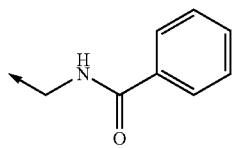 | 762 (M − H) | 748 (M − H) | 686 (M + H) |
| R² | R³ |
|---|---|
| | 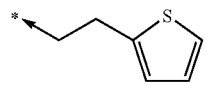 |
| 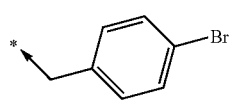 | 726 (M + H)<br>728 |
| 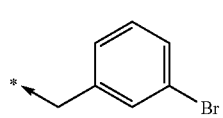 | 726 (M + H)<br>728 |
| 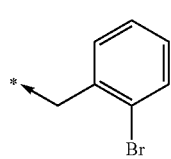 | 726 (M + H)<br>728 |

-continued
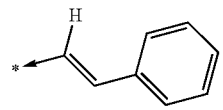  660 (M + H)
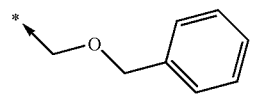  678 (M + H)
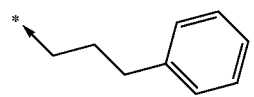  676 (M + H)
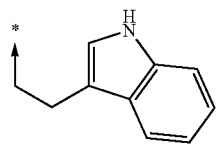  701 (M + H)
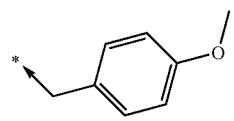  678 (M + H)
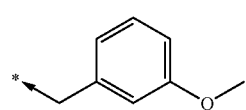  678 (M + H)
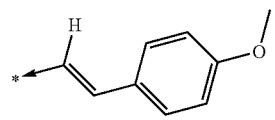  690 (M + H)
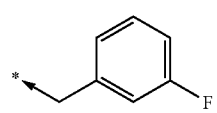  666 (M + H)
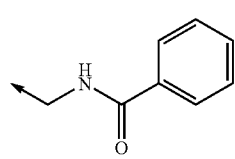  691 (M + H)

-continued
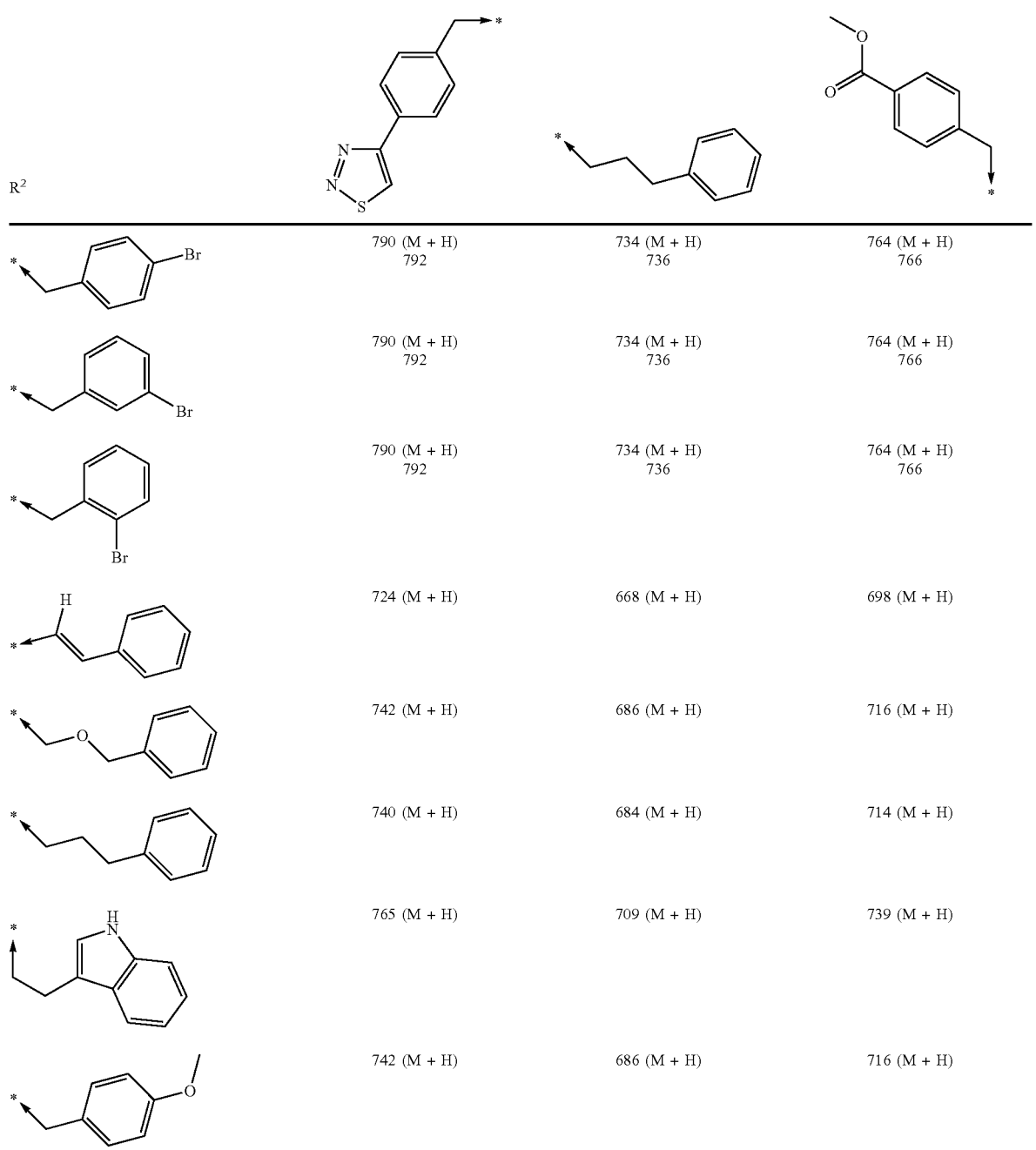

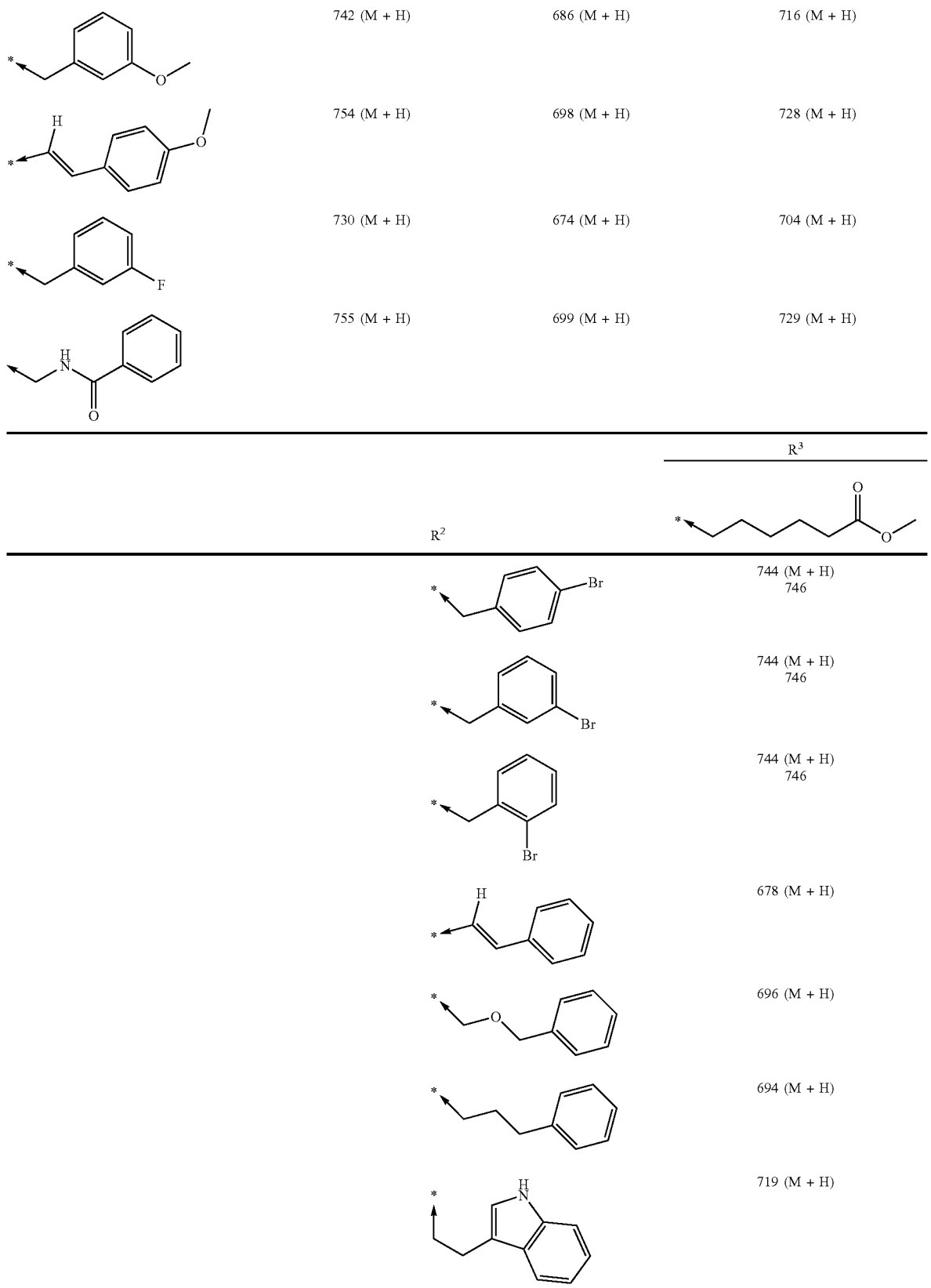

-continued
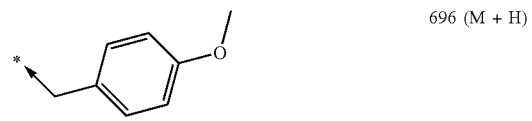 696 (M + H)
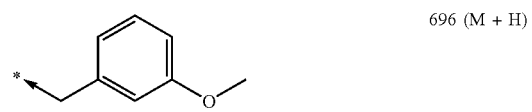 696 (M + H)
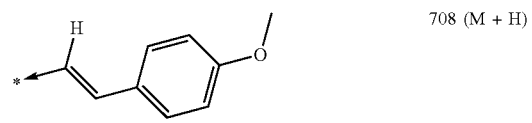 708 (M + H)
 684 (M + H)
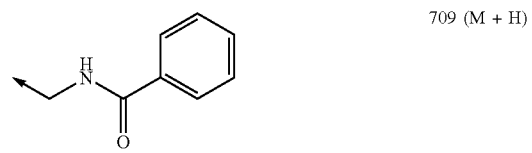 709 (M + H)
-continued
| Root Structure | Root Structure |
|---|---|
| 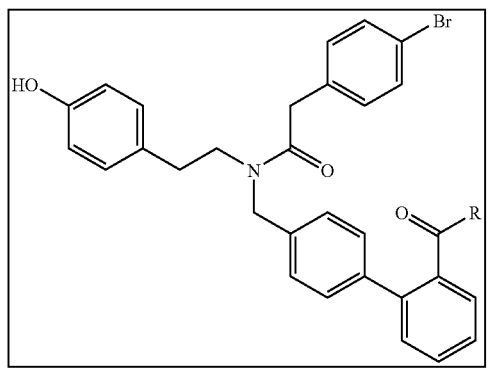 | 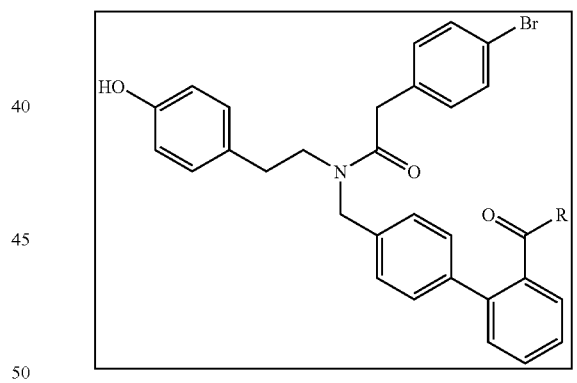 |
| R | MS (AP-CI+) | R | MS (AP-CI+) |
|---|---|---|---|
| 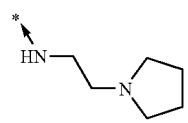 | 640 (M + H), 642 | 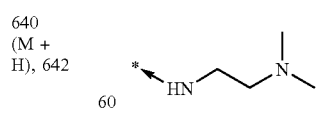  | 614 (M + H), 616 |
| 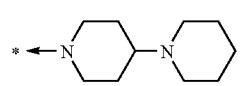 | 694 (M + H), 696 | 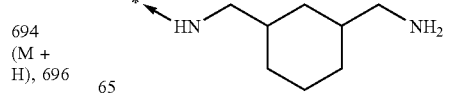 | 668 (M + H), 670 |

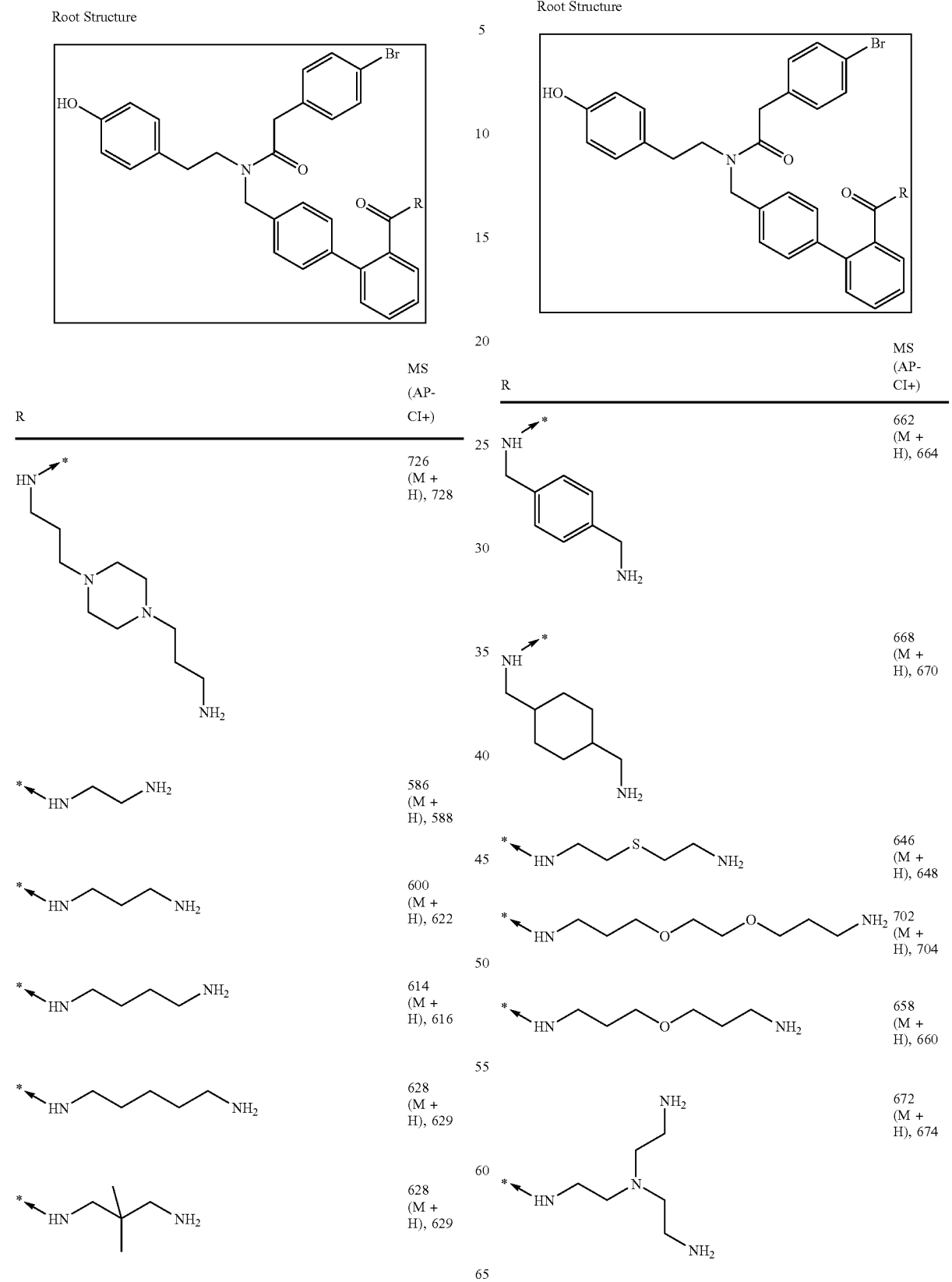

-continued
Root Structure
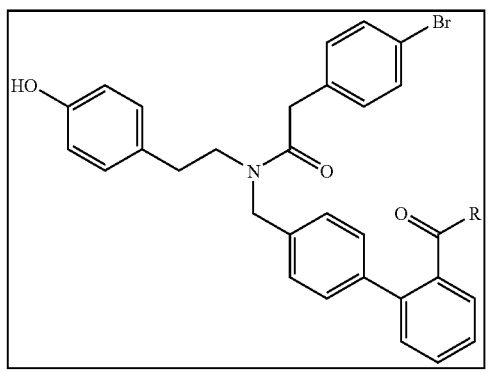
| R | MS (APCI+) |
|---|---|
| 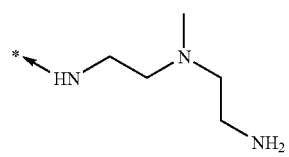 | 643 (M + H), 645 |
| 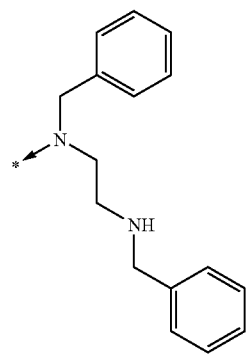 | 766 (M + H), 768 |
| 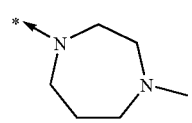 | 640 (M + H), 642 |
| 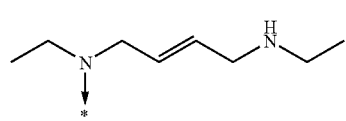 | 668 (M + H), 670 |
| 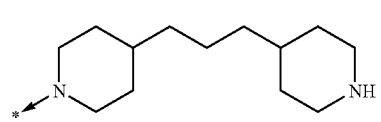 | 736 (M + H), 738 |
-continued
Root Structure
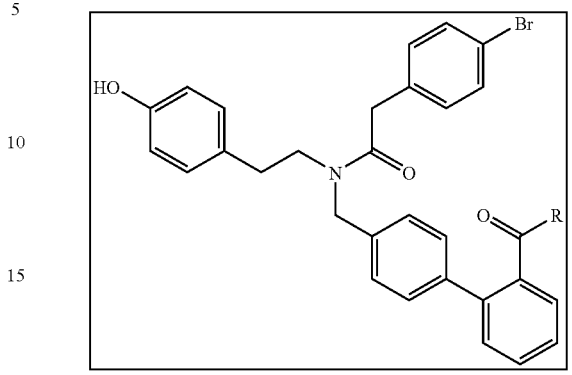
| R | MS (APCI+) |
|---|---|
| 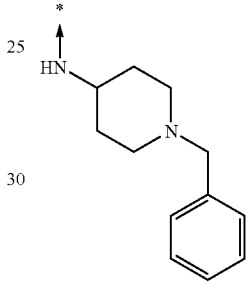 | 716 (M + H), 718 |
| 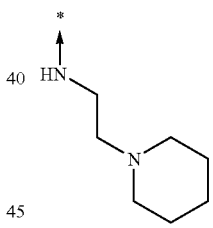 | 654 (M + H), 656 |
| 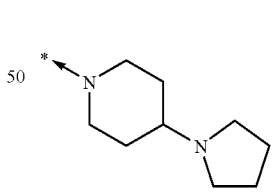 | 680 (M + H), 682 |
| 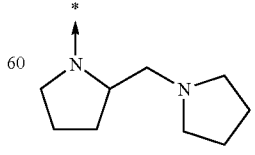 | 680 (M + H), 682 |

181
-continued
Root Structure
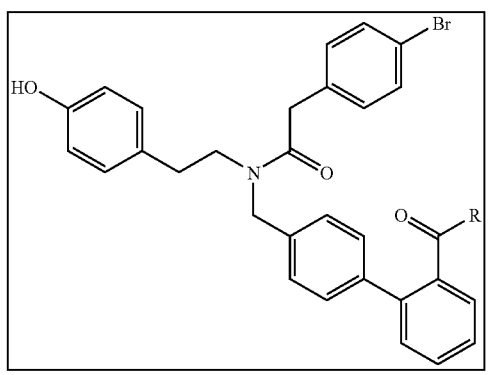
| R | MS (APCI+) |
|---|---|
| 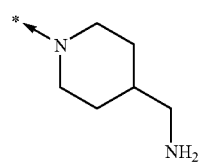 | 640 (M + H), 642 |
| 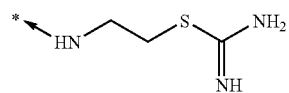 | 645 (M + H), 647 |
| 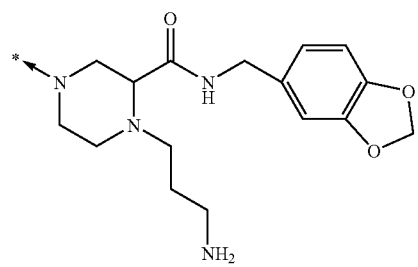 | 846 (M + H), 848 |
| 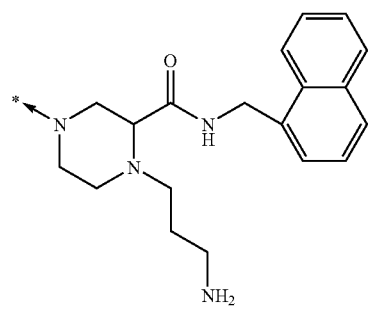 | 852 (M + H), 854 |
182
Root Structure
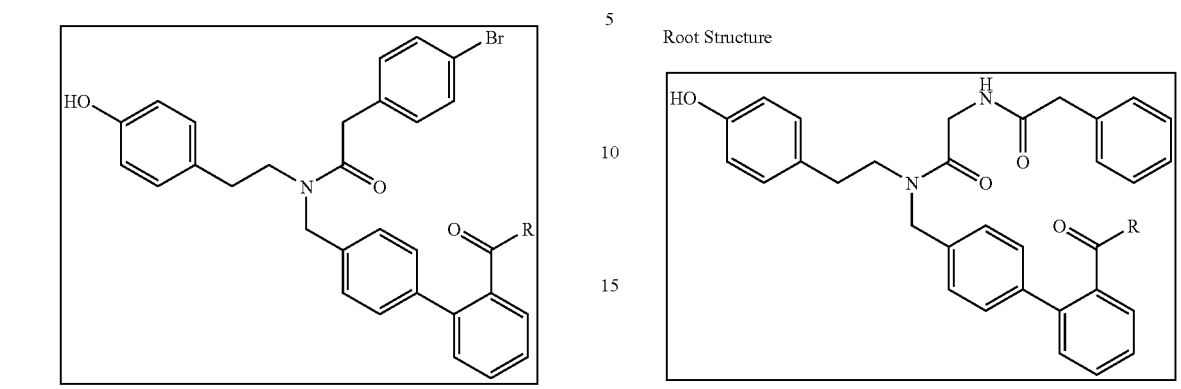
| R | MS (APCI+) |
|---|---|
| 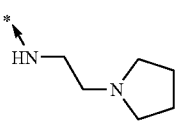 | 619 (M + H) |
| 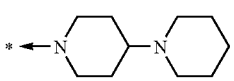 | 673 (M + H) |
| 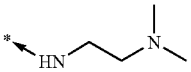 | 593 (M + H) |
| 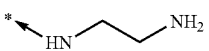 | 565 (M + H) |
| 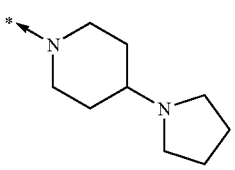 | 659 (M + H) |

Root Structure
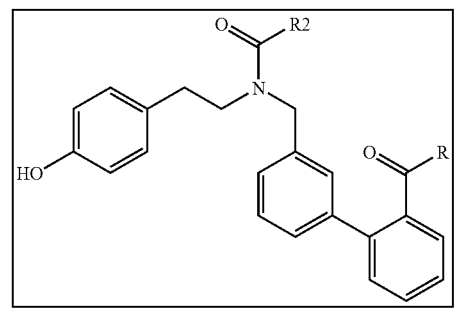
MS (APCI+)
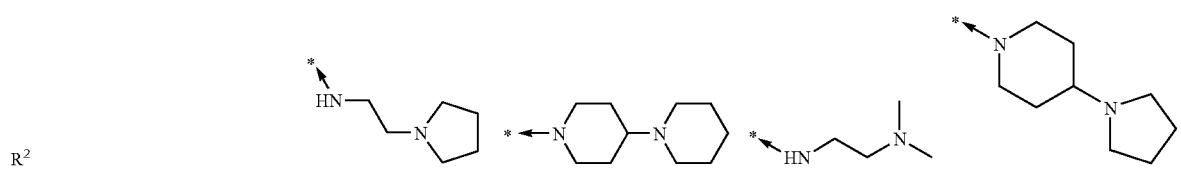
| R² | | | | |
|---|---|---|---|---|
| 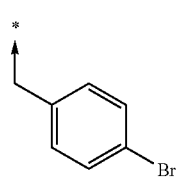 | 640 (M + H)<br>642 | 694 (M + H)<br>696 | 614 (M + H)<br>616 | 680 (M + H)<br>682 |
| 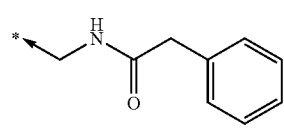 | 619 (M + H) | 673 (M + H) | 593 (M + H) | 658 (M + H) |
| 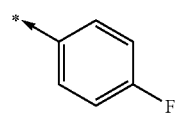 | 566 (M + H) | 620 (M + H) | 540 (M + H) | 606 (M + H) |
| 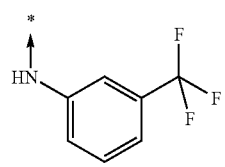 | 631 (M + H) | 685 (M + H) | 605 (M + H) | 671 (M + H) |

185

Root Structure

[Root structure: N-(4-hydroxyphenethyl)-N-((2'-(C(O)R)-biphenyl-3-yl)methyl)-2-(4-bromophenyl)acetamide]

| R | MS (APCI+) |
|---|---|
| *–HN–CH₂CH₂CH₂–NH₂ | 600 (M + H), 602 |
| *–HN–CH₂CH₂CH₂–O–CH₂CH₂CH₂–NH₂ | 658 (M + H), 660 |
| *–HN–CH₂CH₂–NH₂ | 586 (M + H), 588 |
| *–HN–(CH₂)₆–NH₂ | 642 (M + H), 644 |
| *–HN–CH₂–(1,3-cyclohexyl)–CH₂–NH₂ | 668 (M + H), 670 |
| NH (to *)–CH₂–(1,4-cyclohexyl)–CH₂–NH₂ | 668 (M + H), 670 |
| NH (to *)–CH₂–(1,4-phenyl)–CH₂–NH₂ | 662 (M + H), 664 |
| *–HN–CH₂–C(CH₃)₂–CH₂–NH₂ | 628 (M + H), 630 |
| *–HN–CH₂CH₂–S–CH₂CH₂–NH₂ | 646 (M + H), 648 |

186 -continued

Root Structure

[Same root structure as 185]

| R | MS (APCI+) |
|---|---|
| bis(piperidin-4-yl)propane linked via N | 736 (M + H), 738 |
| piperazine–CH₂CH₂–NH₂ | 655 (M + H), 656 |
| 4-(aminomethyl)piperidine via N | 640 (M + H), 642 |
| *–HN–CH₂–C(=NH)–NH₂ | 600 (M + H), 602 |
| *–HN–CH₂CH₂–S–C(=NH)–NH₂ | 646 (M + H), 648 |
| *–HN–(CH₂)₄–NH₂ | 614 (M + H), 616 |
| *–HN–(CH₂)₅–NH₂ | 628 (M + H), 630 |
| *–HN–CH₂CH₂–N(CH₂CH₂NH₂)₂ | 672 (M + H), 674 |

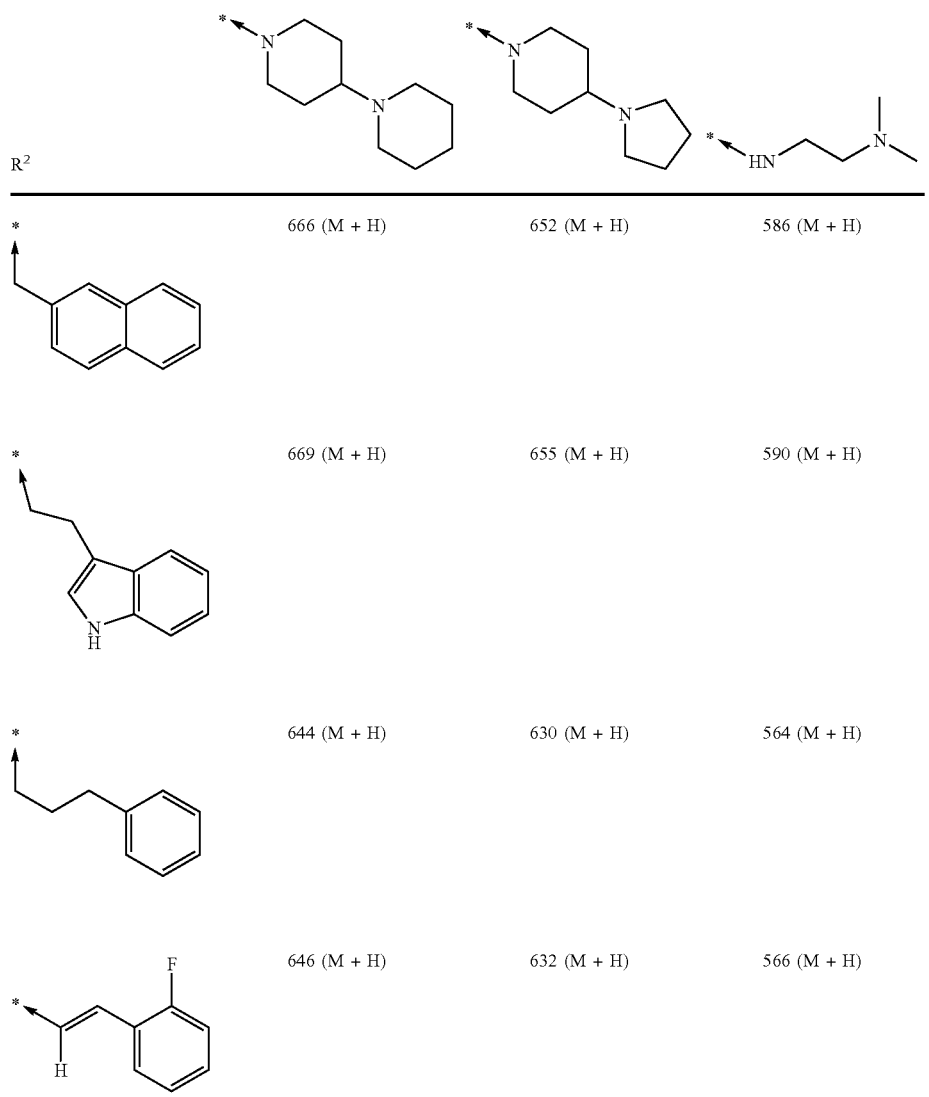

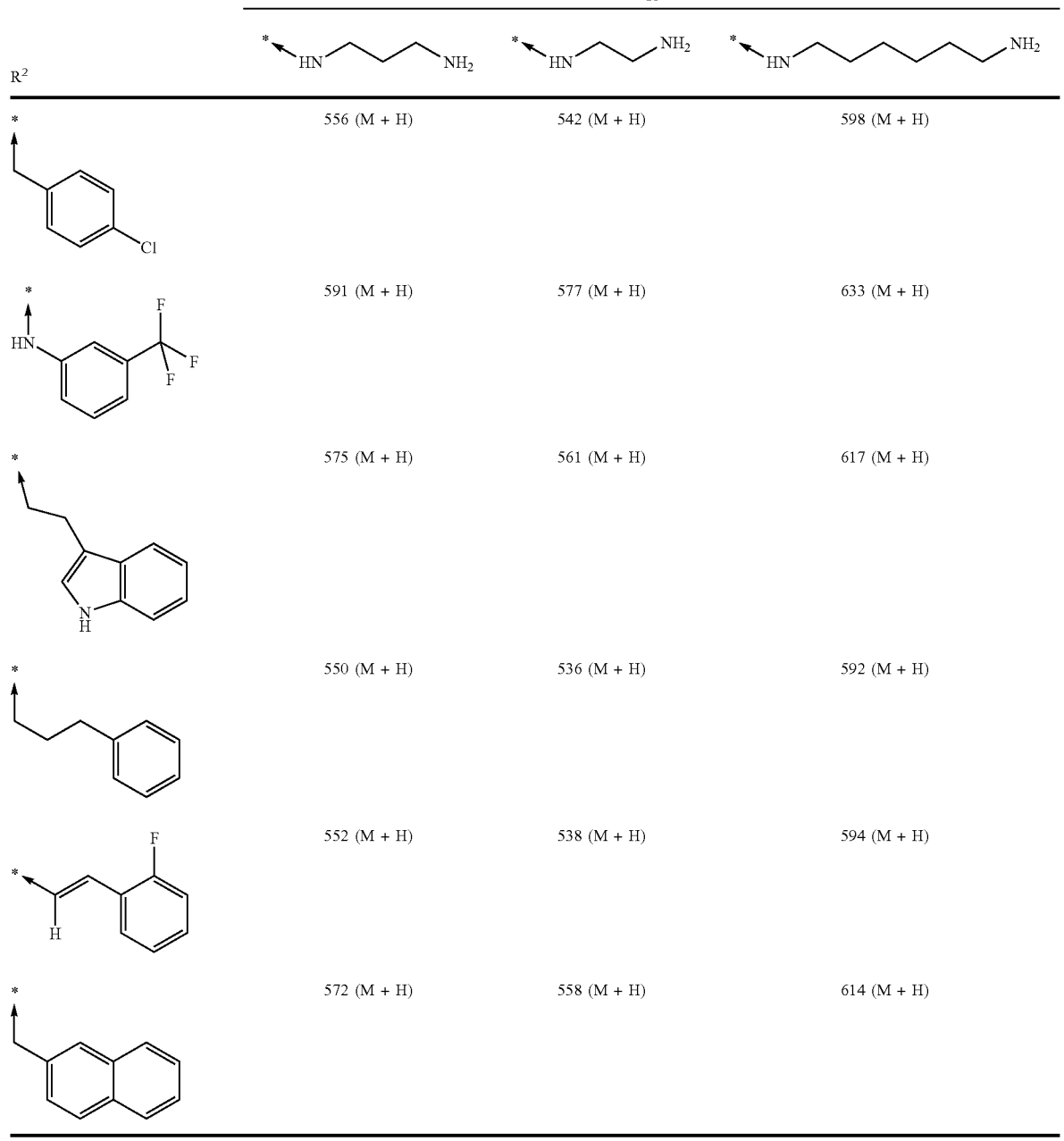

-continued
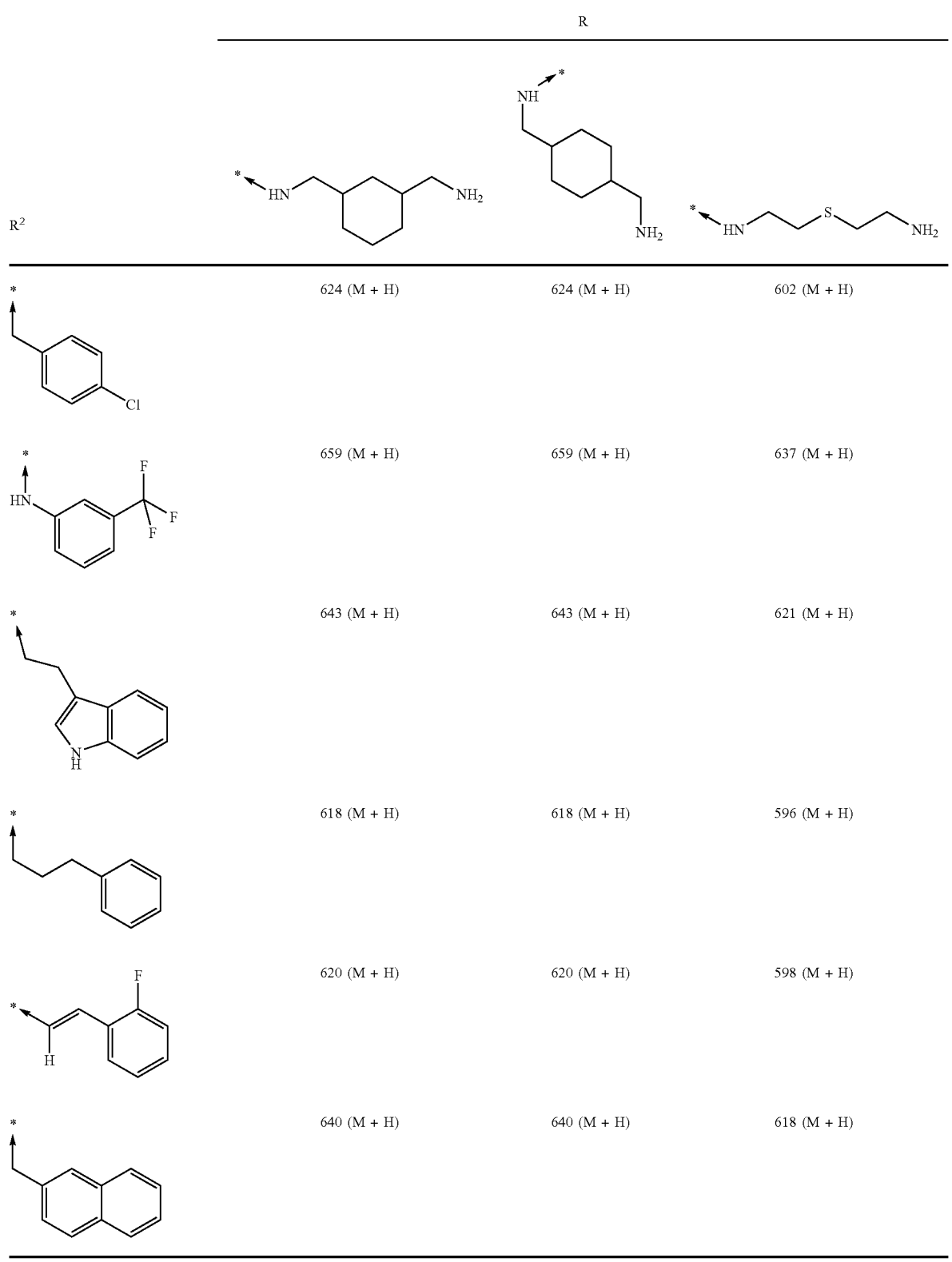
| R² | R | | |
|---|---|---|---|
| | *←HN—CH₂—[cyclohexane-1,3-diyl]—CH₂—NH₂ | *—NH—CH₂—[cyclohexane-1,4-diyl]—CH₂—NH₂ | *←HN—CH₂CH₂—S—CH₂CH₂—NH₂ |
| *—CH₂—C₆H₄—Cl (4-Cl benzyl) | 624 (M + H) | 624 (M + H) | 602 (M + H) |
| 3-CF₃-phenyl-NH—* | 659 (M + H) | 659 (M + H) | 637 (M + H) |
| *—CH₂CH₂—(1H-indol-3-yl) | 643 (M + H) | 643 (M + H) | 621 (M + H) |
| *—CH₂CH₂CH₂—phenyl | 618 (M + H) | 618 (M + H) | 596 (M + H) |
| *—CH=CH—(2-F-phenyl) | 620 (M + H) | 620 (M + H) | 598 (M + H) |
| *—CH₂—(naphthalen-2-yl) | 640 (M + H) | 640 (M + H) | 618 (M + H) |

-continued
| R² | R |||
|---|---|---|---|
| | piperidine-propyl-piperidine | HN-(CH₂)₄-NH₂ | HN-(CH₂)₅-NH₂ |
| 4-chlorobenzyl | 692 (M + H) | 570 (M + H) | 584 (M + H) |
| 3-(trifluoromethyl)phenylamino | 727 (M + H) | 605 (M + H) | 619 (M + H) |
| 2-(1H-indol-3-yl)ethyl | 711 (M + H) | 589 (M + H) | 603 (M + H) |
| 3-phenylpropyl | 686 (M + H) | 564 (M + H) | 578 (M + H) |
| 2-fluorostyryl | 688 (M + H) | 566 (M + H) | 580 (M + H) |
| naphthalen-2-ylmethyl | 708 (M + H) | 586 (M + H) | 600 (M + H) |
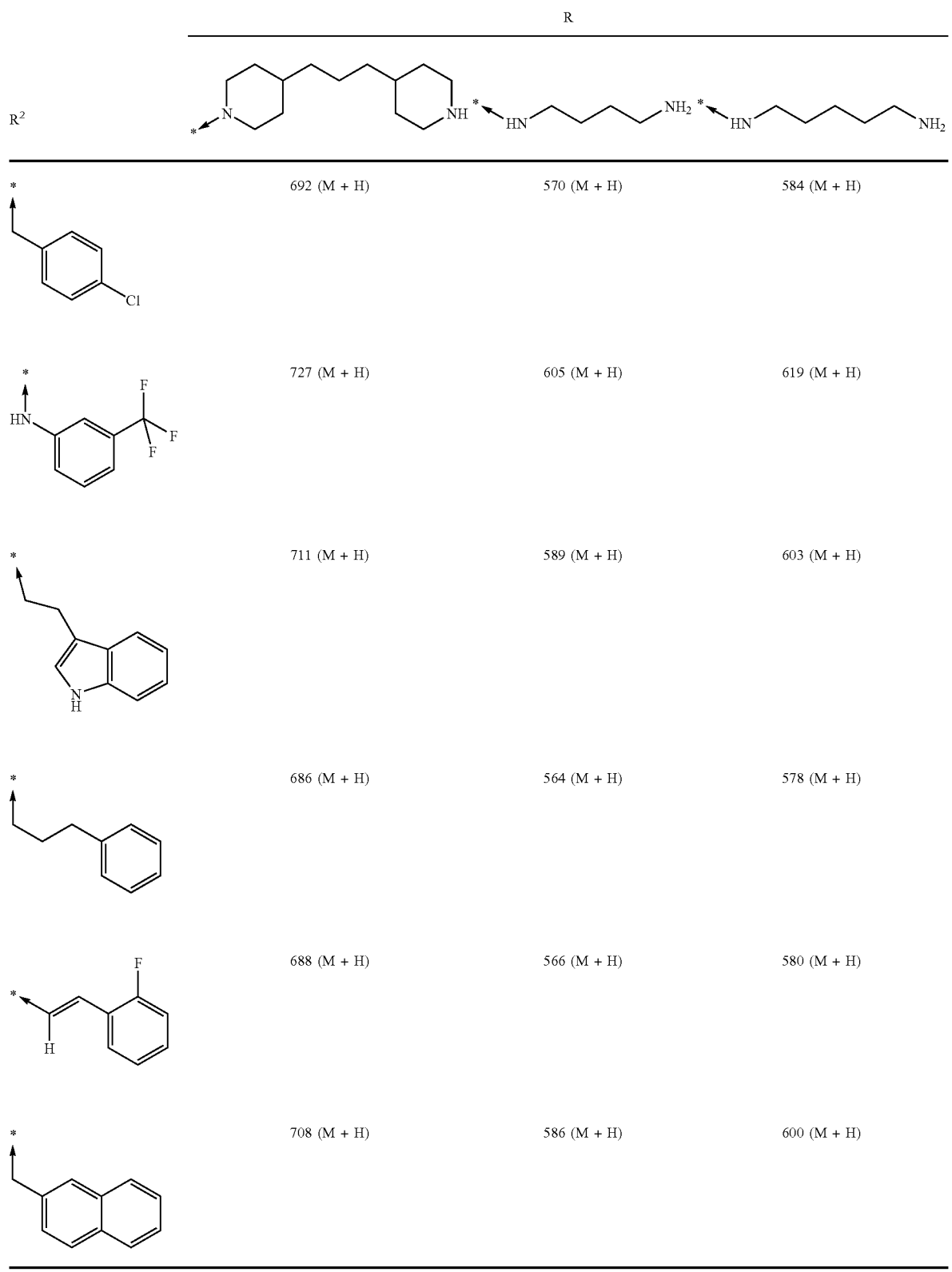

| Root Structure | | |
|---|---|---|
| 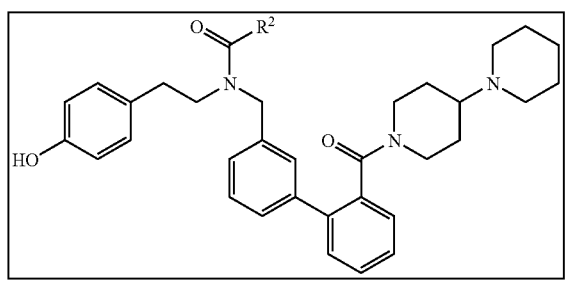 | | |
| R² | | MS (APCI+) |
| 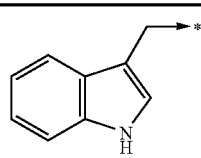 | | 655 (M + H) |
| 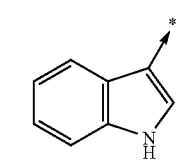 | | 641 (M + H) |
| 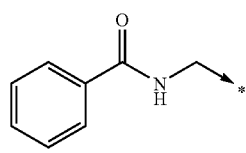 | | 659 (M + H) |
| 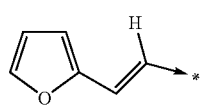 | | 618 (M + H) |
| 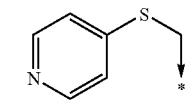 | | 649 (M + H) |
| 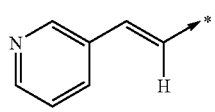 | | 629 (M + H) |
| 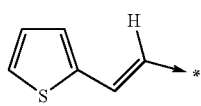 | | 634 (M + H) |
| 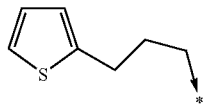 | | 650 (M + H) |
| 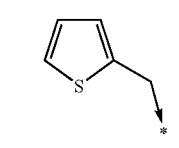 | | 622 (M + H) |
-continued
| Root Structure | | |
|---|---|---|
| 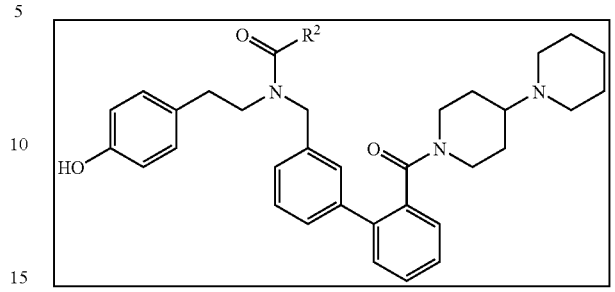 | | |
| R² | | MS (APCI+) |
| 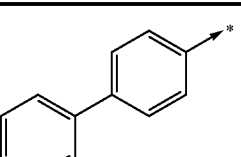 | | 678 (M + H) |
| 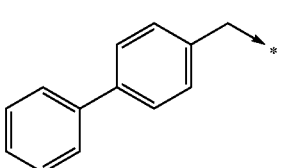 | | 692 (M + H) |
| 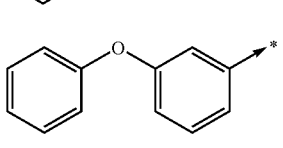 | | 694 (M + H) |
| 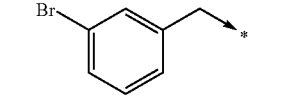 | | 694 (M + H), 696 |
| 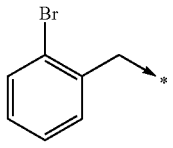 | | 694 (M + H), 696 |
| 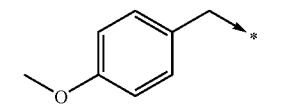 | | 646 (M + H) |
| 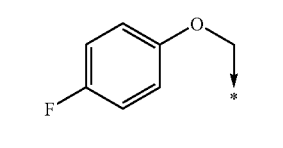 | | 650 (M + H) |
| 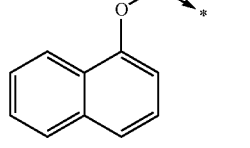 | | 682 (M + H) |

-continued
Root Structure
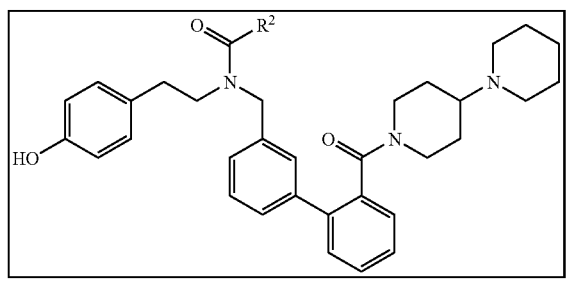
| R² | MS (APCI+) |
|---|---|
| 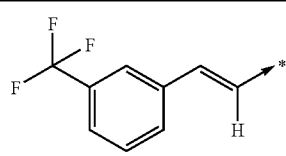 | 696 (M + H) |
| 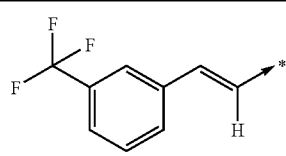 | 646 (M + H) |
| 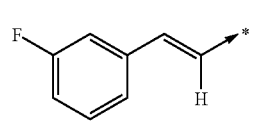 | 646 (M + H) |
| 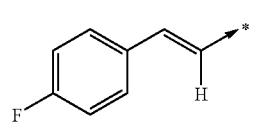 | 706 (M + H), 708 |
| 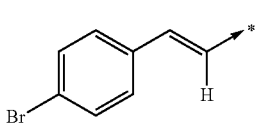 | 660 (M + H) |
| 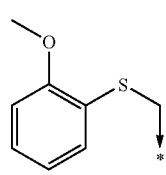 | 660 (M + H) |
| 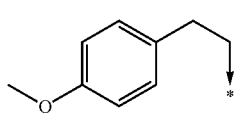 | 666 (M + H) |
| 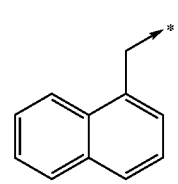 | |
-continued
Root Structure
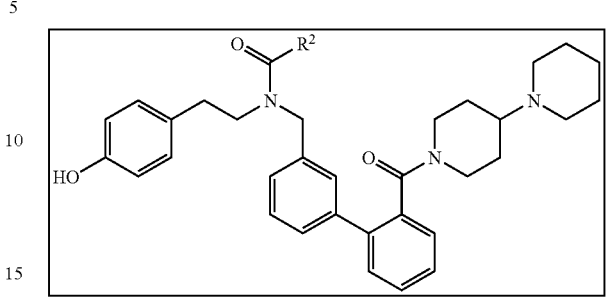
| R² | MS (APCI+) |
|---|---|
| 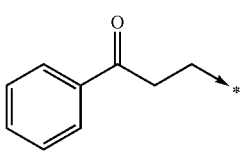 | 658 (M + H) |
| 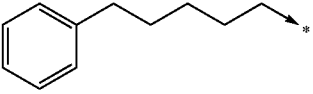 | 672 (M + H) |
| 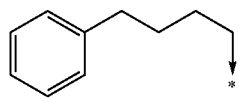 | 658 (M + H) |
| 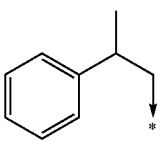 | 644 (M + H) |
| 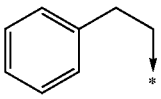 | 630 (M + H) |
| 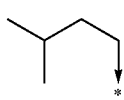 | 596 (M + H) |

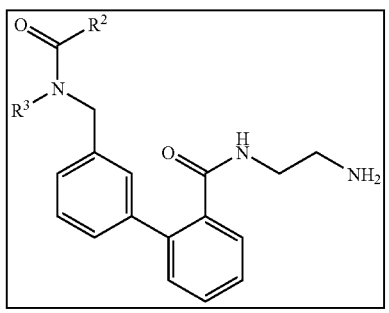
Root Structure
MS (APCI+)
| R² | R³ 4-MeO-PhCH₂CH₂-* | PhCH₂-* | PhCH₂CH₂-* | PhCH₂CH₂CH₂-* |
|---|---|---|---|---|
| 4-Br-PhCH₂-* | 600 (M + H) 602 | 556 (M + H) 558 | 570 (M + H) 572 | 584 (M + H) 586 |
| Ph(CH₂)₃-* | 550 (M + H) | 506 (M + H) | 520 (M + H) | 534 (M + H) |
| 2-thienyl-(CH₂)₃-* | 556 (M + H) | 512 (M + H) | 526 (M + H) | 540 (M + H) |
| 4-F-PhCH=CH-* | 552 (M + H) | 508 (M + H) | 522 (M + H) | 536 (M + H) |
| 3-CF₃-PhCH=CH-* | 602 (M + H) | 558 (M + H) | 572 (M + H) | 586 (M + H) |
| 3-indolyl-CH₂CH₂-* | 575 (M + H) | 531 (M + H) | 545 (M + H) | 559 (M + H) |
| PhCH₂C(O)NHCH₂-* | 579 (M + H) | 535 (M + H) | 549 (M + H) | 563 (M + H) |
| PhC(O)NHCH₂-* | 565 (M + H) | 521 (M + H) | 535 (M + H) | 549 (M + H) |

-continued

| | R³ | | | |
|---|---|---|---|---|
| R² | Ph(CH₂)₄-* | PhCH(CH₃)CH₂-* | benzodioxole-CH₂-* | 2-F-C₆H₄-CH₂-* |
| 4-Br-C₆H₄-CH₂-* | 598 (M + H) 600 | 584 (M + H) 586 | 600 (M + H) 602 | 574 (M + H) 576 |
| Ph(CH₂)₃-* | 548 (M + H) | 534 (M + H) | 550 (M + H) | 524 (M + H) |
| 2-thienyl-(CH₂)₃-* | 554 (M + H) | 540 (M + H) | 556 (M + H) | 530 (M + H) |
| 4-F-C₆H₄-CH=CH-* | 550 (M + H) | 536 (M + H) | 552 (M + H) | 526 (M + H) |
| 3-CF₃-C₆H₄-CH=CH-* | 600 (M + H) | 586 (M + H) | 602 (M + H) | 576 (M + H) |
| indol-3-yl-CH₂CH₂-* | 573 (M + H) | 559 (M + H) | 575 (M + H) | 549 (M + H) |
| PhCH₂C(O)NHCH₂-* | 577 (M + H) | 563 (M + H) | 579 (M + H) | 553 (M + H) |
| PhC(O)NHCH₂-* | 563 (M + H) | 549 (M + H) | 565 (M + H) | 539 (M + H) |

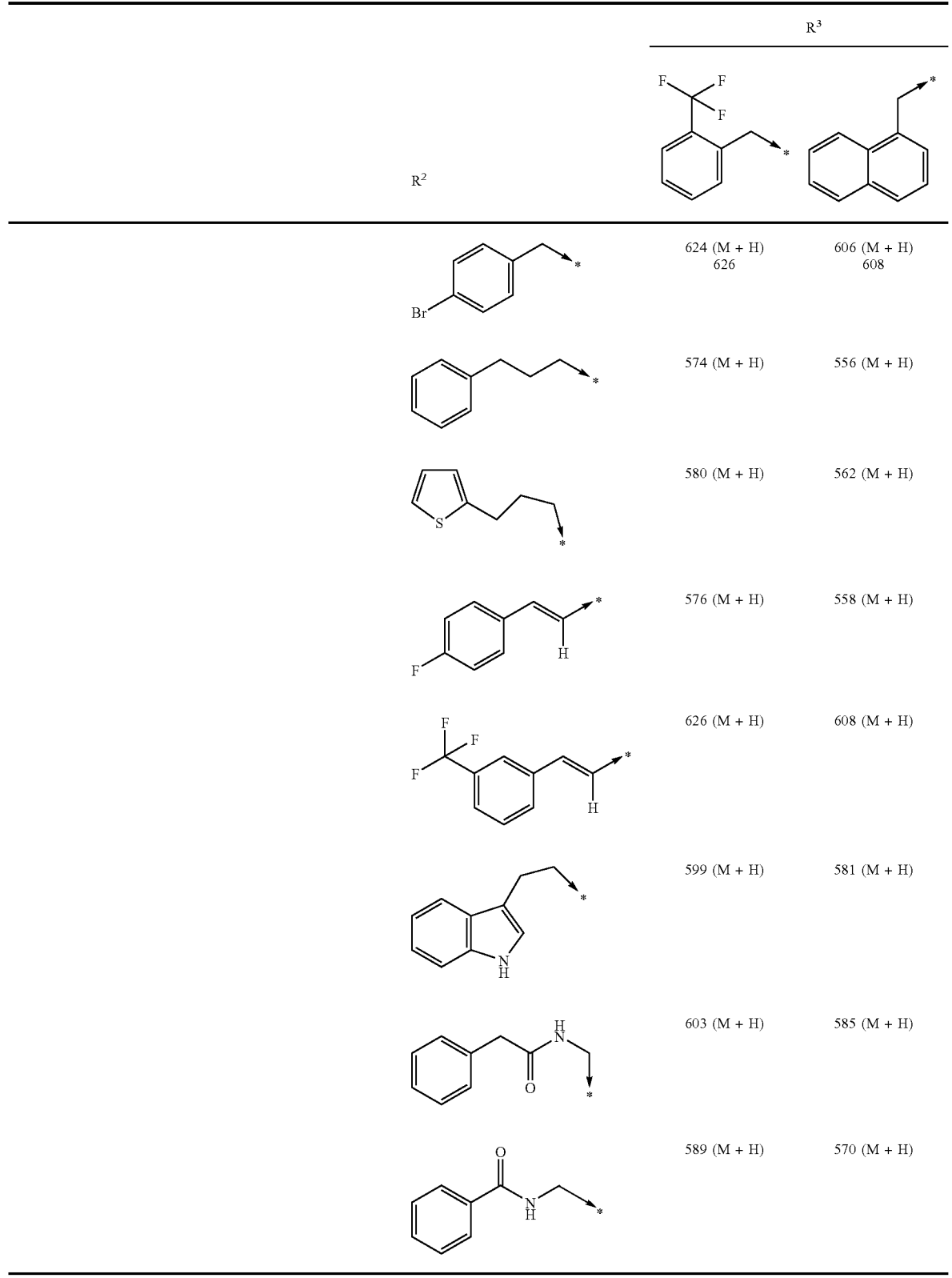

Root Structure
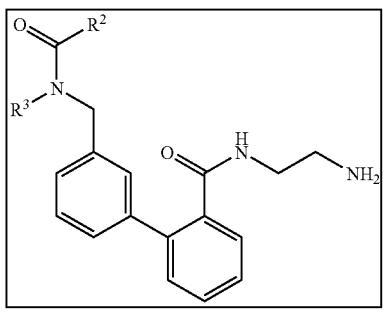
MS (APCI+)
| R² | R³ 2,4-dichlorophenethyl | R³ 2-thienylethyl | R³ N-methyl-N-phenyl-aminopropyl |
|---|---|---|---|
| 4-bromobenzyl | 638 (M + H) / 640 | 576 (M + H) / 578 | 613 (M + H) / 615 |
| phenylpropyl | 588 (M + H) | 526 (M + H) | 563 (M + H) |
| 2-thienylpropyl | 594 (M + H) | 532 (M + H) | 569 (M + H) |
| 4-fluorostyryl | 590 (M + H) | 528 (M + H) | 565 (M + H) |
| 3-trifluoromethylstyryl | 640 (M + H) | 578 (M + H) | 615 (M + H) |
| phenylacetamidomethyl | 617 (M + H) | 555 (M + H) | 592 (M + H) |
| benzamidomethyl | 603 (M + H) | 541 (M + H) | 578 (M + H) |

-continued
| R² | R³ 1 (diphenylpropyl) | R³ 2 (methyl benzyl ester) | R³ 3 (methoxyphenyl) |
|---|---|---|---|
| 4-Br-benzyl | 660 (M + H)<br>662 | 628 (M + H)<br>630 | 572 (M + H)<br>574 |
| phenylpropyl | 610 (M + H) | 578 (M + H) | 522 (M + H) |
| thienylpropyl | 616 (M + H) | 584 (M + H) | 528 (M + H) |
| 4-F-styryl | 612 (M + H) | 580 (M + H) | 524 (M + H) |
| 3-CF₃-styryl | 662 (M + H) | 630 (M + H) | 574 (M + H) |
| PhCH₂C(O)NHCH₂ | 639 (M + H) | 607 (M + H) | 551 (M + H) |
| PhC(O)NHCH₂ | 625 (M + H) | 593 (M + H) | 537 (M + H) |
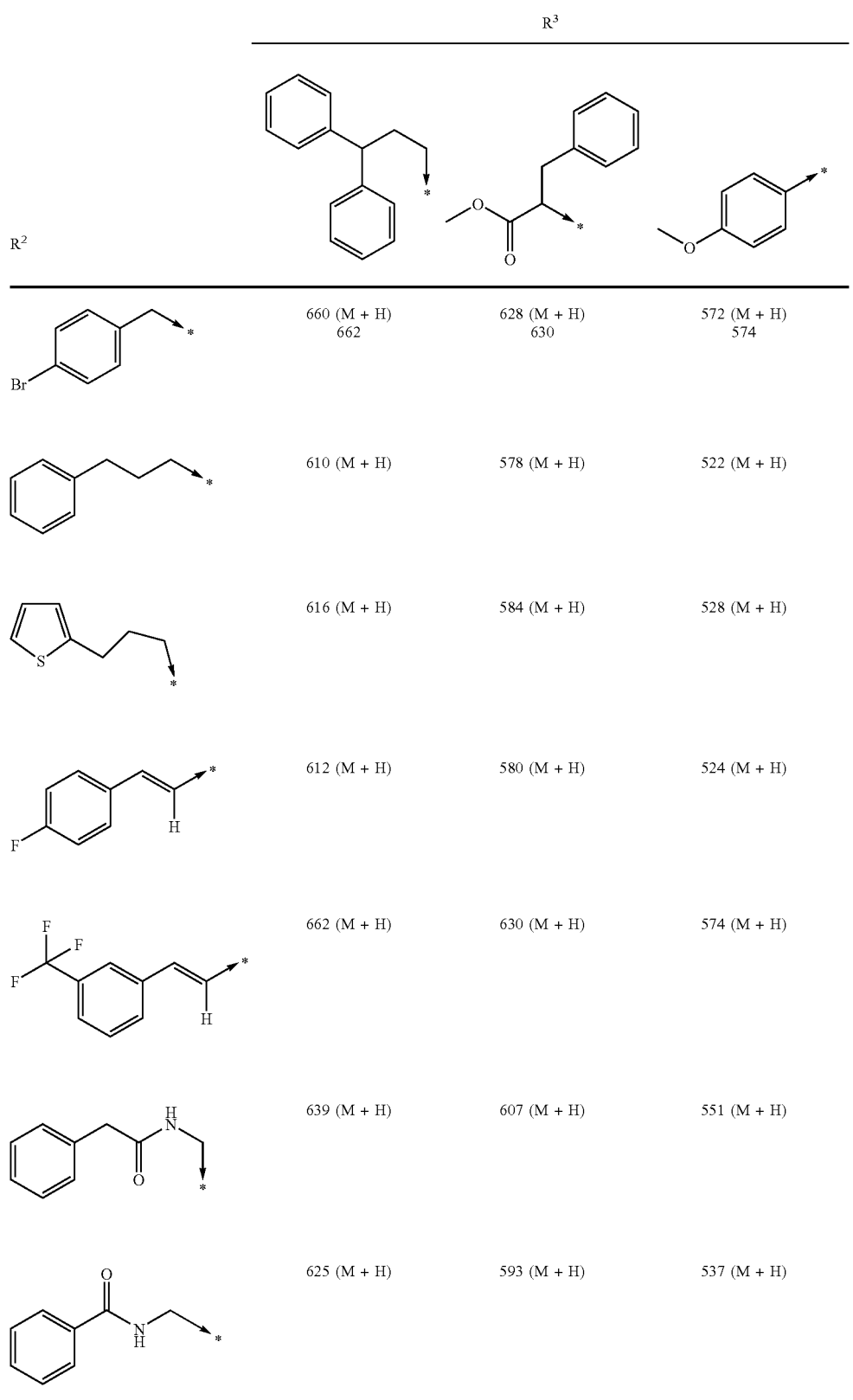

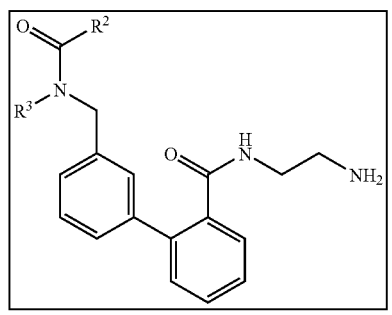
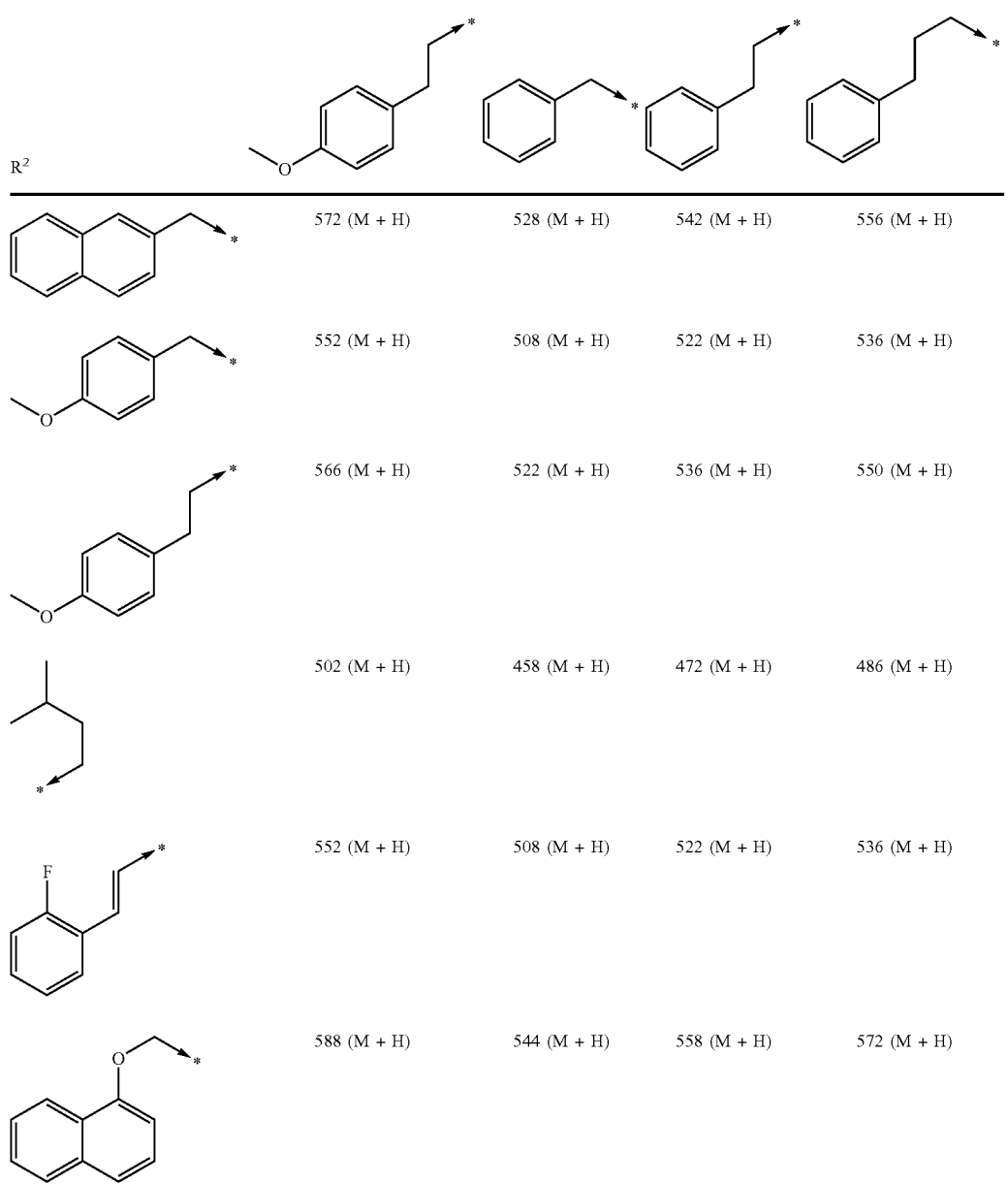
| R² | R³ | | | |
|---|---|---|---|---|
| | 4-methoxyphenethyl | benzyl | phenethyl | phenylpropyl |
| 2-naphthylmethyl | 572 (M + H) | 528 (M + H) | 542 (M + H) | 556 (M + H) |
| 4-methoxybenzyl | 552 (M + H) | 508 (M + H) | 522 (M + H) | 536 (M + H) |
| 4-methoxyphenethyl | 566 (M + H) | 522 (M + H) | 536 (M + H) | 550 (M + H) |
| isopentyl | 502 (M + H) | 458 (M + H) | 472 (M + H) | 486 (M + H) |
| 2-fluorostyryl | 552 (M + H) | 508 (M + H) | 522 (M + H) | 536 (M + H) |
| 1-naphthyloxymethyl | 588 (M + H) | 544 (M + H) | 558 (M + H) | 572 (M + H) |

-continued

| R² | | | | | |
|---|---|---|---|---|---|
| (phenyl propanoyl) | 564 (M + H) | 520 (M + H) | 534 (M + H) | 548 (M + H) | |
| (2-trifluoromethylanilino) | 591 (M + H) | 547 (M + H) | 561 (M + H) | 575 (M + H) | |

| | R³ | | | |
|---|---|---|---|---|
| R² | 4-phenylbutyl | 2-fluorobenzyl | 2-trifluoromethylbenzyl | 2-(tetrahydrothiophen-2-yl)ethyl |
| 2-naphthylmethyl | 570 (M + H) | 546 (M + H) | 596 (M + H) | 548 (M + H) |
| 4-methoxybenzyl | 550 (M + H) | 526 (M + H) | 576 (M + H) | 528 (M + H) |
| 2-(4-methoxyphenyl)ethyl | 564 (M + H) | 540 (M + H) | 590 (M + H) | 542 (M + H) |
| isopentyl | 500 (M + H) | 476 (M + H) | 526 (M + H) | 478 (M + H) |
| 2-fluorostyryl | 550 (M + H) | 526 (M + H) | 576 (M + H) | 528 (M + H) |
| (naphthalen-1-yloxy)methyl | 586 (M + H) | 562 (M + H) | 612 (M + H) | 564 (M + H) |

-continued
| R² | | | R³ | | |
|---|---|---|---|---|---|
| | 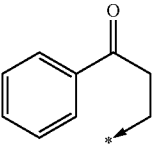 (phenyl propanone) | 562 (M + H) | 538 (M + H) | 588 (M + H) | 540 (M + H) |
| | 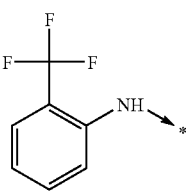 (2-CF₃ anilino) | 589 (M + H) | 565 (M + H) | 615 (M + H) | 567 (M + H) |
| R² | R³: imidazolyl-butyl | N-methyl-N-phenyl-aminobutyl | diphenyl-propyl | methyl benzyl ester |
|---|---|---|---|---|
| 2-naphthylmethyl | 546 (M + H) | 585 (M + H) | 632 (M + H) | 600 (M + H) |
| 4-methoxybenzyl | 526 (M + H) | 565 (M + H) | 612 (M + H) | 580 (M + H) |
| 4-methoxyphenethyl | 540 (M + H) | 579 (M + H) | 626 (M + H) | (M + H) |
| isopentyl | 476 (M + H) | 515 (M + H) | 562 (M + H) | (M + H) |
| 2-fluorostyryl | 526 (M + H) | 565 (M + H) | 612 (M + H) | 580 (M + H) |
| 1-naphthyloxymethyl | 562 (M + H) | 601 (M + H) | (M + H) | 616 (M + H) |

-continued
| | 538 (M + H) | 577 (M + H) | (M + H) | 592 (M + H) |
|---|---|---|---|---|
| | 565 (M + H) | 604 (M + H) | 651 (M + H) | 619 (M + H) |
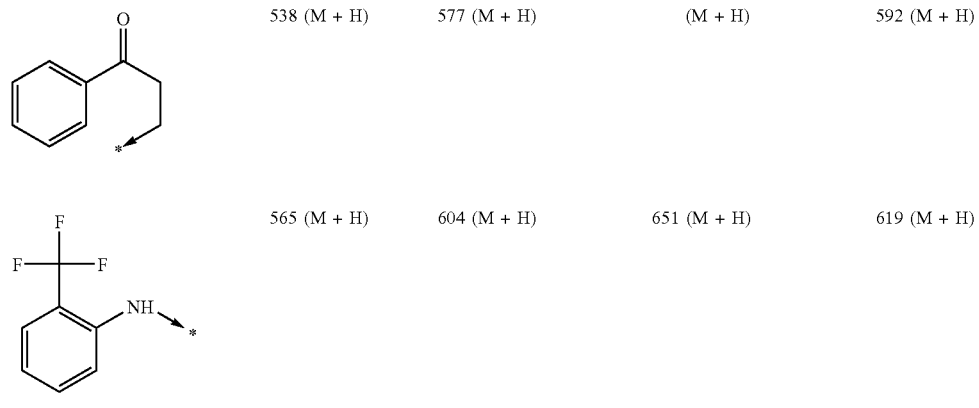
Root Structure
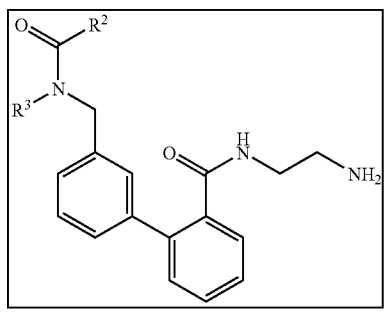
MS (APCI+)
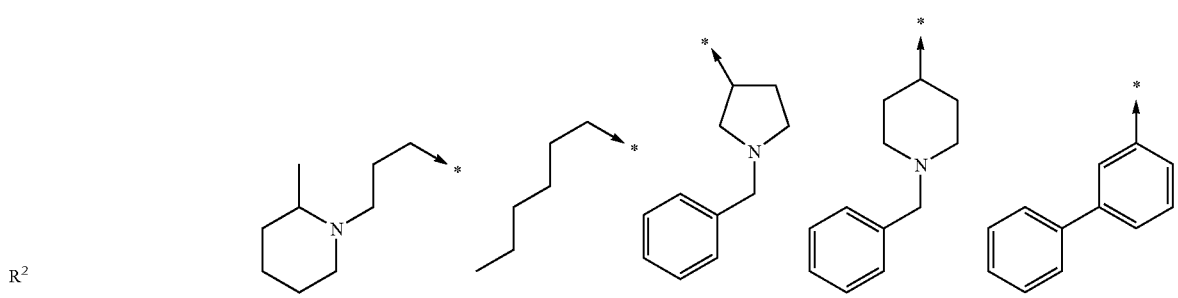
| R² | | | | | |
|---|---|---|---|---|---|
| 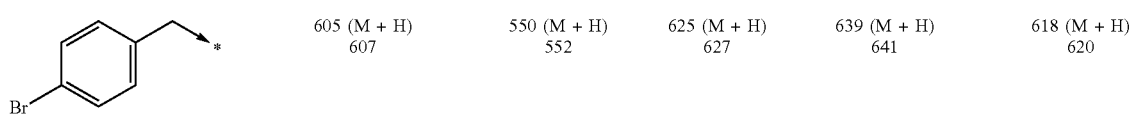 | 605 (M + H) 607 | 550 (M + H) 552 | 625 (M + H) 627 | 639 (M + H) 641 | 618 (M + H) 620 |
| 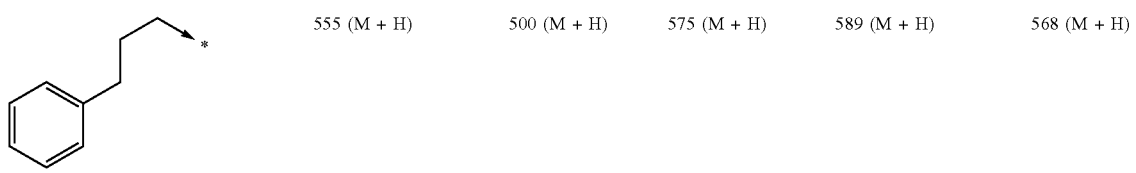 | 555 (M + H) | 500 (M + H) | 575 (M + H) | 589 (M + H) | 568 (M + H) |

-continued
| R² | | | | | |
|---|---|---|---|---|---|
| 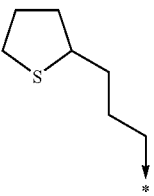 | 561 (M + H) | 506 (M + H) | 581 (M + H) | 595 (M + H) | 574 (M + H) |
| 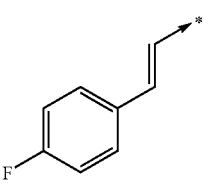 | 557 (M + H) | 502 (M + H) | 577 (M + H) | 591 (M + H) | 570 (M + H) |
| 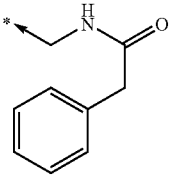 | 584 (M + H) | 529 (M + H) | 604 (M + H) | 618 (M + H) | 597 (M + H) |
| 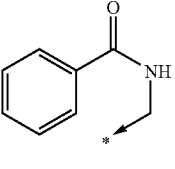 | 570 (M + H) | 515 (M + H) | 590 (M + H) | 604 (M + H) | 583 (M + H) |
| 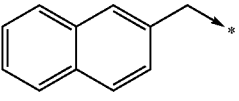 | 577 (M + H) | 522 (M + H) | 597 (M + H) | 611 (M + H) | 590 (M + H) |
| 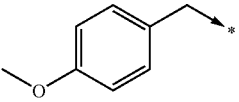 | 557 (M + H) | 502 (M + H) | 577 (M + H) | 591 (M + H) | 570 (M + H) |
| | R³ | | |
|---|---|---|---|
| R² | 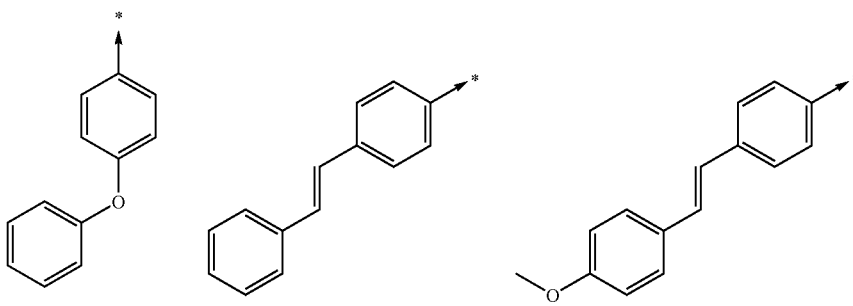 | 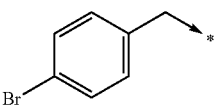 | |
|  | 634 (M + H) 636 | 644 (M + H) 646 | 674 (M + H) 676 |

-continued
| | | | |
|---|---|---|---|
| 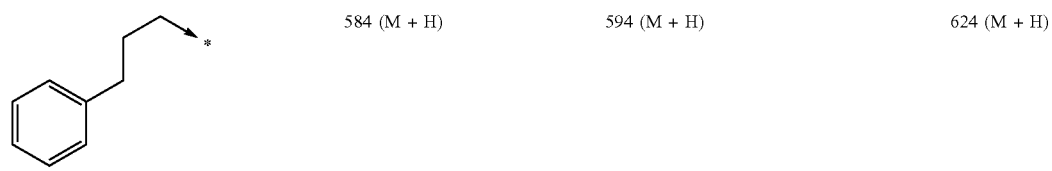 | 584 (M + H) | 594 (M + H) | 624 (M + H) |
| 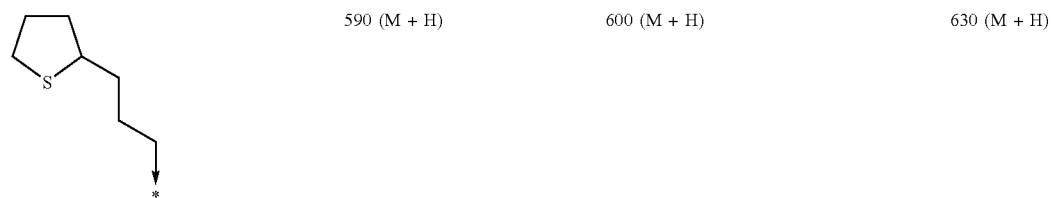 | 590 (M + H) | 600 (M + H) | 630 (M + H) |
| 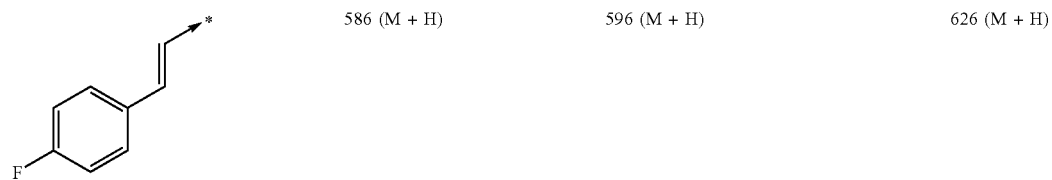 | 586 (M + H) | 596 (M + H) | 626 (M + H) |
| 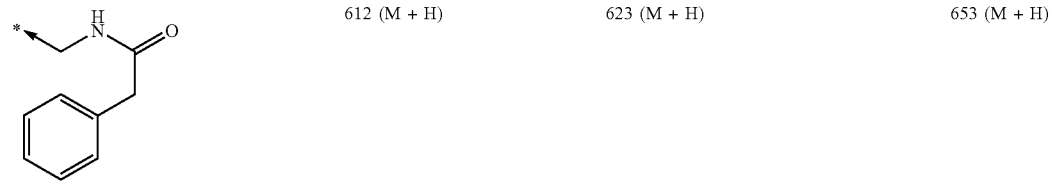 | 612 (M + H) | 623 (M + H) | 653 (M + H) |
|  | 599 (M + H) | 609 (M + H) | 639 (M + H) |
|  | 606 (M + H) | 616 (M + H) | 646 (M + H) |
|  | 586 (M + H) | 596 (M + H) | 626 (M + H) |

Root Structure
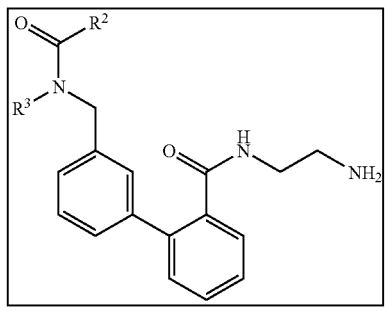
MS (APCI+)
| R² | R³ 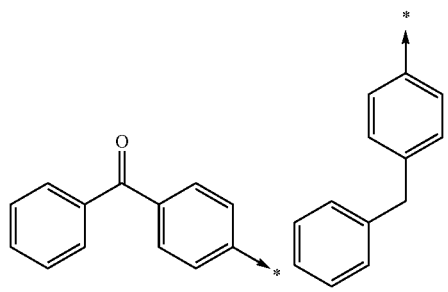 | |
|---|---|---|
| 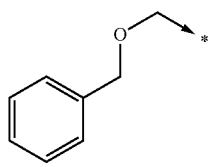 | 598 (M + H) | 584 (M + H) |
|  | 574 (M + H) | 560 (M + H) |
| 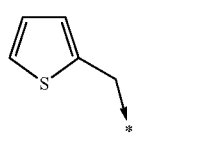 | 644 (M + H) | 630 (M + H) |
| 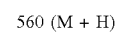 | 604 (M + H) | 590 (M + H) |
| 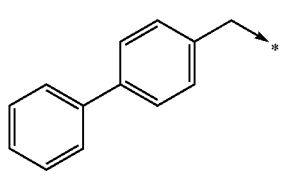 | 598 (M + H) | 584 (M + H) |

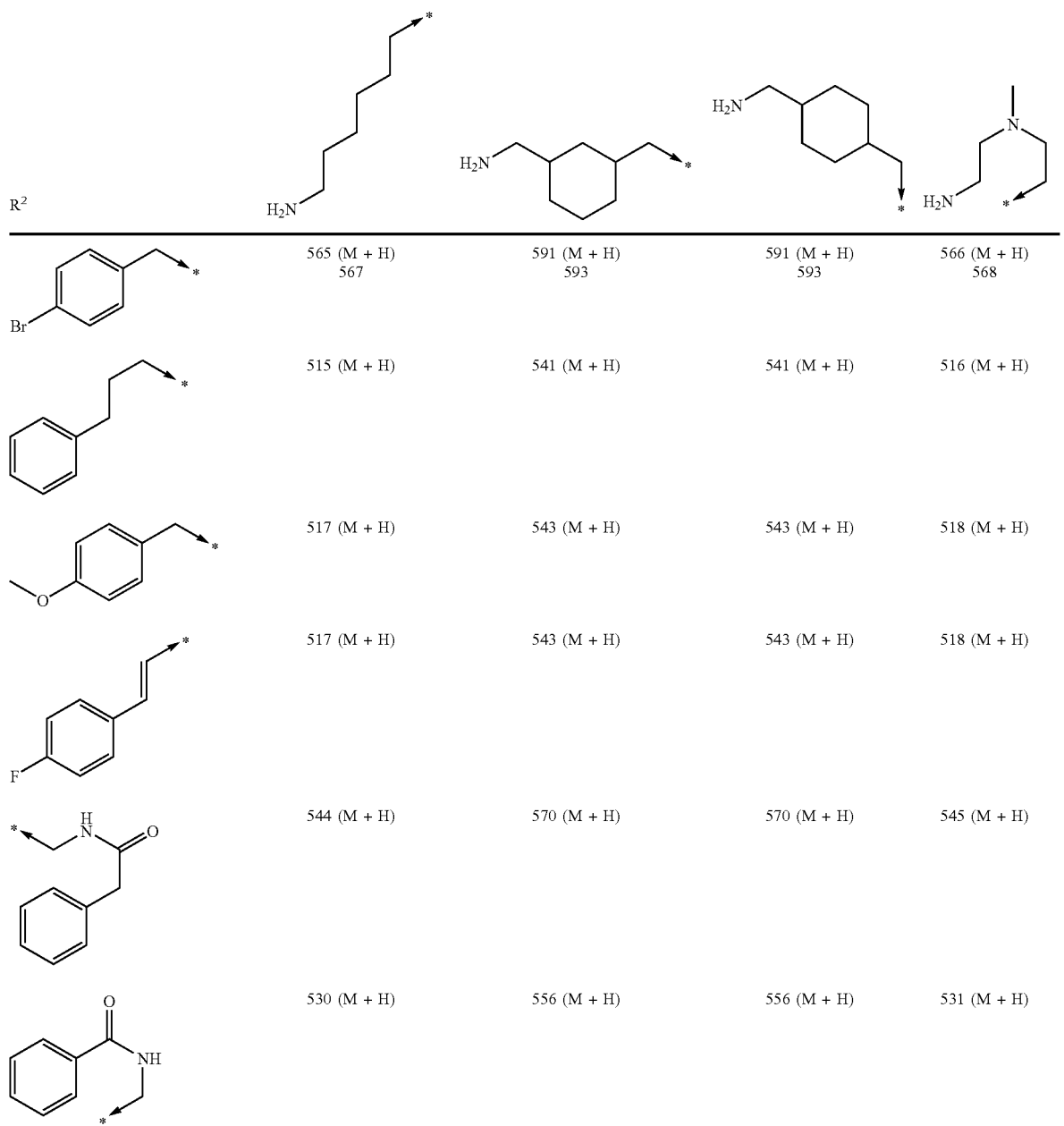

-continued

| R² | | | |
|---|---|---|---|
| naphthalen-2-ylmethyl | 537 (M + H) | 563 (M + H) | 563 (M + H) | 538 (M + H) |
| 3-(trifluoromethyl)phenylamino | 556 (M + H) | 582 (M + H) | 582 (M + H) | 557 (M + H) |

| R² | R³ 4-sulfamoylbenzyl | R³ ethyl (S)-2-(4-hydroxybenzyl) acetate | R³ 4-sulfamoylphenethyl |
|---|---|---|---|
| 4-bromobenzyl | 635 (M + H) 637 | 658 (M + H) 660 | 649 (M + H) 651 |
| 3-phenylpropyl | 585 (M + H) | 608 (M + H) | 599 (M + H) |
| 4-methoxybenzyl | 587 (M + H) | 610 (M + H) | 601 (M + H) |
| (E)-4-fluorostyryl | 587 (M + H) | 610 (M + H) | 601 (M + H) |
| phenylacetamidomethyl | 614 (M + H) | 637 (M + H) | 628 (M + H) |
| benzamidomethyl | 600 (M + H) | 623 (M + H) | 614 (M + H) |
| naphthalen-2-ylmethyl | 607 (M + H) | 630 (M + H) | 621 (M + H) |

-continued
| | 626 (M + H) | 649 (M + H) | 640 (M + H) |
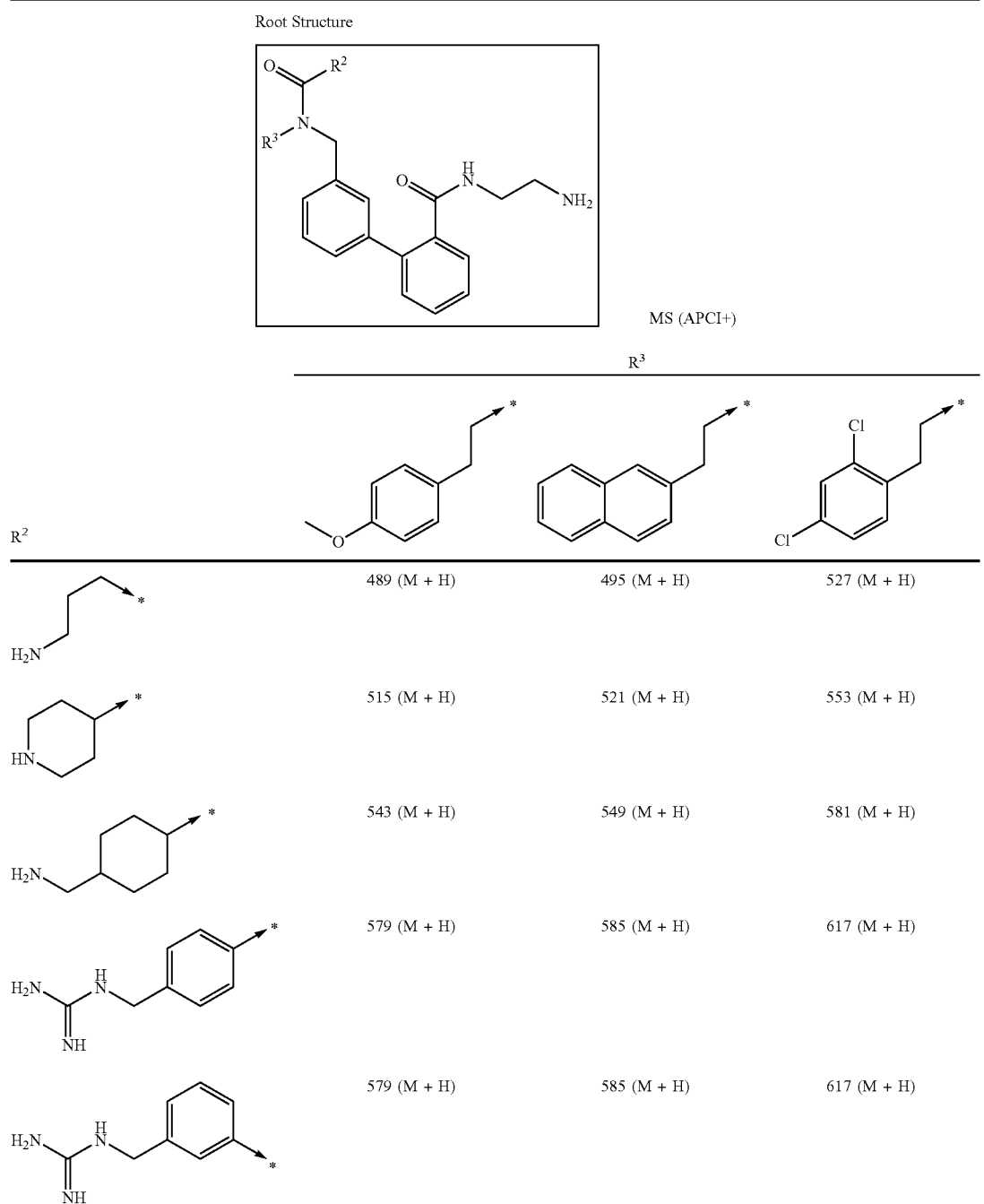

-continued
| | | | |
|---|---|---|---|
| 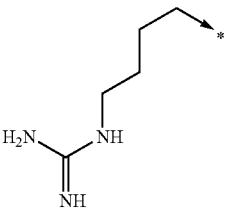 | 545 (M + H) | 551 (M + H) | 583 (M + H) |
| 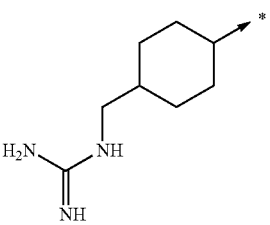 | 585 (M + H) | 591 (M + H) | 623 (M + H) |
| 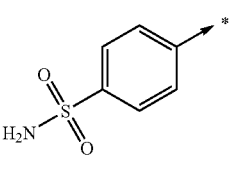 | 587 (M + H) | 591 (M + H) | 623 (M + H) |
| 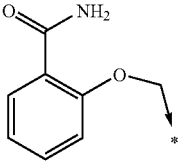 | 581 (M + H) | 587 (M + H) | 619 (M + H) |
| 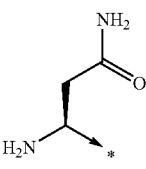 | 518 (M + H) | 524 (M + H) | 556 (M + H) |
| 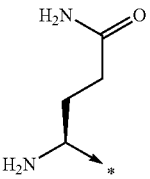 | 532 (M + H) | 538 (M + H) | 570 (M + H) |
| 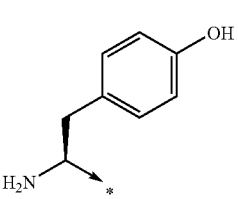 | 567 (M + H) | 573 (M + H) | 605 (M + H) |

-continued
| R² \ R³ | 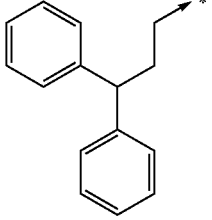 | 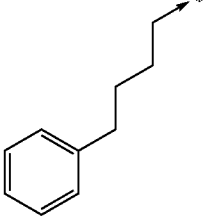 | 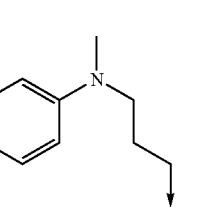 |
|---|---|---|---|
| 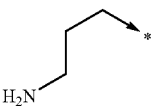 | 549 (M + H) | 487 (M + H) | 502 (M + H) |
| 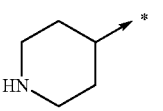 | 575 (M + H) | 513 (M + H) | 528 (M + H) |
| 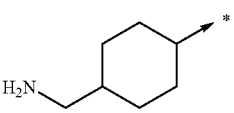 | 603 (M + H) | 541 (M + H) | 556 (M + H) |
| 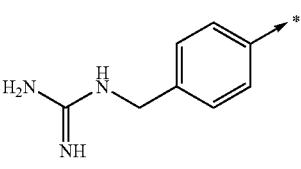 | 639 (M + H) | 577 (M + H) | 592 (M + H) |
| 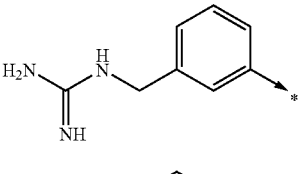 | 639 (M + H) | 577 (M + H) | 592 (M + H) |
| 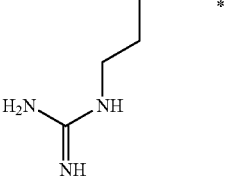 | 605 (M + H) | 543 (M + H) | 558 (M + H) |
| 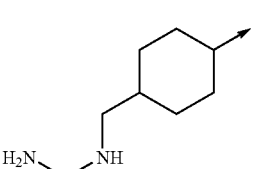 | 645 (M + H) | 583 (M + H) | 598 (M + H) |
| 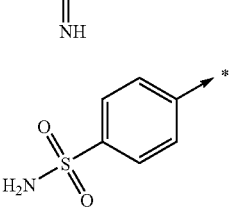 | 647 (M + H) | 585 (M + H) | 600 (M + H) |

| | 233 | | 234 |
|---|---|---|---|
| -continued | | | |
| [benzamide with O-CH2-* ortho to CONH2] | 641 (M + H) | 579 (M + H) | 594 (M + H) |
| [H2N-CH(*)-CH2-C(O)NH2] | 578 (M + H) | 516 (M + H) | 531 (M + H) |
| [H2N-CH(*)-CH2-CH2-C(O)NH2] | 592 (M + H) | 530 (M + H) | 545 (M + H) |
| [H2N-CH(*)-CH2-C6H4-OH (tyrosine-like)] | 627 (M + H) | 565 (M + H) | 580 (M + H) |
Root Structure
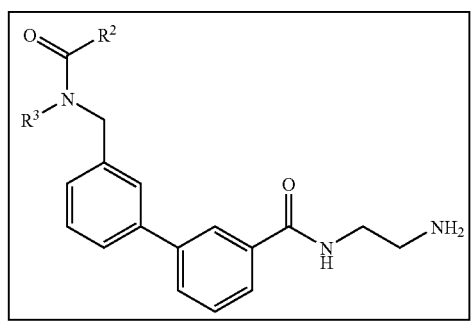
MS (APCI+)
| | R³ | | |
|---|---|---|---|
| R² | 4-methoxyphenethyl-* | 2,4-dichlorophenethyl-* | 2-naphthylethyl-* |
| 4-bromobenzyl-* | 600 (M + H)<br>602 | 638 (M + H)<br>640 | 606 (M + H)<br>608 |

-continued
| | 235 | | 236 |
|---|---|---|---|
| 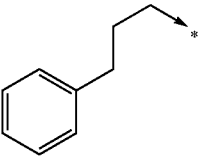 | 550 (M + H) | 588 (M + H) | 556 (M + H) |
| 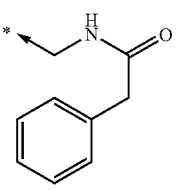 | 579 (M + H) | 617 (M + H) | 585 (M + H) |
| 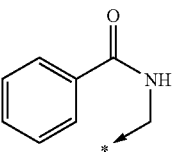 | 565 (M + H) | 603 (M + H) | 571 (M + H) |
| 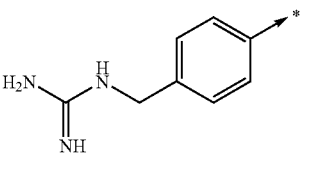 | 579 (M + H) | 617 (M + H) | 585 (M + H) |
| 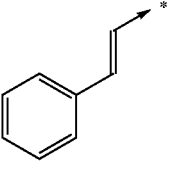 | 534 (M + H) | 572 (M + H) | 540 (M + H) |
| 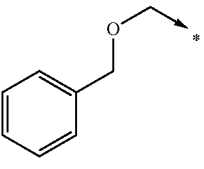 | 552 (M + H) | 590 (M + H) | 558 (M + H) |
| 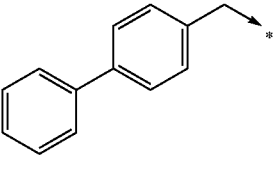 | 508 (M + H) | 636 (M + H) | 604 (M + H) |

-continued

| R² | R³ (Ph₂CH-CH₂-CH₂-*) | R³ (Ph-(CH₂)₄-*) | R³ (PhN(Me)-(CH₂)₃-*) |
|---|---|---|---|
| 4-Br-C₆H₄-CH₂-* | 660 (M + H)<br>662 | 598 (M + H)<br>600 | 613 (M + H)<br>615 |
| Ph-(CH₂)₂-CH₂-* | 610 (M + H) | 548 (M + H) | 563 (M + H) |
| *-CH₂-NH-C(O)-CH₂-Ph | 639 (M + H) | 577 (M + H) | 592 (M + H) |
| Ph-C(O)-NH-CH₂-* | 525 (M + H) | 563 (M + H) | 578 (M + H) |
| H₂N-C(=NH)-NH-CH₂-C₆H₄-* | 539 (M + H) | 577 (M + H) | 592 (M + H) |
| Ph-CH=CH-* | 594 (M + H) | 532 (M + H) | 547 (M + H) |
| Ph-CH₂-O-CH₂-* | 612 (M + H) | 550 (M + H) | 565 (M + H) |

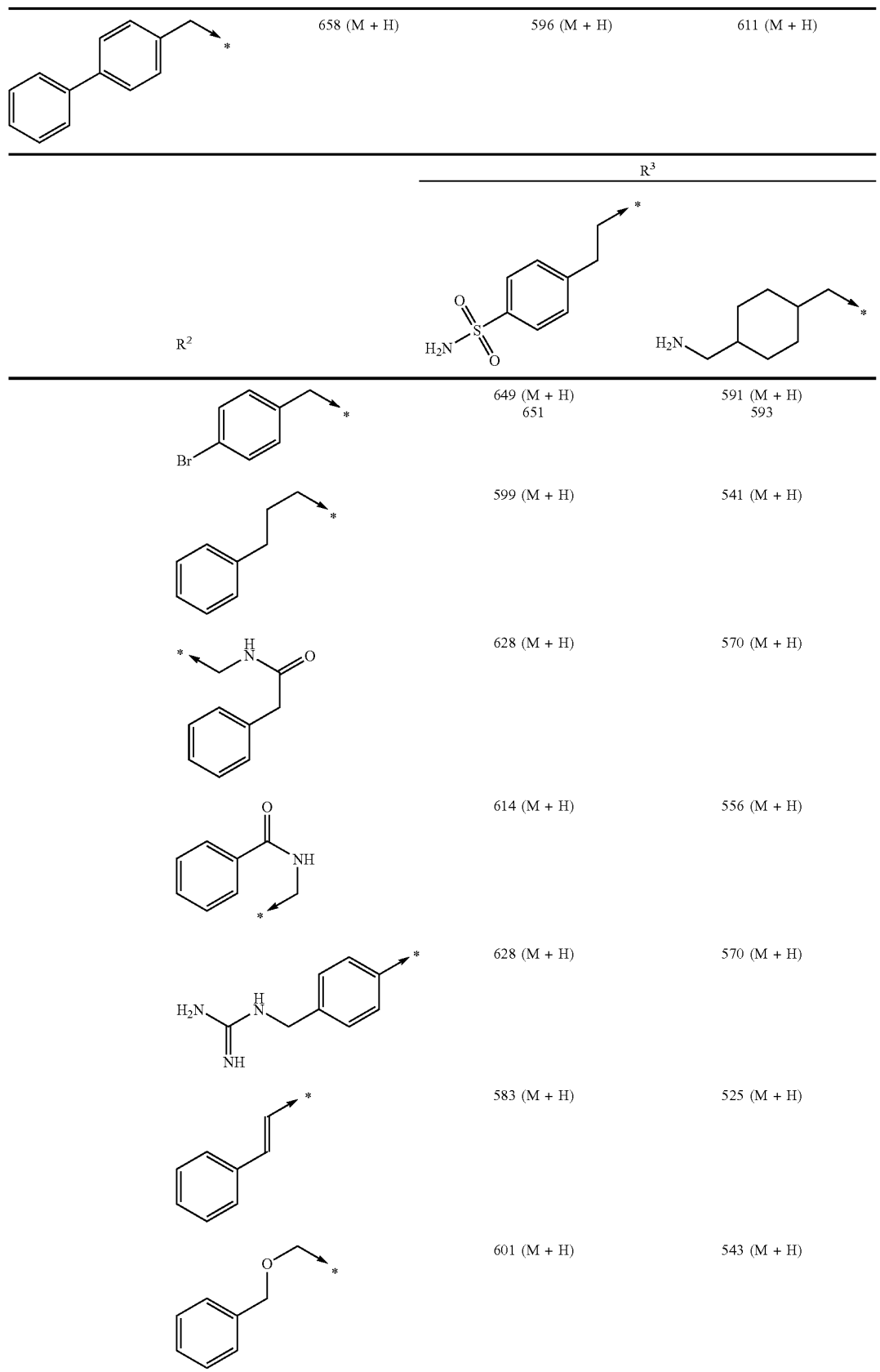

-continued
| | | | |
|---|---|---|---|
| 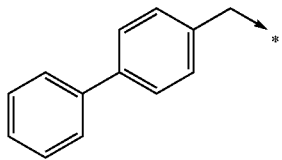 | 647 (M + H) | | 589 (M + H) |
Root Structure
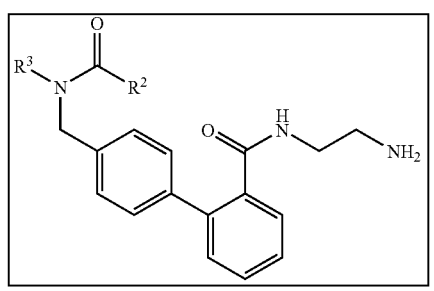
| R² | R³ | | |
|---|---|---|---|
| | 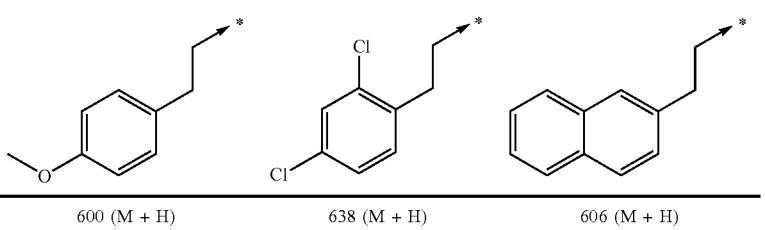 | | |
| 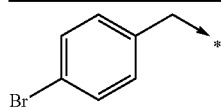 | 600 (M + H)<br>602 | 638 (M + H)<br>640 | 606 (M + H)<br>608 |
| 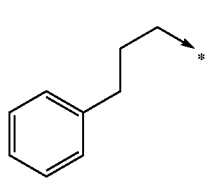 | 550 (M + H) | 588 (M + H) | 556 (M + H) |
| 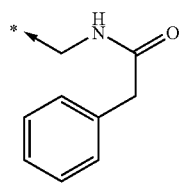 | 579 (M + H) | 617 (M + H) | 585 (M + H) |
| 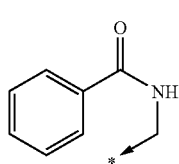 | 565 (M + H) | 603 (M + H) | 571 (M + H) |
| 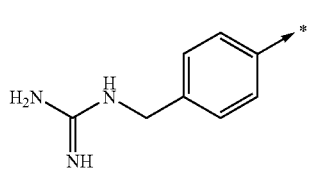 | 579 (M + H) | 617 (M + H) | 585 (M + H) |

-continued
| R² | | | |
|---|---|---|---|
| 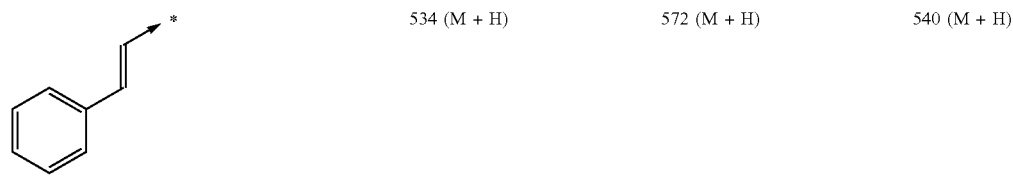 | 534 (M + H) | 572 (M + H) | 540 (M + H) |
| 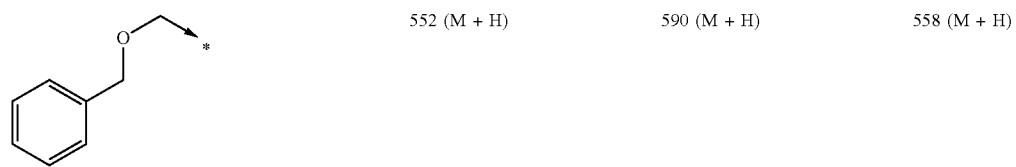 | 552 (M + H) | 590 (M + H) | 558 (M + H) |
| 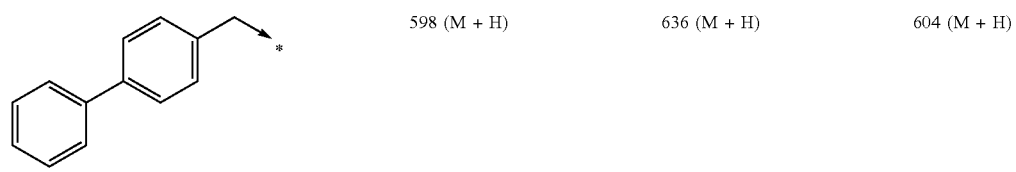 | 598 (M + H) | 636 (M + H) | 604 (M + H) |
| | R³ | | |
|---|---|---|---|
| R² | 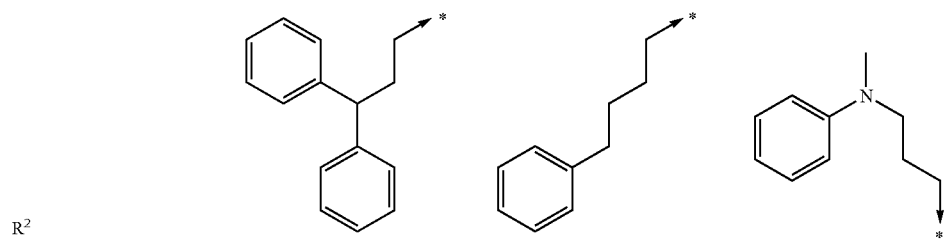 | | |
|  | 660 (M + H)<br>662 | 598 (M + H)<br>600 | 613 (M + H)<br>615 |
| 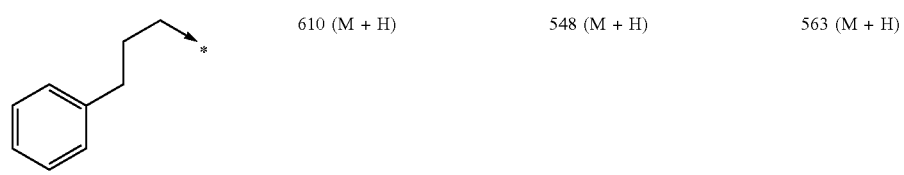 | 610 (M + H) | 548 (M + H) | 563 (M + H) |
| 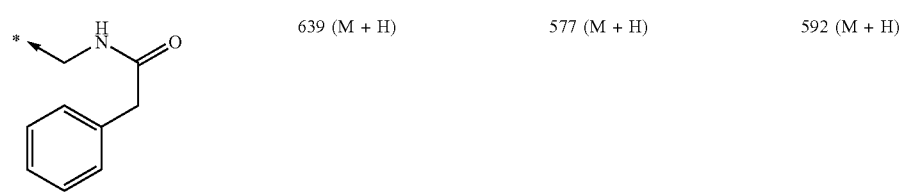 | 639 (M + H) | 577 (M + H) | 592 (M + H) |
| 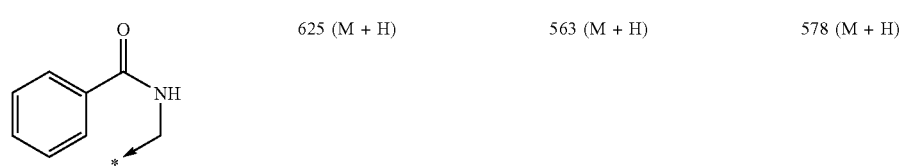 | 625 (M + H) | 563 (M + H) | 578 (M + H) |

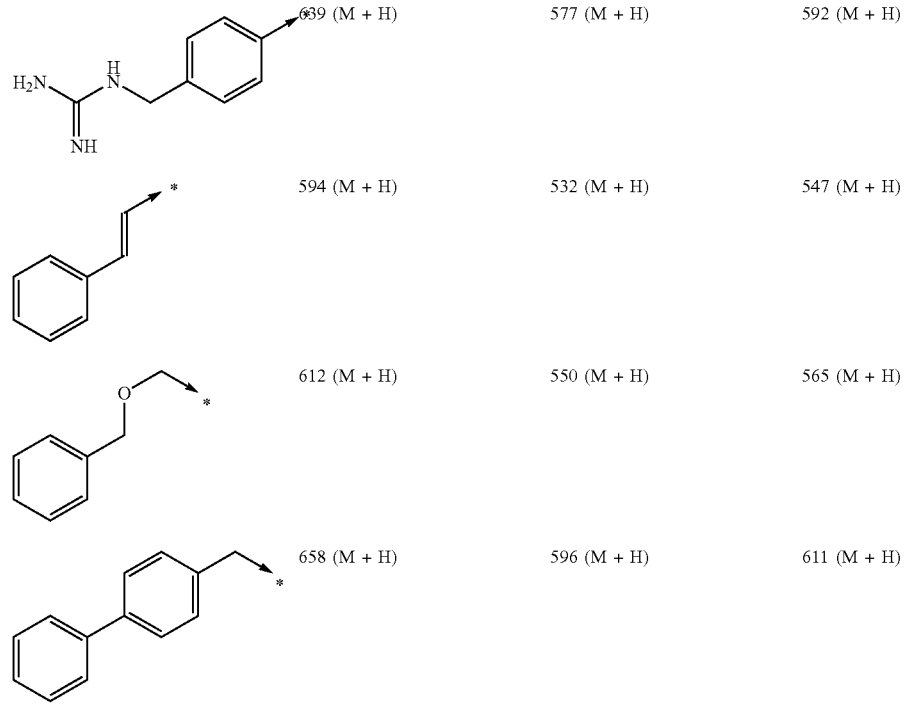

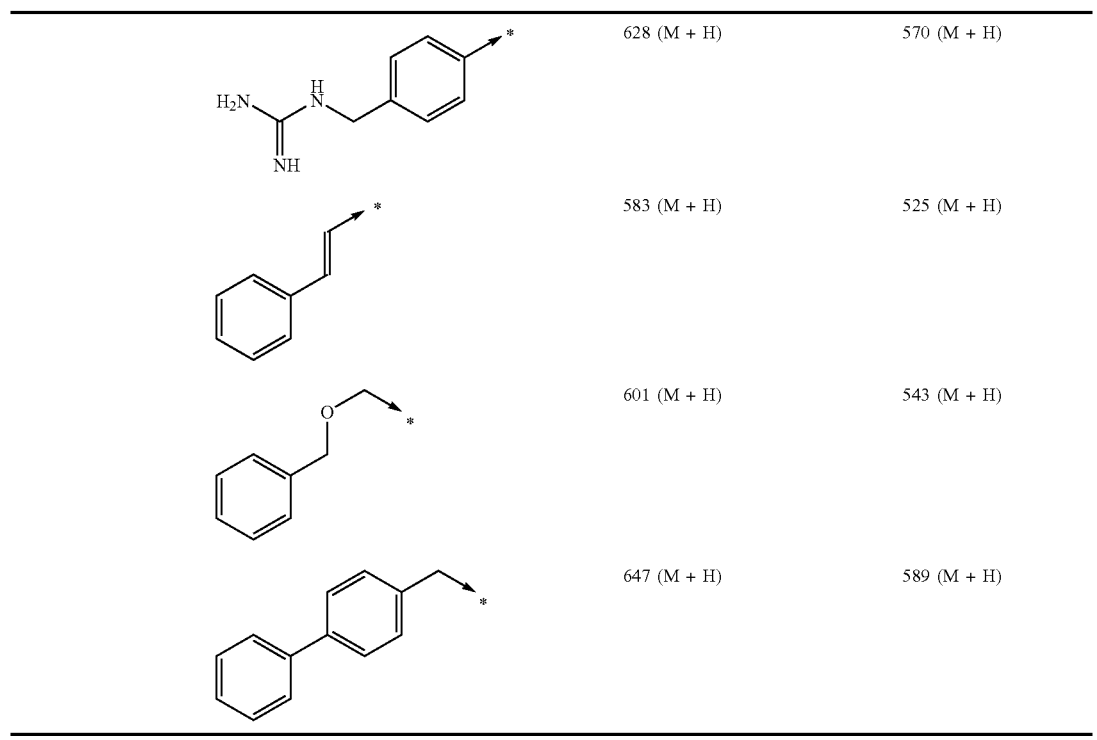

Hereinafter, the pharmaceutical activity of the compounds of the present invention is specifically illustrated, but is not limited thereto. The gene manipulation procedures using *Escherichia coli* were carried out according to the methods described in the Molecular Cloning, 1989 edition (Molecular Cloning, T. Maniatis et al.).

REFERENCE EXAMPLE 4

Cloning of Human Somatostatin Receptor Protein Subtype 5 (SSTR5) DNA

On the basis of a known nucleotide sequence of human SSTR5 cDNA [Biochem. Biophys. Res. Commun., 195: 844–852, 1993], DNA oligomers, S5-1 and S5-2 were synthesized. The sequence of S5-1 is 5'-GGTCGACCAC-CATGGAGCCCCTGTTCCC-3' (SEQ-ID NO:5) and the sequence of S5-2 was 5'-CCGTCGACACTCTCACAGCT-TGCTGG-3' (SEQ ID NO:6). As a template, human chromosomal DNA (Catalog No. CL6550-1, Clontech) was used. 25 pmol of Each of the above DNA oligomers was added to 0.5 ng of the template DNA and subjected to polymerase chain reaction with 2.5 U of Pfu DNA polymerase (Stratagene). The composition of the reaction mixture followed instructions attached to the Pfu DNA polymerase. In the reaction, 35 cycles each consisting of heating at 94° C. for 1 minute, at 66° C. for 1 minute and at 75° C. for 2 minutes were carried out. Electrophoresis of the reaction mixture on 1% agarose gel indicated that a DNA fragment of intended size (about 1.1 kb) was specifically amplified. This DNA fragment was recovered in a usual manner from the agarose gel, then ligated to pUC118 previously cleaved at its Hinc II site, and transformed into competent cells, *Escherichia coli* JM109. A transformant having a plasmid containing the DNA fragment was selected, and the nucleotide sequence of the insert DNA fragment, confirmed by an automatic nucleotide sequencer ALF DNA sequencer (Pharmacia) using a fluorescent coloring matter, indicated that an amino acid sequence deduced from the nucleotide sequence agreed completely with a sequence described in the literature supra.

REFERENCE EXAMPLE 5

Construction of Human Somatostatin Receptor Protein Subtype 5 (SSTR5) DNA Expression Plasmid As an expression vector in CHO (Chinese hamster ovary) cells, pAKKO-111 was used. pAKKO-111 was constructed in the following manner. pTB1417 described in JP 5-076385 A was treated with Hind III and Cla I to give a 1.4 kb DNA fragment containing an SR• promoter and a polyA-added signal. Separately, pTB348 (Biochem. Biophys. Res. Commun., 128: 256–264, 1985) was treated with Cla I and Sal I, to give a 4.5 kb DNA fragment containing a dihydrofolate reductase (DHFR) gene. These DNA fragments were blunt-ended by treatment with T4 polymerase and then ligated to each other by treatment with T4 ligase, to construct pAKKO-111 plasmid. 5 •g of Plasmid having the human SSTR5 DNA fragment obtained in Reference Example 4 was digested with a restriction enzyme Sal I and then subjected to 1% agarose gel electrophoresis, and a 1.1 kb DNA fragment encoding human SSTR5 was recovered. Then, 1 •g of the expression vector pAKKO-111 (5.5 kb) was digested with Sal I, to prepare a cloning site for the inserting human SSTR5 DNA fragment into it. This expression vector fragment and the 1.1 kb DNA fragment were ligated to each other with T4 DNA ligase, and the reaction mixture was introduced into *E. coli* JM109 by calcium chloride method, and an expression plasmid pA-1-11-

SSTR5 having the human SSTR5 DNA fragment inserted in the normal direction into the promoter was obtained from the resultant transformant.

REFERENCE EXAMPLE 6

Introduction of Human Somatostatin Receptor Protein Subtype 5 (SSTR5) DNA into CHO (dhfr⁻) Cells and Expression of the DNA $1 \times 10^6$ CHO (dhfr⁻) cells were cultured for 24 hours in HAM F12 medium containing 10% fetal bovine serum in a Petri dish of 8 cm in diameter, and 10 •g of the human SSTR5 cDNA expression plasmid pA-1-11-SSTR5 obtained in Reference Example 5 was introduced into the cells by phosphate calcium method. 24 Hours after this introduction, the medium was exchanged with a DMEM medium containing 10% dialyzed fetal bovine serum, and colony-forming cells in the medium (that is, DHFR⁺ cells) were selected. A single cell obtained by limiting dilution from the selected cells was cloned and measured for the ability to express a somatostatin receptor protein in the following manner. The human SSTR5 cDNA-expressing cell strain was diluted with a measurement buffer [50 mM Tris-HCl buffer (pH 7.5) containing 1 mM EDTA, 5 mM magnesium chloride, 0.1% BSA, 0.2 mg/ml bacitracin, 10 •g/ml leupeptin, 1 •g/ml pepstatin, 200 units/ml aprotinin], to prepare a cell suspension containing $2 \times 10^4$ cells/200 •l. In to a tube, 200 •l of the cell suspension was pipetted, and 2 •l of 5 nM [$^{125}$I]-somatostatin (2000 Ci/mmol, Amersham) was added thereto and incubated at 25° C. for 60 minutes. To measure non-specific binding (NSB), a tube containing 2 •l ($10^{-4}$ M) of somatostatin-14 was also incubated. 1.5 ml of Washing buffer [50 mM Tris-HCl buffer (pH 7.5) containing 1 mM EDTA, 5 mM magnesium chloride] was added to the sample which was then filtered with a GF/F glass fiber filter paper (Whatman) and then washed with the same buffer. [$^{125}$I] of the filter paper was measured by a •-counter. SSTR5-32-4 was selected as a cell strain having a higher somatostatin binding activity.

EXPERIMENTAL EXAMPLE 5

Preparation of CHO Cell Membrane Fraction Containing Human Somatostatin Receptor Protein Subtype 5 (SSTR5)

The human somatostatin receptor protein subtype 5-expressing CHO cell strain, SSTR5-32-4 ($10^9$ cells), were suspended in phosphate-buffered physiological saline containing 5 mM EDTA (PBS-EDTA) and centrifuged. To the cell pellet, 10 ml of homogenate buffer (10 mM NaHCO₃, 5 mM EDTA, pH 7.5) was added, which was then homogenated with a polytron homogenizer. The homogenate was centrifuged at 400×g for 15 minutes, and the resultant supernatant was further centrifuged at 100,000×g for 1 hour, to give precipitates of the membrane fraction. The precipitates were suspended in 2ml of assay buffer [25 mM Tris-HCl buffer (pH 7.5) containing 1 mM EDTA, 0.1% BSA (bovine serum albumin), 0.25 mM PMSF, 1 •g/ml pepstatin, 20 •g/ml leupeptin, 10 •g/ml phosphoramidon) and centrifuged at 100,000×g for 1 hour. The membrane fraction recovered as precipitates was suspended again in 20 ml of assay buffer, pipetted, stored at −80° C. and thawed just before use.

EXPERIMENTAL EXAMPLE 6

Measurement of the Degree of Inhibition of Binding to [$^{125}$I]-Somatostatin

The SSTR5-expressing CHO cell membrane fraction prepared in Example 5 was diluted with the assay buffer to prepare a solution at a concentration of 3 •g/ml and pipetted into tubes (173 •l/tube). Two •l of compound dissolved in DMSO and 25 •l of 200 pM [$^{125}$I]-somatostatin (Amersham) were added simultaneously thereto. To measure the maximum binding, a reaction mixture containing 2 •l of DMSO and 25 •l of 200 pM [$^{125}$I]-somatostatin was prepared. To measure nonspecific binding, a reaction mixture containing 2 •l of 100 •M somatostatin in DMSO and 25 •l of 200 pM [$^{125}$I]-somatostatin was also simultaneously prepared. Each reaction mixture was reacted at 25° C. for 60 minutes and then filtered under suction with a polyethylene imine-treated Whatman glass filter (GF/B). After filtration, the radioactivity of [$^{125}$I]-somatostatin remaining on the glass filer was measured with a • counter.

The degree of inhibition of binding (%) by each test substance was determined according to the following equation:

The degree of inhibition of binding (%)=(radioactivity when the compound was added−radioactivity when *DMSO* solution was added)/(radioactivity when somatostatin was added−radioactivity when *DMSO* solution was added)× 100.

While the concentration of the test substance was changed, the concentration of the test substance at which 50% binding was inhibited (IC₅₀ value) was calculated from Hill plots.

The results are shown below:

| Test Compound | IC$_{50}$ |
| --- | --- |
| Example 325 | 6 nM |
| Example 328 | 3 nM |

INDUSTRIAL APPLICABILITY

Since the compounds [compounds of the formula (I) or salts thereof] having an antagonistic activity on GPR14 of the present invention have a strong antagonistic activity on GPR14, they can be advantageously used as various vasoactive drugs (preferably vasoconstriction inhibitor) and for treating various diseases (preferably treating ischemic myocardial infarction, congestive heart failure and the like).

Further since the compounds of the formula (I) or salts thereof of the present invention have an excellent somatostatin receptor-binding activity. Accordingly, compound (I) is useful for treating abnormalities (e.g., diseases accompanied by excessive promotion or suppression) in the intracellular information transmission system of mammals, diseases accompanied by abnormalities in regulation of cell proliferation, and diseases accompanied by abnormalities in production and/or secretion of hormones, growth factors, physiologically active substances, etc.

The invention claimed is:

1. A compound represented by the formula (I):

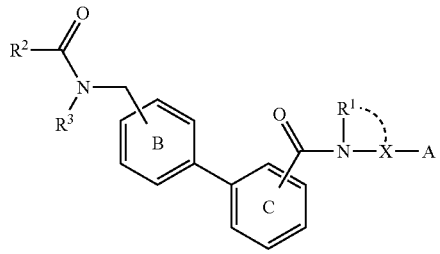

(I)

wherein $R^1$ is (1) hydrogen atom;

(2) $C_{1-10}$alkyl which may have 1 to 3 substituents selected from (1') halogen atom, (2') nitro, (3') cyano, (4') oxo, (5') hydroxyl group, (6') thiol, (7') $C_{1-4}$alkylthio, (8') amino group, (9') mono-$C_{1-4}$alkylamino, (10') di-$C_{1-4}$ alkylamino, (11') 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (12') phenyl-$C_{1-4}$alkyl, (13') $C_{3-7}$cycloalkyl, (14') carboxyl, (15') $C_{1-4}$alkoxy-carbonyl, (16') $C_{7-10}$aralkyloxy-carbonyl, (17') carbamoyl, (18') mono-$C_{1-4}$alkylcarbamoyl, (19') di-$C_{1-4}$alkylcarbamoyl, (20') $C_{1-4}$alkyl which may be substituted with a halogen atom or $C_{1-4}$alkoxy, (21') $C_{1-4}$alkoxy which may be substituted with a halogen atom or $C_{1-4}$alkoxy, (22') $C_{1-4}$alkylenedioxy, (23') formyl, (24') $C_{2-4}$alkanoyl, (25') $C_{1-4}$alkylsulfonyl, (26') $C_{1-4}$alkylsulfinyl, (27') sulfamoyl, (28') mono-$C_{1-4}$alkylsulfamoyl, (29') di-$C_{1-4}$alkylsulfamoyl, (30') $C_{6-14}$aryl (which may be substituted with a substituent(s) selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole and imidazole, (11") phenyl-$C_{1-4}$alkyl, (12") $C_{3-7}$cycloalkyl, (13") carboxyl group, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl and (29") 5- to 6-membered aromatic monocyclic heterocyclic group), and (31') 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1") halogen, (2") nitro, (3") cyano, (4") oxo, (5") hydroxyl group, (6") thiol, (7") $C_{1-4}$alkylthio, (8") amino, (9") mono-$C_{1-4}$alkylamino, (10") di-$C_{1-4}$alkylamino, (11") 5- to 6-membered cyclic amino selected from tetrahydropyrrole, piperazine, piperidine, morpholine, thiomorpholine, pyrrole and imidazole, (12") phenyl-$C_{1-4}$alkyl, (13") $C_{3-7}$cycloalkyl, (14") carboxyl, (15") $C_{1-4}$alkoxy-carbonyl, (16") $C_{7-10}$aralkyloxy-carbonyl, (17") carbamoyl, (18") mono-$C_{1-4}$alkyl-carbamoyl, (19") di-$C_{1-4}$ alkyl-carbamoyl, (20") $C_{1-4}$alkyl which may be substituted with a halogen atom or $C_{1-4}$alkoxy, (21") $C_{1-4}$alkoxy which may be substituted with a halogen atom or $C_{1-4}$alkoxy, (22") $C_{1-4}$alkylenedioxy, (23") formyl, (24") $C_{2-4}$alkanoyl, (25") $C_{1-4}$alkylsulfonyl, and (26") $C_{1-4}$alkylsulfinyl) (hereinafter referred to as substituent group A);

(3) $C_{3-8}$cycloalkyl which may have 1 to 3 substituents selected from the substituent group A;

(4) $C_{2-10}$alkenyl which may have 1 to 3 substituents selected from the substituent group A;

(5) $C_{3-8}$cycloalkenyl which may have 1 to 3 substituents selected from the substituent group A;

(6) $C_{2-10}$alkynyl which may have 1 to 3 substituents selected from the substituent group A;

(7) $C_{6-14}$aryl which may have 1 to 3 substituents selected from the substituent group A;

(8) $C_{6-14}$aryl-$C_{1-6}$alkyl which may have 1 to 3 substituents selected from the substituent group A;

(9) di-$C_{6-14}$aryl-$C_{1-6}$alkyl which may have 1 to 3 substituents selected from the substituent group A;

(10) tri-$C_{6-14}$aryl-$C_{1-6}$alkyl which may have 1 to 3 substituents selected from the substituent group A;

(11) a group represented by the formula —X'''—G—$(CH_2)_n$—J wherein X''' represents $C_{1-4}$alkylene or $C_{2-4}$alkenylene, G is a bond, —O—, —S—, —CO—NH— or —NH—CO—, n is an integer of 0 to 3, J represents (a) $C_{6-14}$aryl (which may have 1 to 3 substituents selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (11") phenyl-$C_{1-4}$alkyl, (12") $C_{3-7}$cycloalkyl, (13") carboxyl, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl, (29") $C_{6-14}$aryl (which may be substituted with a substituent(s) selected from (1''') halogen, (2''') nitro, (3''') cyano, (4''') hydroxyl group, (5''') thiol, (6''') $C_{1-4}$alkylthio, (7''') amino, (8''') mono-$C_{1-4}$alkylamino, (9''') di-$C_{1-4}$alkylamino, (10''') 5- to 6-membered cyclic amino selected from tetrahydropyrrole, piperazine, piperidine, morpholine, thiomorpholine, pyrrole and imidazole, (11''') phenyl-$C_{1-4}$alkyl, (12''') $C_{3-7}$cycloalkyl, (13''') carboxyl group, (14''') $C_{1-4}$alkoxy-carbonyl, (15''') $C_{7-10}$aralkyloxy-carbonyl, (16''') carbamoyl, (17''') mono-$C_{1-4}$alkyl-carbamoyl, (18''') di-$C_{1-4}$alkyl-carbamoyl, (19''') $C_{1-4}$alkyl which may be substituted with a halogen atom or $C_{1-4}$alkoxy, (20''') $C_{1-4}$alkoxy which may be substituted with a halogen atom or $C_{1-4}$alkoxy, (21''') $C_{1-4}$alkylenedioxy, (22''') formyl, (23''') $C_{2-4}$alkanoyl, (24''') $C_{1-4}$alkylsulfonyl, (25''') $C_{1-4}$alkylsulfinyl, (26''') sulfamoyl, (27''') mono-$C_{1-4}$alkylsulfamoyl, (28''') di-$C_{1-4}$alkylsulfamoyl, and (29''') 5- to 6-membered aromatic monocyclic heterocyclic group), and (30") 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1''') halogen, (2''') nitro, (3''') cyano, (4''') oxo, (5''') hydroxyl group, (6''') thiol, (7''') $C_{1-4}$alkylthio, (8''') amino, (9''') mono-$C_{1-4}$alkylamino, (10''') di-$C_{1-4}$alkylamino, (11''') 5- to 6-membered cyclic amino selected from tetrahydropyrrole, piperazine, piperidine, morpholine, thiomorpholine, pyrrole and imidazole, (12''') phenyl-$C_{1-4}$alkyl, (13''') $C_{3-7}$cycloalkyl, (14''') carboxyl, (15''') $C_{1-4}$alkoxy-carbonyl, (16''') $C_{7-10}$aralkyloxy-carbonyl, (17''') carbamoyl, (18''') mono-$C_{1-4}$alkyl-carbamoyl, (19''') di-$C_{1-4}$alkyl-carbamoyl, (20''') $C_{1-4}$alkyl which may be substituted with a halogen atom or $C_{1-4}$alkoxy, (21''') $C_{1-4}$alkoxy which may be substituted with a halogen atom or $C_{1-4}$alkoxy, (22''') $C_{1-4}$alkylenedioxy, (23''') formyl, (24''') $C_{2-4}$alkanoyl, (25''') $C_{1-4}$alkylsulfonyl and (26''') $C_{1-4}$alkylsulfinyl) (hereinafter referred to as substituent group B), or (b) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B); or

(12) a group represented by the formula —X''''—L—$(CH_2)_n$—M wherein X'''' represents a bond or a $C_{1-4}$alkylene group which may have 1 to 3 substituents selected from the substituent group A, L represents (a) a bond, (b) $C_{6-10}$aryl which may have 1 to 3 substituents selected from the substituent group B, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, and M represents amino group, guanidino group, sulfamoyl group, carbamoyl group or hydroxyl group, X represents:

(1) —$(CH_2)_{f1}$—, wherein f1 represents an integer of 1 to 12, (2) —$(CH_2)_{g1}$—$X^1$—$(CH_2)_{g2}$—, wherein g1 and g2 are the same or different, and represent an integer of 0 to 11, provided that the sum of g1 and g2 is 0 to 11, and $X^1$ represents NH, O, S, SO or $SO_2$, or (3) —$(CH_2)_{h1}$—$X^1$—$(CH_2)_{h2}$—$X^2$—$(CH_2)_{h3}$— wherein h1, h2 and h3 are the same or different, and represent an integer of 0 to 10, provided that the sum of h1, h2 and h3 is 0 to 10, and $X^1$ and $X^2$ each represents NH, O, S, SO or $SO_2$ provided that when h2 is 0, $X^1$ $_{and/or}$ $x^2$ preferably represent NH, A represents (1) amino which may have 1 to 2 substituents selected from (a) $C_{1-10}$alkyl which may have 1 to 3 substituents selected from (1") halogen, (2") nitro, (3") cyano, (4") oxo, (5") hydroxyl group, (6") thiol, (7") $C_{1-4}$alkylthio, (8") amino, (9") mono-$C_{1-4}$alkylamino, (10") di-$C_{1-4}$ alkylamino, (11") 5- to 6-membered cyclic amino selected from tetrahydropyrrole, piperazine, piperidine, morpholine, thiomorpholine, pyrrole and imidazole, (12") phenyl-$C_{1-4}$alkyl, (13") $C_{3-7}$cycloalkyl, (14") carboxyl, (15") $C_{1-4}$alkoxy-carbonyl, (16") $C_{7-10}$aralkyloxy-carbonyl, (17") carbamoyl, (18") mono-$C_{1-4}$alkyl-carbamoyl, (19") di-$C_{1-4}$alkyl-carbamoyl, (20") $C_{1-4}$alkyl which may be substituted with a halogen atom or $C_{1-4}$alkoxy, (21") $C_{1-4}$alkoxy which may be substituted with a halogen atom or $C_{1-4}$alkoxy, (22") $C_{1-4}$alkylenedioxy, (23") formyl, (24") $C_{2-4}$alkanoyl, (25") $C_{1-4}$alkylsulfonyl and (26") $C_{1-4}$alkylsulfinyl (hereinafter referred to as substituent group C), (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$ aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), and (l) acyl groups wherein a 5- to 8-membered aromatic heterocyclic group or saturated or unsaturated non-aromatic heterocyclic group containing a least one of 1 to 3 kinds of heteroatoms selected from oxygen atom, sulfur atom and nitrogen atom has been bound to carbonyl or sulfonyl (said acyl optionally having 1 to 3 substituents selected from the substituent group C); or (2) 5- or 6-membered cyclic amino which may have 1 to 3 substituents selected from (a) halogen, (b) nitro, (c) cyano, (d) hydroxyl group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl; or (3) a heterocyclic group formed by removing one hydrogen atom from a 5- to 8-membered aromatic monocyclic heterocyclic ring or saturated or unsaturated non-aromatic monocyclic heterocyclic ring containing one nitrogen atom and one to three kinds of 1 to 4 heteroatoms selected from oxygen atom, sulfur atom and nitrogen atom or by removing one hydrogen atom from a ring wherein 2 or 3 the same or different rings selected from the above monocyclic rings have been fused (said heterocyclic group optionally having 1 to 3 substituents selected from the substituent group C), $R^2$ represents (1) $C_{1-10}$alkyl which may have 1 to 3 substituents selected from the substituent group A;

(2) $C_{3-8}$cycloalkyl which may have 1 to 3 substituents selected from the substituent group A;

(3) $C_{2-10}$alkenyl which may have 1 to 3 substituents selected from the substituent group A;

(4) $C_{3-8}$cycloalkenyl which may have 1 to 3 substituents selected from the substituent group A;

(5) $C_{2-10}$alkynyl which may have 1 to 3 substituents selected from the substituent group A;

(6) $C_{6-14}$aryl which may have 1 to 3 substituents selected from the substituent group A;

(7) $C_{6-14}$aryl-$C_{1-6}$alkyl which may have 1 to 3 substituents selected from the substituent group A;

(8) di-$C_{6-14}$aryl-$C_{1-6}$alkyl which may have 1 to 3 substituents selected from the substituent group A;

(9) tri-$C_{6-14}$aryl-$C_{1-6}$alkyl which may have 1 to 3 substituents selected from the substituent group A;

(10) a group represented by the formula —X'''—G—(CH$_2$)$_n$—J, wherein X''' represents $C_{1-4}$alkylene or $C_{2-4}$alkenylene, G represents a bond, —O—, —S—, —CO—NH— or —NH—CO—, n is an integer of 0 to 3, and J represents (a) $C_{6-14}$aryl (which may have 1 to 3 substituents selected from the substituent group B) or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group B);

(11) a group represented by the formula —X''''—L—(CH$_2$)$_n$—M, wherein X'''' represents a bond or $C_{1-4}$alkylene which may have 1 to 3 substituents selected from the substituent group A, and L represents (a) a bond, (b) $C_{6-10}$aryl which may have 1 to 3 substituents selected from the substituent group B, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, M represents an amino group, guanidino group, sulfamoyl group, carbamoyl group or hydroxyl group; or

(12) amino which may have 1 to 2 substituents selected from (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), and (l) acyl groups wherein a 5- to 8-membered aromatic heterocyclic group or saturated or unsaturated non-aromatic heterocyclic group containing a least one of 1 to 3 kinds of heteroatoms selected from oxygen atom, sulfur atom and nitrogen atom has been bound to a carbonyl or sulfonyl group (said acyl optionally having 1 to 3 substituents selected from the substituent group C), $R^3$ represents (1) $C_{1-10}$alkyl which may have 1 to 3 substituents selected the substituent group A;

(2) $C_{3-8}$cycloalkyl which may have 1 to 3 substituents selected from the substituent group A;

(3) $C_{2-10}$alkenyl which may have 1 to 3 substituents selected from the substituent group A;

(4) $C_{3-8}$cycloalkenyl which may have 1 to 3 substituents selected from the substituent group A;

(5) $C_{2-10}$alkynyl which may have 1 to 3 substituents selected from the substituent group A;

(6) $C_{6-14}$aryl which may have 1 to 3 substituents selected from the substituent group A;

(7) $C_{6-14}$aryl-$C_{1-6}$alkyl which may have 1 to 3 substituents selected from the substituent group A;

(8) di-$C_{6-14}$aryl-$C_{1-6}$alkyl which may have 1 to 3 substituents selected from the substituent group A;

(9) tri-$C_{6-14}$aryl-$C_{1-6}$alkyl which may have 1 to 3 substituents selected from the substituent group A;

(10) a group represented by the formula —X'"—G—(CH$_2$)$_n$—J, wherein X'" represents $C_{1-4}$alkylene or $C_{2-4}$alkenylene, G represents a bond, —O—, —S—, —CO—NH— or —NH—CO—, n is an integer of 0 to 3, and J represents (a) a $C_{6-14}$aryl group (which may have 1 to 3 substituents selected from the substituent group B) or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group B); or

(11) a group represented by the formula —X""—L—(CH$_2$)$_n$—M, wherein X"" represents a bond or $C_{1-4}$alkylene which may have 1 to 3 substituents selected from the substituent group A, and L represents (a) a bond, (b) $C_{6-10}$aryl (which may have 1 to 3 substituents selected from the substituent group B), or (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, M represents amino group, guanidino group, sulfamoyl group, carbamoyl group or hydroxyl group; and rings B and C each represent a benzene ring which may further have 1 to 4 substituents selected from (1) $C_{1-10}$alkyl which may have 1 to 3 substituents selected from the substituent group A;

(2) $C_{3-8}$cycloalkyl which may have 1 to 3 substituents selected from the substituent group A;

(3) $C_{2-10}$alkenyl which may have 1 to 3 substituents selected from the substituent group A;

(4) $C_{3-8}$cycloalkenyl which may have 1 to 3 substituents selected from the substituent group A;

(5) $C_{2-10}$alkynyl which may have 1 to 3 substituents selected from the substituent group A;

(6) $C_{6-14}$aryl which may have 1 to 3 substituents selected from the substituent group A;

(7) $C_{6-14}$aryl-$C_{1-6}$alkyl which may have 1 to 3 substituents selected from the substituent group A;

(8) di-$C_{6-14}$aryl-$C_{1-6}$alkyl which may have 1 to 3 substituents selected from the substituent group A;

(9) tri-$C_{6-14}$aryl-$C_{1-6}$alkyl which may have 1 to 3 substituents selected from the substituent group A;

(10) a heterocyclic group formed by removing one hydrogen atom from a 5- to 8-membered aromatic monocyclic heterocyclic ring or saturated or unsaturated non-aromatic monocyclic heterocyclic ring containing at least 1 of one to three kinds of heteroatoms selected from oxygen atom, sulfur atom and nitrogen atom or by removing one hydrogen atom from a ring wherein 2 or 3 of the same or different rings selected from the above monocyclic rings and 5- to 8-membered cyclic hydrocarbons have been fused (said heterocyclic group optionally having 1 to 3 substituents selected from the substituent group A);

(11) a halogen atom;

(12) amino which may have 1 to 2 substituents selected from (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), and (l) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group C);

(13) 5- or 6-membered cyclic amino which may have 1 to 3 substituents selected from (a) halogen, (b) nitro, (c) cyano, (d) hydroxyl group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl;

(14) a group represented by the formula: $R^6$—Y— (wherein Y is O, S, S(O) or S(O)$_2$, and $R^6$ is (i) $C_{1-10}$alkyl which may have 1 to 3 substituents selected from the substituent group A; (ii) $C_{3-8}$cycloalkyl which may have 1 to 3 substituents selected from the substituent group A; (iii) $C_{2-10}$alkenyl which may have 1 to 3 substituents selected from the substituent group A; (iv) $C_{3-8}$cycloalkenyl which may have 1 to 3 substituents selected from the substituent group A; (v) $C_{2-10}$alkynyl which may have 1 to 3 substituents selected from the substituent group A; (vi) $C_{6-14}$aryl which may have 1 to 3 substituents selected from the substituent group A; (vii) $C_{6-14}$aryl-$C_{1-6}$alkyl which may have 1 to 3 substituents selected from the substituent group A; (viii) di-$C_{6-14}$aryl-$C_{1-6}$alkyl which may have 1 to 3 substituents selected from the substituent group A; (ix) tri-$C_{6-14}$ aryl-$C_{1-6}$alkyl which may have 1 to 3 substituents selected from the substituent group A; or (x) a heterocyclic group formed by removing one hydrogen atom from a 5- to 8-membered aromatic monocyclic heterocyclic ring or saturated or unsaturated non-aromatic monocyclic heterocyclic ring containing at least 1 of one to three kinds of heteroatoms selected from oxygen atom, sulfur atom and nitrogen atom or by removing one hydrogen atom from a ring wherein 2 or 3 of the same or different rings selected from the above monocyclic rings and 5- to 8-membered cyclic hydrocarbons have been fused (said heterocyclic group optionally having 1 to 3 substituents selected from the substituent group A));

(15) cyano group;

(16) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C);

(17) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group C);

(18) carboxyl; and

(19) carbamoyl which may have 1 to 2 substituents selected from (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C and (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C;

or a salt thereof, provided that (1) a compound represented by the formula:

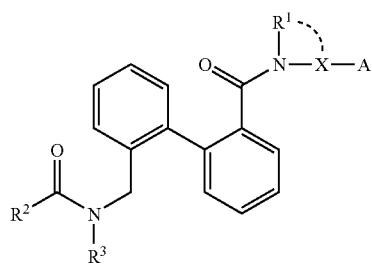

wherein each symbol is as defined above and (2) 4'-[[(methoxyacetyl)methylamino]methyl]-N-[4-methoxy-3-(4-methyl-1-piperazinyl)phenyl]-2'-methyl-[1,1'-biphenyl]-4-carboxamide are excluded.

2. A compound represented by formula (I):

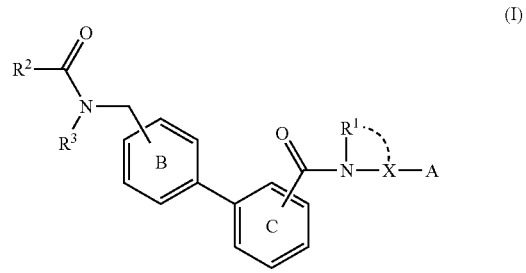

wherein $R^1$ is (1) hydrogen atom;

(2) $C_{1-10}$alkyl which may have 1 to 3 substituents selected from (1') halogen atom, (2') nitro, (3') cyano, (4') oxo, (5') hydroxyl group, (6') thiol, (7') $C_{1-4}$alkylthio, (8') amino group, (9') mono-$C_{1-4}$alkylamino, (10') di-$C_{1-4}$alkylamino, (11') 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (12') phenyl-$C_{1-4}$alkyl, (13') $C_{3-7}$cycloalkyl, (14') carboxyl, (15') $C_{1-4}$alkoxy-carbonyl, (16') $C_{7-10}$aralkyloxy-carbonyl, (17') carbamoyl, (18') mono-$C_{1-4}$alkylcarbamoyl, (19') di-$C_{1-4}$alkylcarbamoyl, (20') $C_{1-4}$alkyl which may be substituted with a halogen atom or $C_{1-4}$alkoxy, (21') $C_{1-4}$alkoxy which may be substituted with a halogen atom or $C_{1-4}$alkoxy, (22') $C_{1-4}$alkylenedioxy, (23') formyl, (24') $C_{2-4}$alkanoyl, (25') $C_{1-4}$alkylsulfonyl, (26') $C_{1-4}$alkylsulfinyl, (27') sulfamoyl, (28') mono-$C_{1-4}$alkylsulfamoyl, (29') di-$C_{1-4}$alkylsulfamoyl, (30') $C_{6-14}$aryl (which may be substituted with a substituent(s) selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole and imidazole, (11") phenyl-$C_{1-4}$alkyl, (12") $C_{3-7}$cycloalkyl, (13") carboxyl group, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl, and (29") 5- to 6-membered aromatic monocyclic heterocyclic group), or (31') 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1''') halogen, (2''') nitro, (3''') cyano, (4''') oxo, (5''') hydroxyl group, (6''') thiol, (7''') $C_{1-4}$alkylthio, (8''') amino, (9''') mono-$C_{1-4}$alkylamino, (10''') di-$C_{1-4}$alkylamino, (11''') 5- to 6-membered cyclic amino selected from tetrahydropyrrole, piperazine, piperidine, morpholine, thiomorpholine, pyrrole and imidazole, (12''') phenyl-$C_{1-4}$alkyl, (13''') $C_{3-7}$cycloalkyl, (14''') carboxyl, (15''') $C_{1-4}$alkoxy-carbonyl, (16''') $C_{7-10}$aralkyloxy-carbonyl, (17''') carbamoyl, (18") mono-$C_{1-4}$alkyl-carbamoyl, (19") di-$C_{1-4}$alkyl-carbamoyl, (20") $C_{1-4}$alkyl which may be substituted with a halogen atom or $C_{1-4}$alkoxy, (21") $C_{1-4}$alkoxy which may be substituted with a halogen atom or $C_{1-4}$alkoxy, (22") $C_{1-4}$alkylenedioxy, (23") formyl, (24") $C_{2-4}$alkanoyl, (25") $C_{1-4}$alkylsulfonyl and (26") $C_{1-4}$alkylsulfinyl) (hereinafter referred to as substituent group D);

(3) $C_{3-8}$cycloalkyl which may have 1 to 3 substituents selected from the substituent group D;

(4) $C_{2-10}$alkenyl which may have 1 to 3 substituents selected from the substituent group D;

(5) $C_{3-8}$cycloalkenyl which may have 1 to 3 substituents selected from the substituent group D;

(6) $C_{2-10}$alkynyl which may have 1 to 3 substituents selected from the substituent group D;

(7) $C_{6-14}$aryl which may have 1 to 3 substituents selected from the substituent group D;

(8) $C_{6-14}$aryl-$C_{1-6}$alkyl which may have 1 to 3 substituents selected from the substituent group D;

(9) di-$C_{6-14}$aryl-$C_{1-6}$alkyl which may have 1 to 3 substituents selected from the substituent group D;

(10) tri-$C_{6-14}$aryl-$C_{1-6}$alkyl which may have 1 to 3 substituents selected from the substituent group D;

(11) a group represented by the formula —X'"—G—$(CH_2)_n$—J, wherein X'" represents $C_{1-4}$alkylene or $C_{2-4}$alkenylene, G is a bond, —O—, —S—, —CO—NH— or —NH—CO—, n is an integer of 0 to 3, J represents (a) $C_{6-14}$aryl (which may have 1 to 3 substituents selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (11") phenyl-$C_{1-4}$alkyl, (12") $C_{3-7}$cycloalkyl, (13") carboxyl, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl, (29") $C_{6-14}$aryl (which may be substituted with a substituent selected from (1'") halogen, (2'") nitro, (3'") cyano, (4'") hydroxyl group, (5'") thiol, (6'") $C_{1-4}$alkylthio, (7'") amino, (8'") mono-$C_{1-4}$alkylamino, (9'") di-$C_{1-4}$alkylamino, (10'") 5- to 6-membered cyclic amino selected from tetrahydropyrrole, piperazine, piperidine, morpholine, thiomorpholine, pyrrole and imidazole, (11'") phenyl-$C_{1-4}$alkyl, (12'") $C_{3-7}$cycloalkyl, (13'") carboxyl group, (14'") $C_{1-4}$alkoxy-carbonyl, (15'") $C_{7-10}$aralkyloxy-carbonyl, (16'") carbamoyl, (17'") mono-$C_{1-4}$alkyl-carbamoyl, (18'") di-$C_{1-4}$alkyl-carbamoyl, (19'") $C_{1-4}$alkyl which may be substituted with a halogen atom or $C_{1-4}$alkoxy, (20'") $C_{1-4}$alkoxy which may be substituted with a halogen atom or $C_{1-4}$alkoxy, (21'") $C_{1-4}$alkylenedioxy, (22'") formyl, (23'") $C_{2-4}$alkanoyl, (24'") $C_{1-4}$alkylsulfonyl, (25'") $C_{1-4}$alkylsulfinyl, (26'") sulfamoyl, (27'") mono-$C_{1-4}$alkylsulfamoyl, (28'") di-$C_{1-4}$alkylsulfamoyl and (29'") 5- to 6-membered aromatic monocyclic heterocyclic group), or (30") 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1'") halogen, (2'") nitro, (3'") cyano, (4'") oxo, (5'") hydroxyl group, (6'") thiol, (7'") $C_{1-4}$alkylthio, (8'") amino, (9'") mono-$C_{1-4}$alkylamino, (10'") di-$C_{1-14}$alkylamino, (11'") 5- to 6-membered cyclic amino selected from tetrahydropyrrole, piperazine, piperidine, morpholine, thiomorpholine, pyrrole and imidazole, (12'") phenyl-$C_{1-4}$alkyl, (13'") $C_{3-7}$cycloalkyl, (14'") carboxyl, (15'") $C_{1-4}$alkoxy-carbonyl, (16'") $C_{7-10}$aralkyloxy-carbonyl, (17'") carbamoyl, (18'") mono-$C_{1-4}$alkyl-carbamoyl, (19'") di-$C_{1-4}$alkyl-carbamoyl, (20'") $C_{1-4}$alkyl which may be substituted with a halogen atom or $C_{1-4}$alkoxy, (21'") $C_{1-4}$alkoxy which may be substituted with a halogen atom or $C_{1-4}$alkoxy, (22'") $C_{1-4}$alkylenedioxy, (23'") formyl, (24'") $C_{2-4}$alkanoyl, (25'") $C_{1-4}$alkylsulfonyl and (26'") $C_{1-4}$alkylsulfinyl) (hereinafter referred to as substituent group E), or (b) a 5- to 8-membered heterocyclic group containing at least one of 1 to 3 kinds of heteroatoms selected from oxygen atom, sulfur atom and nitrogen atom, said aromatic heterocyclic group optionally having 1 to 3 substituents selected from the substituent group E; or

(12) a group represented by the formula —X""—L—$(CH_2)_n$—M, wherein X"" represents a bond or a $C_{1-4}$alkylene group which may have 1 to 3 substituents selected from the substituent group D, L represents (a) a bond, (b) $C_{6-10}$aryl which may have 1 to 3 substituents selected from the substituent group E, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group E), (d) —O—, (e) —S—, (f) —CO—NH— or (g) —NH—CO—, n is an integer of 0 to 3, and M represents an amino group, guanidino group, sulfamoyl group, carbamoyl group or hydroxyl group, X represents:

(1) —$(CH_2)_{f1}$—, wherein f1 represents an integer of 1 to 8, (2) —$(CH_2)_{g1}$—$X^1$—$(CH_2)_{g2}$—, wherein g1 and g2 are the same or different, and represent an integer of 0 to 7, provided that the sum of g1 and g2 is 0 to 7, and $X^1$ represents NH, O, S, SO or $SO_2$, or (3) —$(CH_2)_{h1}$—$X^1$—$(CH_2)_{h2}$—$X^2$—$(CH_2)_{h3}$—, wherein h1, h2 and h3 are the same or different, and represent an integer of 0 to 6, provided that the sum of h1, h2 and h3 is 0 to 6, and $X^1$ and $X^2$ each represent NH, O, S, SO or $SO_2$ provided that when h2 is 0, $X^1$ and/or $X^2$ preferably represent NH, A represents (1) amino which may have 1 to 2 substituents selected from (a) $C_{1-10}$alkyl which may have 1 to 3 substituents selected from (1") halogen, (2") nitro, (3") cyano, (4") oxo, (5") hydroxyl group, (6") thiol, (7") $C_{1-4}$alkylthio, (8") amino, (9") mono-$C_{1-4}$alkylamino, (10") di-$C_{1-4}$alkylamino, (11") 5- to 6-membered cyclic amino selected from tetrahydropyrrole, piperazine, piperidine, morpholine, thiomorpholine, pyrrole and imidazole, (12") phenyl-$C_{1-4}$alkyl, (13") $C_{3-7}$cycloalkyl, (14") carboxyl, (15") $C_{1-4}$alkoxy-carbonyl, (16") $C_{7-10}$aralkyloxy-carbonyl, (17") carbamoyl, (18") mono-$C_{1-4}$alkyl-carbamoyl, (19") di-$C_{1-4}$alkyl-carbamoyl, (20") $C_{1-4}$alkyl which may be substituted with a halogen atom or $C_{1-4}$alkoxy, (21") $C_{1-4}$alkoxy which may be substituted with a halogen atom or $C_{1-4}$alkoxy, (22") $C_{1-4}$alkylenedioxy, (23") formyl, (24") $C_{2-4}$alkanoyl, (25") $C_{1-4}$alkylsulfonyl and (26") $C_{1-4}$alkylsulfinyl (hereinafter referred to as substituent group F), (b) $C_{3-8}$cycloalkyl which may have 1 to 3 substituents selected from the substituent group F, (c) $C_{2-10}$alkenyl which may have 1 to 3 substituents selected from the substituent group F, (d) $C_{3-8}$cycloalkenyl which may have 1 to 3 substituents selected from the substituent group F, (e) $C_{2-10}$alkynyl which may have 1 to 3 substituents selected from the substituent group F, (f) $C_{6-14}$aryl which may have 1 to 3 substituents selected from the substituent group F, (g) $C_{6-14}$aryl-$C_{1-6}$alkyl which may have 1 to 3 substituents selected from the substituent group F, (h) di-$C_{6-14}$aryl-$C_{1-6}$alkyl which may have 1 to 3 substituents selected from the substituent group F, (i) tri-$C_{6-14}$aryl-$C_{1-6}$alkyl which may have 1 to 3 substituents selected from the substituent group F, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group F, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group F, and (l) acyl wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group F); or (2) 5- or 6-membered cyclic amino which may have 1 to 3 substituents selected from (a) halogen, (b) nitro, (c) cyano, (d) hydroxyl group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl; or (3) a heterocyclic group formed by removing one hydrogen atom from a 5- to 8-membered aromatic monocyclic heterocyclic ring or saturated or unsaturated non-aromatic monocyclic heterocyclic ring containing one nitrogen atom and one to three kinds of 1 to 4 heteroatoms selected from an oxygen atom, a sulfur atom and a nitrogen atom or by removing one hydrogen atom from a ring wherein 2 or 3 the same or different rings selected from the above monocyclic rings have been condensed (said heterocyclic group optionally having 1 to 3 substituents selected from the substituent group F), $R^2$ and $R^3$ each represents (1) $C_{1-10}$alkyl which may have 1 to 3 substituents selected from the substituent group D;
(2) $C_{3-8}$cycloalkyl which may have 1 to 3 substituents selected from the substituent group D;
(3) $C_{2-10}$alkenyl which may have 1 to 3 substituents selected from the substituent group D;
(4) $C_{3-8}$cycloalkenyl which may have 1 to 3 substituents selected from the substituent group D;
(5) $C_{2-10}$alkynyl which may have 1 to 3 substituents selected from the substituent group D;
(6) $C_{6-14}$aryl which may have 1 to 3 substituents selected from the substituent group D;
(7) $C_{6-14}$aryl-$C_{1-6}$alkyl which may have 1 to 3 substituents selected from the substituent group D;
(8) di-$C_{6-14}$aryl-$C_{1-6}$alkyl which may have 1 to 3 substituents selected from the substituent group D;
(9) tri-$C_{6-14}$aryl-$C_{1-6}$alkyl which may have 1 to 3 substituents selected from the substituent group D;
(10) a group represented by the formula —X'''—$(CH_2)_n$—J, wherein X''' represents $C_{1-4}$alkylene or $C_{2-4}$alkenylene, G represents a bond, —O—, —S—, —CO—NH— or —NH—CO—, n is an integer of 0 to 3, and J represents (a) $C_{6-14}$aryl which may have 1 to 3 substituents selected from the substituent group E or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group E), or
(11) a group represented by the formula —X''''—L—$(CH_2)_n$—M, wherein X'''' represents a bond or $C_{1-4}$alkylene which may have 1 to 3 substituents selected from the substituent group D, and L represents (a) a bond, (b) $C_{6-10}$aryl which may have 1 to 3 substituents selected from the substituent group E, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group E), (d) —O—, (e) —S—, (f) —CO—NH— or (g) —NH—CO—, n is an integer of 0 to 3, M represents an amino group, guanidino group, sulfamoyl group, carbamoyl group or hydroxyl group; and rings B and C each represent a benzene ring which may further have 1 to 4 substituents selected from (1) $C_{1-10}$alkyl which may have 1 to 3 substituents selected from the substituent group D;
(2) $C_{3-8}$cycloalkyl which may have 1 to 3 substituents selected from the substituent group D;
(3) $C_{2-10}$alkenyl which may have 1 to 3 substituents selected from the substituent group D;
(4) $C_{3-8}$cycloalkenyl which may have 1 to 3 substituents selected from the substituent group D;
(5) $C_{2-10}$alkynyl which may have 1 to 3 substituents selected from the substituent group D;
(6) $C_{6-14}$aryl which may have 1 to 3 substituents selected from the substituent group D;
(7) $C_{6-14}$aryl-$C_{1-6}$alkyl which may have 1 to 3 substituents selected from the substituent group D;
(8) di-$C_{6-14}$aryl-$C_{1-6}$alkyl which may have 1 to 3 substituents selected from the substituent group D;
(9) tri-$C_{6-14}$aryl-$C_{1-6}$alkyl which may have 1 to 3 substituents selected from the substituent group D;
(10) a heterocyclic group formed by removing one hydrogen atom from a 5- to 8-membered aromatic monocyclic heterocyclic ring or saturated or unsaturated non-aromatic monocyclic heterocyclic ring containing at least 1 of one to three kinds of heteroatoms selected from oxygen atom, sulfur atom and nitrogen atom or by removing one hydrogen atom from a ring wherein 2 or 3 of the same or different rings selected from the above monocyclic rings and 5- to 8-membered cyclic hydrocarbons have been fused (said heterocyclic group optionally having 1 to 3 substituents selected from the substituent group D);
(11) a halogen atom;
(12) amino which may have 1 to 2 substituents selected from (a) $C_{1-10}$alkyl which may have 1 to 3 substituents selected from the substituent group F, (b) $C_{3-8}$cycloalkyl which may have 1 to 3 substituents selected from the substituent group F, (c) $C_{2-10}$alkenyl which may have 1 to 3 substituents selected from the substituent group F, (d) C$_{3-8}$cycloalkenyl which may have 1 to 3 substituents selected from the substituent group F, (e) C$_{2-10}$alkynyl which may have 1 to 3 substituents selected from the substituent group F, (f) C$_{6-14}$aryl which may have 1 to 3 substituents selected from the substituent group F, (g) C$_{6-14}$aryl-C$_{1-6}$alkyl which may have 1 to 3 substituents selected from the substituent group F, (h) di-C$_{6-14}$aryl-C$_{1-6}$alkyl which may have 1 to 3 substituents selected from the substituent group F, (i) tri-C$_{6-14}$aryl-C$_{1-6}$alkyl which may have 1 to 3 substituents selected from the substituent group F, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group F, (k) acyl selected from formyl, C$_{1-10}$alkyl-carbonyl, C$_{3-8}$cycloalkyl-carbonyl, C$_{2-10}$alkenyl-carbonyl, C$_{3-8}$cycloalkenyl-carbonyl, C$_{2-10}$alkynyl-carbonyl, C$_{6-14}$aryl-carbonyl, C$_{6-14}$aryl-C$_{1-6}$alkyl-carbonyl, di-C$_{6-14}$aryl-C$_{1-6}$alkyl-carbonyl, tri-C$_{6-14}$aryl-C$_{1-6}$alkyl-carbonyl, C$_{1-10}$alkylsulfonyl, C$_{3-8}$cycloalkylsulfonyl, C$_{2-10}$alkenylsulfonyl, C$_{3-8}$cycloalkenylsulfonyl, C$_{2-10}$alkynylsulfonyl, C$_{6-14}$arylsulfonyl, C$_{6-14}$aryl-C$_{1-6}$alkylsulfonyl, di-C$_{6-14}$aryl-C$_{1-6}$alkylsulfonyl or tri-C$_{6-14}$aryl-C$_{1-6}$alkylsulfonyl (said acyl optionally having 1 to 3 substituents selected from the substituent group F), and (l) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group F);

(13) 5- or 6-membered cyclic amino which may have 1 to 3 substituents selected from (a) halogen, (b) nitro, (c) cyano, (d) hydroxyl group, (e) thiol, (f) amino, (g) carboxyl, (h) optionally halogenated C$_{1-4}$alkyl, (i) optionally halogenated C$_{1-4}$alkoxy, (j) formyl, (k) C$_{2-4}$alkanoyl and (l) C$_{1-4}$alkylsulfonyl;

(14) a group represented by the formula: R$^6$—Y— (wherein Y is O, S, S(O) or S(O)$_2$, and R$^6$ is (i) C$_{1-10}$alkyl which may have 1 to 3 substituents selected the substituent group D; (ii) C$_{3-8}$cycloalkyl which may have 1 to 3 substituents selected from the substituent group D; (iii) C$_{2-10}$alkenyl which may have 1 to 3 substituents selected from the substituent group D; (iv) C$_{3-8}$cycloalkenyl which may have 1 to 3 substituents selected from the substituent group D; (v) C$_{2-10}$alkynyl which may have 1 to 3 substituents selected from the substituent group D; (vi) C$_{6-14}$aryl which may have 1 to 3 substituents selected from the substituent group D; (vii) C$_{6-14}$aryl-C$_{1-6}$alkyl which may have 1 to 3 substituents selected from the substituent group D; (viii) di-C$_{6-14}$aryl-C$_{1-6}$alkyl which may have 1 to 3 substituents selected from the substituent group D; (ix) tri-C$_{6-14}$aryl-C$_{1-6}$alkyl which may have 1 to 3 substituents selected from the substituent group D; or (x) a heterocyclic group formed by removing one hydrogen atom from a 5- to 8-membered aromatic monocyclic heterocyclic ring or saturated or unsaturated non-aromatic monocyclic heterocyclic ring containing at least 1 of one to three kinds of heteroatoms selected from oxygen atom, sulfur atom and nitrogen atom or by removing one hydrogen atom from a ring wherein 2 or 3 of the same or different rings selected from the above monocyclic rings and 5- to 8-membered cyclic hydrocarbons have been fused (said heterocyclic group optionally having 1 to 3 substituents selected from the substituent group D));

(15) cyano group;

(16) acyl selected from formyl, C$_{1-10}$alkyl-carbonyl, C$_{3-8}$cycloalkyl-carbonyl, C$_{2-10}$alkenyl-carbonyl, C$_{3-8}$cycloalkenyl-carbonyl, C$_{2-10}$alkynyl-carbonyl, C$_{6-14}$aryl-carbonyl, C$_{6-14}$aryl-C$_{1-6}$alkyl-carbonyl, di-C$_{6-14}$aryl-C$_{1-6}$alkyl-carbonyl, tri-C$_{6-14}$aryl-C$_{1-6}$alkyl-carbonyl, C$_{1-10}$alkylsulfonyl, C$_{3-8}$cycloalkylsulfonyl, C$_{2-10}$alkenylsulfonyl, C$_{3-8}$cycloalkenylsulfonyl, C$_{2-10}$alkynylsulfonyl, C$_{6-14}$arylsulfonyl, C$_{6-14}$aryl-C$_{1-6}$alkylsulfonyl, di-C$_{6-14}$aryl-C$_{1-6}$alkylsulfonyl or tri-C$_{6-14}$aryl-C$_{1-6}$alkylsulfonyl (said acyl optionally having 1 to 3 substituents selected from the substituent group F);

(17) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group F);

(18) carboxyl; and

(19) carbamoyl which may have 1 to 2 substituents selected from (a) C$_{1-10}$alkyl which may have 1 to 3 substituents selected from the substituent group F, (b) C$_{3-8}$cycloalkyl which may have 1 to 3 substituents selected from the substituent group F, (c) C$_{2-10}$alkenyl which may have 1 to 3 substituents selected from the substituent group F, (d) C$_{3-8}$cycloalkenyl which may have 1 to 3 substituents selected from the substituent group F, (e) C$_{2-10}$alkynyl which may have 1 to 3 substituents selected from the substituent group F, (f) C$_{6-14}$aryl which may have 1 to 3 substituents selected from the substituent group F, (g) C$_{6-14}$aryl-C$_{1-6}$alkyl which may have 1 to 3 substituents selected from the substituent group F, (h) di-C$_{6-14}$aryl-C$_{1-6}$alkyl which may have 1 to 3 substituents selected from the substituent group F, (i) tri-C$_{6-14}$aryl-C$_{1-6}$alkyl which may have 1 to 3 substituents selected from the substituent group F and (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group F; or a salt thereof, provided that 4'-[[(methoxyacetyl)methylamino]methyl]-N-[4-methoxy-3-(4-methyl-1-piperazinyl)phenyl]-2'-methyl-[1,1'-biphenyl]-4-carboxamide is excluded.

3. A compound represented by the formula:

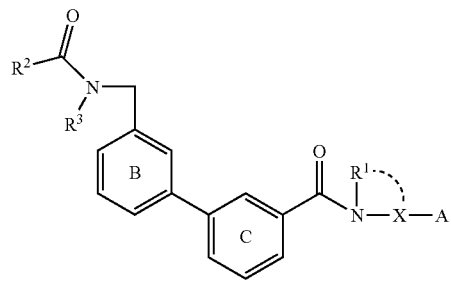

wherein each symbol is as defined in claim 2, or a salt thereof.

4. A compound represented by the formula:

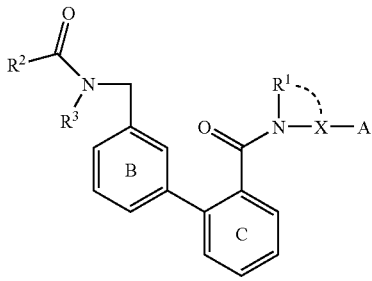

wherein each symbol is as defined in claim 2, or a salt thereof.

5. A compound represented by the formula:

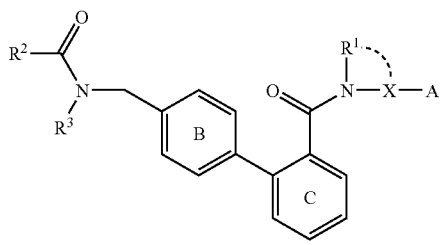

wherein each symbol is as defined in claim 2, or a salt thereof.

6. The compound according to claim 2, wherein the group represented by the formula:

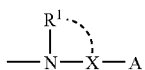

is a group represented by the formula:

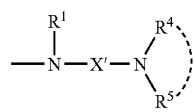

wherein
R$^1$ represents (1) hydrogen atom, (2) C$_{1-10}$alkyl, (3) C$_{3-8}$cycloalkyl, (4) C$_{2-10}$alkenyl, (5) C$_{3-8}$cycloalkenyl, (6) C$_{2-10}$alkynyl, (7) C$_{6-14}$aryl, (8) C$_{6-14}$aryl-C$_{1-6}$alkyl, (9) di-C$_{6-14}$aryl-C$_{1-6}$alkyl, (10) tri-C$_{6-14}$aryl-C$_{1-6}$alkyl, (11) a group represented by the formula —X'"—G—(CH$_2$)$_n$—J, wherein X'" represents a C$_{1-4}$alkylene group or C$_{2-4}$alkenylene group, G represents a bond, —O—, —S—, —CO—NH— or —NH—CO—, n is an integer of 0 to 3, J represents (a) C$_{6-14}$aryl or (b) a 5- to 8-membered aromatic heterocyclic group containing at least one of 1 to 3 kinds of heteroatoms selected from oxygen atom, sulfur atom and nitrogen atom, or (12) a group represented by the formula —X""—L—(CH$_2$)$_n$—M, wherein X"" represents a bond or a C$_{1-4}$alkylene group, L represents (a) a bond, (b) C$_{6-10}$aryl, (c) a 5- to 8-membered aromatic heterocyclic group containing at least one of 1 to 3 kinds of heteroatoms selected from oxygen atom, sulfur atom and nitrogen atom, (d) —O—, (e) —S—, (f) —CO—NH— or (g) —NH—CO—, n is an integer of 0 to 3, and M represents an amino group, guanidino group, sulfamoyl group, carbamoyl group or hydroxyl group,
X' represents C$_{1-6}$alkylene,
R$^4$ and R$^5$ each represents hydrogen atom or C$_{1-6}$alkyl (which may have 1 to 3 substituents selected from (i) halogen, (ii) nitro, (iii) cyano, (iv) hydroxyl group, (v) thiol, (vi) C$_{1-4}$alkylthio, (vii) amino, (viii) mono-C$_{1-4}$alkylamino, (ix) di-C$_{1-4}$alkylamino, (x) 5- to 6-membered cyclic amino selected from tetrahydropyrrole, piperazine, piperidine, morpholine, thiomorpholine, pyrrole and imidazole, (xi) carboxyl, (xii) C$_{1-4}$alkoxy-carbonyl, (xiii) C$_{7-10}$aralkyloxy-carbonyl, (xiv) carbamoyl, (xv) mono-C$_{1-4}$alkyl-carbamoyl, (xvi) di-C$_{1-4}$alkyl-carbamoyl, (xvii) C$_{1-4}$alkyl which may be substituted with a halogen atom or C$_{1-4}$alkoxy, (xviii) C$_{1-4}$alkoxy which may be substituted with a halogen atom or C$_{1-4}$alkoxy, (xix) C$_{1-4}$alkylenedioxy, (xx) phenyl-C$_{1-4}$alkyl, (xxi) C$_{3-7}$cycloalkyl, (xxii) formyl, (xxiii) C$_{2-4}$alkanoyl, (xxiv) C$_{1-4}$alkylsulfonyl and (xxv) C$_{1-4}$alkylsulfinyl), and R$^4$ and R$^5$ together with their adjacent nitrogen atom may be bound to each other to form a 3- to 8-membered cyclic amino group.

7. The compound according to claim 6, wherein each of R$^4$ and R$^5$ is hydrogen atom.

8. The compound according to claim 6, wherein R$^4$ and R$^5$ are bound to each other to form a 3- to 8-membered saturated nitrogen-containing heterocyclic ring.

9. The compound according to claim 2, wherein the group represented by the formula:

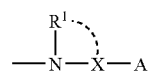

is a group represented by the formula:

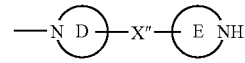

wherein X" represents a bond or C$_{1-4}$alkylene, and
rings D and E each represents a 3- to 8-membered saturated nitrogen-containing heterocyclic ring.

10. The compound according to claim 2, wherein R$^2$ is a group represented by the formula —X'"—G—(CH$_2$)$_n$—J wherein X'" represents a C$_{1-4}$alkylene group or C$_{2-4}$alkenylene group, G represents a bond, —O—, —S—, —CO—NH— or —NH—CO—, n is an integer of 0 to 3, J represents (a) a C$_{6-14}$aryl group (which may have 1 to 3 substituents selected from (i) halogen, (ii) hydroxyl group, (iii) C$_{1-4}$alkyl which may be substituted with a halogen atom or C$_{1-4}$alkoxy, (iv) C$_{1-4}$alkoxy which may be substituted with a halogen atom or C$_{1-4}$alkoxy and (v) sulfamoyl), or (b) a 5- to 8-membered aromatic heterocyclic group containing at least one of 1 to 3 kinds of heteroatoms selected from oxygen atom, sulfur atom and nitrogen atom.

11. The compound according to claim 2, wherein R$^2$ is a group represented by the formula —X""—L—(CH$_2$)$_n$—M wherein X"" represents a bond or a C$_{1-4}$alkylene group, L represents (a) a bond, (b) C$_{6-14}$aryl, (c) a 5- to 8-membered aromatic heterocyclic group containing at least one of 1 to 3 kinds of heteroatoms selected from oxygen atom, sulfur atom and nitrogen atom, (d) —O—, (e) —S—, (f) —CO—NH— or (g) —NH—CO—, n is an integer of 0 to 3, and M represents an amino group, guanidino group, sulfamoyl group, carbamoyl group or hydroxyl group.

12. The compound according to claim 2, wherein $R^3$ represents a group represented by the formula —$(CH_2)_p$—T, wherein p is an integer of 1 to 6, T represents (a) $C_{6-14}$aryl (which may have 1 to 3 substituents selected from (i) halogen, (ii) hydroxyl group, (iii) phenyl-$C_{1-4}$alkyl, (iv) carboxyl, (v) $C_{1-4}$alkoxy-carbonyl, (vi) $C_{1-4}$alkyl which may be substituted with a halogen atom or $C_{1-4}$alkoxy, (vii) $C_{1-4}$alkoxy which may be substituted with a halogen atom or $C_{1-4}$alkoxy, (viii) $C_{1-4}$alkylenedioxy, (ix) sulfamoyl, (x) $C_{1-4}$alkylsulfamoyl, (xi) di-$C_{1-4}$alkylsulfamoyl and (xii) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, or (b) a 5- to 8-membered aromatic heterocyclic group containing at least one of 1 to 3 kinds of heteroatoms selected from oxygen atom, sulfur atom and nitrogen atom.

13. The compound according to claim 12, wherein T is phenyl group substituted with hydroxyl group, sulfamoyl, $C_{1-4}$alkylsulfamoyl or di-$C_{1-4}$alkylsulfamoyl.

14. 3'-{[{2-[4-(Aminosulfonyl)phenyl]ethyl}(4-phenylbutanoyl)amino]methyl}-N-[2-(1-pyrrolidinyl)ethyl]-[1,1'-biphenyl]-3-carboxamide or a salt thereof.

15. 3'-({{2-[4-(Aminosulfonyl)phenyl]ethyl}-[(benzyloxy)acetyl]amino}methyl)-N-[2-(1-pyrrolidinyl)-ethyl][1,1'-biphenyl]-3-carboxamide or a salt thereof.

16. N-(2-Aminoethyl)-3'-{[[3-({[amino(imino)methyl]amino}methyl)benzoyl](1-naphthylmethyl)amino]methyl}-1,1'-biphenyl]-2-carboxamide or a salt thereof.

17. N-(2-Aminoethyl)-3'-{[[4-(aminosulfonyl)benzoyl]-(1-naphthylmethyl)amino]methyl}-1,1'-biphenyl-2-carboxamide or a salt thereof.

18. A prodrug of the compound according to claim 1 or 2 or a salt thereof.

19. A pharmaceutical composition comprising a compound represented by the formula (I):

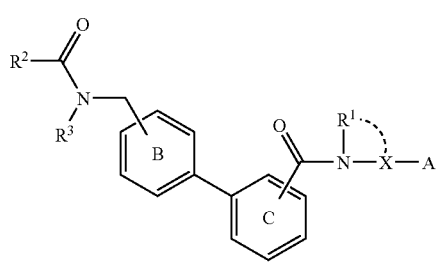

wherein $R^1$ is (1) hydrogen atom;
(2) $C_{1-10}$alkyl which may have 1 to 3 substituents selected from (1') halogen atom, (2') nitro, (3') cyano, (4') oxo, (5') hydroxyl group, (6') thiol, (7') $C_{1-4}$alkylthio, (8') amino group, (9') mono-$C_{1-4}$alkylamino, (10') di-$C_{1-4}$alkylamino, (11') 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (12') phenyl-$C_{1-4}$alkyl, (13') $C_{3-7}$cycloalkyl, (14') carboxyl, (15') $C_{1-4}$alkoxy-carbonyl, (16') $C_{7-10}$aralkyloxy-carbonyl, (17') carbamoyl, (18') mono-$C_{1-4}$alkylcarbamoyl, (19') di-$C_{1-4}$alkylcarbamoyl, (20') $C_{1-4}$alkyl which may be substituted with a halogen atom or $C_{1-4}$alkoxy, (21') $C_{1-4}$alkoxy which may be substituted with a halogen atom or $C_{1-4}$alkoxy, (22') $C_{1-4}$alkylenedioxy, (23') formyl, (24') $C_{2-4}$alkanoyl, (25') $C_{1-4}$alkylsulfonyl, (26') $C_{1-4}$alkylsulfinyl, (27') sulfamoyl, (28') mono-$C_{1-4}$alkylsulfamoyl, (29') di-$C_{1-4}$alkylsulfamoyl, (30') $C_{6-14}$aryl (which may be substituted with a substituent(s) selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole and imidazole, (11") phenyl-$C_{1-4}$alkyl, (12") $C_{3-7}$cycloalkyl, (13") carboxyl group, (14") $C_{1-4}$alkoxy-carbonyl, (15") $C_{7-10}$aralkyloxy-carbonyl, (16") carbamoyl, (17") mono-$C_{1-4}$alkyl-carbamoyl, (18") di-$C_{1-4}$alkyl-carbamoyl, (19") $C_{1-4}$alkyl which may be substituted with a halogen atom or $C_{1-4}$alkoxy, (20") $C_{1-4}$alkoxy which may be substituted with a halogen atom or $C_{1-4}$alkoxy, (21") $C_{1-4}$alkylenedioxy, (22") formyl, (23") $C_{2-4}$alkanoyl, (24") $C_{1-4}$alkylsulfonyl, (25") $C_{1-4}$alkylsulfinyl, (26") sulfamoyl, (27") mono-$C_{1-4}$alkylsulfamoyl, (28") di-$C_{1-4}$alkylsulfamoyl and (29") 5- to 6-membered aromatic monocyclic heterocyclic group), and (31') 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1") halogen, (2") nitro, (3") cyano, (4") oxo, (5") hydroxyl group, (6") thiol, (7") $C_{1-4}$alkylthio, (8") amino, (9") mono-$C_{1-4}$alkylamino, (10") di-$C_{1-4}$alkylamino, (11") 5- to 6-membered cyclic amino selected from tetrahydropyrrole, piperazine, piperidine, morpholine, thiomorpholine, pyrrole and imidazole, (12") phenyl-$C_{1-4}$alkyl, (13") $C_{3-7}$cycloalkyl, (14") carboxyl, (15") $C_{1-4}$alkoxy-carbonyl, (16") $C_{7-10}$aralkyloxy-carbonyl, (17") carbamoyl, (18") mono-$C_{1-4}$alkyl-carbamoyl, (19") di-$C_{1-4}$alkyl-carbamoyl, (20") $C_{1-4}$alkyl which may be substituted with a halogen atom or $C_{1-4}$alkoxy, (21") $C_{1-4}$alkoxy which may be substituted with a halogen atom or $C_{1-4}$alkoxy, (22") $C_{1-4}$alkylenedioxy, (23") formyl, (24") $C_{2-4}$alkanoyl, (25") $C_{1-4}$alkylsulfonyl, and (26") $C_{1-4}$alkylsulfinyl)(hereinafter referred to as substituent group A);

(3) $C_{3-8}$cycloalkyl which may have 1 to 3 substituents selected from the substituent group A;
(4) $C_{2-10}$alkenyl which may have 1 to 3 substituents selected from the substituent group A;
(5) $C_{3-8}$cycloalkenyl which may have 1 to 3 substituents selected from the substituent group A;
(6) $C_{2-10}$alkynyl which may have 1 to 3 substituents selected from the substituent group A;
(7) $C_{6-14}$aryl which may have 1 to 3 substituents selected from the substituent group A;
(8) $C_{6-14}$aryl-$C_{1-6}$alkyl which may have 1 to 3 substituents selected from the substituent group A;
(9) di-$C_{6-14}$aryl-$C_{1-6}$alkyl which may have 1 to 3 substituents selected from the substituent group A;
(10) tri-$C_{6-14}$aryl-$C_{1-6}$alkyl which may have 1 to 3 substituents selected from the substituent group A;
(11) a group represented by the formula —X'"—G—$(CH_2)_n$—J wherein X'" represents $C_{1-4}$alkylene or $C_{2-4}$alkenylene, G is a bond, —O—, —S—, —CO—NH— or —NH—CO—, n is an integer of 0 to 3, J represents (a) $C_{6-14}$aryl (which may have 1 to 3 substituents selected from (1") halogen, (2") nitro, (3") cyano, (4") hydroxyl group, (5") thiol, (6") $C_{1-4}$alkylthio, (7") amino, (8") mono-$C_{1-4}$alkylamino, (9") di-$C_{1-4}$alkylamino, (10") 5- to 6-membered cyclic amino selected from tetrahydropyrrole, piperazine, piperidine, morpholine, thiomorpholine, pyrrole, imidazole, 2-oxo-1-pyrrolidinyl and 2-oxo-1-piperidinyl, (11″) phenyl-$C_{1-4}$alkyl, (12″) $C_{3-7}$cycloalkyl, (13″) carboxyl, (14″) $C_{1-4}$alkoxy-carbonyl, (15″) $C_{7-10}$aralkyloxy-carbonyl, (16″) carbamoyl, (17″) mono-$C_{1-4}$alkyl-carbamoyl, (18″) di-$C_{1-4}$alkyl-carbamoyl, (19″) $C_{1-4}$alkyl which may be substituted with a halogen atom or $C_{1-4}$alkoxy, (20″) $C_{1-4}$alkoxy which may be substituted with a halogen atom or $C_{1-4}$alkoxy, (21″) $C_{1-4}$alkylenedioxy, (22″) formyl, (23″) $C_{2-4}$alkanoyl, (24″) $C_{1-4}$alkylsulfonyl, (25″) $C_{1-4}$alkylsulfinyl, (26″) sulfamoyl, (27″) mono-$C_{1-4}$alkylsulfamoyl, (28″) di-$C_{1-4}$alkylsulfamoyl, (29″) $C_{6-14}$aryl (which may be substituted with a substituent(s) selected from (1‴) halogen, (2‴) nitro, (3‴) cyano, (4‴) hydroxyl group, (5‴) thiol, (6‴) $C_{1-4}$alkylthio, (7‴) amino, (8‴) mono-$C_{1-4}$alkylamino, (9‴) di-$C_{1-4}$alkylamino, (10‴) 5- to 6-membered cyclic amino selected from tetrahydropyrrole, piperazine, piperidine, morpholine, thiomorpholine, pyrrole and imidazole, (11‴) phenyl-$C_{1-4}$alkyl, (12‴) $C_{3-7}$cycloalkyl, (13‴) carboxyl group, (14‴) $C_{1-4}$alkoxy-carbonyl, (15‴) $C_{7-10}$aralkyloxy-carbonyl, (16‴) carbamoyl, (17‴) mono-$C_{1-4}$alkyl-carbamoyl, (18‴) di-$C_{1-4}$alkyl-carbamoyl, (19‴) $C_{1-4}$alkyl which may be substituted with a halogen atom or $C_{1-4}$alkoxy, (20‴) $C_{1-4}$alkoxy which may be substituted with a halogen atom or $C_{1-4}$alkoxy, (21‴) $C_{1-4}$alkylenedioxy, (22‴) formyl, (23‴) $C_{2-4}$alkanoyl, (24‴) $C_{1-4}$alkylsulfonyl, (25‴) $C_{1-4}$alkylsulfinyl, (26‴) sulfamoyl, (27‴) mono-$C_{1-4}$alkylsulfamoyl, (28‴) di-$C_{1-4}$alkylsulfamoyl, and (29‴) 5- to 6-membered aromatic monocyclic heterocyclic group), and (30″) 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom (said heterocyclic group may have 1 to 3 substituents selected from (1‴) halogen, (2‴) nitro, (3‴) cyano, (4‴) oxo, (5‴) hydroxyl group, (6‴) thiol, (7‴) $C_{1-4}$alkylthio, (8‴) amino, (9‴) mono-$C_{1-4}$alkylamino, (10‴) di-$C_{1-4}$alkylamino, (11‴) 5- to 6-membered cyclic amino selected from tetrahydropyrrole, piperazine, piperidine, morpholine, thiomorpholine, pyrrole and imidazole, (12‴) phenyl-$C_{1-4}$alkyl, (13‴) $C_{3-7}$cycloalkyl, (14‴) carboxyl, (15‴) $C_{1-4}$alkoxy-carbonyl, (16‴) $C_{7-10}$aralkyloxy-carbonyl, (17‴) carbamoyl, (18‴) mono-$C_{1-4}$alkyl-carbamoyl, (19‴) di-$C_{1-4}$alkyl-carbamoyl, (20‴) $C_{1-4}$alkyl which may be substituted with a halogen atom or $C_{1-4}$alkoxy, (21‴) $C_{1-4}$alkoxy which may be substituted with a halogen atom or $C_{1-4}$alkoxy, (22‴) $C_{1-4}$alkylenedioxy, (23‴) formyl, (24‴) $C_{2-4}$alkanoyl, (25‴) $C_{1-4}$alkylsulfonyl and (26‴) $C_{1-4}$alkylsulfinyl) (hereinafter referred to as substituent group B), or (b) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B); or

(12) a group represented by the formula —X″″—L—$(CH_2)_n$—M wherein X″″ represents a bond or a $C_{1-4}$alkylene group which may have 1 to 3 substituents selected from the substituent group A, L represents (a) a bond, (b) $C_{6-10}$aryl which may have 1 to 3 substituents selected from the substituent group B, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, and M represents amino group, guanidino group, sulfamoyl group, carbamoyl group or hydroxyl group, X represents:

(1) —$(CH_2)_{f1}$—, wherein f1 represents an integer of 1 to 12, (2) —$(CH_2)_{g1}$—$X^1$—$(CH_2)_{g2}$—, wherein g1 and g2 are the same or different, and represent an integer of 0 to 11, provided that the sum of g1 and g2 is 0 to 11, and $X^1$ represents NH, O, S, SO or $SO_2$, or (3) —$(CH_2)_{h1}$—$X^1$—$(CH_2)_{h2}$—$X^2$—$(CH_2)_{h3}$— wherein h1, h2 and h3 are the same or different, and represent an integer of 0 to 10, provided that the sum of h1, h2 and h3 is 0 to 10, and $X^1$ and $X^2$ each represents NH, O, S, SO or $SO_2$ provided that when h2 is 0, $X^1$ and/or $X^2$ preferably represent NH, A represents (1) amino which may have 1 to 2 substituents selected from (a) $C_{1-10}$alkyl which may have 1 to 3 substituents selected from (1″) halogen, (2″) nitro, (3″) cyano, (4″) oxo, (5″) hydroxyl group, (6″) thiol, (7″) $C_{1-4}$alkylthio, (8″) amino, (9″) mono-$C_{1-4}$alkylamino, (10″) di-$C_{1-4}$alkylamino, (11″) 5- to 6-membered cyclic amino selected from tetrahydropyrrole, piperazine, piperidine, morpholine, thiomorpholine, pyrrole and imidazole, (12″) phenyl-$C_{1-4}$alkyl, (13″) $C_{3-7}$cycloalkyl, (14″) carboxyl, (15″) $C_{1-4}$alkoxy-carbonyl, (16″) $C_{7-10}$aralkyloxy-carbonyl, (17″) carbamoyl, (18″) mono-$C_{1-4}$alkyl-carbamoyl, (19″) di-$C_{1-4}$alkyl-carbamoyl, (20″) $C_{1-4}$alkyl which may be substituted with a halogen atom or $C_{1-4}$alkoxy, (21″) $C_{1-4}$alkoxy which may be substituted with a halogen atom or $C_{1-4}$alkoxy, (22″) $C_{1-4}$alkylenedioxy, (23″) formyl, (24″) $C_{2-4}$alkanoyl, (25″) $C_{1-4}$alkylsulfonyl and (26″) $C_{1-4}$alkylsulfinyl (hereinafter referred to as substituent group C), (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), and (1) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group C); or (2) 5- or 6-membered cyclic amino which may have 1 to 3 substituents selected from (a) halogen, (b) nitro, (c) cyano, (d) hydroxyl group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl; or (3) a heterocyclic group formed by removing one hydrogen atom from a 5- to 8-membered aromatic monocyclic heterocyclic ring or saturated or unsaturated non-aromatic monocyclic heterocyclic ring containing one nitrogen atom and one to three kinds of 1 to 4 heteroatoms selected from oxygen atom, sulfur atom and nitrogen atom or by removing one hydrogen atom from a ring wherein 2 or 3 of the same or different rings selected from the above monocyclic rings have been fused (said heterocyclic group optionally having 1 to 3 substituents selected from the substituent group C), $R^2$ represents (1) $C_{1-10}$alkyl which may have 1 to 3 substituents selected from the substituent group A;

(2) $C_{3-8}$cycloalkyl which may have 1 to 3 substituents selected from the substituent group A;

(3) $C_{2-10}$alkenyl which may have 1 to 3 substituents selected from the substituent group A;

(4) $C_{3-8}$cycloalkenyl which may have 1 to 3 substituents selected from the substituent group A;

(5) $C_{2-10}$alkynyl which may have 1 to 3 substituents selected from the substituent group A;

(6) $C_{6-14}$aryl which may have 1 to 3 substituents selected from the substituent group A;

(7) $C_{6-14}$aryl-$C_{1-6}$alkyl which may have 1 to 3 substituents selected from the substituent group A;

(8) di-$C_{6-14}$aryl-$C_{1-6}$alkyl which may have 1 to 3 substituents selected from the substituent group A;

(9) tri-$C_{6-14}$aryl-$C_{1-6}$alkyl which may have 1 to 3 substituents selected from the substituent group A;

(10) a group represented by the formula —X'''—G—(CH$_2$)$_n$—J, wherein X''' represents $C_{1-4}$alkylene or $C_{2-4}$alkenylene, G represents a bond, —O—, —S—, —CO—NH— or —NH—CO—, n is an integer of 0 to 3, and J represents (a) $C_{6-14}$aryl (which may have 1 to 3 substituents selected from the substituent group B) or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group B);

(11) a group represented by the formula —X''''—L—(CH$_2$)$_n$—M, wherein X'''' represents a bond or $C_{1-4}$alkylene which may have 1 to 3 substituents selected from the substituent group A, and L represents (a) a bond, (b) $C_{6-10}$aryl which may have 1 to 3 substituents selected from the substituent group B, (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—O—, n is an integer of 0 to 3, M represents an amino group, guanidino group, sulfamoyl group, carbamoyl group or hydroxyl group; or

(12) amino which may have 1 to 2 substituents selected from (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), and (l) acyl groups wherein a 5- to 8-membered aromatic heterocyclic group or saturated or unsaturated non-aromatic heterocyclic group containing a least one of 1 to 3 kinds of heteroatoms selected from oxygen atom, sulfur atom and nitrogen atom has been bound to a carbonyl or sulfonyl group (said acyl optionally having 1 to 3 substituents selected from the substituent group C), $R^3$ represents (1) $C_{1-10}$alkyl which may have 1 to 3 substituents selected the substituent group A;

(2) $C_{3-8}$cycloalkyl which may have 1 to 3 substituents selected from the substituent group A;

(3) $C_{2-10}$alkenyl which may have 1 to 3 substituents selected from the substituent group A;

(4) $C_{3-8}$cycloalkenyl which may have 1 to 3 substituents selected from the substituent group A;

(5) $C_{2-10}$alkynyl which may have 1 to 3 substituents selected from the substituent group A;

(6) $C_{6-14}$aryl which may have 1 to 3 substituents selected from the substituent group A;

(7) $C_{6-14}$aryl-$C_{1-6}$alkyl which may have 1 to 3 substituents selected from the substituent group A;

(8) di-$C_{6-14}$aryl-$C_{1-6}$alkyl which may have 1 to 3 substituents selected from the substituent group A;

(9) tri-$C_{6-14}$aryl-$C_{1-6}$alkyl which may have 1 to 3 substituents selected from the substituent group A;

(10) a group represented by the formula —X'''—G—(CH$_2$)$_n$—J, wherein X''' represents $C_{1-4}$alkylene or $C_{2-4}$alkenylene, G represents a bond, —O—, —S—, —CO—NH— or —NH—CO—, n is an integer of 0 to 3, and J represents (a) a $C_{6-14}$aryl group (which may have 1 to 3 substituents selected from the substituent group B) or (b) a 5- to 8-membered aromatic heterocyclic group which may have at least one of 1 to 3 kinds of heteroatoms selected from oxygen atom, sulfur atom and nitrogen atom (said aromatic heterocyclic group optionally having 1 to 3 substituents selected from the substituent group B); or

(11) a group represented by the formula —X''''—L—(CH$_2$)$_n$—M, wherein X'''' represents a bond or $C_{1-4}$alkylene which may have 1 to 3 substituents selected from the substituent group A, and L represents (a) a bond, (b) $C_{6-10}$aryl (which may have 1 to 3 substituents selected from the substituent group B), or (c) a 5- to 8-membered aromatic heterocyclic group containing at least one of 1 to 3 kinds of heteroatoms selected from oxygen atom, sulfur atom and nitrogen atom (said aromatic heterocyclic group optionally having 1 to 3 substituents selected from the substituent group B), (d) —O—, (e) —S—, (f) —CO—NH— or (g) —NH—CO—, n is an integer of 0 to 3, M represents amino group, guanidino group, sulfamoyl group, carbamoyl group or hydroxyl group; and rings B and C each represent a benzene ring which may further have 1 to 4 substituents selected from (1) $C_{1-10}$alkyl which may have 1 to 3 substituents selected the substituent group A;

(2) $C_{3-8}$cycloalkyl which may have 1 to 3 substituents selected from the substituent group A;

(3) $C_{2-10}$alkenyl which may have 1 to 3 substituents selected from the substituent group A;

(4) $C_{3-8}$cycloalkenyl which may have 1 to 3 substituents selected from the substituent group A;

(5) $C_{2-10}$alkynyl which may have 1 to 3 substituents selected from the substituent group A;

(6) $C_{6-14}$aryl which may have 1 to 3 substituents selected from the substituent group A;

(7) $C_{6-14}$aryl-$C_{1-6}$alkyl which may have 1 to 3 substituents selected from the substituent group A;

(8) di-$C_{6-14}$aryl-$C_{1-6}$alkyl which may have 1 to 3 substituents selected from the substituent group A;

(9) tri-$C_{6-14}$aryl-$C_{1-6}$alkyl which may have 1 to 3 substituents selected from the substituent group A;

(10) a heterocyclic group formed by removing one hydrogen atom from a 5- to 8-membered aromatic monocyclic heterocyclic ring or saturated or unsaturated non-aromatic monocyclic heterocyclic ring containing at least 1 of one to three kinds of heteroatoms selected from oxygen atom, sulfur atom and nitrogen atom or by removing one hydrogen atom from a ring wherein 2 or 3 of the same or different rings selected from the above monocyclic rings and 5- to 8-membered cyclic hydrocarbons have been fused (said heterocyclic group optionally having 1 to 3 substituents selected from the substituent group A);

(11) a halogen atom;

(12) amino which may have 1 to 2 substituents selected from (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C, (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C, (k) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C), and (l) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group C);

(13) 5- or 6-membered cyclic amino which may have 1 to 3 substituents selected from (a) halogen, (b) nitro, (c) cyano, (d) hydroxyl group, (e) thiol, (f) amino, (g) carboxyl, (h) optionally halogenated $C_{1-4}$alkyl, (i) optionally halogenated $C_{1-4}$alkoxy, (j) formyl, (k) $C_{2-4}$alkanoyl and (l) $C_{1-4}$alkylsulfonyl;

(14) a group represented by the formula: $R^6$—Y— (wherein Y is O, S, S(O) or S(O)$_2$, and $R^6$ is (i) $C_{1-10}$alkyl which may have 1 to 3 substituents selected the substituent group A; (ii) $C_{3-8}$cycloalkyl which may have 1 to 3 substituents selected from the substituent group A; (iii) $C_{2-10}$alkenyl which may have 1 to 3 substituents selected from the substituent group A; (iv) $C_{3-8}$cycloalkenyl which may have 1 to 3 substituents selected from the substituent group A; (v) $C_{2-10}$alkynyl which may have 1 to 3 substituents selected from the substituent group A; (vi) $C_{6-14}$aryl which may have 1 to 3 substituents selected from the substituent group A; (vii) $C_{6-14}$aryl-$C_{1-6}$alkyl which may have 1 to 3 substituents selected from the substituent group A; (viii) di-$C_{6-14}$aryl-$C_{1-6}$alkyl which may have 1 to 3 substituents selected from the substituent group A; (ix) tri-$C_{6-14}$aryl-$C_{1-6}$alkyl which may have 1 to 3 substituents selected from the substituent group A; or (x) a heterocyclic group formed by removing one hydrogen atom from a 5- to 8-membered aromatic monocyclic heterocyclic ring or saturated or unsaturated non-aromatic monocyclic heterocyclic ring containing at least 1 of one to three kinds of heteroatoms selected from oxygen atom, sulfur atom and nitrogen atom or by removing one hydrogen atom from a ring wherein 2 or 3 of the same or different rings selected from the above monocyclic rings and 5- to 8-membered cyclic hydrocarbons have been fused (said heterocyclic group optionally having 1 to 3 substituents selected from the substituent group A));

(15) cyano group;

(16) acyl selected from formyl, $C_{1-10}$alkyl-carbonyl, $C_{3-8}$cycloalkyl-carbonyl, $C_{2-10}$alkenyl-carbonyl, $C_{3-8}$cycloalkenyl-carbonyl, $C_{2-10}$alkynyl-carbonyl, $C_{6-14}$aryl-carbonyl, $C_{6-14}$aryl-$C_{1-6}$alkyl-carbonyl, di-$C_{6-14}$aryl-$C_{1-6}$alkyl-carbonyl, tri-$C_{6-14}$aryl-$C_{1-6}$alkyl-carbonyl, $C_{1-10}$alkylsulfonyl, $C_{3-8}$cycloalkylsulfonyl, $C_{2-10}$alkenylsulfonyl, $C_{3-8}$cycloalkenylsulfonyl, $C_{2-10}$alkynylsulfonyl, $C_{6-14}$arylsulfonyl, $C_{6-14}$aryl-$C_{1-6}$alkylsulfonyl, di-$C_{6-14}$aryl-$C_{1-6}$alkylsulfonyl or tri-$C_{6-14}$aryl-$C_{1-6}$alkylsulfonyl (said acyl optionally having 1 to 3 substituents selected from the substituent group C);

(17) acyl groups wherein a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom has been bound to carbonyl or sulfonyl (said acyl optionally having 1 to 3 substituents selected from the substituent group C);
(18) carboxyl; and
(19) carbamoyl which may have 1 to 2 substituents selected from (a) $C_{1-10}$alkyl which may have 1 to 3 substituents selected from the substituent group C, (b) $C_{3-8}$cycloalkyl which may have 1 to 3 substituents selected from the substituent group C, (c) $C_{2-10}$alkenyl which may have 1 to 3 substituents selected from the substituent group C, (d) $C_{3-8}$cycloalkenyl which may have 1 to 3 substituents selected from the substituent group C, (e) $C_{2-10}$alkynyl which may have 1 to 3 substituents selected from the substituent group C, (f) $C_{6-14}$aryl which may have 1 to 3 substituents selected from the substituent group C, (g) $C_{6-14}$aryl-$C_{1-6}$alkyl which may have 1 to 3 substituents selected from the substituent group C, (h) di-$C_{6-14}$aryl-$C_{1-6}$alkyl which may have 1 to 3 substituents selected from the substituent group C, (i) tri-$C_{6-14}$aryl-$C_{1-6}$alkyl which may have 1 to 3 substituents selected from the substituent group C and (j) a 5- to 8-membered aromatic heterocyclic group or saturated or unsaturated non-aromatic heterocyclic group containing at least one of 1 to 3 kinds of heteroatoms selected from oxygen atom, sulfur atom and nitrogen atom, which may have 1 to 3 substituents selected from the substituent group C;
provided that (1) a compound represented by the formula:

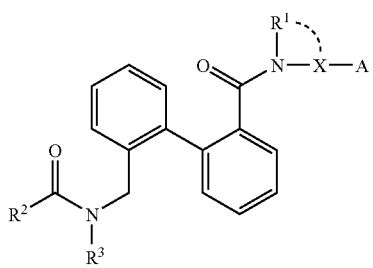

wherein each symbol has the same meaning as defined above, and
(2) 4'-[[(methoxyacetyl)methylamino]methyl]-N-[4-methoxy-3-(4-methyl-1-piperazinyl)phenyl]-2'-methyl-[1,1'-biphenyl]-4-carboxamide are excluded,
or a salt thereof or a prodrug thereof.

20. A method for inhibiting vasoconstriction comprising administering an effective amount of a compound of claim 1 to a mammal in need thereof.

21. A method for treating hypertension, arteriosclerosis, cardiac hypertrophy, myocardial infarction or heart failure, comprising administering an effective amount of a compound of claim 1 to a mammal in need thereof.

22. A process for producing the compound according to claim 1 or a salt thereof, which comprises (i) reacting a compound represented by the formula:

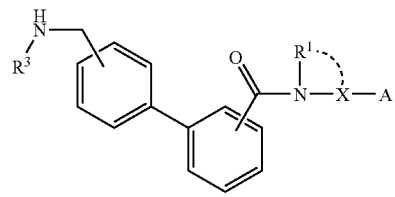

wherein each symbol is as defined in claim 1, or a salt thereof, with a compound represented by the formula: $R^2COOH$ wherein $R^2$ is as defined in claim 1, or a salt thereof, or a reactive derivative thereof, or (ii) reacting a compound represented by formula:

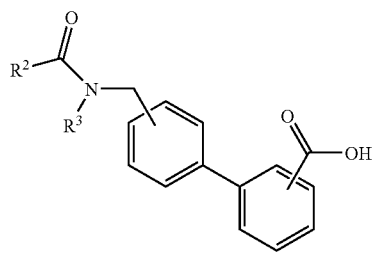

wherein each symbol is as defined in claim 1, or a salt thereof or a reactive derivative thereof, with a compound represented by the formula:

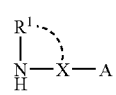

wherein each symbol is as defined in claim 1, or a salt thereof.

* * * * *